United States Patent [19]
Yoshida et al.

[11] Patent Number: 5,719,303
[45] Date of Patent: Feb. 17, 1998

[54] PHOSPHONIC ACID DERIVATIVES

[75] Inventors: Ichirou Yoshida; Hironori Ikuta; Yoshio Fukuda; Yoshihito Eguchi; Makoto Kaino, all of Ibaraki, Japan; Katsuya Tagami, Arlington, Mass.; Naoki Kobayashi, Ibaraki, Japan; Kenji Hayashi, Ibaraki, Japan; Hironobu Hiyoshi, Ibaraki, Japan; Issei Ohtsuka, Ibaraki, Japan; Makoto Nakagawa, Ibaraki, Japan; Shinya Abe, Ibaraki, Japan; Shigeru Souda, Ibaraki, Japan

[73] Assignee: Eisai Co., Ltd., Tokyo, Japan

[21] Appl. No.: 530,311

[22] PCT Filed: Mar. 4, 1994

[86] PCT No.: PCT/JP94/00354

§ 371 Date: Sep. 6, 1995

§ 102(e) Date: Sep. 6, 1995

[87] PCT Pub. No.: WO94/20508

PCT Pub. Date: Sep. 15, 1994

[30] Foreign Application Priority Data

Mar. 8, 1993 [JP] Japan .................. 5-46389

[51] Int. Cl.$^6$ .................. C07F 9/40; C07F 9/38
[52] U.S. Cl. .................. 558/158; 562/13
[58] Field of Search .................. 562/13; 558/158

[56] References Cited

FOREIGN PATENT DOCUMENTS

| 0541037 | 3/1992 | European Pat. Off. . |
| 9304073 | 3/1993 | WIPO . |

OTHER PUBLICATIONS

CA 108:94778 Abstract & structures pp. 1-9 for Oct. 28, 1987 EP Patent — 243173.

*Primary Examiner*—C. Warren Ivy
*Assistant Examiner*—Jean F. Vollamo
*Attorney, Agent, or Firm*—Birch, Stewart, Kolasch & Birch, LLP

[57] ABSTRACT

A phosphonic acid derivative which is useful for medically treating hyperlipemia, represented by the following general formula (I) or a pharmacologically acceptable salt thereof:

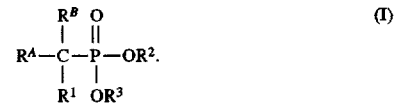

Representative example of the compound according to the present invention is one represented by the following formula:

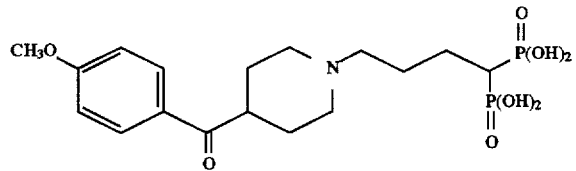

21 Claims, No Drawings

PHOSPHONIC ACID DERIVATIVES

This is the U.S. National Stage application of PCT/JP94/00354 filed Mar. 4, 1994 published as WO94/20508 Sep. 15, 1994.

1. Field of the Invention

The present invention relates to a novel phosphonic acid derivative and a pharmacologically acceptable salt thereof. More particularly, it relates to a phosphonic acid derivative and a pharmacologically acceptable salt thereof which are useful as a medicine, a use of the phosphonic acid derivative or the pharmacologically acceptable salt thereof and a method for medically treating a disease which comprises administering a therapeutically effective amount of the phosphonic acid derivative or the pharmacologically acceptable salt thereof to a patient.

2. Description of the Related Art

Ischemic heart diseases such as myocardial infarction still account for a high proportion of the death causes of the middle-aged and the elderly. Ischemic heart diseases are known to be induced by hyperlipemia which is a primary factor of atherosclerosis which is one of the adult diseases. Accordingly, the medical treatment of hyperlipemia which is a stage precedent to ischemic heart diseases such as myocardial infarction is essential, so that studies have been made for many years to develop an excellent therapeutic medicine for hyperlipemia.

Recently, an HMG-CoA reductase inhibitor has been developed as a therapeutic medicine for hyperlipemia and has been ascertained to have an excellent cholesterol level lowering activity. However, this inhibitor also hinders the biosynthesis of $CoQ_{10}$ or dolichol, so that it is in danger of causing adverse effects such as cardiac hypofunction, muscle ache and infirmity. Meanwhile, a desmosterol reductase inhibitor, which is also a therapeutic medicine for hyperlipemia, also causes a serious adverse effect such as cataract owing to the accumulation of desmosterol.

Under these circumstances, it is still expected to develop a therapeutic medicine for hyperlipemia which is free from the above adverse effects and has an excellent cholesterol level lowering activity.

Under the above circumstances, the present inventors have started the search and studies for a medicine having a squalene synthetase inhibiting action and have found that a specific phosphonic acid derivative can attain the object. The present invention has been accomplished on the basis of this finding.

Although phosphorus-containing hydrocarbon compounds useful as medicines are disclosed in Japanese Patent Publication-A Nos. 56492/1990 and 138288/1990, these compounds are different from those of the present invention in both structure and drug efficacy. Further, phosphorus-containing isoprenoid derivatives useful as medicines are also disclosed in Japanese Patent Publication-A Nos. 101088/1990 and 235821/1990. However, these derivatives are different from those of the present invention in structure.

Constitution of the Invention

The present invention relates to a phosphonic acid derivative represented by the following general formula (I) or a pharmacologically acceptable salt thereof:

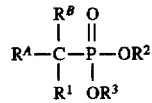

(I)

wherein $R^1$ represents a hydrogen atom, a hydroxyl group, an acyloxyalkyl group, an alkyloxycarbonyl group, a lower alkyl group which may have a substituent or a lower alkoxy group which may have a substituent;

$R^2$ and $R^3$ may be the same or different from each other and each represents a hydrogen atom, a lower alkyl group which may have a substituent, an alkali metal or a prodrug ester forming group;

$R^A$ represents a group represented by the formula:

(wherein $R^4$ represents a hydrogen atom, a lower alkyl group, an alkali metal or an acyloxyalkyl group which may have a substituent), a group represented by the formula:

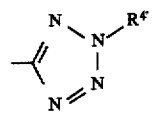

(wherein $R^{4'}$ represents a hydrogen atom, a lower alkyl group or an alkali metal) or a group represented by the formula:

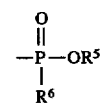

wherein $R^5$ represents a hydrogen atom, a lower alkyl group, an alkali metal or a prodrug ester forming group; and $R^6$ represents a lower alkyl group or a group represented by the formula: —$OR^7$ (wherein $R^7$ represents a hydrogen atom, a lower alkyl group, an alkali metal or a prodrug ester forming group)]; and $R^B$ represents a group represented by the formula: S—T— [wherein S represents an alkenyl group which may have a substituent or a group represented by the formula:

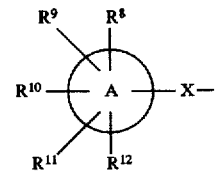

(wherein ring A represents an aromatic ring; $R^8$, $R^9$, $R^{10}$, $R^{11}$ and $R^{12}$ may be the same or different from one another and each represents (1) a hydrogen atom,
(2) an alkyl group which may have a substituent,
(3) an alkenyl group which may have a substituent,
(4) a lower alkoxy group which may have a substituent,
(5) a carbamoyl group which may have a substituent,
(6) a carbamoyloxy group which may have a substituent,
(7) a hydroxyl group,
(8) an acyl group,
(9) a halogen atom,

(10) a group represented by the following formula:

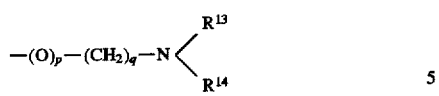

(wherein $R^{13}$ and $R^{14}$ may be the same or different from each other and each represents a lower alkyl group which may have a substituent, or alternatively $R^{13}$ and $R^{14}$ may form together with the nitrogen atom to which they are bonded, a ring which may further contain an oxygen atom, a sulfur atom or a nitrogen atom and which may have one or two, mono- or divalent substituent(s); p is 0 or 1; and q is an integer of 0 to 4) or (11) a group represented by the formula:

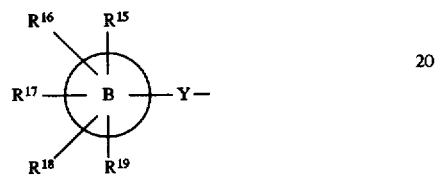

(wherein $R^{15}$, $R^{16}$, $R^{17}$, $R^{18}$ and $R^{19}$ may be the same or different from one another and each represents a hydrogen atom, a hydroxyl group, a lower alkyl group or a lower alkoxy group which may have a substituent; ring B represents an aromatic ring; and Y represents an alkylene chain which may have a substituent, an alkenylidene chain which may have a substituent, an alkynylidene chain which may have a substituent, a group represented by the formula:

a group represented by the formula: —O—, or a single bond), or alternatively two adjacent groups of $R^8$, $R^9$, $R^{10}$, $R^{11}$ and $R^{12}$ may together form a ring; and X represents a single bond, an alkylene chain which may have a substituent, an alkenylidene chain which may have a substituent or a group represented by the formula: —(CH$_2$)$_u$—Z—(CH$_2$)$_v$— (wherein Z is a group represented by the formula:

(wherein r is an integer of 0 to 2), a group represented by the formula:

a group represented by the formula: —O—, a group represented by the formula:

(wherein $R^{20}$ represents a hydrogen atom, a lower alkyl group which may have a substituent or a lower alkenyl group which may have a substituent), a group represented by the formula:

(wherein $R^{21}$ represents a hydrogen atom, a lower alkyl group which may have a substituent, a lower alkenyl group which may have a substituent or a group represented by the formula:

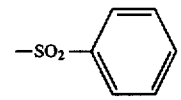

or a group represented by the formula:

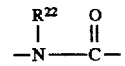

(wherein $R^{22}$ represents a hydrogen atom, a lower alkyl group which may have a substituent or a lower alkenyl group which may have a substituent); u is an integer of 0 to 3;

and v is an integer of 0 to 6); and T represents (1) a single bond, (2) a group represented by the formula:

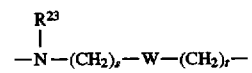

(wherein $R^{23}$ represents a hydrogen atom, a cycloalkyl group, a cycloalkylalkyl group, a lower alkyl group which may have a substituent or a lower alkenyl group which may have a substituent; W represents a group represented by the formula: —O—, a group represented by the formula:

a group represented by the formula: —NH—, a group represented by the formula:

a group represented by the formula:

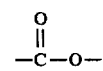

or a single bond; and s and t are independent of each other and are each an integer of 0 to 4), (3) a group represented by the formula:

$$-\underset{\underset{OH}{|}}{CH}-\underset{|}{\overset{R^{29}}{CH}}-\underset{|}{\overset{R^{23}}{N}}-(CH_2)_s-W-(CH_2)_t-$$

(wherein $R^{23}$ W, s and t are each as defined above; and $R^{29}$ represents a hydrogen atom, a cycloalkyl group, a cycloalkylalkyl group, a lower alkyl group which may have a substituent or a lower alkenyl group which may have a substituent), (4) a group represented by the formula:

$$-\underset{|}{\overset{R^{25}}{N}}-$$

(wherein $R^{25}$ represents a hydrogen atom, a cycloalkyl group, a lower alkyl group which may have a substituent or a lower alkenyl group which may have a substituent), or (5) a group represented by the formula:

$$=D\underset{(CH_2)_y}{\overset{(CH_2)_x}{\diagup\diagdown}}E-(CH_2)_w-F-(CH_2)_z-$$

(wherein D represents a carbon atom or a nitrogen atom, E represents a nitrogen atom or a group represented by the formula:

$$\overset{\diagdown}{\underset{\diagup}{}}CH-;$$

F represents a group represented by the formula: —O—, a group represented by the formula:

$$-\overset{\overset{O}{\|}}{C}-,$$

a group represented by the formula: —NH—, a group represented by the formula:

$$-\underset{\underset{}{}}{\overset{OH}{\underset{|}{CH}}}-,$$

a group represented by the formula:

$$-\overset{\overset{O}{\|}}{C}-O-$$

or a single bond; x and y are independent of each other and are each an integer of 0 to 3, with the proviso that the case wherein both x and y are 0 is excepted; w and z are each an integer of 0 to 4; and the symbol: ......... represents a single bond or a double bond when D is a carbon atom and a single bond when D is a nitrogen atom), with the proviso that S must be a group selected from among those described above except an alkenyl group which may have a substituent, when T is a group represented by the formula:

$$=D\underset{(CH_2)_y}{\overset{(CH_2)_x}{\diagup\diagdown}}E-(CH_2)_w-F-(CH_2)_z-$$

(wherein D, E, F, x, y, w and z are each as defined above)].

Preferable examples of the phosphonic acid derivative or the pharmacologically acceptable salt thereof described above include those represented by the general formula (I) wherein T defined with respect to $R^B$ represents (1) a single bond,
(2) a group represented by the formula:

$$-\underset{|}{\overset{R^{23}}{N}}-(CH_2)_s-W-(CH_2)_t-$$

(wherein $R^{23}$ W, s and t are each as defined above), (4) a group represented by the formula:

$$-\underset{|}{\overset{R^{25}}{N}}-$$

(wherein $R^{25}$ is as defined above), or (5) a group represented by the formula:

$$=D\underset{(CH_2)_y}{\overset{(CH_2)_x}{\diagup\diagdown}}E-(CH_2)_w-F-(CH_2)_z-$$

(wherein D, F, x, y, w and z are each as defined above, and E is a carbon atom or a nitrogen atom, or is a nitrogen atom or a group represented by the formula:

$$\overset{\diagdown}{\underset{\diagup}{}}CH-).$$

Preferable examples of the phosphonic acid derivative or the pharmacologically acceptable salt thereof described above include those represented by the general formula (I) wherein the prodrug ester forming group is a group represented by the formula:

$$-\underset{|}{\overset{R^{27}}{CH}}-O-\overset{\overset{O}{\|}}{C}-^{28}$$

(wherein $R^{27}$ represents a hydrogen atom or a lower alkyl group; and $R^{28}$ represents an alkyl group which has 1 to 12 carbon atoms and may have a substituent, a cycloalkyl group, an aryl group which may have a substituent, an alkoxy group which has 1 to 12 carbon atoms and may have a substituent, a cycloalkyloxy group, an aryloxy group which may have a substituent, an alkylamino group which has 1 to 12 carbon atoms and may have a substituent, a cycloalkylamino group, a piperidinyl group, a pyrrolidinyl group or an aromatic amino group which may have a substituent).

Further, the present invention relates to (A) a squalene synthetase inhibitor comprising the phosphonic acid derivative or the pharmacologically acceptable salt thereof described above as the active ingredient, (B) a preventive or therapeutic medicine for diseases against which a squalene synthetase inhibiting action is efficacious, which comprises the phosphonic acid derivative or the pharmacologically acceptable salt thereof described above as the active ingredient, (C) a preventive or therapeutic medicine for hyperlipemia which comprises the phosphonic acid derivative or the pharmacologically acceptable salt thereof described above as the active ingredient, (D) a preventive or therapeutic medicine for hypertension which comprises the phosphonic acid derivative or the pharmacologically acceptable salt thereof described above as the active ingredient, (E) a pharmaceutical composition which comprises a therapeutically effective amount of the phosphonic acid derivative or the pharmacologically acceptable salt thereof described above and a pharmaceutically acceptable filler, (F) a use of the phosphonic acid derivative or the pharmacologically acceptable salt thereof described above for making a medicament for medically treating a disease against which a squalene synthetase inhibiting action is efficacious, (G) a use of the phosphonic acid derivative or the pharmacologically acceptable salt thereof described above for making a medicament for hyperlipemia, (H) a use of the phosphonic acid derivative or the pharmacologically acceptable salt thereof described above for making a medicament for hypertension, (I) a method for medically treating a disease which comprises administering a therapeutically effective amount of the phosphonic acid derivative or the pharmacologically acceptable salt thereof described above to a patient suffering from a disease against which a squalene synthetase inhibiting action is efficacious, (J) a method for medically treating a disease which comprises administering a therapeutically effective amount of the phosphonic acid derivative or the pharmacologically acceptable salt thereof described above to a patient suffering from hyperlipemia, and (K) a method for medically treating a disease which comprises administering a therapeutically effective amount of the phosphonic acid derivative or the pharmacologically acceptable salt thereof described above to a patient suffering from hypertension.

The explanation with respect to the general formula (I) will be described hereinafter.

The lower alkyl group defined with respect to $R^4$, $R^{4'}$, $R^5$, $R^6$, $R^7$, $R^{15}$, $R^{16}$, $R^{17}$, $R^{18}$, $R^{19}$ and $R^{27}$ is a linear or branched alkyl group having 1 to 6 carbon atoms such as methyl group, ethyl group, propyl group, isopropyl group, butyl group, isobutyl group, secbutyl group, tert-butyl group, pentyl group (amyl group), isopentyl group, neopentyl group, tert-pentyl group, 2-methylbutyl group, 3-methylbutyl group, hexyl group, isohexyl group, 2-methylpentyl group, 3-methylpentyl group, 1,1-dimethylbutyl group, 2,2-dimethylbutyl group, 2,3-dimethylbutyl group, 3,3-dimethylbutyl group, 2-ethylbutyl group, 1,1,2-trimethylpropyl group, 1-ethyl-1-methylpropyl group and 2-ethyl-3-methylpropyl group.

The lower alkyl group constituting the "lower alkyl group which may have a substituent" as defined with respect to $R^1$, $R^2$, $R^3$, $R^{13}$, $R^{14}$, $R^{20}$, $R^{21}$, $R^{22}$, $R^{23}$, $R^{25}$ and $R^{29}$ is the same as the one defined above, while the substituent constituting it includes aryl groups such as phenyl group, o-tolyl group, m-tolyl group, p-tolyl group, 1-naphthyl group and 2-naphthyl group; hydroxyl group; cyano group; heteroaryl groups such as pyridyl group, pyrrolyl group, furanyl group, imidazolyl group, thiazolyl group, thienyl group, oxazolyl group, isoxazolyl group and pyrimidinyl group; cycloalkyl groups having 3 to 8 carbon atoms; lower alkoxy groups; amino group and mono- and dialkylamino groups. These substituents may each be bonded to any carbon atom of the lower alkyl group.

The alkyl group constituting the "alkyl group which may have a substituent" as defined with respect to $R^8$, $R^9$, $R^{10}$, $R^{11}$ and $R^{12}$ is a linear or branched alkyl group having 1 to 20 carbon atoms. Among them, alkyl groups having 1 to 15 carbon atoms are preferred. The substituent constituting it is the same as the one defined above with respect to the lower alkyl group which may have a substituent.

The lower alkoxy group constituting the "lower alkoxy group which may have a substituent" as defined with respect to $R^1$, $R^8$, $R^9$, $R^{10}$, $R^{11}$, $R^{12}$, $R^{15}$, $R^{16}$, $R^{17}$, $R^{18}$ and $R^{19}$ is one derived from the above lower alkyl group, and examples thereof include methoxy group, ethoxy group, n-butoxy group, isobutoxy group, secbutoxy group, tert-butoxy group, 2-methylbutoxy group, 3-methylbutoxy group, 2,3-dimethylpropoxy group, hexyloxy group and octyloxy group. The substituent constituting it includes lower alkoxy groups such as methoxy group and ethoxy group; amino group; dialkylamino group; monoalkylamino group, cyano group and hydroxyl group.

The lower alkenyl group constituting the "lower alkenyl group which may have a substituent" as defined with respect to $R^{20}$, $R^{21}$, $R^{22}$, $R^{23}$, $R^{25}$ and $R^{29}$ is one derived from the above lower alkyl group. In other words, the lower alkenyl group is one derived from the above lower alkyl group by replacing one or two of the carbon-carbon single bonds by double bond(s). The substituent constituting it is the same as the one defined above with respect to the lower alkyl group which may have a substituent.

The alkenyl group constituting the "alkenyl group which may have a substituent" as defined with respect to S, $R^8$, $R^9$, $R^{10}$, $R^{11}$ and $R^{12}$ is a linear or branched one having 2 to 20 carbon atoms and 1 to 3 double bonds. Among them, alkenyl groups having 5 to 15 carbon atoms are preferred. The substituent constituting it includes cycloalkyl groups having 3 to 8 carbon atoms, hydroxyl group and cyano group.

The alkali metal defined with respect to $R^2$, $R^3$, $R^4$, $R^{4'}$, $R^5$ and $R^7$ includes lithium, sodium, potassium and rubidium, among which lithium, sodium and potassium are preferable, with sodium being most preferable.

The acyl group defined with respect to $R^8$, $R^9$, $R^{10}$, $R^{11}$ and $R^{12}$ includes those derived from aliphatic saturated carboxylic acids having 1 to 8 carbon atoms, e.g., formyl group, acetyl group and propionyl group; those derived from aliphatic unsaturated carboxylic acids having 1 to 8 carbon atoms, e.g., acryloyl group, propioloyl group, methacryloyl group, crotonoyl group and isocrotonoyl group; those derived from carbocyclic carboxylic acids having 1 to 8 carbon atoms, e.g., benzoyl group and toluoyl group; and those derived from heterocyclic carboxylic acids having 1 to 8 carbon atoms, e.g., furoyl group, thenoyl group, nicotinoyl group and isonicotinoyl group. In short, the acyl group may be any one derived from a carboxylic acid having 1 to 8 carbon atoms.

The acyloxy group constituting the "acyloxyalkyl group" defined with respect to $R^1$ is one derived from the above acyl group, while the alkyl group constituting it is the same as the one defined above with respect to the lower alkyl group.

The alkyl group constituting the "alkyloxycarbonyl group" defined with respect to $R^1$ is the same as the one defined above with respect to the lower alkyl group.

The acyloxy group constituting the "acyloxyalkyl group which may have a substituent" as defined with respect to $R^4$ is one derived from the above acyl group, while the alkyl group constituting it is the same as the one described above with respect to the lower alkyl group.

The halogen atom defined with respect to $R^8$, $R^9$, $R^{10}$, $R^{11}$ and $R^{12}$ includes fluorine atom, chlorine atom, bromine atom and iodine atom.

The cycloalkyl group defined with respect to $R^{23}$, $R^{25}$, $R^{28}$ and $R^{29}$ is one having 3 to 8 carbon atoms.

The cycloalkyl group constituting the "cycloalkylalkyl group" defined with respect to $R^{23}$ and $R^{29}$ is the same as the one described above. The alkyl group constituting it is the same as the one described above with respect to the lower alkyl group.

Preferable examples of the substituent constituting the "carbamoyl group which may have a substituent" or "carbamoyloxy group which may have a substituent" as defined with respect to $R^8$, $R^9$, $R^{10}$, $R^{11}$ and $R^{12}$ include lower alkyl groups, aminoalkyl groups, mono- and dialkylaminoalkyl groups, alkylcarbamoyl groups and arylcarbamoyl groups. The alkylene chain constituting the "alkylene chain which may have a substituent" as defined with respect to X and Y is one having 1 to 6 carbon atoms, while the substituent constituting it includes hydroxyl group, lower alkoxy groups, lower alkyl groups, lower acyloxy groups, alkylcarbamoyloxy groups and arylcarbamoyloxy groups.

The alkenylidene chain constituting the "alkenylidene chain which may have a substituent" as defined with respect to X and Y is one which is derived from the above alkylene chain and which has 1 to 6 carbon atoms and 1 to 3 double bonds. The substituent constituting it includes hydroxyl group, lower alkoxy groups, lower alkyl groups, lower acyloxy groups, alkylcarbamoyloxy groups and arylcarbamoyloxy groups.

The alkynylidene chain constituting the "alkynylidene chain which may have a substituent" as defined with respect to Y is one which is derived from the above alkylene chain and which has 1 to 6 carbon atoms and one or two triple bonds. The substituent constituting it includes hydroxyl group, lower alkyl groups, lower alkoxy groups, lower acyloxy groups, alkylcarbamoyloxy groups and arylcarbamoyloxy groups.

x and y are independent of each other and are each an integer of 0 to 3 and it is preferable that the sum of x and y be 3 or 4. The case wherein the sum of x and y is 0 is excepted.

Specific examples of the group represented by the formula:

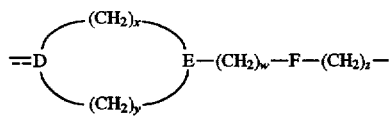

(wherein D, E, F, x, y, w and z are each as defined above) as defined with respect to T include the following groups (a) to (j), among which the groups (c), (d) and (e) are preferable, with the groups (d) and (e) being still preferable:

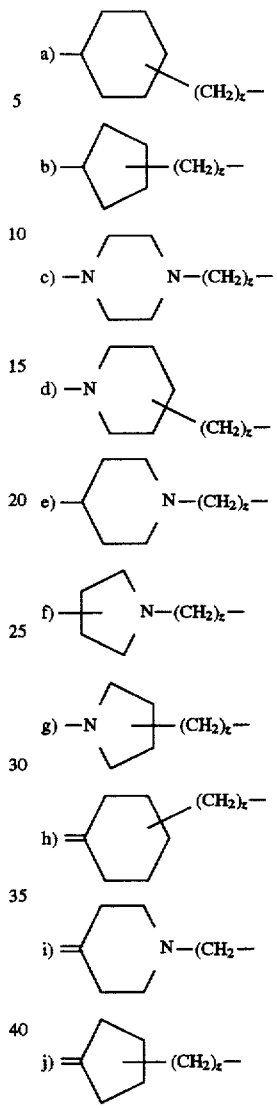

wherein z is an integer of 0 to 4, preferably 2 or 3.

As defined above, $R^{13}$ and $R^{14}$ may form, together with the nitrogen atom to which they are bonded, a ring which may contain an oxygen atom, a sulfur atom or a nitrogen atom, and examples of the ring are as follows, though the ring according to the present invention is not limited to them:

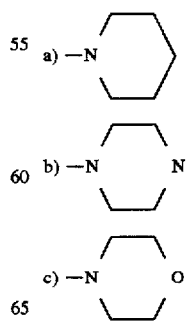

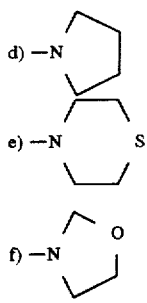

These rings described above may have a mono- or divalent substituent and preferable examples of the substituent include lower alkyl groups, lower alkenyl groups, a group represented by the formula: =O and a group represented by the formula: =S.

The rings A and B as defined with respect to S each represents an aromatic ring and examples thereof include benzene ring, thiophene ring, furan ring, naphthalene ring, quinoline ring, pyridine ring, pyrrole ring, imidazole ring, thiazole ring, oxazole ring, isoxazole ring, pyrimidine ring, benzimidazole ring and benzofuran ring.

The pharmacologically acceptable salt according to the present invention includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate.

Further, the phosphonic acid derivative of the present invention may form a metal salt such as calcium salt and magnesium salt. The pharmacologically acceptable salt of the present invention includes these metal salts.

Although the phosphonic acid derivative of the present invention may be present as geometrical isomers (including cis- and trans-isomers) owing to its structure, the present invention includes both of the isomers.

Representative processes for preparing the phosphonic acid derivative of the present invention will now be described.

Preparation process 1

A compound represented by the general formula (I) wherein $R^2$ and $R^3$ are each a lower alkyl group; $R^4$ is a group represented by the formula:

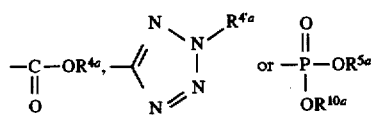

(wherein $R^{4a}$, $R^{4'a}$, $R^{5a}$ and $R^{7a}$ are each a lower alkyl group); $R^1$ is a hydrogen atom; and $R^B$ is a group represented by the formula:

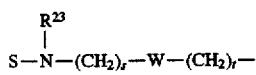

(wherein S, W, $R^{23}$, s and t are each as defined above) or a group represented by the formula:

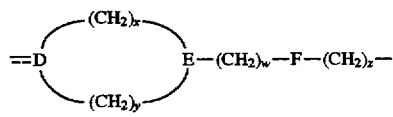

(wherein S, D, E, F, x, y, w and z are each as defined above) can be prepared by the following Methods 1 or 2. The following Methods 1 and 2 include, needless to say, methods for preparing a compound represented by the general formula (I) wherein E represents a nitrogen atom and others are each as defined above.

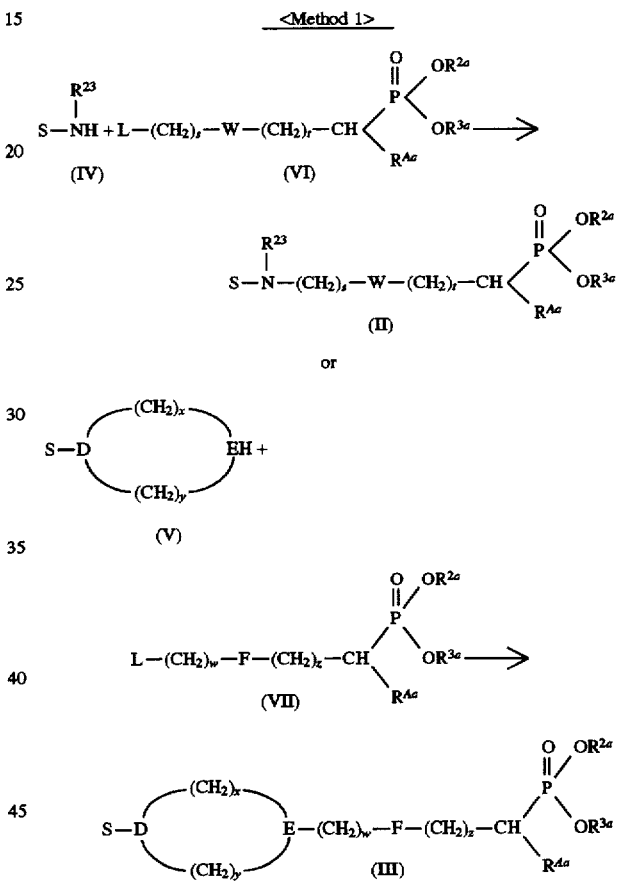

wherein S, W, $R^{23}$, D, E, F, s, t, x, y, w and z are each as defined above; $R^{2a}$ and $R^{3a}$ are each a lower alkyl group; $R^{Aa}$ is a group represented by the formula:

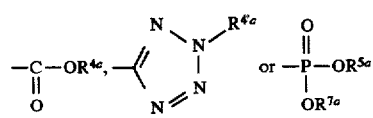

(wherein $R^{4a}$, $R^{4'a}$, $R^{5a}$ and $R^{7a}$ are each as defined above); and L represents a halogen atom or a leaving group such as tosyloxy group, acetoxy group and mesyloxy group.

Specifically, the Method 1 is one which comprises conducting the reaction of an amine represented by the general formula (IV) with a compound represented by the general formula (VI) or that of an amine represented by the general formula (V) with a compound represented by the general formula (VII) in the presence of a base and further, if necessary, a catalyst under stirring to prepare the compounds (II) or (III).

The solvent usable in the above reaction includes dimethylformamide, dimethylsulfoxide, dichloromethane, chloroform and tetrahydrofuran.

Preferable examples of the base usable in the reaction include inorganic bases such as sodium carbonate an potassium carbonate; and organic bases such as triethylamine and diisopropylamine.

Preferable examples of the catalyst usable in the reaction include organic palladium catalysts such as tetrakis (triphenylphosphine) palladium, palladium acetate and bis (triphenylphosphine) palladium chloride; and organic nickel catalysts such as dichloro[1,3-bis(triphenylphosphino) propane] nickel (II) and bis(acetylacetonate) nickel.

The reaction temperature may range from room temperature to 100° C., preferably from room temperature to 60° C.

<Method 2>

$$S-L + HN-(CH_2)_s-W-(CH_2)_t-CH\overset{O}{\underset{R^{Aa}}{\overset{\|}{P}}}\overset{OR^{2a}}{\underset{OR^{3a}}}$$
(IX)   (X)

$$S-N-(CH_2)_s-W-(CH_2)_t-CH\overset{O}{\underset{R^{Aa}}{\overset{\|}{P}}}\overset{OR^{2a}}{\underset{OR^{3a}}}$$
(II)

$$S-L + H-D \overset{(CH_2)_x}{\underset{(CH_2)_y}{\bigcirc}} \quad E-(CH_2)_w-F-(CH_2)_z-CH\overset{O}{\underset{R^{Aa}}{\overset{\|}{P}}}\overset{OR^{2a}}{\underset{OR^{3a}}}$$
(IX)   (XI)

$$S-D \overset{(CH_2)_x}{\underset{(CH_2)_y}{\bigcirc}} \quad E-(CH_2)_w-F-(CH_2)_z-CH\overset{O}{\underset{R^{Aa}}{\overset{\|}{P}}}\overset{OR^{2a}}{\underset{OR^{3a}}}$$
(III)

wherein S, W, $R^{23}$, D, E, F, L, $R^{Aa}$, $R^{2a}$, $R^{3a}$, s, t, x, y, w and z are each as defined above.

Specifically, the above compounds (II) or (III) can also be prepared by reacting a compound represented by the general formula (IX) with an amine represented by the general formulas (X) or (XI) in the presence of a base under stirring.

The base usable in the above reaction includes inorganic bases such as potassium carbonate and sodium carbonate; and organic bases represented by tertiary amines such as triethylamine and diisopropylethylamine.

Although the solvent to be used in the reaction may be any one inert to the reaction, preferable examples of the solvent include organic solvents such as dimethylformamide, dimethylsulfoxide, dichloromethane, chloroform and tetrahydrofuran. The reaction temperature is preferably from room temperature to 100° C., still preferably room temperature to 60° C.

Preparation process 2

A compound represented by the general formulas (II) or (III) wherein W or F is a group represented by the formula:

$$\underset{-CH-}{\overset{OH}{|}};$$

E is an nitrogen atom and s or w is 1 can also be prepared by the following process:

$$\underset{(XII)}{\overset{R^{23}}{\underset{|}{S-NH}}} \text{ or } + S-D\overset{(CH_2)_x}{\underset{(CH_2)_y}{\bigcirc}}NH$$
(XIII)

-continued $$\overset{O}{\underset{}{\longrightarrow}}(CH_2)_t-CH\overset{O}{\underset{R^{Aa}}{\overset{\|}{P}}}\overset{OR^{2a}}{\underset{OR^{3a}}} \overset{heat}{\longrightarrow}$$
(XIV)

$$S-\underset{|}{\overset{R^{23}}{N}}-CH_2-\overset{OH}{\underset{|}{CH}}-(CH_2)_t-CH\overset{O}{\underset{R^{Aa}}{\overset{\|}{P}}}\overset{OR^{2a}}{\underset{OR^{3a}}} \text{ or }$$
(XV)

$$S-D\overset{(CH_2)_x}{\underset{(CH_2)_y}{\bigcirc}}N-CH_2-\overset{OH}{\underset{|}{CH}}-(CH_2)_t-CH\overset{O}{\underset{R^{Aa}}{\overset{\|}{P}}}\overset{OR^{2a}}{\underset{OR^{3a}}}$$
(XVI)

wherein $R^{2a}$, $R^{3a}$, $R^{Aa}$, $R^{23}$, S, D, t, x and y are each as defined above.

Specifically, this process is one which comprises heating a mixture comprising an amine represented by the general formulas (XII) or (XIII) and a carbonic ester represented by the general formula (XIV) in the absence of any solvent to prepare an objective compounds (XV) or (XVI).

Preparation process 3-1

A compound represented by the general formula (I) wherein T in the definition of $R^B$ is a group represented by the formula: —NH—, or a compound represented by the general formula (III) wherein F is a group represented by the formula: —NH—; z is 0 and $R^{Aa}$ is a group represented by the formula:

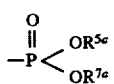

(wherein $R^{5a}$ and $R^{7a}$ are each as defined above) can also be prepared by the following process:

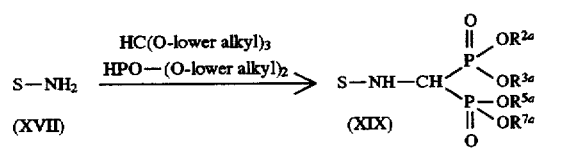

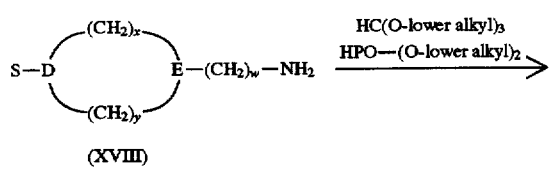

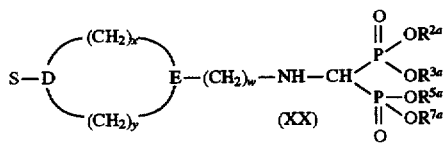

wherein S, $R^{2a}$, $R^{3a}$, $R^{5a}$, $R^{7a}$, D, E and w are each as defined above.

Specifically, this method is one which comprises condensing an amine represented by the general formulas (XVII) or (XVIII) with a phosphonic ester in the conventional manner to prepare the objective compounds (XIX) or (XX).

Preparation process 3-2

A compound represented by the general formula (II) or (III) wherein E is a nitrogen atom; W or F is a group represented by —NH—; t or z is 0; and $R^{Aa}$ is a group represented by the formula:

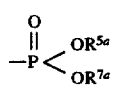

(wherein $R^{5a}$ and $R^{7a}$ are each as defined above) can also be prepared by the following process:

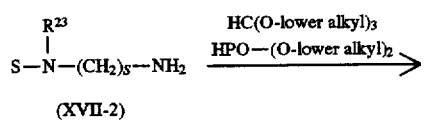

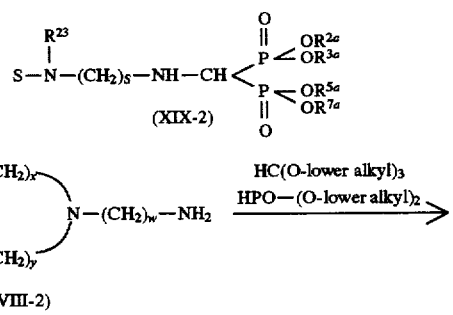

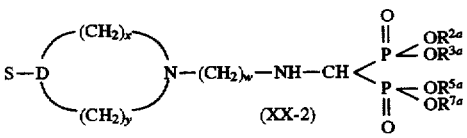

wherein S, $R^{23}$, $R^{2a}$, $R^{3a}$, $R^{5a}$, $R^{7a}$, D, s and w are each as defined above.

Specifically, this method is one which comprises condensing an amine represented by the general formulas (XVII-2) or (XVIII-2) with a phosphonic ester in the conventional manner to prepare the objective compounds (XIX-2) or (XX-2).

Preparation process 4

A compound represented by the general formula (I) wherein T in the definition of $R^B$ is a single bond can also be prepared by the following process:

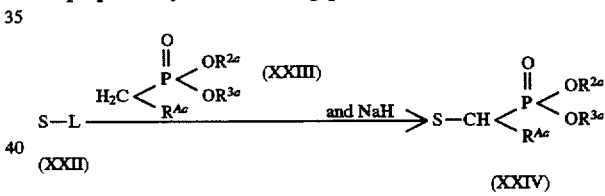

wherein S, L, $R^{2a}$, $R^{3a}$ and $R^{Aa}$ are each as defined above.

Specifically, the objective compound (XXIV) can be prepared by condensing a compound represented by the general formula (XXII) with a phosphonic acid derivative represented by the general formula (XXIII) in the presence of a base.

The base is preferably an alkali metal hydride such as sodium hydride and potassium hydride, or an alkali metal alcoholate such as sodium methoxide, sodium ethoxide and potassium tert-butoxide, though it may be any conventional one.

Preferable examples of the solvent usable in the above reaction include N,N-dimethylformamide, N,N-dimethylacetamide, N-methylpyrrolidone, tetrahydrofuran and 1,2-dimethoxyethane, though the solvent may be any one inert to the reaction. The reaction temperature is preferably about 0° to 100° C., still preferably 20° to 80° C.

Preparation process 5

A compound represented by the general formula (I) wherein $R^2$ and $R^3$ are each a lower alkyl group; $R^4$ is a group represented by the formula:

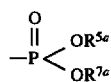

(wherein $R^{5a}$ and $R^{7a}$ are each as defined above) and $R^B$ is a group represented by the formula:

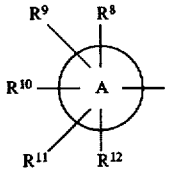

(wherein A, $R^8$, $R^9$, $R^{10}$, $R^{11}$ and $R^{12}$ are each as defined above) can be prepared by the following process:

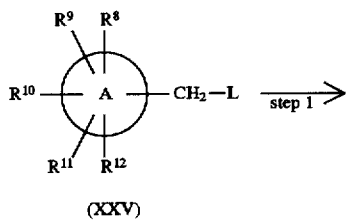

(XXV)

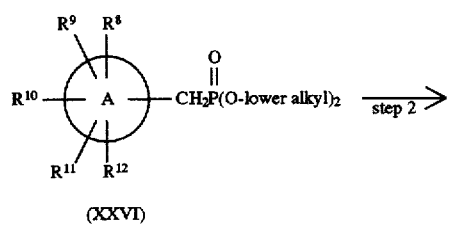

(XXVI)

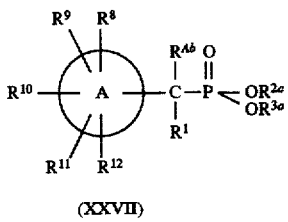

(XXVII)

wherein ring A, $R^1$, $R^8$, $R^9$, $R^{10}$, $R^{11}$, $R^{12}$, $R^{2a}$, $R^{3a}$ and L are each as defined above; and $R^{Ab}$ is a group represented by the formula:

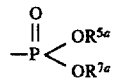

(wherein $R^{5a}$ and $R^{7a}$ are each as defined above).

Specifically, this process is one which comprises converting a compound represented by the general formula (XXV) into a phosphonate (XXVI) in the first step of and reacting the phosphonate with an acid chloride of a lower alkyl ester of phosphorous acid in the presence of a base in the second step to prepare the objective compound (XXVII). Preferable examples of the base include n-butyllithium and lithium diisopropylamide. The reaction temperature is preferably from −80° C. to room temperature.

Preparation process 6

A compound represented by the general formula (I) wherein $R^2$ and $R^3$ may be the same or different from each other and each represent a hydrogen atom or an alkali metal; and $R^A$ is a group represented by the formula:

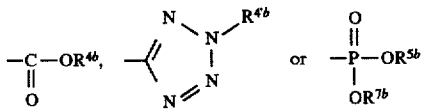

(wherein $R^{4b}$, $R^{4'b}$, $R^{5b}$ and $R^{7b}$ are each a hydrogen atom or an alkali metal) or a compound as defined above wherein at least one of $R^2$, $R^3$, $R^{4b}$, $R^{4'b}$, $R^{5b}$ and $R^{7b}$ is a hydrogen atom or an alkali metal and the others thereof are each a lower alkyl group can also be prepared by the following process:

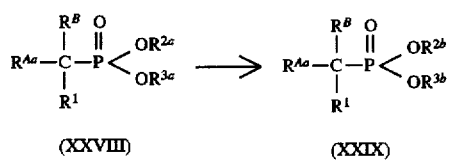

(XXVIII)            (XXIX)

wherein $R^1$, $R^{Aa}$, $R^B$ $R^{2a}$ and $R^{3a}$ are each as defined above; $R^{Ac}$ represents a group represented by the formula:

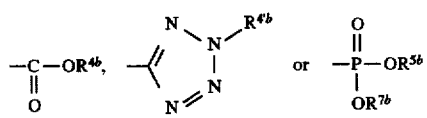

(wherein $R^{4b}$, $R^{4'b}$, $R^{5b}$ and $R^{7b}$ are each as defined above); and $R^{2b}$ and $R^{3b}$ are each a hydrogen atom or an alkali metal.

Specifically, this process is one which comprises dealkylating an alkyl phosphonate derivative represented by the general formula (XXVIII) in the conventional manner.

This process is one which comprises, e.g., treating the compound (XXVIII) with excess of a trimethylsilyl halide and treating the obtained compound with water or an alcohol to prepare the objective compound (XXIX).

In the above reaction, it is preferable to use a nonaqueous solvent such as dichloromethane, chloroform, carbon tetrachloride, benzene and acetonitrile. The reaction temperature is preferably from about −20° C. to room temperature.

Further the compound (XXIX) can be converted into the corresponding phosphonic acid through acidic hydrolysis in the conventional manner. The acidic hydrolysis is preferably conducted by adding concentrated hydrochloric acid to the compound (XXIX) and heating the resulting mixture under reflux.

A compound represented by the formula (XXVIII) wherein $R^{Aa}$ is a group represented by the formula: —COOR$^{4a}$ (wherein $R^{4a}$ is as defined above) can be converted into a compound represented by the formula (XXIX) wherein $R^{Ac}$ is a group represented by the formula: —COOR$^{4b}$ (wherein $R^{4b}$ is as defined above) by the conventional alkaline hydrolysis with sodium hydroxide or potassium hydroxide.

Further the compound (XXVIII) can also be converted into a partial ester by changing the reaction conditions, for example, by reducing the amount of the trimethylsilyl halide to be added to the compound (XXVIII), or by conducting ester cleavage (i.e., dealkylation of the trialkylphosphate) at a temperature of as low as −10° C. or below.

Preparation process 7

A compound represented by the general formula (I) wherein at least one of $R^2$, $R^3$, $R^4$, $R^5$ and $R^7$ is a benzyl group, a picolyl group, an alkyl group which may have a substituent, a lower alkyl group which may have a substituent, an acyloxyalkyl group, an alkyloxycarbonyloxyalkyl group or hydrogen atom can be prepared by the following process:

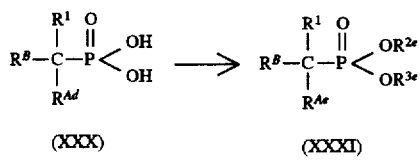

(XXX)  (XXXI)

wherein $R^{Ad}$ is a group represented by the formula:

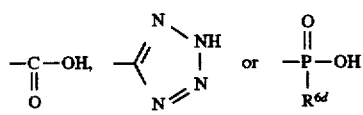

(wherein $R^{6d}$ represents a lower alkyl group or a hydroxyl group); $R^B$ and $R^1$ are each as defined above; $R^{2e}$ and $R^{3e}$ each represents a benzyl group, a picolyl group, an alkyl group which may have a substituent, a lower alkyl group which may have a substituent, an acyloxyalkyl group, an alkyloxycarbonyloxyalkyl group or a hydrogen atom; and $R^{Ae}$ represents a group represented by the formula:

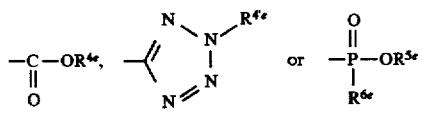

wherein $R^{4e}$ and $R^{4'e}$ each represents a benzyl group, a picolyl group, an alkyl group which may have a substituent, a lower alkyl group which may have a substituent, an acyloxyalkyl group or a prodrug ester forming group; and $R^{6e}$ represents a lower alkyl group or a group represented by the formula: —$OR^{7e}$ (wherein $R^{7e}$ represents a benzyl group, a picolyl group, an alkyl group which may have a substituent, a lower alkyl group which may have a substituent, an acyloxyalkyl group or a prodrug ester forming group)].

Specifically, the objective compound (XXXI) can be prepared by heating a mixture of a phosphonic acid derivative represented by the general formula (XXX) with an alkyl halide in the presence of a base.

The base is preferably a tertiary amine such as diisopropylethylamine and triethylamine, though it is not limited to them.

The solvent to be used in the above reaction is preferably a nonaqueous solvent such as dimethylformamide and dimethyl sulfoxide, though it may be any one inert to the reaction.

Preparation process 8

A compound represented by the general formulas (II) or (III) wherein W or F is a group represented by the formula:

$$\overset{O}{\underset{\|}{-C-O-}};$$

E represents a nitrogen atom and s or w is 0 can be prepared by the following process:

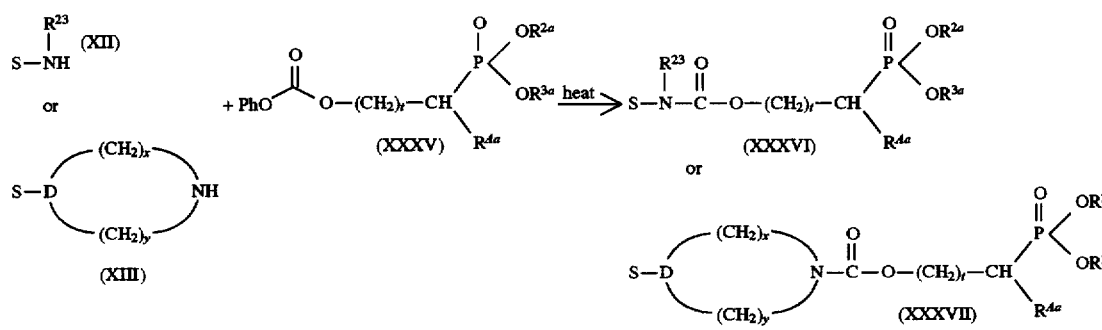

wherein $R^{2a}$, $R^{3a}$, $R^{Aa}$, $R^{23}$, S, D, t, x and y are each as defined above; and Ph is a phenyl group.

Specifically, the objective compounds (XXXVI) or (XXXVII) can be prepared by heating a mixture of an amine (XII) or an amine (XIII) with a carbonic ester (XXXV) in the absence of any solvent. The reaction temperature is generally from room temperature to 100° C., preferably 40° to 70° C.

Preparation process 9

A compound represented by the general formulas (I) wherein $R^2$ and $R^3$ are each a lower alkyl group, $R^4$ is a group represented by the formulas:

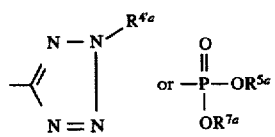

(wherein $R^{4a}$, $R^{4'a}$, $R^{5a}$ and $R^{7a}$ each represents a lower alkyl group), $R^1$ represents a hydrogen atom and $R^B$ is a group selected among groups represented by the formula:

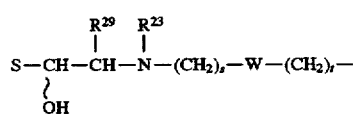

(wherein S, W, $R^{23}$, $R^{29}$, s and t are each as defined above) and groups represented by the formula:

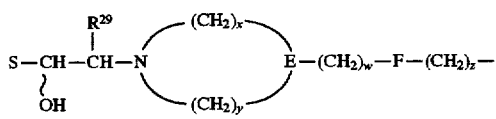

(wherein S, E, F, x, y, w and z are each as defined above) can be prepared by the following process:

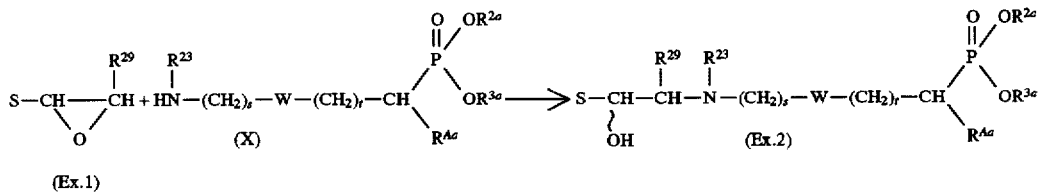

or

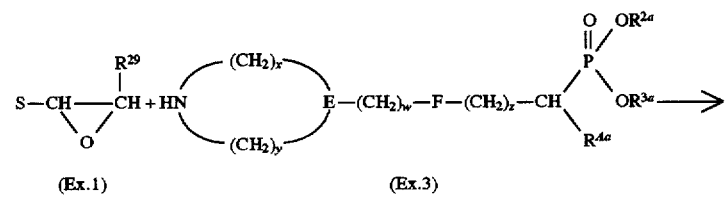

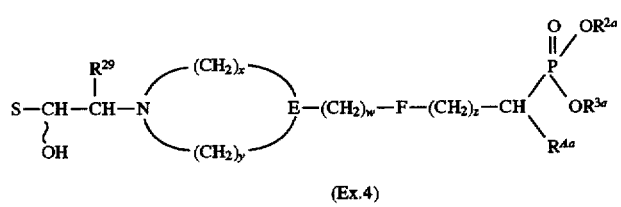

wherein S, W, $R^{23}$, E, F, $R^{4a}$, $R^{2a}$, $R^{3a}$, $R^{29}$, s, t, x, y, w and z are each as defined above.

That is, this process is one which comprises heating a mixture comprising an epoxide represented by the general formula (Ex. 1) and an amine represented by the general formulas (X) or (Ex. 3) in the absence of any solvent or in the presence of a solvent inert to the reaction to thereby prepare the objective compound (Ex. 4).

Preferable examples of the solvent usable in the above reaction include dichloromethane, chloroform, benzene, toluene, methanol, ethanol, tetrahydrofuran, dimethylformamide and dimethylsulfoxide. The reaction temperature is preferably 40° to 200° C., more preferably 40° to 100° C.

Preparation process 10

A compound represented by the general formula (I) wherein T in the definition of $R^B$ is a group represented by the formula:

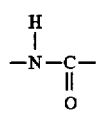

can also be prepared by the following process:

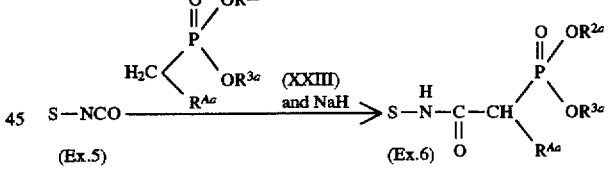

wherein S, $R^{2a}$, $R^{3a}$ and $R^{4a}$ are each as defined above.

That is, the objective compound (Ex. 6) can be prepared by condensing an isocyanate compound represented by the general formula (Ex. 5) and a phosphonic acid derivative represented by the general formula (XXIII) in the presence of a base.

The base is preferably an alkali metal hydride such as sodium hydride and potassium hydride, or an alkali metal alcoholate such as sodium methoxide, sodium ethoxide and potassium t-butoxide, though it may be any conventional one.

Preferable examples of the reaction solvent usable in the above reaction include N,N-dimethylformamide, N,N-dimethylacetamide, N-methylpyrrolidone, tetrahydrofuran and 1,2-dimethoxyethane, though the solvent may be any one inert to the reaction. The reaction temperature is preferably 0° to 100° C., more preferably 20° to 80° C.

Preparation process 11

A compound represented by the general formula (I) wherein $R^2$ and $R^3$ are each a lower alkyl group; $R^4$ is a group represented by the formulas:

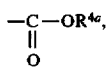

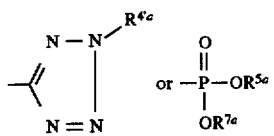

(wherein $R^{4a}$, $R^{4'a}$, $R^{5a}$ and $R^{7a}$ are each a lower alkyl group), $R^1$ represents a hydrogen atom and $R^B$ is a group represented by the formula:

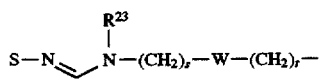

(wherein S, W, $R^{23}$, s and t are each as defined above) can be prepared by the following process:

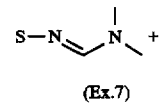

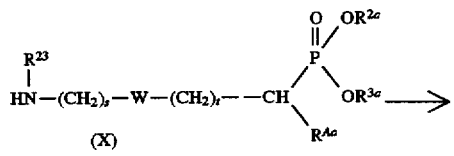

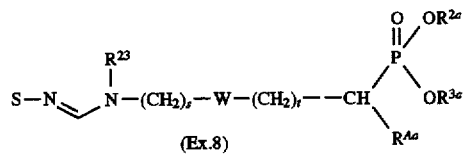

wherein S, W, $R^{23}$, $R^{2a}$, $R^{3a}$, $R^{Aa}$, s and t are each as defined above.

That is, the objective compound (Ex. 8) can be prepared by heating a mixture of a formamidine derivative represented by the general formula (Ex. 7) and an amine represented by the general formula (X).

Examples of the solvent to be used in the above reaction include preferably benzene, toluene, dimethylformamide and dimethylsulfoxide, though it may be any one inert to the reaction. The temperature is preferably 60° to 200° C., more preferably 100° to 150° C. The presence of a catalytic amount of a salt can accelerate the reaction, and ammonium sulfate and sodium chloride can be used as the salt.

The preparation processes of representative raw materials used in the above Preparation processes will now be described.

Preparation process A

The compound (VI) used in the Preparation process 1 can be prepared by the procedure represented by the following reaction scheme:

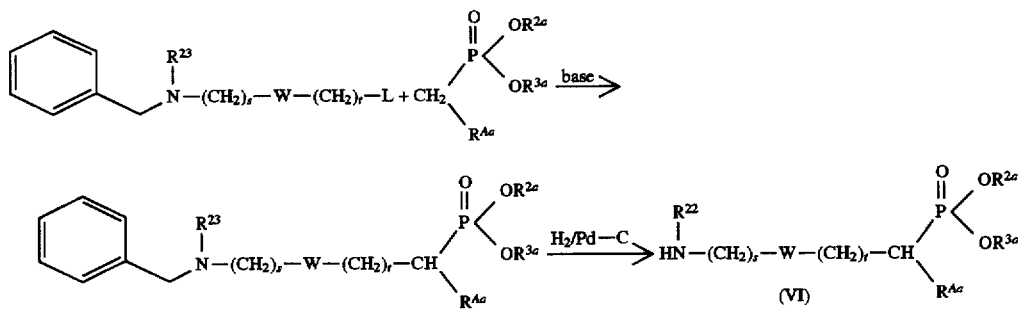

wherein $R^{Aa}$, $R^{2a}$, $R^{3a}$, $R^{23}$, W, L, s and t are each as defined above.

Preparation process B

The compound (XXXV) used in the Preparation process 8 can be prepared by the procedure represented by the following reaction scheme:

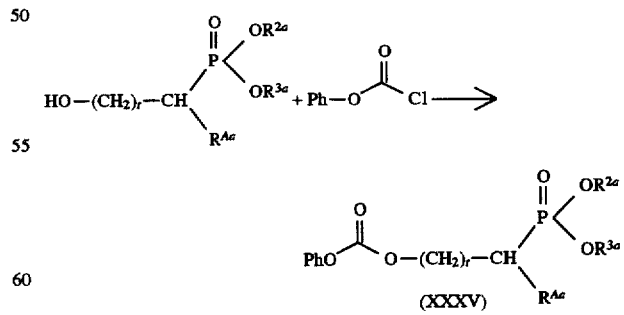

wherein $R^{Aa}$, $R^{2a}$, $R^{3a}$, t and Ph are each as defined above.

A pharmacological experimental example will now be described to illustrate the effect of the invention.

Pharmacological Experimental Example

1. Experimental method

50 μl of 500 mM Tris-HCl (pH: 7.4), 50 μl of 10 mM magnesium chloride, 50 μl of 2 mM potassium fluoride, 50 μl of 10 mM nicotinamide adenine dinucleotide phosphate (hereinafter abbreviated to "NADPH"), 100 μl of a sample solution of five-fold concentration, 100 μl of distilled water and 50 μl of a 1 mg/ml rat liver microsome were put in a centrifuge tube, with the liver microsome being one prepared by the method which will be described below.

The above mixture was preincubated at 37° C. for 5 minutes. 50 μl of 100 μM 3H-FPP (10 mCi/mmol, NEN) was added to the resulting mixture to initiate a reaction. After 10 minutes, 1 ml of 4N sodium hydroxide was added to the mixture to stop the reaction, followed by the addition of 1 ml of ethanol. The obtained mixture was incubated at 80° C. for 12 hours, cooled with ice and extracted with petroleum ether twice. The petroleum ether phases were separated from the aqueous phase and evaporated to dryness with nitrogen gas. The residue was dissolved in 25 μl of chloroform containing squalene, farnesol and cholesterol as markers. The obtained solution was applied to TLC (Empore: 412001-1) and developed with benzene/isopropyl ether (1:1) for 6 minutes and with heptane for 15 minutes.

The band of squalene was cut from the plate and examined for radioactivity with a liquid scintillation counter to determine the inhibitory ratio.

<Preparation of rat liver microsome>

The rate liver microsome used in the above experiment was prepared as follows.

A Sqraque-Dawley rat was fed with a feed containing 2% of cholestyramine (Dowex 1-X2) for at least 5 days to enhance the cholesterol biosynthesis activity. At midnight (0:00), the liver was extirpated from the rat. A 1.15 (w/v) % potassium chloride solution was circulated in the blood vessel of the liver extirpated under cooling with ice to remove the blood. The resulting liver was cut into small pieces with scissors, homogenized with a Teflon homogenizer of loose fitting type and subjected to centrifugation (700 g, 10 minutes). The obtained supernatant was further subjected to centrifugation (15000 g, 20 minutes) and the obtained supernatant was subjected to centrifugation (105000 g, 60 minutes) to be separated into a microsome fraction and a supernatant. This microsome fraction was washed with a 0.1M potassium phosphate buffer (pH: 7.4) once, and suspended in the same buffer in a liver concentration of 3 g/ml. The obtained suspension was examined for protein content by the Lowry method and the protein content of the suspension was adjusted to 20 mg/ml.

2. Experimental results

The squalene synthetase inhibiting activities of representative compounds according to the present invention are given in Table A. The data of the Table A reveal that the compounds of the present invention act as an effective squalene synthetase inhibitor.

TABLE A

| Inhibitory activity against squalene synthetase | |
| --- | --- |
| Ex. No. | Inhibitory activity $IC_{50}$ (nM) |
| 14 | 2.4 |
| 15 | 0.81 |
| 16 | 0.28 |
| 19 | 170 |
| 32 | 1.4 |
| 41 | 5.0 |
| 42 | 1.8 |

TABLE A-continued

| Inhibitory activity against squalene synthetase | |
| --- | --- |
| Ex. No. | Inhibitory activity $IC_{50}$ (nM) |
| 114 | 2.4 |
| 201 | 0.91 |
| 209 | 1.3 |
| 210 | 4.0 |
| 223 | 1.0 |
| 230 | 3.0 |
| 238 | 0.54 |
| 246 | 3.1 |

It can be understood from the above experimental results that the phosphonic acid derivatives according to the present invention are useful as preventive and therapeutic medicines for diseases against which a squalene synthetase inhibiting action is efficacious. Accordingly, the compounds according to the present invention are effective in the prevention and treatment of all diseases against which a squalene synthetase inhibiting action is efficacious. For example, the compounds of the present invention are effective in the prevention and treatment of hyperlipemia and prevent the evolution of atherosclerosis to regress thereof. Thus, the compounds of the present invention can also prevent the development and evolution of ischemic heart diseases such as myocardial infarction to treat medically thereof. Further, the compounds of the present invention inhibit squalene synthetases of eumycetes, so that they are useful as antifugal agents. Thus, they can be used in the prevention and treatment of all diseases to which eumycetes participate.

There is known that the prenylation to give a ras protein plays an important role in the activation of the ras protein which is a carcinogenic one. The compounds of the present invention have the activity to interfere the prenylation to give a ras protein. In addition, the compounds of the present invention also interfere the enzymes which catalyze the synthesis of a prenyl diphosphate such as farnesyl diphosphate and geranylgeranyl diphosphate which plays as a substrate in the prenylation to give a ras protein. Therefore, the compounds of the present invention can prevent the development and evolution of carcinomas and cancers to regress thereof and are also useful as carcinostaic agents.

Further, the compounds of the present invention having a bisphosphonic acid structure exhibit a calcium metabolism regulating activity and therefore are effective in medically treating osteoporosis, Parget's disease, carcinomatous hypercalcemia, arthritic calculus and calcareous metastasis. Furthermore, they are useful as therapeutic medicines for diabetes mellitus and rheumatism, and as anti-inflammatory agents, anticholelithogenic agents, hypotensive agents, hypoglycemic agents, diuretic agents and antimicrobial agents.

The compounds of the present invention can use together with a HMG-CoA reductase inhivitor and the like which is another cholesterol-lowering agent. The combination use of the compound of the present invention with the HMG-CoA reductase inhivitor and the like brings a strong reduction in cholesterol concentration in blood, and therefore, hyperlipemia can medically be treated.

The compounds of the present invention are less toxic and highly safe, thus being valuable also in this sence.

When the compound of the present invention is used as a squalene synthetase inhibitor for the treatment and prevention of various diseases, it may be administered orally in the form of powder, granule, capsule or syrup, or alternatively parenterally in the form of suppository, injection, external preparation or drop. The dose thereof remarkably varies depending upon symptom; the sex, weight, age and sensitivity of a patient; the route of administration; the kind of preparation; and the kind of liver disease, and is not particularly limited. When the compound is administered orally, the dose per adult a day is about 0.1 to 1000 mg, which may be administered in one to several portions. When it is administered as an injection, the dose is about 0.3 to 100 µg/kg.

The preparations according to the present invention are prepared by the use of the conventional carriers in the conventional manners.

More precisely, a solid preparation for oral administration according to the present invention is prepared by adding a filler and, if necessary, a binder, disintegrator, lubricant, color and/or corrigent to an active ingredient and shaping the obtained mixture into a tablet, coated tablet, granule, powder or capsule.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant include magnesium stearate, talc, polyethylene glycol, silica and hardened vegetable oil; those of the color include those authorized as pharmaceutical additives; and those of the corrigent include cocoa powder, mentha herb, aromatic powder, mentha oil, borneol and powdered cinnamon bark. Of course, the tablet and granule may be suitably coated with sugar, gelatin or the like, if necessary.

An injection according to the present invention is prepared by adding a pH regulator, buffer, stabilizer and/or solubilizing agent to an active ingredient at need and formulating the mixture into an injection for subcutaneous, intramuscular or intravenous administration by the conventional process.

EXAMPLES

Examples will now be described, though it is needless to say that the present invention is not limited to them. In the Examples, Me represents a methyl group, Et an ethyl group and Tos a tosyl group; and $^1$H-NMR spectra were determined with a Varian UNITY 400. When $CDCl_3$, $CD_3OD$ or DMSO-$d_6$ was used as the solvent, each value was determined with $Me_4Si$ (δ=0) as the internal reference. When D20 was used as the solvent, each value was determined by taking the δ value of $D_2O$ as 4.65, unless otherwise stated. In each case wherein DSS is described as the internal reference, sodium 3-(trimethylsilyl)-1-propane-sulfonate was used as the internal reference (δ=0).

Preparative Example 1

Tetraethyl 4-methylaminobutylindenediphosphonate (a) 3-(N-Methylbenzylamino)1-chloropropane

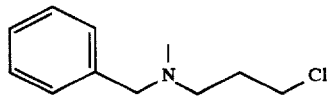

60 ml of 1-bromo-3-chloropropane was added to a mixture comprising 60 g of N-methylbenzylamine, 100 g of anhydrous potassium carbonate and 200 ml of N,N-dimethylformamide, while maintaining the mixture at room temperature on a water bath. The obtained mixture was stirred at that temperature overnight to conduct a reaction. The reaction mixture was extracted with ethyl acetate/water. The ethyl acetate phase was washed with water and a saturated aqueous solution of common salt, dried over anhydrous magnesium sulfate and concentrated. The residue was subjected to silica gel column chromatography (0 to 1.5% methanol/chloroform) to give 69 g of the title compound.

$^1$H-NMR δ($CDCl_3$): 1.97(2H, quint, J=7 Hz), 2.20(3H, s), 2.53(2H, t, J=7 Hz), 3.50(2H, s), 3.61(2H, t, J=7 Hz), 7.20~7.35(5H, m)

(b)Tetraethyl 4-(N-methylbenzylamino) butylindenediphosphonate

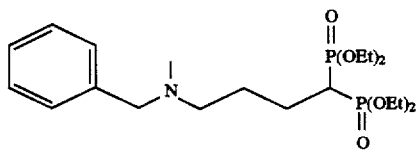

10 g of tetraethyl methylenediphosphonate was dropwise added to a mixture comprising 1.5 g of sodium hydride and 30 ml of N,N-dimethylformamide. After the resulting mixture bubbled and turned into a transparent solution, 7.0 g of the 3-(N-methylbenzylamino)-1-chloropropane prepared in the step (a) was added to the transparent solution and the obtained mixture was heated on an oil bath at 80° C. for 10 hours to conduct a reaction. The reaction mixture was extracted with ethyl acetate/water. The ethyl acetate phase was washed with water and a saturated aqueous solution of common salt, dried over anhydrous magnesium sulfate and concentrated. The residue was subjected to silica gel column chromatography [1 to 3% (1% concentrated aqueous ammonia/methanol)/chloroform] to give 7.7 g of the title compound.

$^1$H-NMR δ($CDCl_3$): 1.34(12H, t, J=7 Hz), 1.75~2.05(4H, m), 2.18(3H, s), 2.35(1H, tt, J=6 Hz, 23 Hz), 2.39(2H, t, J=7 Hz), 3.48(2H, s), 4.12~4.22(8H, m), 7.20~7.33(5H, m)

(c) Tetraethyl 4-methylaminobutylidenediphosphonate

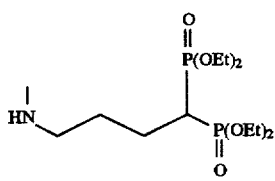

A mixture comprising 1 g of the tetraethyl 4-(N-methylbenzylamino)butylidenediphosphonate prepared in the step (b), a catalytic amount of 10% palladium/carbon and 10 ml of ethanol was stirred in a hydrogen atmosphere at room temperature for 6 hours to conduct a reaction. The catalyst was filtered out and the filtrate was concentrated to give 700 mg of the title compound.

$^1$H-NMR δ($CDCl_3$): 1.35(12H, t, J=7 Hz), 1.72~1.85(2H, m), 1.89~2.05(2H, m), 2.32(1H, tt, J=6 Hz, 24 Hz), 2.43(3H, s), 2.61(2H, t, J=7z), 4.12~4.23(8H, m)

Preparative Example 2

Tetraethyl 2-(4-piperidinyl)ethylidene-1,1-diphosphonate (a) N-Benzyloxycarbonyl-4-hydroxymethylpiperidine

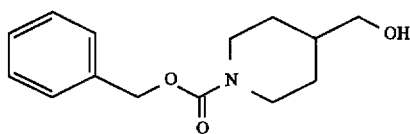

A solution of 25 g of sodium hydrogencarbonate in 200 ml of water was added to a solution of 15 g of 4-hydroxymethylpiperidine in 150 ml of dichloromethane. 25.7 ml of benzyloxycarbonyl chloride was dropwise added to the obtained mixture under vigorous stirring at room temperature. The resulting mixture was stirred for 2 hours. The organic phase was dried and distilled to remove the solvent. The residue was purified by silica gel column chromatography [dichloromethane/methanol (100:2)]to give 20 g of the title compound.

$^1$H-NMR $\delta$(CDCl$_3$): 1.05~1.28(2H, m), 1.60~1.79(3H, m), 3.50(2H, s), 4.22(2H, s), 5.14(2H, s), 7.28~7.38(5H, m)

(b) N-Benzyloxycarbonyl4-(methanesulfonyloxymethyl)piperidine

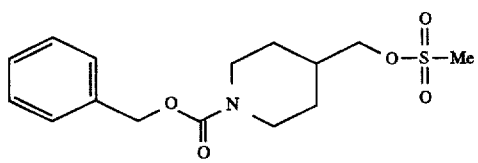

2.6 ml of methanesulfonyl chloride was dropwise added to a mixture comprising 7.5 g of the N-benzyloxycarbonyl-4-hydroxymethylpiperidine prepared in the step (a), 4.6 ml of triethylamine and 100 ml of tetrahydrofuran under cooling with ice. After one hour, the resulting mixture was extracted with ethyl acetate. The organic phase was washed with water, dried and distilled to remove the solvent. 10.5 g of the title compound was obtained as a colorless oil, which was used in the subsequent step without further purification.

(c) N-Benzyloxycarbonyl-4-bromomethylpiperidine

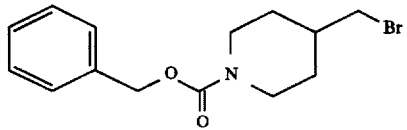

A mixture comprising 6.6 g of the N-benzyloxycarbonyl-4-(methanesulfonyloxymethyl)piperidine, 5.2 g of lithium bromide and 70 ml of tetrahydrofuran was refluxed for 2 hours to conduct a reaction. After the completion of the reaction, water was added to the reaction mixture. The resulting mixture was extracted with ethyl acetate. The organic phase was dried and distilled to remove the solvent. The residue was purified by silica gel column chromatography [hexane/ ethyl acetate (3:1)] to give 5.4 g of the title compound as a colorless oil.

1H-NMR $\delta$(CDCl$_3$): 1.14~1.30(2H, m), 1.75~1.90(3H, m), 2.68~2.85(2H, m), 3.30(2H, d, J=8 Hz), 4.22(2H, s), 5.13(2H, s), 7.18~7.28(5H, m)

(d) Tetraethyl 2-(N-benzyloxycarbonyl-4-piperidinyl)ethylidene-1,1-diphosphonate

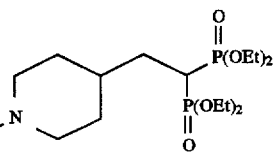

3.2 g of the N-benzyloxycarbonyl-4-bromomethylpiperidine prepared in the step (c) was dropwise added to a solution of 3.2 g of tetraethyl methylenediphosphonate and 0.46 g of sodium hydride (60% oil dispersion) in 20 ml of anhydrous dimethylformamide at room temperature. The obtained mixture was stirred at 60° C. for 3 fours and poured into chilled water. The resulting mixture was extracted with ethyl acetate. The organic phase was dried and distilled to remove the solvent. The residue was purified by silica gel column chromatography [benzene/ acetone (75:25)] to give 2.5 g of the title compound as a colorless oil.

$^1$H-NMR $\delta$(CDCl$_3$): 1.00~1.15(2H, m), 1.33(12H, t, J=7 Hz), 1.68~1.90(5H, m), 2.47(1H, tt, J=24 Hz, 7 Hz), 2.76 (2H, s), 4.10~4.22(10H, m), 5.11(2H, s), 7.28~7.36(5H, m)

(e) Tetraethyl 2-(4-piperidinyl)ethylidene-1,1-diphosphonate

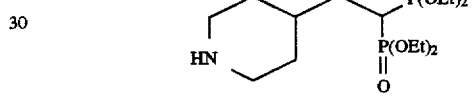

2.5 g of the tetraethyl 2-(N-benzyloxycarbonyl-4-piperidinyl)ethylidene- 1,1-diphosphonate prepared in the step (d) was dissolved in 50 ml of methanol, followed by the addition of 0.3 g of palladium/carbon. The obtained mixture was stirred at room temperature in a hydrogen atmosphere for one hour. After the completion of the reaction, the reaction mixture was filtered. The filtrate was subjected to vacuum distillation to remove the solvent, giving 1.7 g of the title compound.

$^1$H-NMR $\delta$(CDCl$_3$): 0.98~1.10(2H, m), 1.32(12H, t, J=7Hz), 1.70~1.90(6H, m), 2.38(1H, tt, J=24 Hz, 7Hz), 2.55(2H, br.d, J=10 Hz), 3.04(2H, br.d, J=12 Hz), 4.10~4.20 (8H, m)

Preparative Example 3

Tetraethyl 4-phenoxycarbonyloxybutylidene-1,1-diphosphonate

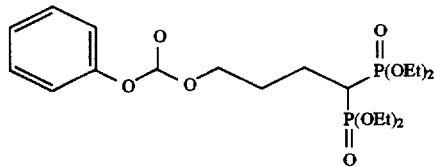

0.70 g of tetraethyl 4-hydroxybutylidene-1,1-diphosphonate was dissolved in 15 ml of anhydrous dichloromethane, followed by the addition of 0.39 ml of triethylamine and 0.30 ml of phenyl chloroformate under cooling with ice. The obtained mixture was stirred for 30 minutes. Water was added to the resulting mixture to cause phase separation. The organic phase was separated from the aqueous phase, dried and subjected to vacuum concentration to give 0.954 g of the title compound.

$^1$H-NMR δ(CDCl$_3$): 1.34(12H, t, J:7 Hz), 1.76~1.86(2H, m), 1.97~2.03(2H, m), 2.37(1H, tt, J=25 Hz, 6 Hz), 3.67(2H, t, J=6 Hz), 4.13~4.24(8H, m), 7.24~7.29(2H, m), 7.38~7.44 (3H, m)

Preparative Example 4

Tetraethyl 4-(4-nitrophenoxy)carbonyloxybutylidene-1,1-diphosphonate

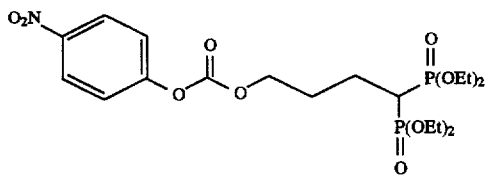

The title compound was prepared in a similar manner to that of the Preparative Example 3.

$^1$H-NMR δ(CDCl$_3$): 1.32~1.43(12H, m), 1.75~1.88(2H, m), 1.93~2.15(2H, m), 2.38(1H, tt, J=24 Hz, 6 Hz), 3.67(2H, t, J=6 Hz), 4.12~4.25(8H, m), 7.48~7.54(2H, m), 8.32~8.38 (2H, m)

Preparative Example 5

Diethyl 1-ethoxycarbonyl-4-hydroxybutylphosphonate
(a) Diethyl 1-ethoxycarbonyl-4(tetrahydropyran-2-yloxy)butylphosphonate

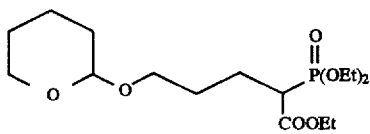

21.5 g of sodium hydride was suspended in 400 ml of dimethylformamide, followed by the addition of 115 g of triethyl phosphonoacetate under cooling with ice. The obtained mixture was stirred at room temperature for 20 minutes, followed by the addition of 100 g of 2-(3-bromopropyloxy)tetrahydropyran. The obtained mixture was stirred at 80° C. for 6 hours. Water (1 l) was added to the resulting mixture, followed by the extraction with ether. The organic phase was washed with a saturated aqueous solution of common salt, dried over anhydrous sodium sulfate and subjected to vacuum concentration. The residue was purified by silica gel column chromatography [acetone/hexane (1:2 to 1:1)] to give 90.5 g of the title compound.

$^1$H-NMR δ(CDCl$_3$): 1.22~1.39(9H, m), 1.46~1.88(6H, m), 1.90~2.10(2H, m), 2.93~3.05(1H, m), 3.34~3.43(1H, m), 3.46~3.53(1H, m), 3.68~3.88(2H, m), 4.08~4.25(6H, m), 4.54~4.59(1H, m)

(b) Diethyl 1-ethoxycarbonyl-4-hydroxybutylphosphonate

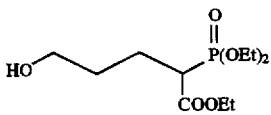

The diethyl 1-ethoxycarbonyl-4-(tetrahydropyran-2-yloxy)butylphosphonate prepared in the step (a) was dissolved in 500 ml of methanol, followed by the addition of 20 g of a cation-exchange resin (Dowex 50w-8, H type). The obtained mixture was mildly refluxed for 7 hours, cooled to room temperature, and filtered to remove the resin. The filtrate was distilled to remove the solvent, giving 68.8 g of the title compound.

$^1$H-NMR δ(CDCl$_3$): 1.26~1.46(9H, m), 1.55~1.82(2H, m), 1.90~2.11(2H, m), 2.93~3.06(1H, m), 3.62~3.68(2H, m), 4.08~4.26(6H, m)

Preparative Example 6

Diethyl 1-ethoxycarbonyl-4-(p-toluenesulfonyloxy)butylphosphonate

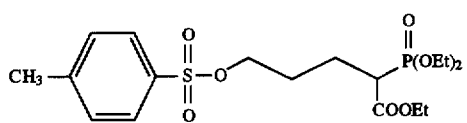

50 g of the diethyl 1-ethoxycarbonyl-4-hydroxybutylphosphonate prepared in the Preparative Example 5 was dissolved in 150 ml of anhydrous pyridine, followed by the addition of 44 g of p-toluenesulfonyl chloride at −20° C. The obtained mixture was stirred for 3 hours and poured onto ice-water. The resulting mixture was neutralized with dilute hydrochloric acid and extracted with ethyl acetate. The organic phase was washed with 2N hydrochloric acid, water, an aqueous solution of sodium hydrogencarbonate and a saturated aqueous solution of common salt successively, dried over anhydrous sodium sulfate and subjected to vacuum concentration. The residue was purified by silica gel column chromatography [dichloromethane/methanol (50:1 to 10:1)] to give 46 g of the title compound.

$^1$H-NMR δ(CDCl$_3$): 1.23~1.35(9H, m), 1.65~2.04(4H, m), 2.45(3H, s), 2.81~2.96(1H, m), 3.97~4.07(2H, m), 4.09~4.24(6H, m), 7.36(2H, d, J=9 Hz), 7.77(2H, d, J=9 Hz)

Preparative Example 7

Diethyl 1-ethoxycarbonyl-4-phenoxycarbonyloxybutylphosphonate

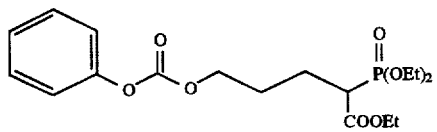

The title compound was prepared from the diethyl 1-ethoxycarbonyl-4-hydroxybutylphosphonate prepared in the Preparative Example 5 and phenyl chloroformate in a similar manner to that of the Preparative Example 3.

$^1$H-NMR δ(CDCl$_3$):

1.27~1.36(9H, m), 1.55~1.84(2H, m), 1.90~2.13(2H, m), 2.93~3.06(1H, m), 3.63~3.68(2H, m), 4.08~4.26 (6H, m), 7.20~7.30(2H, m), 7.35~7.44(3H, m)

Preparative Example 8

Diethyl 1-ethoxycarbonyl-4-(4-nitrophenoxycarbonyloxy)butylphosphonate

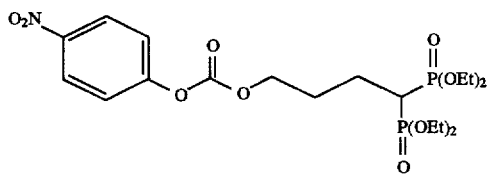

The title compound was prepared from the diethyl 1-ethoxycarbonyl-4-hydroxybutylphosphonate prepared in the Preparative Example 5 and 4'-nitrophenyl chloroformate in a similar manner to that of the Preparative Example 7.

$^1$H-NMR $\delta$(CDCl$_3$): 1.25~1.38(9H, m), 1.57~2.18(4H, m), 2.92~3.12(1H, m), 3.75~3.65(2H, t, J=6 Hz), 4.10~4.30 (6H, m), 7.48~7.53(2H, m), 8.32~8.37(2H, m)

Preparative Example 9

Triethyl 3,4-epoxy-1-carboxybutylphosphonate

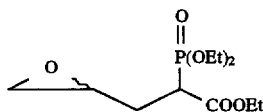

A mixture comprising 5.7 g of triethyl 1-carboxy-3-butenylphosphonate and 100 ml of dichloromethane was stirred, followed by the addition of 5 g of 80% m-chloroperbenzoic acid. The obtained mixture was reacted at room temperature overnight. An aqueous solution of sodium hydrogencarbonate and a small amount of sodium sulfite were added to the reaction mixture successively, followed by stirring for 30 minutes. The dichloromethane phase was recovered, washed with an aqueous solution of sodium hydrogencarbonate and a saturated aqueous solution of common salt successively, dried over anhydrous magnesium sulfate, and concentrated. The residue was subjected to silica gel column chromatography (50 to 100% ethyl acetate/hexane) to give 3.9 g of the title compound.

$^1$H-NMR $\delta$(CDCl$_3$): 1.27~1.37(9H, m), 1.88~1.98(0.6H, m), 2.10~2.28(0.8H, m), 2.32~2.42(0.6H, m), 2.50(0.4H, dd, J=2 Hz, 5 Hz), 2.56(0.6H, dd, J=2 Hz, 5 Hz), 2.75~2.80 (1H, m), 2.95~3.01(0.6H, m), 3.03~3.09(0.4H, m), 3.10 (0.4H, ddd, J=5 Hz, 9 Hz, 22 Hz), 3.15(0.6H, ddd, J=3 Hz, 12 Hz, 23 Hz), 4.10~4.30(6H, m)

Preparative Example 10

N-Methyl-4-[4-(1-hydroxyethyl)benzyl]benzylamine
(a) 2-[4-[α-Hydroxy-4-(1-methoxymethyloxyethyl)benzyl]phenyl]-1,3-dioxolane

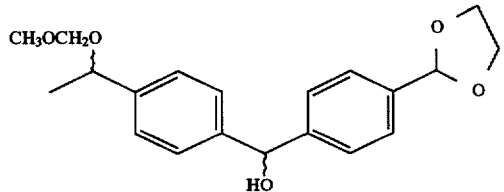

36 ml of a 2.5M solution of n-butyllithium in hexane was dropwise added to a solution of 20 g of 4-bromo(1-methoxymethyloxyethyl)benzene in 200 ml of anhydrous tetrahydrofuran, while the mixture was maintained at −50° C. or below. The obtained mixture was stirred at −60° C. for one hour, and 50 ml of a solution of 14.5 g of 4-(1,3-dioxolan-2-yl)benzaldehyde in anhydrous tetrahydrofuran was dropwise added to the resulting mixture while maintaining the mixture at −60° C. or below. The obtained mixture was stirred at −50° C. for 30 minutes and poured onto ice-water. The obtained mixture was extracted with ethyl acetate. The organic phase was dried and distilled to remove the solvent. The residue was purified by silica gel column chromatography [hexane/ethyl acetate (75:25)] to give 22.8 E of the title compound as a colorless oil.

$^1$H-NMR $\delta$(CDCl$_3$): 1.45(3H, d, J=7 Hz), 3.36(3H, s), 4.01~4.08(2H, m), 4.08~4.14(2H, m), 4.52(1H, d, J=7 Hz), 4.56(1H, d, J=7 Hz), 4.73(1H, q, J=7 Hz), 5.80(1H, s), 5.86(1H, d, J=4 Hz), 7.28(2H, d, J=8 Hz), 7.33(2H, d, J=8 Hz), 7.41(2H, d, J=8 Hz), 7.45(2H, d, J=8 Hz)

(b) 2-[4-[4-(1-Methoxymethyloxyethyl)benzyl]phenyl]-1,3-dioxolane

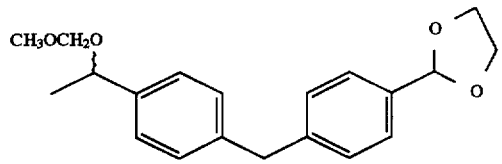

20 ml of acetic anhydride was dropwise added to a comprising 22.8 g of the 2-[4-[α-hydroxy-4-(1-methoxymethyloxyethyl)benzyl]phenyl]-1,3-dioxolane prepared in the step (a) and 30 ml of pyridine, and the obtained mixture was stirred at room temperature for 3 hours. After the completion of the reaction, 10 ml of water was added to the reaction mixture and the obtained mixture was further stirred for 30 minutes and poured onto ice-water. The resulting mixture was extracted with ethyl acetate. The organic phase was washed with 1N hydrochloric acid, water, an aqueous solution of sodium hydrogencarbonate and a saturated aqueous solution of common salt successively, dried and distilled to remove the solvent, giving a colorless oil. 2 ml of pyridine, 100 ml of ethanol and 3 g of palladium/carbon were added to the oil and the obtained mixture was stirred in a hydrogen atmosphere at room temperature for 3 hours. After the completion of the reaction, the reaction mixture was filtered and the filtrate was subjected to vacuum distillation to remove the solvent. The residue was purified by silica gel column chromatography [hexane/ethyl acetate (85:15)] to give 21 g of the title compound.

$^1$H-NMR $\delta$(CDCl$_3$): 1.45(3H, d, J=7 Hz), 3.36(3H, s), 3.98(2H, s), 4.00~4.06(2H, m), 4.09~4.15(2H, m), 4.52(1H, d, J=7 Hz), 4.56(1H, d, J=7 Hz), 4.72(1H, q, J=7 Hz), 7.14(2H, d, J=8 Hz), 7.21(2H, d, J=8 Hz), 7.23(2H, d, J=8 Hz), 7.40(2H, d, J=8 Hz)

(c) 4-[4-(1-Hydroxyethyl)benzyl]benzaldehyde

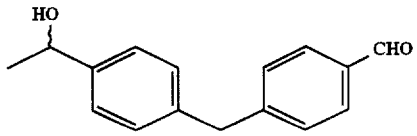

210 ml of tetrahydrofuran and 45 ml of 5N hydrochloric acid were added to 21 g of the 2-[4-[4-(1-methoxymethyloxyethyl)benzyl]phenyl]-1,3-dioxolane prepared in the step (b). The obtained mixture was stirred at 50°

C. for 2 hours to complete a reaction. The reaction mixture was poured into water and the resulting mixture was extracted with ethyl acetate. The organic phase was washed with an aqueous solution of sodium hydrogencarbonate to conduct hydration. The resulting organic phase was washed with a saturated aqueous solution of common salt, dried and distilled to remove the solvent. The residue was purified by silica gel column chromatography [hexane/ethyl acetate (70:30)] to give 9.8 g of the title compound as a colorless oil.

$^1$H-NMR δ(CDCl$_3$): 1.50(3H, d, J=6 Hz), 4.05(2H, s), 4.80~4.92(1H, m), 7.17(2H, d, J=8 Hz), 7.32(2H, d, J=8 Hz), 7.35(2H, d, J=8 Hz), 7.80(2H, d, J=8 Hz), 9.99(1H, s)

(d) N-Methyl-4-[4-(1-hydroxyethyl)benzyl]benzylamine

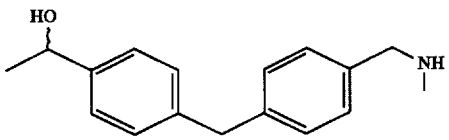

9.8 g of the 4-[4-(1-hydroxyethyl)benzyl]benzaldehyde prepared in the step (c) and 3.7 ml of methylamine (40% methanolic solution) were stirred together in 20 ml of methanol at room temperature. After one hour, the resulting mixture was cooled with ice, followed by the addition of 0.93 g of sodium borohydride. The obtained mixture was stirred at room temperature for 30 minutes. 5 ml of acetone was dropwise added to the resulting mixture under cooling with ice to treat excess sodium borohydride therewith. The reaction mixture was poured into water and the resulting mixture was extracted with dichloromethane. The organic phase was washed with water and a saturated aqueous solution of common salt, dried and distilled to dryness. The residue was recrystallized from ether/isopropyl ether to give 10.2 g of the title compound as a colorless solid.

$^1$H-NMR δ(CDCl$_3$): 1.47(3H, d, J=6 Hz), 1.76(1H, br.s), 3.69(2H, s), 4.00(2H, s), 4.86(1H, q, J=6 Hz), 7.14(2H, d, J=8 Hz), 7.16(2H, d, J=8 Hz), 7.21(2H, d, J=8 Hz), 7.29(2H d, J=8 Hz)

Preparative Example 11

(E)-1-Bromo-3-methyl-5-(2-naphthyl)-2-pentene (a) 2-Bromomethylnaphthalene

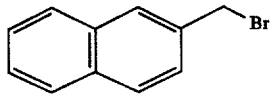

A mixture comprising 200 g of 2-methylnaphthalene, 260 g of N-bromosuccinimide and 600 ml of carbon tetrachloride was stirred under heating together with a small amount of benzoyl peroxide for 1.5 hours. The reaction mixture was cooled and filtered to remove insolubles. The filtrate was filtered through a silica bed and the silica gel was washed with hexane. The filtrate and washings were concentrated together. The obtained residue was used in the subsequent step without any particular purification.

$^1$H-NMR δ(CDCl$_3$): 4.67(2H, s)

(b) 4-(2-Naphthyl)-2-butanone

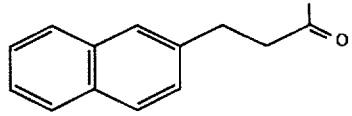

200 ml of ethyl acetoacetate was dropwise added to a solution of 33 g of metallic sodium in 700 ml of ethanol under cooling with ice. The obtained mixture was stirred at that temperature for 30 minutes, followed by the addition of the whole 2-bromomethylnaphthalene prepared in the step (a). The obtained mixture was stirred at room temperature overnight to conduct a reaction. The reaction mixture was acidified with concentrated hydrochloric acid and filtered to remove insolubles. The filtrate was concentrated, followed by the addition of 500 ml of acetic acid, 100 ml of concentrated hydrochloric acid and 100 ml of water. The obtained mixture was heated on an oil bath at 110° C. for 10 hours, concentrated and extracted with ethyl acetate/water. The ethyl acetate phase was washed with water, an aqueous solution of sodium hydrogencarbonate and a saturated aqueous solution of common salt, dried over anhydrous magnesium sulfate and concentrated. The residue was subjected to silica gel column chromatography (2.5 to 7.5% ethyl acetate/hexane) and thereafter recrystallized from ethyl acetate/hexane to give 122 g of the title compound.

$^1$H-NMR δ(CDCl$_3$): 2.15(3H, s), 2.84(2H, t, J=7 Hz), 3.06(2H, t, J=7 Hz), 7.31(1H, dd, J=2 Hz, 8 Hz), 7.39~7.48 (2H, m), 7.61(1H, d, J=2 Hz), 7.73~7.81(3H, m)

(c) Ethyl (E)-3-methyl-5-(2-naphthyl)-2-pentenoate

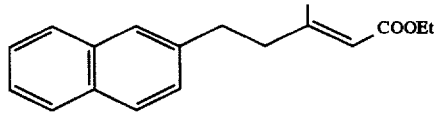

160 ml of triethyl phosphonoacetate was dropwise added to a mixture comprising 30 g of sodium hydride and 700 ml of tetrahydrofuran under stirring. After the resulting mixture turned transparent, 122 g of the 4-(2-naphthyl)-2-butanone prepared in the step (b) was added thereto. The obtained mixture was heated on an oil bath at 50° C. for 3 hours to conduct a reaction. The reaction mixture was extracted with ethyl acetate/water. The organic phase was washed with a saturated aqueous solution of common salt, dried over anhydrous magnesium sulfate and concentrated. The residue was subjected to silica gel column chromatography (1 to 3% ethyl acetate/hexane) to give 57 g of the title compound.

$^1$H-NMR δ(CDCl$_3$): 1.27(3H, t, J=7 Hz), 2.24(3H, d, J=1 Hz), 2.53(2H, t, J=8 Hz), 2.95(2H, t, J=8 Hz), 4.14(2H, q, J=7 Hz), 5.72(1H, q, J=1 Hz), 7.31(1H, dd, J=2 Hz, 8 Hz), 7.40~7.48(2H, m), 7.61(1H, d, J=2 Hz), 7.75~7.82(3H, m)

(d) (E)-3-Methyl-5-(2-naphthyl)-2-penten-1-ol

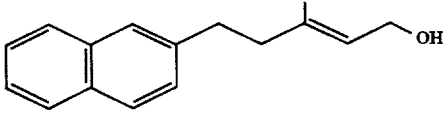

A mixture comprising 57 g of the ethyl (E)-3-methyl-5-(2-naphthyl)-2-pentenoate prepared in the step (c) and 700 ml of toluene was cooled to −40° C., followed by the dropwise addition of 300 ml of a 1.5M solution of diisobutylaluminum hydride in toluene. The obtained mixture was maintained at that temperature for one hour to conduct a reaction. The temperature of the reaction mixture was raised to −20° C., followed by the addition of 40 ml of methanol. 50% water/methanol was added to the resulting mixture in portions to form a white precipitate. The resulting mixture was stirred as such for 2 hours and filtered to remove insolubles, and the insolubles were washed with ethyl acetate. The filtrate and washings were washed with water and a saturated aqueous solution of common salt, dried over anhydrous magnesium sulfate and concentrated. The residue was recrystallized from ethyl acetate/hexane to give 40 g of the title compound.

$^1$H-NMR δ(CDCl$_3$): 1.76(3H, d, J=1 Hz), 2.42(2H, t, J=8 Hz), 2.91(2H, t, J=8 Hz), 4.14(2H, d, J=7Hz),5.44(1H, tq, J=7Hz, 1 Hz), 7.32(1H, dd, J=2 Hz, 8 Hz), 7.39~7.47(2H, m), 7.61(1H, s), 7.75~7.82(3H, m)

(e) (E)-1-Bromo-3-methyl-5-(2-naphthyl)-2-pentene

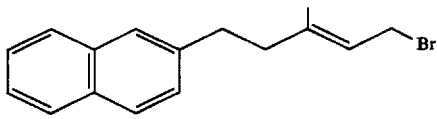

1.6 ml of phosphorus tribromide was dropwise added to a mixture comprising 10 g of the (E)-3-methyl-5-(2-naphthyl)-2-penten-1-ol prepared in the step (d) and 100 ml of diethyl ether under cooling with ice. The obtained mixture was maintained at that temperature for 20 minutes to conduct a reaction, followed by the addition of 200 ml of hexane. The obtained mixture was filtered through a silica gel bed and the silica gel was washed with hexane. The filtrate and washings were combined and concentrated to give 11.1 g of the title compound.

$^1$H-NMR δ(CDCl$_3$): 1.80(3H, d, J=1 Hz), 2.45(2H, t, J=8 Hz), 2.90(2H, t, J=8 Hz), 4.01(2H, d, J=7 Hz), 5.56(1H, tq, J=7 Hz, 1 Hz), 7.31(1H, dd, J=2 Hz, 8 Hz), 7.38~7.47(2H, m), 7.60(1H, d, J=2 Hz), 7.72~7.82(3H, m)

Preparative Example 12

2-Acetoxy-4-bromomethylbenzophenone (a) 3-Methylphenyl benzoate

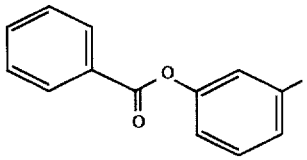

35 ml of benzoyl chloride was added to a mixture comprising 25 g of m-cresol, 25 ml of pyridine and 200 ml of ethyl acetate at room temperature. The obtained mixture was stirred overnight, followed by the addition of water. The resulting mixture was stirred for 30 minutes. The ethyl acetate phase was recovered, washed with dilute hydrochloric acid, an aqueous solution of sodium hydrogencarbonate and a saturated aqueous solution of common salt successively, dried over anhydrous magnesium sulfate and filtered through a silica gel bed. The filtrate was concentrated to give 41.5 g of the title compound.

$^1$H-NMR δ(CDCl$_3$): 2.39(3H, s), 6.99~7.11(3H, m), 7.31 (1H, t, J=8 Hz), 7.51(2H, t, J=8 Hz), 7.63(1H, tt, J=1 Hz, 8 Hz), 8.20(2H, dd, J=1 Hz, 8 Hz)

(b) 2-Hydroxy-4-methylbenzophenone

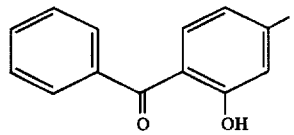

A mixture comprising 21.2 g of the 3-methylphenyl benzoate prepared in the step (a) and 13.1 g of aluminum chloride was stirred on an oil bath at 180 to 200° C. for one hour, cooled and extracted with dilute hydrochloric acid/ethyl acetate. The ethyl acetate phase was washed with water arid a saturated aqueous solution of common salt, dried over anhydrous magnesium sulfate and concentrated. The residue was subjected to silica gel column chromatography (0 to 4% ethyl acetate/hexane) to give 14.1 g of the title compound.

$^1$H-NMR δ(CDCl$_3$): 2.38(3H, s), 6.68(1H, d, J=8 Hz), 6.88(1H, s), 7.45~7.52(3H, m), 7.55~7.60(1H, m), 7.63~7.68(2H, m), 12.12(1H, s)

(c) 2-Acetoxy-4-methylbenzophenone

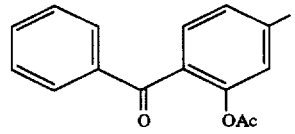

A mixture comprising 14.1 g of the 2-hydroxy-4-methylbenzophenone prepared in the step (b), 20 ml of pyridine and 9 ml of acetic anhydride was allowed to stand at room temperature overnight. The obtained reaction mixture was subjected to vacuum concentration and extracted with ethyl acetate/water. The ethyl acetate phase was washed with water, dilute hydrochloric acid and an aqueous solution of sodium hydrogencarbonate successively, dried over anhydrous magnesium sulfate and concentrated. The residue was subjected to silica gel column chromatography (5 to 0% ethyl acetate/hexane) to give 16.8 g of the title compound.

$^1$H-NMR δ(CDCl$_3$): 1.95(3H, s), 2.43(3H, s), 7.00(1H, s), 7.18(1H, d, J=8 Hz), 7.42~7.47(3H, m), 7.56(1H, tt, J=1 Hz, 8 Hz), 7.75(2H, dd, J=1 Hz, 8 Hz)

(d) 2-Acetoxy-4-bromomethylbenzophenone

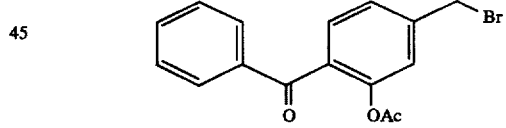

A mixture comprising 1.3 g of the 2-acetoxy-4-methylbenzophenone prepared in the step (c), 910 mg of N-bromosuccinimide and 20 ml of carbon tetrachloride was heated under reflux together with a small amount of benzoyl peroxide for one hour. The reaction mixture was cooled and filtered through a silica gel bed, and the silica gel was washed with 20% ethyl acetate/hexane. The filtrate and washings were concentrated together. The residue was subjected to silica gel column chromatography (7 to 10% ethyl acetate/hexane) to give 1.08 g of the title compound.

$^1$H-NMR δ(CDCl$_3$): 1.95(3H, s), 4.51(2H, s), 7.25(1H, d, J=2 Hz), 7.35(1H, dd, J=2 Hz, 8 Hz), 7.43~7.49(2H, m), 7.52(1H, d, J=8 Hz), 7.59(1H, tt, J=1 Hz, 8 Hz), 7.75~7.78 (2H, m)

Preparative Example 13

2-[(1E, 5E)-2,6,10-Trimethyl-1,5,9-undecatrienyl]-benzyl bromide (a) Ethyl 2-[(1E, 5E)-2,6,10-trimethyl-1,5,9-undecatrienyl] benzoate

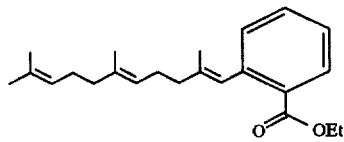

6.7 g of potassium t-butoxide was added to a solution of 12.5 g of diethyl 2-ethoxycarbonylbenzylphosphonate in 50 ml of dimethylformamide. The obtained mixture was stirred at 50° C. for one hour, followed by the addition of 9.7 g of all-E-geranylacetone. The obtained mixture was stirred for one hour and poured into water. The resulting mixture was extracted with ethyl acetate. The solvent was distilled off and the residue was subjected to silica gel column chromatography [ethyl acetate/hexane (0.4:100)] to give 6.8 g of a mixture of the title compound with ethyl 2-[(1Z, 5E)-2,6,10-trimethyl-1,5,9-undecatrienyl]benzoate.

(b) 2-[(1E, 5E)-2,6,10-Trimethyl-1,5,9-undecatrienyl] benzyl alcohol

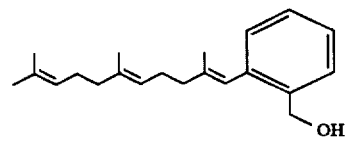

6.8 g of the mixture of ethyl 2-[(1E, 5E)-2,6,10-trimethyl-1,5,9-undecatrienyl]benzoate with ethyl 2-[(1Z, 5E)-2,6,10-trimethyl-1,5,9-undecatrienyl]-benzoate prepared in the step (a) was dropwise added to a solution of 2.4 g of aluminum lithium hydride in 40 ml of tetrahydrofuran. The obtained mixture was stirred at room temperature for 30 minutes, followed by the addition of 2.4 ml of water, 2.4 ml of a 5N aqueous solution of sodium hydroxide and 7.2 ml of water. The formed precipitate was filtered out and the solvent was distilled off. The obtained residue was purified by silica gel column chromatography [hexane/ethyl acetate (100:2)] to give 1.9 g of the title compound.

$^1$H-NMR δ(CDCl$_3$): 1.60(3H, s), 1.65(3H, s), 1.67(3H, s), 1.68(3H, d, J=<1 Hz), 1.99–2.13(4H, m), 2.22–2.26(4H, m), 4.64(2H, d, J=6 Hz), 5.07–5.15(1H, m), 5.15–5.22(1H, m), 6.34(1H, s) 7.13–7.18(1H, m), 7.23–7.19(2H, m), 7.17–7.21 (1H, m)

(c) 2-[(1E, 5E)-2,6,10-Trimethyl-1,5,9-undecatrienyl] benzyl bromide

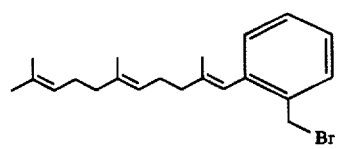

0.57 ml of methanesulfonyl chloride was dropwise added to a solution of 1.9 g of the 2-[(1E, 5E)-2,6,10-trimethyl-1,5,9-undecatrienyl]benzyl alcohol prepared in the step (b) and 1.02 ml of triethylamine in 10 ml anhydrous dichloromethane under cooling with ice. The obtained mixture was stirred for 30 minutes and poured into mater. The resulting mixture was extracted with dichloromethane. The organic phase was dried and distilled to remove the solvent. 10 ml of tetrahydrofuran and 1.57 g of lithium bromide were added to the residue. The obtained mixture was stirred at 50° C. for 4 hours and pouted into water. The resulting mixture was extracted with ethyl acetate and the organic phase was distilled to remove the solvent. The residue was purified by silica gel column chromatography [hexane/ethyl acetate (100:1)] to give 2.1 g of the title compound.

$^1$H-NMR δ(CDCl$_3$): 1.60(3H, s), 1.63(3H, s), 1.67–1.70 (6H, m), 1.99–2.16(4H, m), 2.23–2.29(4H, m), 4.48(2H, s), 5.09–5.17(1H, m), 5.19–5.23(1H, m), 6.38(1H, s), 7.12–7.17(1H, m), 7.17–7.29(2H, m), 7.34–7.39(1H, m)

Preparative Example 14

Tetraethyl 5-acetoxy-(E)-3-pentenylidene-1,1-bisphosphonate (a) 3:1 Mixture of 4-(1,1-dimethylethyl/diphenyl-silyloxy-1-acetoxy-(E)-2-butene and 4-(1,1-dimethylethyl) diphenylsilyloxy-1-acetoxy-(Z)-2-butene

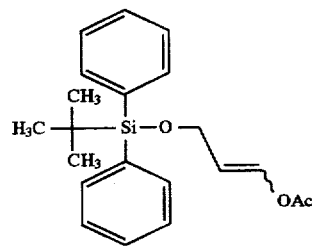

25 g of 1,4-Butenediol (mixture of E:Z=3:1) was dissolved in 200 ml of DMF, and then 22 g of imidazole and 78 g of t-butyldiphenylsilyl chloride were added thereto, followed by stirring at room temperature for 8 hours. Water was added to the reaction mixture thus obtained and the resultant solution was extracted three times with ethyl acetate. The organic phases were put together, washed twice with water and once with a saturated aqueous solution of common salt, dried over anhydrous sodium sulfate and concentrated under a reduced pressure. The oily substance thus obtained was purified by silica gel column chromatography (2 to 20 % ethyl acetate/hexane) to give 42 g of the corresponding mono-t-butyldiphenylsilyl compound. This mono-t-butyldiphenylsilyl compound was dissolved in 80 ml of pyridine to give a solution. Acetic anhydride was gradually added to the solution, followed by stirring at room temperature for 3 hours. The reaction solution was concentrated under a reduced pressure to thereby give 47 g of the title mixture.

$^1$H-NMR δ(CDCl$_3$): 1.02(2.25H, s), 1.04(6.75H, s), 2.01 (0.75H, s), 2.07(2.25H, s), 4.21(1.50 H, d, J=1 Hz), 4.27 (0.50H, d, J=7 Hz), 4.47(0.50H, d, J=7 Hz), 4.58(1.50H, d, J=7 Hz), 5.50–5.60(0.25H, m), 5.76–5.95(1.75H, m), 7.35–7.45(6H, m), 7 63–7.68(4H, m)

(b) Tetraethyl 5-(1,1-dimethylethyl)diphenylsilyloxy(E)-3-pentenylidene-1,1-diphosphonate

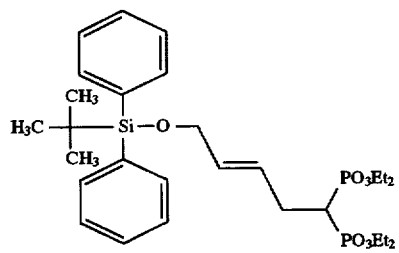

18.4 g of the mixture prepared in the step (a) was dissolved in 150 ml of THF, followed by the addition of 20.5 g of bis(trimethylsilyl)actamide, 29 g of tetraethyl methylenediphosphonate, 720 mg of triphenylphosphine and 1.65 g of tetrakis(triphenylphosphine) palladium. The obtained mixture was heated under reflux for 8 hours under a nitrogen flow. The reaction solution thus obtained was concentrated under a reduced pressure, and the residue was purified by silica gel column chromatography [isopropanol/hexane (1:4)] to thereby give 25 g of the title compound as a single compound.

$^1$H-NMR δ(CDCl$_3$): 1.02(9H, s), 1.32(12H, t, J=7 Hz), 2.35(1H, tt, J=23 Hz, 7 Hz), 2.61~2.75(2H, m), 4.13~4.21 (10H, m), 5.65(1H, dt, J=16 Hz, 5 Hz), 5.82(1H, dt, J=16 Hz, 7 Hz), 7.35~7.42(6H, m), 7.63~7.69(4H, m)

(c) Tetraethyl 5-hydroxy-(E)-3-pentenylidene-1,1-diphosphonate

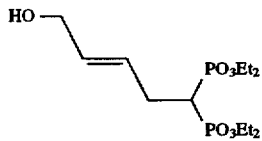

25 g of the compound prepared in the step (b) was dissolved in 200 ml of THF, and then 42 ml of a solution of 1N tetra-n-butylammonium chloride in THF was added thereto. The obtained mixture was stirred at room temperature for 3 hours. The reaction solution thus obtained was concentrated under a reduced pressure, and the residue was purified by silica gel column chromatography (5 to 20% methanol/dichloromethane) to thereby give 12 g of the title compound.

$^1$H-NMR δ(CDCl$_3$): 1.35(12H, t, J=7 Hz), 2.40(1H, tt, J=23 Hz, 7 Hz), 2.61~2.77(2H, m), 4.08(2H, d, J=6 Hz), 4.12~4.22 (8H, m), 5.76(1H, td, J=5 Hz, 16 Hz), 5.83(1H, td, J=7 Hz, 16 Hz)

(d) Tetraethyl 5-acetoxy-(E)-3-pentenylidene-1,1-diphosphonate

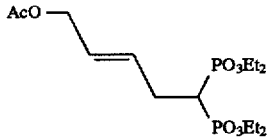

12 g of the compound prepared in the step (c) was dissolved in 100 ml of pyridine to give a solution. 100 ml of acetic anhydride was gradually added to the solution, followed by stirring at room temperature for 3 hours. The reaction solution thus obtained was concentrated under a reduced pressure, and the residue was purified by silica gel column chromatography (5 to 10 methanol/dichloromethane) to thereby give 13 g of the title compound.

$^1$H-NMR δ(CDCl$_3$): 1.35(12H, t, J=7 Hz), 2.05(3H, s), 2.38(1H, tt, J=23 Hz, 7 Hz), 2.62~2.77(2H, m), 4.13~4.23 (8H, m), 4.52(2H, d, J=7 Hz), 5.68(1H, dt, J=15 Hz, 6 Hz), 5.92(1H, dt, J=15 Hz, 7 Hz)

Preparative Example 15

1,1-dimethyl-3-[2-(2-methoxyphenyl)ethyl]formamidine

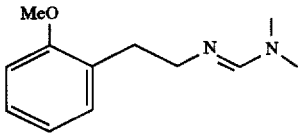

9.5 ml of dimethyl sulfate was added to 7.7 ml of N,N-dimethylformamide at room temperature. The resulting mixture was heated in an oil bath of 90° C. for 2.5 hours under stirring. The reaction solution thus obtained was cooled with ice and then a solution of 15.1 g of 2-(2-methoxyphenyl)ethylamine in 20 ml of dichloromethane was dropwise added thereto over a period of 30 minutes. Thereafter, the resulting solution was heated under reflux in an oil bath of 50° C. for 3 hours. The reaction solution was cooled and then poured into a 20 % aqueous solution of sodium hydroxide. The dichloromethane phase was separated and the aqueous phase was extracted with 10 ml of dichloromethane. The dichloromethane phases were put together and washed with a saturated aqueous solution of common salt, dried over anhydrous magnesium sulfate, concentrated and distilled under a reduced pressure (113°to 114° C./0.5 mmHg) to give 10.1 g of the title compound.

$^1$H-NMR δ((d$_6$-DMSO): 2.64(2H, t, J=8 Hz), 2.72(6H, s), 3.28(2H, t, J=8 Hz), 3.77(3H, s), 6.84(1H, t, J=8 Hz), 6.93(1H, d, J=8 Hz), 7.11(1H, dd, J=8 Hz, 2 Hz), 7.16(1H, dt, J=2 Hz, 8 Hz), 7.28(1H, s)

Example 1

Tetraethyl-4-[N-Methyl-4-[4-(1-hydroxyethyl)benzyl] benzylamino]butylidene-1,1-diphosphonate

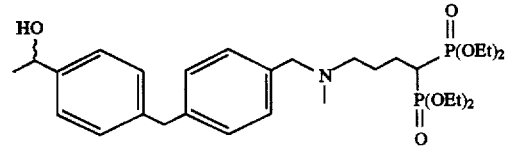

7 g of the N-methyl-4-[4-(1-hydroxyethyl)benzyl] benzylamine prepared in the Preparative Example 10, 13 g of tetraethyl 4-(p-tolylsulfonyloxy)butylidene-1,1-diphosphonate and 8 g of potassium carbonate were stirred together in 30 ml of dimethylformamide for 24 hours to conduct a reaction. After the completion of the reaction, the reaction mixture was poured into water and the resulting mixture was extracted with ethyl acetate. The organic phase was washed with water, dried and distilled to remove the solvent. The residue was purified by silica gel column chromatography [dichloromethane/methanol (100:5)] to give 7.3 g of the title compound.

$^1$H-NMR δ(CDCl$_3$): 1.32(12H, t, J=7 Hz), 1.48(3H, d, J=7 Hz), 1.73~1.82(2H, m), 1.88~2.03(2H, m), 2.16(3H, s), 2.32(1H, tt, J=24 Hz, 6 Hz), 2.36(2H, t, J=7 Hz), 3.43(2H, s), 3.95(2H, s), 4.10~4.20(8H, m), 4.87(1H, quart, J=7 Hz), 7.12(2H, d, J=8 Hz), 7.17(2H, d, J=8 Hz), 7.22(2H, d, J=8 Hz), 7.30(2H, d, J=8 Hz)

Example 2

Tetraethyl 4-[4-methoxybenzoyl)piperidino]butylidene-1,1-diphosphonate

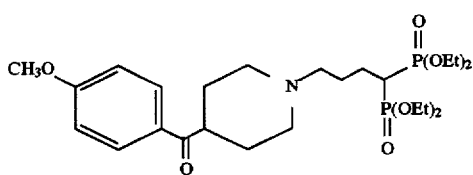

The title compound was prepared from 4-(4-methoxy) benzoylpiperidine in a similar manner to that of the Example 1.

¹H-NMR δ(CDCl₃): 1.35(12H, t, J=7 Hz), 1.75~2.14 (10H, m), 2.30~2.48(3H, m), 3.00(2H, br.d, J=12 Hz), 3.14~3.24(1H, m), 3.88(3H, s), 4.13~4.23(8H, m), 6.94(2H, dt, J=9 Hz, 2 Hz), 7.93(2H, dt, J=9 Hz, 2 Hz )

Example 3

Diethyl 1-ethoxycarbonyl-4-[N-methyl-(3-benzyl) benzylamino]butylphosphonate

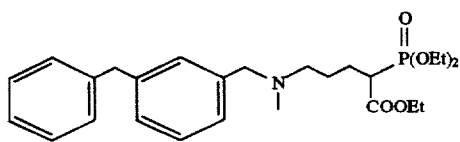

1.3 g of N-methyl-(3-benzyl)benzylamine and 2.6 g of the diethyl 1-ethoxycarbonyl-4-(p-toluenesulfonyloxy) butylphosphonate prepared in the Preparative Example 6 were dissolved in 20 ml of dimethylformamide, followed by the addition of 2 g of potassium carbonate. The obtained mixture was heated to 60° C. and stirred for 4 hours, followed by the addition of water. The resulting mixture was extracted with ethyl acetate thrice. The combined ethyl acetate phases were washed with water and a saturated aqueous solution of common salt successively, dried over magnesium sulfate and subjected to vacuum concentration to give a crude oil. This oil was purified by silica gel column chromatography [aqueous ammonia/methanol/ dichloromethane (1:300)] to give 1.8 g of the title compound. ¹H-NMR δ(CDCl₃): 1.22~1.38(9H, m), 1.45~1.70 (2H, m), 1.82~2.08(2H, m), 2.17(3H, s), 2.37(2H, t, J=7 Hz), 2.90~3.04(1H, m), 3.43(2H, s), 3.97(2H, s), 4.08~4.22(6H, m), 7.02~7.35(9H, m)

Example 4

Tetraethyl 4-[N-methyl-(3-acetoxy-4-benzoylbenzyl)-amino]butylidenediphosphonate

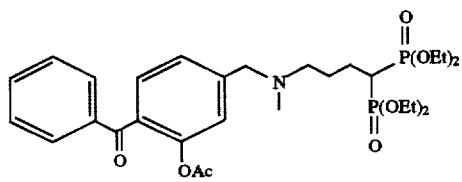

A mixture comprising 650 mg of the 2-acetoxy-4-bromomethylbenzophenone prepared in the Preparative Example 12, 700 mg of the tetraethyl 4-methylaminobutylidenedihosphonate prepared in the Preparative Example 1, 600 mg of anhydrous potassium carbonate and 10 ml of N,N-dimethylformamide was stirred at room temperature overnight to conduct a reaction. The reaction mixture was extracted with ethyl acetate/water. The ethyl acetate phase was washed with water and a saturated aqueous solution of common salt, successively, dried over anhydrous magnesium sulfate and concentrated. The residue was subjected to silica gel column chromatography [0 to 5% (1% concentrated aqueous ammonia/methanol)/chloroform] to give 600 mg of the title compound.

¹H-NMR δ(CDCl₃): 1.32(12H, t, J=7 Hz), 1.75~1.88(2H, m), 1.94(3H, s), 1.90~2.05(2H, m), 2.20(3H, s), 2.35(1H, tt, J=7 Hz, 24 Hz), 2.38~2.47(2H, m), 3.54(2H, s), 4.12~4.22 (8H, m), 7.17(1H, s), 7.25~7.35(1H, m), 7.41~7.52(3H, m), 7.58(1H, t, J=8 Hz), 7.77(2H, d, J=8 Hz)

Example 5

Tetraethyl 2-[N-(3-styrylbenzyl)piperidin-4-yl]-ethylidene-1,1-diphosphonate

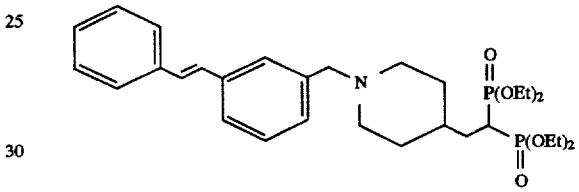

A mixture comprising 0.45 g of 3-styrylbenzyl bromide, 0.23 ml of triethylamine, 0.55 g of the tetraethyl 2-(4-piperidinyl)ethylidene-1,1-diphosphonate prepared in the Preparative Example 2 and 10 ml of dimethylformamide was stirred at room temperature overnight. After the completion of the reaction, water was poured into the reaction mixture, followed by the extraction with ethyl acetate. The organic phase was washed with water, dried and distilled to remove the solvent. The residue was purified by silica gel column chromatography [dichloromethane/methanol (100:1.5)] to give 0.6 g of the title compound as a colorless oil.

¹H-NMR δ(CDCl₃): 1.14~1.27(2H, m), 1.33(12H, t, J=7 Hz), 1.60~1.75(3H, m), 1.77~1.90(2H, m), 1.96(2H, dt, J=11 Hz, 2 Hz), 2.39(1H, tt, J=24 Hz, 7 Hz), 2.91(2H, br.d, J=11 Hz), 4.10~4.21(8H, m), 7.11(2H, s), 7.20(1H, dt, J=8 Hz, <1 Hz), 7.26(1H, tt, J=8 Hz, <1 Hz), 7.30(1H, t, J=8 Hz), 7.36(2H, tt, J=8 Hz, <1 Hz), 7.41(1H, dt, J=8 Hz, <1 Hz), 7.46(1H, br.s), 7.52(2H, dt, J=8 Hz, <1 Hz)

Example 6

(A) Diethyl 1-ethoxycarbonyl-4-[N-methyl-3methyl-5-(2-naphthyl)-2-pentenylamino]-3-hydroxybutylphosphonate (diastereomeric mixture)

(B) Diethyl 5-[N-methyl-3-methyl-5-(2-naphthyl)-2-pentenylamino]methyl-2oxotetrahdrofuran-3-ylphosphonate (diastereomeric mixture)

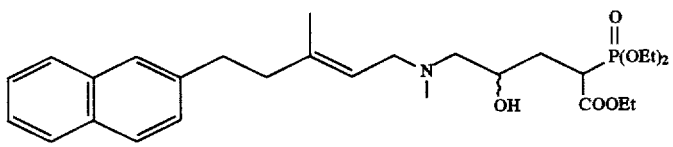
compound (A)

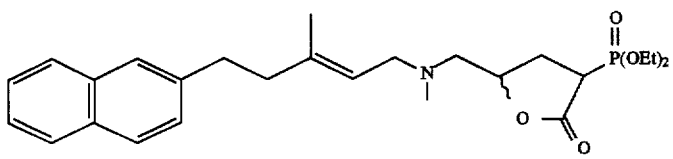
compound (B)

A mixture comprising 340 mg of the triethyl 3,4-epoxy-1-carboxybutylphosphonate prepared in the Preparative Example 9, 290 mg of N-methyl-3-methyl-5-(2-naphthyl)-2-pentenylamine and 2 ml of N,N-dimethylformamide was heated on an oil bath at 50° C. for 8 hours to conduct a reaction. The obtained reaction mixture was extracted with ethyl acetate/water. The ethyl acetate phase was washed with water and a saturated aqueous solution of common salt, dried over anhydrous magnesium sulfate and concentrated. The residue was subjected to silica gel column chromatography [0 to 5% (1% concentrated aqueous ammonia/methanol)/chloroform] to give 140 mg of the title compound (A) and 120 mg of the title compound (B).

Compound (A)

¹H-NMR δ(CDCl₃): 1.25~1.40(9H, m), 1.70(3H, s), 2.11 (1.2H, s), 2.12(1.8H, s), 2.18~2.33(2H, m), 2.42(2H, t, J=8 Hz), 2.90(2H, t, J=8 Hz), 2.92~3.11(2H, m), 3.17(0.4H, ddd, J=5 Hz, 9 Hz, 23 Hz), 3.42(0.6H, ddd, J=3 Hz, 12 Hz, 23 Hz), 3.52~3.61(0.6H, m), 3.68~3.78(0.4H, m), 4.10~4.30 (6H, m), 5.18~5.25(1H, m), 7.33(1H, dd, J=2 Hz, 8 Hz), 7.37~7.48(2H, m), 7.60(1H, s), 7.73~7.82(3H, m)

Compound (B)

¹H-NMR δ(CDCl₃): 1.26~1.39(6H, m), 1.71(3H, s), 2.20 (3H, s), 2.90(2H, t, J=8 Hz), 2.98~3.04(2H, m), 3.20(0.4H, ddd, J=8 Hz, 12 Hz, 24 Hz), 4.1~4.3(4H, m), 4.37~4.45 (0.4H, m), 4.61~4.69(0.6H, m), 5.17~5.26(1H, m), 7.33(1H, dd, J=2 Hz, 8 Hz), 7.37~7.47(2H, m), 7.60(1H, s), 7.72~7.82 (3H, m)

Example 7

Tetraethyl 4-[N-methyl-[(2E)-3,7-dimethyl-2,6-octadienyl]carbamoyloxy]butylene-1,1-diphosphonate

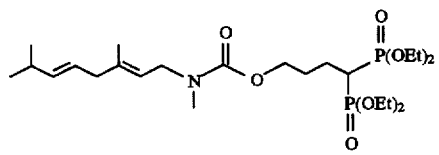

A mixture comprising 0.645 g of the tetraethyl 4-phenoxycarbonyloxybutylidene-1,1-diphosphonate prepared in the Preparative Example 3 and 0.4 ml of N-methyl [(2E)-3,7-dimethyl-2,6-octadienyl]amine was stirred at 90° C. for 2 hours and the obtained product was purified by silica gel column chromatography [chloroform/methanol/water (90:10:1)] to give 0.180 g of the title compound.

¹H-NMR δ(CDCl₃): 1.33(12H, t, J=7 Hz), 1.61(6H, s), 1.68(3H, s), 1.90~2.13(8H, m), 2.32(1H, tt, J=25 Hz, 6 Hz), 2.81(3H, s), 3.83~3.91(2H, m), 4.08(2H, t, J=7 Hz), 4.13~4.22(8H, m), 5.03~5.16(2H, m)

Example 8

Diethyl 1-ethoxycarbonyl-4-[N-methyl-(2E)-3,7-dimethyl-2,6-octadienyl]carbamoyloxy]butylphosphonate

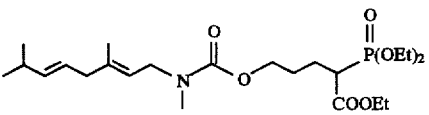

The title compound was prepared from the diethyl 1-ethoxycarbonyl-4-phenoxycarbonyloxybutylphosphonate prepared in the Preparative Example 7 and N-methyl[(2E)-3,7-dimethyl-2,6-octadienyl]amine in a similar manner to that of the Example 7.

¹H-NMR δ(CDCl₃): 1.25~1.37(9H, m), 1.60(3H, s), 1.63~1.88(8H, m), 1.90~2.17(6H, m), 2.82(3H, br.s), 2.90~3.05(1H, m), 3.72~3.75(2H, m), 3.80~3.92(2H, m), 4.03~4.26(6H, m), 5.04~5.18(2H, m)

Example 9

Tetraethyl [3-(4-phenyl-5-methylimidizol-1-yl)propylamino]methylenediphosphonate

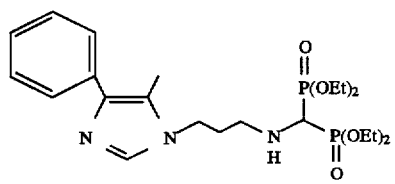

A mixture comprising 5 g of 3-(4-phenyl-5-methylimidazol-1-yl)propylamine, 4.6 ml of ethyl orthoformate and 12.0 ml of diethyl phosphite was stirred at 150° C. for 2 hours to conduct a reaction. The reaction mixture was subjected to vacuum concentration and the residue was purified by silica gel column chromatography [dichloromethane/methanol mixture with the methanol content rising from 1 to 4% stepwise] to give 3.5 g of the title compound.

¹H-NMR δ(CDCl₃): 1.35(12H, t, J=7 Hz), 1.90(2H, quint, J=7 Hz), 2.40(3H, s), 2.90(2H, t, J=7 Hz), 3.23(1H, t, J=22 Hz), 4.04(2H, t, J=7 Hz), 4.15~4.25(8H, m), 7.25(1H, t, J=8 Hz), 7.40(2H, t, J=8 Hz), 7.54(1H, s), 7.65(2H, d, J=8 Hz)

Example 10

Tetraethyl (E)-4-methyl-6-(2-naphthyl)-3-hexenylidene-1,1-diphosphonate

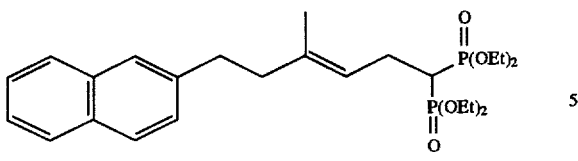

4.4 g of the (E)-1-bromo-3-methyl-5-(2-naphthyl)-2-pentene prepared in the Preparative Example 11 was dropwise added to a mixture comprising 4.38 g of tetraethyl methylenediphosphonate, 0.6 g of sodium hydride (55% oil dispersion) and 50 ml of anhydrous dimethylformamide under cooling with ice. After the completion of the dropwise adding, the obtained mixture was stirred at room temperature for one hour and water was poured into the reaction mixture. The resulting mixture was extracted with ethyl acetate and the ethyl acetate phase was distilled to remove the solvent. The residue was purified by silica gel column chromatography (benzene/acetone mixture with the acetone content rising from 5 to 20%) to give 3 g of the title compound as a colorless oil.

$^1$H-NMR δ(CDCl$_3$): 1.31(12H, m), 1.73(3H, s), 2.28(1H, tt, J=24 Hz, 6 Hz), 2.37(2H, t, J=7.5 Hz), 2.64(2H, tt, J=17 Hz, 6.5 Hz), 2.87(2H, m), 4.13(8H, m), 5.37(1H, t, J=6.5 Hz), 7.31(1H, dd, J=8 Hz, 1.5 Hz), 7.31(1H, dd, J=8 Hz, 1.5 Hz), 7.38~7.46(2H, m), 7.60(1H, s), 7.73~7.81(3H, m)

Example 11

Diethyl 2-[(1E, 5E)-2,6,10-trimethyl-1,5,9-undecatrienyl]benzylphosphonate

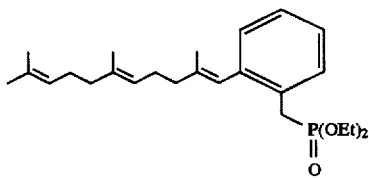

A mixture comprising 0.76 g of the 2-[(1E, 5E)-2,6,10-trimethyl-1,5,9-undecatrienyl]benzyl bromide prepared in the Preparative Example 13 and 1.0 ml of triethyl phosphite was heated to 140° C. and maintained at that temperature for 30 minutes. The obtained reaction mixture was distilled to remove unreacted triethyl phosphite. The residue was purified by silica gel column chromatography (dichloromethane/methanol) to give 0.74 g of the title compound.

$^1$H-NMR δ(CDCl$_3$): 1.22(6H, t, J=7 Hz), 1.60~1.70(12H, m), 1.97~2.15(4H, m), 2.20~2.26(4H, m), 3.18(2H, d, J=20 Hz), 3.92~4.08(4H, m), 5.07~5.16(1H, m), 5.17~5.23(1H, m), 6.38(1H, s), 7.11~7.20(3H, m), 7.34~7.39(1H, m)

Example 12

Tetraethyl 2-[(1E, 5E)-2,6,10-trimethyl-1,5,9-undecatrienyl]benzylidene-1,1-diphosphonate

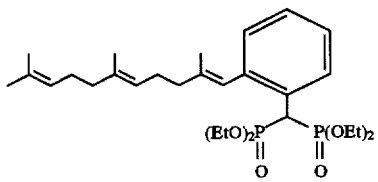

0.3 g of the diethyl 2-[(1E, 5E)-2,6,10-trimethyl-1,5,9-undecatrienyl]benzylphosphonate prepared in the Example 11 was dissolved in 3 ml of anhydrous tetrahydrofuran, followed by the dropwise addition of 1 ml of a 1.6M solution of n-butyllithium in hexane at −50° C. The obtained mixture was stirred at −50° C. for 30 minutes, followed by the addition of 0.11 ml of diethyl chlorophosphate. The obtained mixture was stirred at −50° C. for 30 minutes and gradually brought to room temperature. After the completion of the reaction, the reaction mixture was poured into water and the obtained mixture was extracted with ethyl acetate. The ethyl acetate phase was distilled to remove the solvent and the residue was purified by silica gel column chromatography (dichloromethane/methanol mixture with the methanol content rising from 0.25 to 0.5%) to give 0.1 g of the title compound.

$^1$H-NMR δ(CDCl$_3$): 1.12(6H, t, J=7 Hz), 1.27(6H, t, J=7 Hz), 1.60(3H, s), 1.62~1.67(6H, m), 1.69(3H, s), 2.00~2.15 (4H, m), 2.20~2.24(4H, m), 3.87~4.24(9H, m), 5.08~5.17 (1H, m), 5.17~5.24(1H, m), 6.25(1H, s), 7.10~7.16 (1H, m), 7.20~7.26(2H, m), 7.82~7.89(1H, m)

Example 13

Tetraethyl 4-[N-methyl-4(4acetylbenzyl)benzyl)benzylamino]-butylidene-1,1-diphosphonate

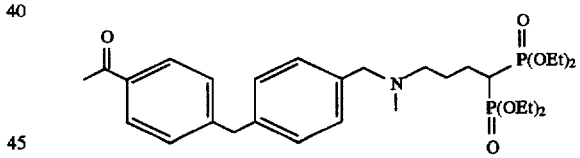

10.6 g of the tetraethyl 4-[N-methyl-4-[4-(1-hydroxyethyl)benzyl]benzylamino]butylidene-1,1-diphosphonate prepared in the Example 1 and 106 g of manganese dioxide were stirred together in 300 ml of chloroform overnight. After the completion of the reaction, the reaction mixture was filtered and the filtrate was distilled to remove the solvent. 7.5 g of the title compound was obtained as a pale-yellow oil.

$^1$H-NMR δ(CDCl$_3$): 1.33(12H, t, J=7 Hz), 1.74~1.83(2H, m), 1.89~2.05(2H, m), 2.15(3H, s), 2.34(1H, tt, J=24 Hz, 7 Hz), 2.37(2H, t, J=7 Hz), 3.44(2H, s), 4.01(2H, s), 4.12~4.22 (8H, m), 7.14(2H, d, J=8 Hz), 7.18(2H, d, J=8 Hz), 7.29(2H, d, J=8 Hz), 7.79(2H, d, J=8 Hz)

Example 14

Tetrasodium 4[N-methyl-4-[4-(1-hydroxyethyl)benzyl]benzylamino]butylidene-1-diphosphonate

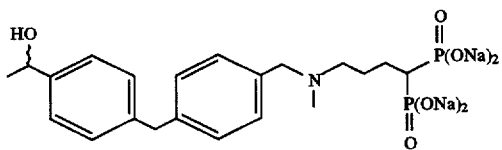

0.87 ml of trimethylsilyl bromide was dropwise added to a mixture comprising 0.5 g of the tetraethyl 4-[N-methyl-4-[4-(1-hydroxyethyl)benzylamino]butylidene-1,1-diphosphonate prepared in the Example 1, 0.5 ml of 2,4,6-collidine and 5 ml of anhydrous dichloromethane under cooling with ice in a nitrogen atmosphere. The obtained mixture was stirred at room temperature for 8 hours and then distilled to remove the solvent. 7 ml of methanol was added to the residue, followed by the addition of 1.5 ml of a 5N aqueous solution of sodium hydroxide. A white solid was formed. This solid was recovered by filtration and washed with methanol and ether successively to give 0.4 g of the title compound as a white solid.

$^1$H-NMR δ(D$_2$O): 1.29(3H, d, J=7 Hz), 1.51~1.70(5H, m), 2.01(3H, s), 2.32(2H, t, J=7 Hz), 3.42(3H, s), 3.85(3H, s), 4.73(1H, q, J=7 Hz), 7.12~7.22(8H, m)

Example 15

Tetrasodium 4-[(E)-N-(3,7-dimethylocta-2,6-dienyl)-N-methylcarbamoyloxybutylidene-1,1-diphosphonate

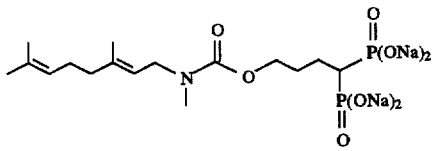

0.12 ml of collidine and 0.28 ml of trimethylsilyl bromide were added to a solution of 0.167 g of tetraethyl 4-[(E)-N-(3,7-dimethylocta-2,6-dienyl)-N-methyl]carbamoyloxybutylidene-1,1-diphosphonate in 5 ml of dichloromethane. The obtained mixture was stirred at room temperature overnight and then distilled to remove the solvent. The residue was dissolved in 5 ml of methanol. The obtained solution was stirred at room temperature for 30 minutes and then distilled to remove the solvent. The residue was dissolved in 5 ml of methanol, followed by the addition of 3 ml of a solution of 60 mg of sodium hydroxide in methanol. The obtained mixture was stirred at room temperature for 30 minutes and then distilled to remove the solvent. The residue was purified by HP-20 column chromatography [acetonitrile/water (1:4)] to give 0.124 g of the title compound.

$^1$H-NMR δ(D$_2$O): 1.45(3H, s), 1.53(6H, s), 1.56~1.79 (5H, m), 1.88~2.04(4H, m), 2.69(3H, s), 3.69~3.80(2H, br.), 3.94(2H, t, J=6 Hz), 4.96~5.07(2H, m)

Example 16

4-[4(4-Methoxybenzoyl)piperidino]butylidene-1,1-diphosphonic acid

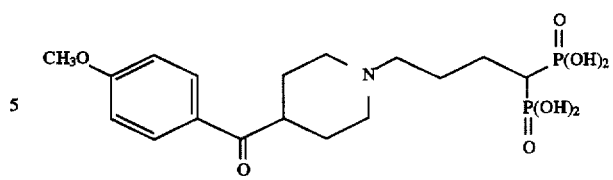

0.95 ml of trimethylsilyl bromide was dropwise added to a solution of 0.6 g of the tetraethyl 4-[4-(4-methoxybenzoylpiperidino]butylidene-1,1-diphosphonate prepared in the Example 2 and 0.48 ml of 2,4,6-collidine in 5 ml of anhydrous dichloromethane in a nitrogen atmosphere. The obtained mixture was stirred overnight and then distilled to remove the solvent. 4 ml of methanol, 0.4 ml of water and 2 ml of diethyl ether were added to the residue to form a solid. This solid was recovered by filtration. 0.42 g of the title compound was obtained.

$^1$H-NMR δ(D$_2$O): 1.66~2.08(9H, m), 2.97~3.10(4H, m), 3.54~3.67(3H, m), 3.77(3H, s), 6.95(2H, d, J=8 Hz), 7.87 (2H, d, J=8 Hz)

Example 17

Diethyl 1-carboxyl-4-[N-methyl-(3-benzyl)benzylaminolbutylphosphonate

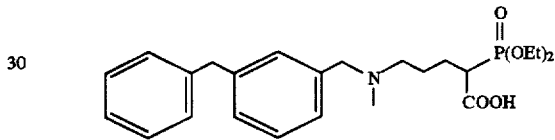

1.8 g of the diethyl 1-ethoxycarbonyl-4-[N-methyl-(3-benzyl)benzylamino]butylphosphonate prepared in the Example 3 was dissolved in 10 ml of ethanol, followed by the addition of 2.5 ml of 2N aqueous sodium hydroxide. The obtained mixture was stirred at 60° C. for 4 hours, neutralized with 5 ml of 1N aqueous hydrochloric acid and then extracted with ethyl acetate thrice. The ethyl acetate phases were combined, washed with a saturated aqueous solution of common salt, dried over magnesium sulfate and subjected to vacuum concentration to give 1.1 g of the title compound.

$^1$H-NMR δ(CDCl$_3$): 1.22~1.32(6H, m), 1.62~1.78(2H, m), 1.90~2.08(2H, m), 2.42(3H, s), 2.80~2.90(1H, m), 3.85~3.95(2H, br.s), 4.00(2H, s), 4.10~4.20(2H, m), 7.10~7.35 (9H, m)

Example 18

Trisodium 1carboxy-4-[N-methyl-3-benzyl)-benzylamino]butylphosphonate

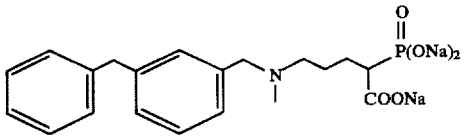

1.12 g of the diethyl 1-carboxy-4-[N-methyl-(3-benzyl)benzylamino]butylphosphonate prepared in the Example 17 was dissolved in 20 ml of dichloromethane. 2 ml of collidine was added to the obtained solution under cooling with ice, followed by the addition of 2 ml of trimethylsilyl bromide. The obtained mixture was stirred overnight, followed by the addition of 10 ml of methanol. The obtained mixture was subjected to vacuum concentration, followed by the addition of 6 ml of 5N aqueous sodium hydroxide. Methanol was added to the resulting mixture by portions to form a precipitate. This precipitate was recovered by filtration and dissolved in 2 ml of water. Methanol was added to the obtained solution by portions to form a precipitate. This precipitate was recovered by filtration and dried under reduced pressure to give 560 mg of the title compound as a white powder.

¹H-NMR δ(D₂O): 1.25~1.55(2H, m), 1.55~1.67(2H, m), 1.98(3H, m), 2.23~2.40(3H, m), 3.40(2H, s), 3.85(2H, s), 7.02~7.22(9H, m)

Example 19

Trisodium 1-carboxy-4-[N-methyl-3-methyl-5-(2-naphthyl)-2-pentenylamino]-3-hydroxybutylphosphonate (diastereomeric mixture)

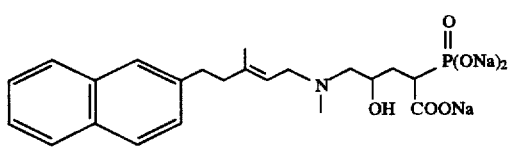

A mixture comprising 140 mg of the diethyl 1-ethoxycarbonyl-4-[N-methyl-3-methyl-5-(2-naphthyl)-2-pentenylamino]-3-hydroxybutylphosphonate prepared in the Example 6, 0.14 ml of 2,4,6-trimethylpyridine, 0.28 ml of trimethylsilyl bromide and 3 ml of dichloromethane was maintained at room temperature overnight to conduct a reaction. The reaction mixture was concentrated, followed by the addition of 2 ml of methanol to prepare a solution, which was further concentrated. 2 ml of 4N aqueous sodium hydroxide was added to the residue. The obtained mixture was heated under reflux for 5 hours, cooled and purified by column chromatography using about 10 ml of MCI gel CHP20P and 10 to 30% acetonitrile/water as the eluent. The obtained fraction was concentrated and freeze-dried to give 120 mg of the title compound.

¹H-NMR δ(D₂O): 1.76(3H, s), 2.14(1.8H, s), 2.18(1.2H, s), 2.40~2.75(5H, m), 3.00(2H, t, J=7 Hz), 3.41~3.48 (2H, m), 3.54~3.62(0.6H, m), 3.78~3.87(0.4H, m), 5.07~5.17 (1H, m), 7.45~7.57(3H, m), 7.74(1H, s), 7.84~7.94(3H, m)

Example 20

Disodium 5-[N-methyl-3-methyl-5-(2-naphthyl)2-pentenylamino]methyl -2-oxotetrahdrofuran-3-ylphosphonate (diastereomeric mixture)

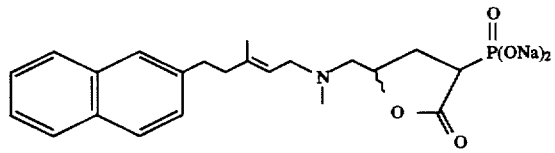

A mixture comprising 120 mg of the diethyl 5-[N-methyl-3-methyl-5-(2-naphthyl)-2-pentenylamino]methyl-2-oxotetrahydrofuran-3-ylphosphonate prepared in the Example 6, 0.14 ml of 2,4,6-trimethylpyridine, 0.28 ml of trimethylsilyl bromide and 3 ml of dichloromethane was maintained at room temperature overnight to conduct a reaction. The reaction mixture was concentrated, followed by the addition of 2 ml of methanol to prepare a solution, which was concentrated. 2 ml of 1N sodium hydroxide was added to the residue to form a sodium salt. The resulting product was purified by column chromatography using about 10 ml of MCl gel CHP20P and 10 to 40% acetonitrile/water as the eluent. The obtained fraction was concentrated and freeze-dried to give 110 mg of the title compound.

¹H-NMR δ(CDCl₃): 1.70(3H, s), 1.96(1.2H, s), 2.00 (1.8H, s), 2.54(2H, t, J=7 Hz), 2.95~3.10(4H, m), 4.28~4.37 (0.4H, m), 4.28~4.37(0.4H, m), 4.62~4.72(0.6H, m), 5.02~5.17(1H, m), 7.44~7.56(3H, m), 7.72(1H, s), 7.83~7.93(3H, m)

Example 21

4-[N-Methyl-4-(4-acetylbenzyl/benzylamino]butylidene-1, 1-diphosphonic acid

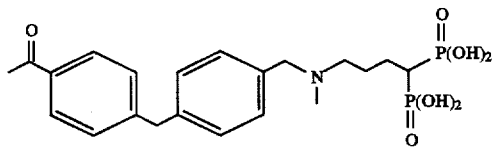

3.1 ml of collidine and 8.5 ml of trimethylsilyl bromide were added to 150 ml of a solution of 5 g of the tetraethyl 4-[N-methyl-4-(4-acetylbenzyl)benzyl-amino]butylidene-1, 1-diphosphonate prepared in the Example 13 in dichloromethane. The obtained mixture was stirred at room temperature for 4 days and distilled to remove the solvent. The residue was dissolved in 100 ml of methanol. The obtained solution was stirred at room temperature for 30 minutes and distilled to remove the solvent. The residue was dissolved in 100 ml of methanol, followed by the addition of 5 ml of propylene oxide. The obtained mixture was stirred at room temperature for 30 minutes and distilled to remove the solvent. The residue was washed with ether and dichloromethane to give 3.2 g of the title compound.

Example 22

(A) Mono(pivaloyloxymethyl) 4-(N-methyl-4-(4-acetylbenzyl)benzylamino]butylidene-1,1-diphosphonate (B) Di(pivaloyloxymethyl) 4-[N-methyl-4-(4-acetylbenzyl)benzylamino]butylidene-1,1-diphosphonate

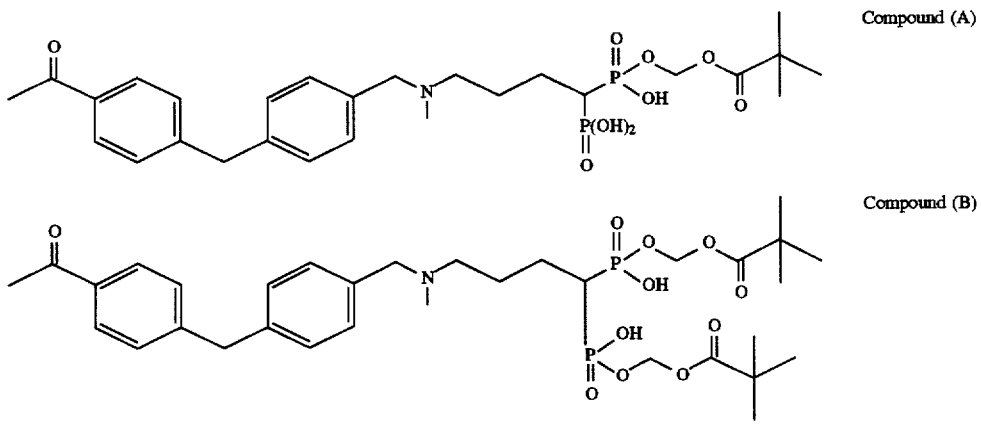

Compound (A)

Compound (B)

3 ml of diisopropylethylamine and 4 g of iodomethyl pivalate were added to of 150 ml of a solution of 3.20 g of the 4-[N-methyl-4-(4-acetylbenzyl)benzylamino] butylidene-1,1-diphosphonic acid prepared in the Example 21 in dimethylformamide. The obtained mixture was stirred at 60° C. for 2 days and then distilled to remove the solvent. The residue was purified by reversed phase silica gel column chromatography (20 to 40% acetonitrile/water) to give 0.20 g of the title compound (A) and 0.37 g of the title compound (B).

Compound (A)

$^1$H-NMR δ(D$_2$O): 0.99(9H, s), 1.58~2.03(5H, m), 2.42 (3H, s), 2.63(3H, s), 2.85~2.94(1H, m), 2.97~3.08(1H, m), 3.90(2H, s), 4.06(1H, br.d, J=14 Hz), 4.18(1H, m), 5.34(2H, dd, J=4 Hz, 14 Hz), 6.98~7.28(6H, m), 7.71(2H, d, J=9 Hz)

Compound (B)

$^1$H-NMR δ(CDCl$_3$): 1.09(18H, s), 1.71~1.91(2H, m), 2.00~2.26(3H, m), 2.57(3H, s), 2.67(3H, br.s), 2.88~3.02 (2H, br), 3.98(2H, s), 4.23(2H, br.s), 5.43~5.62(4H, m), 7.18(2H, d, J=8 Hz), 7.24(2H, d, J=9 Hz), 7.43(2H, br.d, J=8 Hz), 7.87(2H, d, J=9 Hz)

Examples 23 to 199

The compounds of Examples 23 to 199 listed in Tables 1 to 61 were prepared by preparing diphosphonic acid ester derivatives in a similar manner to that of the Example 1 and deprotecting the ester derivatives in a similar manner to that of the Example 14.

TABLE 1

| Ex. No. | Chemical Structure | $^1$H-NMRδ(D$_2$O) |
|---|---|---|
| 23 | (structure with OH, P(ONa)$_2$ groups) | 1.46(3H, d, J=7Hz), 1.70~1.93(5H, m) 2.40(3H, s), 2.72~2.80(2H, m), 3.88(2H, s), 4.93(1H, q, J=7Hz) 7.38~7.46(4H, m) |
| 24 | (benzodioxole structure with P(ONa)$_2$ groups) | 1.50~1.70(5H, m), 2.01(3H, m) 2.25~2.35(2H, m), 3.38(3H, m) 6.71~6.75(2H, m), 6.78(1H, s) |
| 25 | (farnesyl-furan structure with P(ONa)$_2$ groups) | 1.48(3H, s), 1.50~1.68(11H, m) 1.92~2.04(4H, m), 2.06(3H, s) 2.31(2H, d, J=7Hz), 3.22(2H, d, J=8Hz) 3.42(2H, s), 5.02~5.08(1H, m) 5.25(1H, t, J=8Hz), 5.90(1H, d, J=3Hz) 6.16(1H, d, J=3Hz) |

TABLE 2

| Ex. No. | Chemical Structure | $^1$H-NMR$\delta$(D$_2$O) |
|---|---|---|
| 26 | (prenyl-geranyl)-thiophene-CH$_2$-N(Me)-(CH$_2$)$_3$-CH(P(ONa)$_2$=O)$_2$ | 1.68(3H, s), 1.50~1.80(5H, m) 1.80~2.20(4H, m), 1.92(3H, s) 2.16(3H, s), 2.24(3H, s) 2.35~2.40(2H, m), 3.60(2H, s) 5.05~5.20(1H, m) 6.28(cis), 6.34(trans)(1H, s) 6.70~6.80(2H, m) |
| 27 | (farnesyl)-thiophene-CH$_2$-N(Me)-(CH$_2$)$_3$-CH(P(ONa)$_2$=O)$_2$ | 1.60(3H, s), 1.66(3H, s) 1.50~1.80(5H, m), 1.80~2.20(8H, m) 1.94(3H, s), 2.18(3H, s), 2.22(3H, s) 2.35~2.40(2H, m), 3.60(2H, s) 5.00~5.18(2H, m) 6.28(cis), 6.34(trans)(1H, s) 6.70~6.80(2H, m) |
| 28 | NC-(CH$_2$)$_2$-O-(m-C$_6$H$_4$)-CH$_2$-N(Me)-(CH$_2$)$_3$-CH(P(ONa)$_2$=O)$_2$ | 1.52~1.70(5H, m), 1.96~2.05(5H, m) 2.32(2H, t, J=8Hz), 2.54(2H, t, J=7Hz) 3.43(2H, s), 4.04(2H, t, J=7Hz) 6.81~6.92(3H, m), 7.21(1H, t, J=8Hz) |

TABLE 3

| Ex. No. | Chemical Structure | $^1$H-NMR$\delta$(D$_2$O) |
|---|---|---|
| 29 | 2-naphthyl-CH$_2$-N(Me)-(CH$_2$)$_3$-CH(P(ONa)$_2$=O)$_2$ | 1.48~1.75(5H, m), 2.06(3H, s) 2.36(2H, t, J=7Hz), 3.61(2H, s) 7.38~7.46(3H m), 7.73(1H, s) 7.76~7.83(3H, m) |
| 30 | 2-quinolyl-CH$_2$-N(Me)-(CH$_2$)$_3$-CH(P(ONa)$_2$=O)$_2$ | 1.44~1.76(5H, m), 2.06(3H, s) 2.38(2H, t, J=7.5Hz), 3.69(2H, s) 7.45~7.51(2H, m) 7.65(1H, ddd, J=1Hz, 7.5Hz, 8Hz) 7.81(1H, d, J=8Hz), 7.85(1H d, J=8Hz) 8.21(1H, d, J=8.5Hz) |
| 31 | 6-MeO-2-naphthyl-CH$_2$-N(Me)-(CH$_2$)$_3$-CH(P(ONa)$_2$=O)$_2$ | 1.50~1.77(5H, m), 2.07(3H, s) 2.37(2H, t, J=8Hz), 3.58(2H, s) 3.80(3H, s), 7.09(1H, m), 7.23(1H, brs) 7.38(1H, d, J=8Hz), 7.65~7.74(3H, m) |

TABLE 4

| Ex. No. | Chemical Structure | $^1$H-NMRδ(D$_2$O) |
|---|---|---|
| 32 | biphenyl-CH$_2$-N(CH$_3$)-(CH$_2$)$_3$-CH[P(ONa)$_2$=O]$_2$ | 1.60~1.80(5H, m), 2.20(3H, s) 2.50~2.60(2H, m), 3.70(2H, s) 7.20~7.60(9H, m) |
| 33 | 3-(pyridin-3-yl)phenyl-CH$_2$-N(CH$_3$)-(CH$_2$)$_3$-CH[P(ONa)$_2$=O]$_2$ | 1.40~1.75(5H, m), 2.00(3H, s) 2.25~2.35(2H, m), 3.50(2H, s) 7.20~7.50(3H, m), 7.86~7.89(1H, m) 8.32~8.37(1H, m), 8.63(1H, s) |
| 34 | 4-(pyrrol-1-yl)phenyl-CH$_2$-N(CH$_3$)-(CH$_2$)$_3$-CH[P(ONa)$_2$=O]$_2$ | 1.40~1.70(5H, m), 2.03(3H, s) 2.25~2.35(2H, m), 3.45(2H, s) 6.25(1H, d, J=2Hz), 7.13(1H, d, J=2Hz) 7.30~7.38(2H, m) |

TABLE 5

| Ex. No. | Chemical Structure | $^1$H-NMRδ(D$_2$O) |
|---|---|---|
| 35 | 4-(pyridin-3-yl)phenyl-CH$_2$-N(CH$_3$)-(CH$_2$)$_3$-CH[P(ONa)$_2$=O]$_2$ | 1.40~1.70(5H, m), 2.00(3H, s) 2.25~2.35(2H, m), 3.46(2H, s) 7.30~7.36(3H, m), 7.46(1H, s) 7.48(1H, s), 7.89(1H, d, J=8Hz) 8.30(1H, d, J=4.8Hz), 8.57(1H, s) |
| 36 | 3-(oxazol-2-yl)phenyl-CH$_2$-N(CH$_3$)-(CH$_2$)$_3$-CH[P(ONa)$_2$=O]$_2$ | 1.40~1.65(5H, m), 2.00(3H, s) 2.23~2.30(2H, m), 3.40(2H, s) 7.18(2H, d, J=8Hz), 7.23~7.27(2H, m) 7.43(1H, d, J=8Hz), 7.46(1H, s) 7.98(1H, s) |
| 37 | 3-(isoxazol-3-yl)phenyl-CH$_2$-N(CH$_3$)-(CH$_2$)$_3$-CH[P(ONa)$_2$=O]$_2$ | 1.40~1.70(5H, m), 2.00(3H, s) 2.24~2.32(2H, m), 3.41(2H, s) 6.57(1H, s), 7.18~7.40(3H, m) 7.53~7.62(2H, m), 8.27(1H, s) |

TABLE 6

| Ex. No. | Chemical Structure | $^1$H-NMRδ(D$_2$O) |
|---|---|---|
| 38 | 4-(pyridin-4-yl)phenyl-CH$_2$-N(CH$_3$)-(CH$_2$)$_3$-CH[P(ONa)$_2$=O]$_2$ | 1.40~1.65(5H, m), 2.20(3H, s) 2.25~2.35(2H, m), 7.34(1H, d, J=8Hz) 7.38(1H, d, J=8Hz), 7.42~7.60(4H, m) 8.30~8.38(1H, m) |

TABLE 6-continued

| Ex. No. | Chemical Structure | $^1$H-NMR$\delta$(D$_2$O) |
|---|---|---|
| 39 | (structure) | 1.40(3H, d, J=8Hz), 1.56~1.75(5H, m) 2.09(3H, s), 2.38(2H, t, J=8Hz) 3.54(2H, s), 4.87(1H, q, J=8Hz) 7.32(1H, br.d, J=8Hz) 7.38(1H, d, J=8Hz) 7.53(1H, br.d, J=8Hz) 7.56~7.60(3H, m) |
| 40 | (structure) | 1.39(3H, d, J=7Hz), 1.55~1.75(5H, m) 2.09(3H, s), 2.37(3H, t, J=8Hz) 3.53(2H, s), 4.82(1H, q, J=7Hz) 7.38(2H, d, J=8Hz) 7.40(2H, d, J=8Hz) 7.61(2H, d, J=8Hz) |

TABLE 7

| Ex. No. | Chemical Structure | $^1$H-NMR$\delta$(D$_2$O) |
|---|---|---|
| 41 | (structure) | 1.40~1.70(5H, m), 2.10(3H, s) 2.25~2.35(2H, m), 3.65(2H, s) 6.91(1H, d, J=3.6Hz) 7.23(1H, d, J=3.6Hz) 7.29(1H, dd, J=5.2Hz, 8Hz) 7.88(1H, d, J=8Hz) 8.24(1H, d, J=5.2Hz) 8.61(1H, s) |
| 42 | (structure) | 1.68(3H, d, J=7Hz), 1.88~2.05(5H, m) 2.45(3H, s), 2.70(2H, t, J=7Hz) 4.03(2H, s), 5.15(1H, q, J=7Hz) 7.27(1H, d, J=4Hz) 7.55(1H, d, J=4Hz) 7.65(2H, d, J=8Hz) 7.92(2H, d, J=7Hz) |
| 43 | (structure) | 1.40~1.70(5H, m), 2.10(3H, s) 2.28~2.38(2H, m), 3.66(2H, s) 7.23(1H, s), 7.26~7.35(1H, m) 7.53(1H, s), 7.86~7.94(1H, m) 8.25~8.29(1H, m), 8.60(1H, s) |

TABLE 8

| Ex. No. | Chemical Structure | $^1$H-NMR$\delta$(D$_2$O) |
|---|---|---|
| 44 | (structure) | 1.40~1.70(5H, m), 2.08(3H, s) 2.26~2.34(2H, m), 3.64(2H, s) 7.23(1H, s), 7.29~7.37(2H, m) 7.39(1H, s)7.44~7.46(1H, m) |

TABLE 8-continued

| Ex. No. | Chemical Structure | $^1$H-NMRδ(D$_2$O) |
|---|---|---|
| 45 | (3-pyridyl-furan-CH$_2$-N(CH$_3$)-(CH$_2$)$_3$-CH(P(ONa)$_2$=O)$_2$) | 1.40~1.70(5H, m), 2.06(3H, s) 2.25~2.32(2H, m), 3.45(2H, s) 6.29(1H, s), 6.63(1H, s) 7.20~7.25(1H, m), 7.80~7.84(1H, m) 8.16~8.20(1H, m), 8.58(1H, s) |
| 46 | (3,3'-bipyridyl-CH$_2$-N(CH$_3$)-(CH$_2$)$_3$-CH(P(ONa)$_2$=O)$_2$) | 1.40~1.70(5H, m), 1.99(3H, s) 2.25~2.33(2H, m), 3.43(2H, s) 7.30(1H, dd, J=4.8Hz, 8.0Hz) 7.74(1H, s), 7.80(1H, d, J=8Hz) 8.25(1H, d, J=2Hz) 8.30(1H, d, J=4.8Hz) 8.37(1H, d, J=2Hz), 8.45(1H, s) |

TABLE 9

| Ex. No. | Chemical Structure | $^1$H-NMRδ(D$_2$O) |
|---|---|---|
| 47 | (4-benzylbenzyl-N(CH$_3$)-(CH$_2$)$_3$-CH(P(ONa)$_2$=O)$_2$) | 1.48~1.68(5H, m), 2.00(3H, s) 2.30(2H, t, J=7Hz), 3.40(2H, s) 3.84(2H, s), 7.08~7.24(9H, m) |
| 48 | (3-benzylbenzyl-N(CH$_3$)-(CH$_2$)$_3$-CH(P(ONa)$_2$=O)$_2$) | 1.45~1.68(5H, m), 1.97(3H, s) 2.28(2H, t, J=7.2Hz), 3.38(2H, s) 3.84(2H, s), 7.05~7.23(9H, m) |
| 49 | (3,4-dimethoxybenzyl-3-benzyl-N(CH$_3$)-(CH$_2$)$_3$-CH(P(ONa)$_2$=O)$_2$) | 1.42~1.68(5H, m), 1.95(3H, s) 2.27(2H, t, J=7Hz), 3.35(2H, s) 3.61(3H, d, J=0.5Hz) 3.63(3H, d, J=0.5Hz), 3.74(2H, s) 6.69(1H, br.d, J=8Hz) 6.75(1H, d, J=2Hz) 6.77(1H, br.d, J=8Hz) 7.02(1H, d, J=7.5Hz) 7.05(1H, d, J=7.5Hz), 7.08(1H, s) 7.15(1H, t, J=7.5Hz) |

TABLE 10

| Ex. No. | Chemical Structure | $^1$H-NMRδ(D$_2$O) |
|---|---|---|
| 50 | (3-(3-pyridylmethyl)benzyl-N(CH$_3$)-(CH$_2$)$_3$-CH(P(ONa)$_2$=O)$_2$) | 1.40~1.68(5H, m), 1.97(3H, s) 2.28(2H, t, J=7Hz), 3.39(2H, s) 3.88(2H, s), 7.04~7.14(3H, m) 7.15~7.25(2H, m) 7.57(1H, br.d, J=8.0Hz) 8.20(1H, d, J=5.5Hz), 8.30(1H, s) |

TABLE 10-continued

| Ex. No. | Chemical Structure | ¹H-NMRδ(D₂O) |
|---|---|---|
| 51 | (HO-CH(Ph)-C₆H₄-CH₂-N(Me)-(CH₂)₃-CH(P(O)(ONa)₂)₂) | 1.45~1.70(5H, m), 1.97(3H, s) 2.25~2.32(2H, m), 3.41(2H, s) 5.76(1H, s), 7.13~7.30(9H, m) |
| 52 | (MeO-CH(Ph)-C₆H₄-CH₂-N(Me)-(CH₂)₃-CH(P(O)(ONa)₂)₂) | 1.45~1.70(5H, m), 1.98(3H, s) 2.29(2H, t, J=7.5Hz), 3.26(3H, s) 3.41(2H, s), 5.34(1H, s) 7.15~7.31(9H, m) |

TABLE 11

| Ex. No. | Chemical Structure | ¹H-NMRδ(D₂O) |
|---|---|---|
| 53 | (MeO-CH(Ph)-C₆H₄-CH₂-N(Me)-(CH₂)₃-CH(P(O)(ONa)₂)₂) | 1.42~1.69(5H, m), 1.96(3H, s) 2.28(2H, t, J=7.5Hz), 3.25(3H, br.s) 3.40(2H, s), 5.33(1H, s) 7.16~7.30(9H, s) |
| 54 | (HO-CH(Ph)-C₆H₄-CH₂-N(Me)-(CH₂)₃-CH(P(O)(ONa)₂)₂) | 1.43~1.68(5H, m), 1.97(3H, s) 2.28(2H, t, J=7.0Hz), 3.40(2H, s) 5.75(1H, s), 7.15~7.30(9H, m) |
| 55 | (3,4,5-(MeO)₃-C₆H₂-CH₂-C₆H₄-CH₂-N(Me)-(CH₂)₃-CH(P(O)(ONa)₂)₂) | 1.48~1.80(5H, m), 1.98(3H, s) 2.30(2H, t, J=7Hz), 3.39(2H, s) 3.57(3H, s), 3.65(6H, s) 3.76(2H, s), 6.50(2H, s) 7.11(2H, d, J=8Hz) 7.15(2H, d, J=8Hz) |

TABLE 12

| Ex. No. | Chemical Structure | ¹H-NMRδ(D₂O) |
|---|---|---|
| 56 | (3,4-(MeO)₂-C₆H₃-CH₂-C₆H₄-CH₂-N(Me)-(CH₂)₃-CH(P(O)(ONa)₂)₂) | 1.42~1.70(5H, m), 1.98(3H, s) 2.28(2H, br.t, J=8Hz), 3.38(2H, s) 3.63(3H, s), 3.65(3H, s), 3.76(2H, s) 6.72(2H, d, J=8Hz), 6.79(1H, s) 6.80(2H, d, J=8Hz) 7.11(2H, d, J=6.5Hz) 7.14(2H, d, J=6.5Hz) |
| 57 | (4-MeO-C₆H₄-CH₂-C₆H₄-CH₂-N(Me)-(CH₂)₃-CH(P(O)(ONa)₂)₂) | 1.44~1.72(5H, m), 1.99(3H, s) 2.29(2H, t, J=7Hz), 3.40(2H, s) 3.65(3H, s), 3.78(2H, s) 6.79(2H, br.d, J=7.5Hz) 7.07~7.13(4H, m), 7.15(2H, d, J=8Hz) |

TABLE 12-continued

| Ex. No. | Chemical Structure | ¹H-NMRδ(D₂O) |
|---|---|---|
| 58 | [pyridin-3-yl-CH₂-phenyl-CH₂-N(Me)-(CH₂)₃-CH(P(ONa)₂=O)₂] | 1.39~1.72(5H, m), 2.00(3H, s) 2.29(2H, m), 3.40(2H, s) 3.87(2H, s), 7.05~7.25(5H, m) 7.56(1H, br.d, J=7Hz) 8.20(1H, br.s), 8.29(1H, s) |

TABLE 13

| Ex. No. | Chemical Structure | ¹H-NMRδ(D₂O) |
|---|---|---|
| 59 | [HO, MeO-phenyl-CH₂-phenyl-CH₂-N(Me)-(CH₂)₃-CH(P(ONa)₂=O)₂] | 1.40~1.76(5H, m), 2.02(3H, s) 2.36(2H, t, J=6.5Hz), 3.45(2H, s) 3.55(3H, s), 3.68(2H, s) 6.41(1H, d, J=8Hz) 6.53(1H, dd, J=8Hz, 1.5Hz) 6.63(1H, d, J=1.5Hz) 7.14(4H, br.s) |
| 60 | [OMe, HO, MeO-phenyl-CH₂-phenyl-CH₂-N(Me)-(CH₂)₃-CH(P(ONa)₂=O)₂] | 1.50~1.78(5H, m), 2.07(3H, s) 2.38~2.46(2H, m), 3.51(2H, s) 3.58(6H, s), 3.70(2H, s) 6.43(2H, br.s), 7.17(4H, br.s) |
| 61 | [MeO-phenyl-CH(CONHMe)-phenyl-CH₂-N(Me)-(CH₂)₃-CH(P(ONa)₂=O)₂] | 1.58~1.76(3H, m), 1.80~1.92(2H, m) 2.54(3H, s), 2.99~3.05(2H, m) 3.23(3H, s), 3.66(3H, s) 4.10~4.15(2H, m), 5.33(1H, s) 6.84(2H, d, J=9Hz) 7.20(2H, d, J=9Hz) |

TABLE 14

| Ex. No. | Chemical Structure | ¹H-NMRδ(D₂O) |
|---|---|---|
| 62 | [pyridin-3-yl-CH₂-thiophene-CH₂-N(Me)-(CH₂)₃-CH(P(ONa)₂=O)₂] | 1.42~1.80(5H, m), 2.30(3H, s) 2.27(2H, br.t, J=6.5Hz) 3.57(2H, s), 4.03(2H, s) 6.63(1H, d, J=3.5Hz) 6.73(1H, d, J=3.5Hz) 7.25(1H, dd, J=7.5Hz, 5Hz) 7.63(1H, br.d, J=7.5Hz) 8.24(1H, d, J=5Hz), 8.32(1H, br.s) |
| 63 | [pyridin-3-yl-CH₂-(MeO,MeO-dimethylphenyl)-CH₂-N(Me)-(CH₂)₃-CH(P(ONa)₂=O)₂] | 1.39~1.78(5H, m), 1.97(6H, s) 2.15(3H, s), 2.43(2H, t, J=7Hz) 3.48(3H, s), 3.50(2H, s) 3.51(3H, s), 3.97(2H, s) 7.15(1H, dd, J=7.5Hz, 5Hz) 7.32(1H, d, J=7.5Hz) 8.15~8.21(2H, m) |

TABLE 14-continued

| Ex. No. | Chemical Structure | $^1$H-NMR$\delta$(D$_2$O) |
|---|---|---|
| 64 | 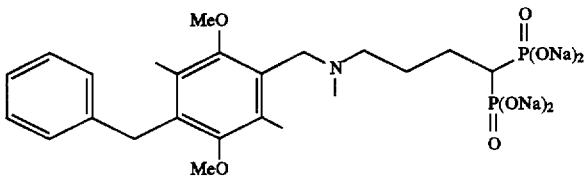 | 1.50~1.77(5H, m), 1.96(3H, s)<br>1.98(3H, s), 2.15(3H, s)<br>2.44(2H, t, J=7Hz), 3.48(3H, s)<br>3.51(5H, s), 3.96(2H, s)<br>6.97(2H, d, J=7Hz)<br>7.07(1H, t, J=7Hz)<br>7.15(2H, t, J=7Hz) |

TABLE 15

| Ex. No. | Chemical Structure | $^1$H-NMR$\delta$(D$_2$O) |
|---|---|---|
| 65 | 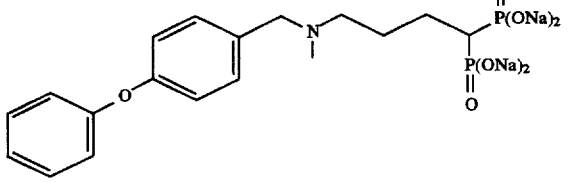 | 1.45~1.70(5H, m), 2.00(3H, s)<br>2.25~2.35(2H, m), 3.41(2H, s)<br>6.87~6.98(4H, m)<br>7.02~7.08(1H, m)<br>7.20~7.35(4H, m) |
| 66 | 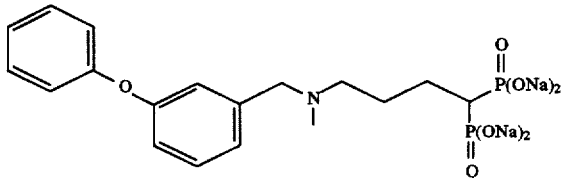 | 1.45~1.65(5H, m), 2.00(3H, s)<br>2.25~2.32(2H, m), 3.40(2H, s)<br>6.80~7.08(6H, m)<br>7.22~7.32(3H, m) |
| 67 | 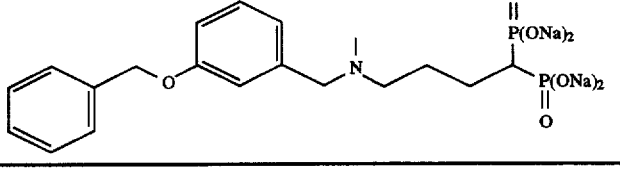 | 1.45~1.65(5H, m), 1.96(3H, s)<br>2.25~2.30(2H, m), 3.40(2H, s)<br>5.00(2H, s), 6.80~6.90(3H, m)<br>7.15~7.38(6H, m) |

TABLE 16

| Ex. No. | Chemical Structure | $^1$H-NMR$\delta$(D$_2$O) |
|---|---|---|
| 68 | 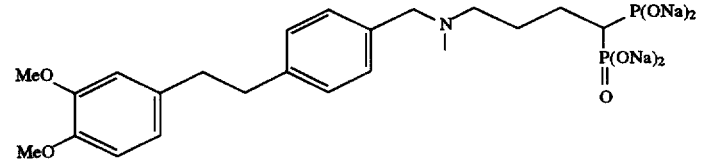 | 1.40~1.78(5H, m), 1.96(3H, s)<br>2.29(2H, t, J=7Hz), 2.63~2.75(4H, m)<br>3.37(2H, s), 3.58(3H, s), 3.62(3H, s)<br>6.60(1H, dd, J=8Hz, 1.5Hz)<br>6.63(1H, d, J=1.5Hz)<br>6.73(1H, d, J=8.0Hz)<br>6.99(2H, d, J=8.0Hz)<br>7.09(2H, d, J=8.0Hz) |

TABLE 16-continued

| Ex. No. | Chemical Structure | $^1$H-NMR$\delta$(D$_2$O) |
|---|---|---|
| 69 | (structure) | 1.26~1.28(3H, d, J=7Hz)<br>1.50~1.69(5H, m), 2.00(3H, d)<br>2.28~2.35(2H, m), 2.77(4H, s)<br>3.39(1H, q, J=7Hz), 3.39~3.44(2H, m)<br>7.04~7.16(8H, m) |
| 70 | (structure) | 1.40~1.70(5H, m), 1.98(3H, s)<br>2.15~2.25(2H, m)<br>2.80(2H, t, J=5Hz), 2.93(2H, t, J=5Hz)<br>3.50(2H, s), 6.40(1H, d, J=3.2Hz)<br>6.60(1H, d, J=3.2Hz)<br>7.16(1H, dd, J=4.8Hz, 7.6Hz)<br>7.46(1H, d, J=7.6Hz), 8.10(1H, s)<br>8.14(1H, d, J=4.8Hz) |

TABLE 17

| Ex. No. | Chemical Structure | $^1$H-NMR$\delta$(D$_2$O) |
|---|---|---|
| 71 | (structure) | 1.50~1.75(5H, m), 2.00(3H, s)<br>2.14~2.35(2H, m), 3.40(2H, s)<br>6.93(1H, d, J=16.4Hz)<br>7.16(1H, d, J=7.0Hz)<br>7.18(1H, d, J=16.4Hz)<br>7.24(1H, t, J=7.0Hz)<br>7.34~7.38(2H, m), 8.70(2H, s)<br>8.74(1H, s) |
| 72 | (structure) | 1.40~1.70(5H, m), 1.92(3H, s)<br>1.96(3H, s), 2.20~2.30(2H, m)<br>3.32(2H, s), 6.50(1H, s)<br>6.95~7.20(5H, m), 7.60(1H, s)<br>8.12~8.35(2H, m) |
| 73 | (structure) | 1.45~1.70(5H, m), 2.00(3H, s)<br>2.26~3.32(2H, m), 3.40(2H, s)<br>6.98(1H, d, J=16.4Hz)<br>7.08(1H, d, J=16.4Hz)<br>7.12~7.36(5H, m), 7.80~7.84(1H, m)<br>8.08(1H, s), 8.40(1H, s) |

TABLE 18

| Ex. No. | Chemical Structure | $^1$H-NMR$\delta$(D$_2$O) |
|---|---|---|
| 74 | (structure) | 1.44~1.70(5H, m), 2.00(8H, s)<br>2.24~2.82(2H, m), 3.40(2H, s)<br>6.95(1H, d, J=16.4Hz)<br>7.06(1H, d, J=16.4Hz)<br>7.18~7.26(3H, m), 7.34~7.42(2H, m)<br>7.78~7.83(1H, m), 8.16~8.20(1H, m)<br>8.40(1H, s) |

TABLE 18-continued

| Ex. No. | Chemical Structure | $^1$H-NMR$\delta$(D$_2$O) |
|---|---|---|
| 75 | (4-(1-hydroxyethyl)phenyl)-CH=CH-(phenyl)-CH$_2$-N(CH$_3$)-(CH$_2$)$_3$-CH(P(O)(ONa)$_2$)$_2$ | 1.56~1.93(5H, m), 1.33(3H, d, J=7Hz) <br> 2.51(3H, s), 2.93~3.00(2H, m) <br> 4.05~4.09(2H, m) <br> 4.89(1H, q, J=7Hz) <br> 7.16(2H, d, J=6Hz) <br> 7.35(2H, d, J=10Hz) <br> 7.29(2H, d, J=10Hz) <br> 7.49(2H, d, J=10Hz) <br> 7.54(2H, d, J=10Hz) |
| 76 | (pyridin-3-yl)-CH=CH-(phenyl)-CH$_2$-N(CH$_3$)-(CH$_2$)$_3$-CH(P(O)(ONa)$_2$)$_2$ | 1.40~1.80(5H, m), 2.00(3H, s) <br> 2.25~2.33(2H, m), 3.40(2H, s) <br> 6.87(1H, d, J=16.4Hz) <br> 7.18~7.30(4H, m) <br> 7.37(1H, d, J=16.4Hz) <br> 7.54(1H, d, J=7.6Hz) <br> 7.87(1H, d, J=7.6Hz) <br> 8.21(1H, d, J=5.2Hz) |

TABLE 19

| Ex. No. | Chemical Structure | $^1$H-NMR$\delta$(D$_2$O) |
|---|---|---|
| 77 | (phenyl)-C(CH$_3$)=CH-(thiophene)-CH$_2$-N(CH$_3$)-(CH$_2$)$_3$-CH(P(O)(ONa)$_2$)$_2$ | 1.60~1.90(5H, m), 2.24(3H, s) <br> 2.38(3H, s), 2.90~3.00(2H, m) <br> 4.28(2H, s), 6.68(1H, s) <br> 7.01(1H, d, J=4Hz), 7.10(1H, d, J=4Hz) <br> 7.21(1H, t, J=7Hz), 7.28(1H, d, J=8Hz) <br> 7.31(1H, d, J=8Hz), 7.43(1H, s) <br> 7.45(1H, s) |
| 78 | (thiazol-2-yl)-C(CH$_3$)=CH-(thiophene)-CH$_2$-N(CH$_3$)-(CH$_2$)$_3$-CH(P(O)(ONa)$_2$)$_2$ | 1.40~1.65(5H, m), 2.05(3H, s) <br> 2.18(3H, s), 2.25~2.32(2H, m) <br> 3.60(2H, s) <br> 6.98(1H, dd, J=3.6Hz, 4.8Hz) <br> 7.10(1H, d, J=3.6Hz), 7.31(1H, s) <br> 7.38(1H, s), 7.39(1H, d, J=4.8Hz) |
| 79 | (pyridin-3-yl)-CH=CH-(thiophene)-CH$_2$-N(CH$_3$)-(CH$_2$)$_3$-CH(P(O)(ONa)$_2$)$_2$ | 1.40~1.70(5H, m), 2.08(3H, s) <br> 2.25~2.35(3H, m), 3.60(2H, s) <br> 6.70(1H, d, J=16Hz), 6.80(1H, s) <br> 6.87(1H, s), 7.24(1H, d, J=16Hz) <br> 7.28(1H, d, J=8Hz), 7.80(1H, d, J=8Hz) <br> 8.18(1H, d, J=4Hz), 8.40(1H, s) |

TABLE 20

| Ex. No. | Chemical Structure | $^1$H-NMR$\delta$(D$_2$O) |
|---|---|---|
| 80 | (furan–C(CH₃)=CH–thiophene–CH₂–N(CH₃)–(CH₂)₃–CH(P(ONa)₂=O)₂) | 1.50~1.80(5H, m), 2.12(3H, s) 2.20(3H, s), 2.45~2.55(2H, m) 3.82(2H, s), 6.39(1H, d, J=3.2Hz) 6.42(1H, d, J=3.6Hz) 6.94(1H, d, J=3.6Hz) 6.95(1H, d, J=3.6Hz), 7.10(1H, s) 7.37(1H, s) |
| 81 | (thiophene–C(CH₃)=CH–thiophene–CH₂–N(CH₃)–(CH₂)₃–CH(P(ONa)₂=O)₂) | 1.50~1.80(5H, m), 2.18(3H, s) 2.27(3H, s), 2.45~2.60(2H, m) 3.87(2H, s), 6.87(1H, d, J=3.6Hz) 6.90~6.94(3H, m) 7.06(1H, d, J=3.6Hz) 7.17(1H, d, J=4.8Hz) |
| 82 | (pyridyl–C(CH₃)=CH–thiophene–CH₂–N(CH₃)–(CH₂)₃–CH(P(ONa)₂=O)₂) | 1.50~1.70(5H, m), 2.18(3H, s) 2.22(3H, s), 2.40~2.50(2H, m) 3.76(2H, s), 6.88(1H, s) 6.73(1H, d, J=3.6Hz) 6.78(1H, d, J=3.6Hz) 7.28(1H, dd, J=4.8Hz, 7.6Hz) 7.82(1H, d, J=7.6Hz) 8.25(1H, d, J=4.8Hz) 8.52(1H, d, J=2.2Hz) |

TABLE 21

| Ex. No. | Chemical Structure | $^1$H-NMR$\delta$(D$_2$O) |
|---|---|---|
| 83 | (3,4-dimethoxyphenyl–C(CH₃)=CH–thiophene–CH₂–N(CH₃)–(CH₂)₃–CH(P(ONa)₂=O)₂) | 1.50~1.70(5H, m), 2.04(3H, s) 2.12(3H, s), 2.26~2.34(2H, m) 3.62(2H, s), 3.64(3H, s) 3.66(3H, s), 6.70(1H, s) 6.79(1H, d, J=8.0Hz), 6.83(2H, s) 6.91(1H, d, J=8.0Hz), 6.93(1H, s) |
| 84 | (pyridyl–C(CH₃)=CH–thiophene–CH₂–N(CH₃)–(CH₂)₃–CH(P(ONa)₂=O)₂) | 1.40~1.70(5H, m), 2.20(3H, s) 2.08(3H, s), 2.25~2.35(2H, m) 3.60(2H, s), 6.64(1H, s) 6.72(1H, d, J=3.6Hz) 6.38(1H, dd, J=4.8Hz, 7.6Hz) 7.62(1H, d, J=7.6Hz) 8.24(1H, d, J=3.6Hz) 8.40(1H, d, J=4.8Hz) |
| 85 | (3,4-dimethoxyphenyl–C(CH₃)=CH–thiophene–CH₂–N(CH₃)–(CH₂)₃–CH(P(ONa)₂=O)₂) | 1.40~1.60(5H, m), 1.92(3H, s) 1.97(3H, s), 2.12~2.20(2H, m) 3.19(2H, s), 3.62(3H, s) 3.72(3H, s), 6.51(1H, s) 6.60(1H, s), 6.64(1H, s) 6.71(1H, d, J=8.4Hz), 6.76(1H, s) 6.93(1H, d, J=8.4Hz) |

TABLE 22

| Ex. No. | Chemical Structure | $^1$H-NMR$\delta$(D$_2$O) |
|---|---|---|
| 86 | 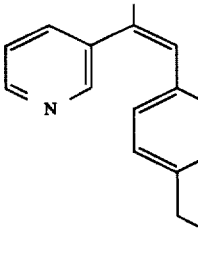 | 1.50~1.70(5H, m), 2.02(3H, s) 2.08(3H, s), 2.30~2.40(2H, m) 3.60(2H, s), 6.63(1H, d, J=3.6Hz) 6.65(1H, s), 6.73(1H, d, J=3.6Hz) 7.37(1H, dd, J=4.8Hz, 7.6Hz) 7.62(1H, d, J=7.6Hz), 8.25(1H, s) 8.38(1H, d, J=4.8Hz) |
| 87 | 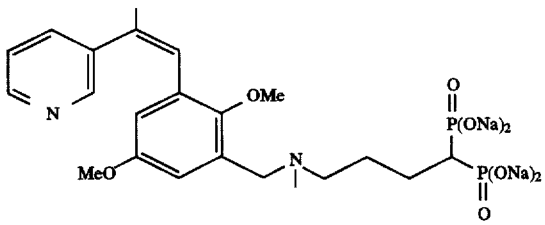 | 1.60~1.98(5H, m), 2.04(3H, s) 2.52(3H, s), 2.98~3.08(2H, m) 3.21(3H, s), 3.52(3H, s) 6.15(1H, s), 6.44(1H, s) 6.79(1H, s), 7.16~7.22(1H, m) 7.48(1H, s), 7.98(1H, s) 8.13~8.19(1H, m) |
| 88 | 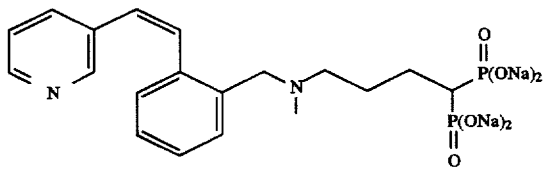 | 1.40~1.70(5H, m), 2.00(3H, s) 2.26~2.37(2H, m), 3.41(2H, s) 6.57(1H, d, J=12Hz) 6.87(1H, d, J=12Hz) 6.96(1H, d, J=7.2Hz), 6.98~7.06(2H, m) 7.19(1H, t, J=7.2Hz), 7.26~7.36(2H, m) 8.06(1H, m), 8.07~8.12(1H, m) |

TABLE 23

| Ex. No. | Chemical Structure | $^1$H-NMR$\delta$(D$_2$O) |
|---|---|---|
| 89 | 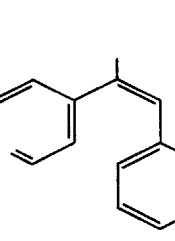 | 1.45~1.65(5H, m), 1.92(3H, s) 2.02(3H, s), 2.25~2.30(2H, m) 3.32(2H, s), 6.49(1H, s) 6.76(2H, d, J=7.2Hz) 6.94(2H, d, J=7.2Hz) 7.15~7.20(1H, m), 7.44~7.50(1H, m) 8.08(1H, s), 8.16~8.20(1H, m) |
| 90 | 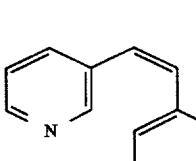 | 1.40~1.65(5H, m), 2.00(3H, s) 2.25~3.35(2H, m), 3.60(2H, s) 6.70(1H, d, J=16.4Hz) 6.88(1H, s), 7.08(1H, d, J=4.8Hz) 7.08(1H, d, J=2.4Hz) 7.19(1H, dd, J=2.4Hz, 4.8Hz) 7.28(1H, s), 7.34(1H, d, J=1.6Hz) 8.30(1H, d, J=1.6Hz) |
| 91 | 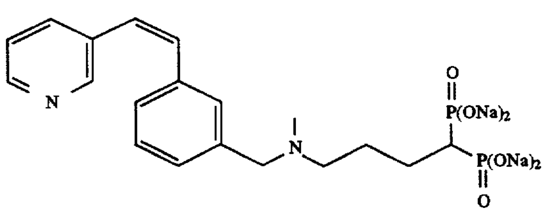 | 1.40~1.65(5H, m), 1.82(3H, s) 2.16~2.28(2H, m), 3.26(2H, s) 6.52(1H, d, J=12Hz) 6.70(1H, d, J=12Hz) 6.92~7.18(5H, m), 7.48(1H, s) 8.10(2H, s) |

TABLE 24

| Ex. No. | Chemical Structure | $^1$H-NMR$\delta$(D$_2$O) |
|---|---|---|
| 92 | (structure: 3,4-dimethoxyphenyl-C(CH₃)=CH-phenyl-CH₂-N(CH₃)-(CH₂)₃-CH[P(O)(ONa)₂]₂) | 1.50~1.62(5H, m), 1.64(3H, s) 2.00(3H, s), 2.16~2.22(2H, m) 3.18(2H, s), 3.43(3H, s) 3.64(3H, s), 6.39(3H, s) 6.59(1H, s), 6.62~6.67(1H, s) 6.74~6.85(2H, m) 6.94~7.04(2H, m) |
| 93 | (structure: 3-pyridyl-CH=CH-phenyl-CH₂-N(CH₃)-(CH₂)₃-CH[P(O)(ONa)₂]₂) | 1.40~1.65(5H, m), 1.92(3H, s) 2.20~2.26(2H, m), 3.30(2H, s) 6.36(1H, d, J=12Hz) 6.56(1H, d, J=12Hz) 6.94~7.05(5H, m), 7.37~7.42(1H, m) 8.06~8.12(2H, m) |
| 94 | (structure: phenyl-C≡C-phenyl-CH₂-N(CH₃)-(CH₂)₃-CH[P(O)(ONa)₂]₂) | 1.60~1.78(3H, m), 1.82~1.92(2H, m) 2.56(3H, s), 2.96~3.06(2H, m) 4.12(2H, s), 7.00~7.48(8H, m) |

TABLE 25

| Ex. No. | Chemical Structure | $^1$H-NMR$\delta$(D$_2$O) |
|---|---|---|
| 95 | (structure: phenyl-C≡C-phenyl-CH₂-N(CH₃)-(CH₂)₃-CH[P(O)(ONa)₂]₂) | 1.55~1.76(3H, m), 2.00~2.10(2H, m) 2.15(3H, s), 2.44~2.57(2H, m) 3.44~3.60(2H, m), 6.94~7.36(8H, m) |
| 96 | (structure: 3,4,5-trimethoxyphenyl-C≡C-phenyl-CH₂-N(CH₃)-(CH₂)₃-CH[P(O)(ONa)₂]₂) | 1.56~1.80(5H, m), 2.02(3H, s) 2.35~2.42(2H, m), 3.38~3.44(2H, m) 3.57(3H, s), 3.59(6H, s) 6.62(2H, s), 7.18~7.30(4H, m) |
| 97 | (structure: thiazol-2-yl-C≡C-phenyl-CH₂-N(CH₃)-(CH₂)₃-CH[P(O)(ONa)₂]₂) | 1.58~1.82(5H, m), 2.28(3H, s) 2.60~2.68(2H, m), 3.77(2H, s) 7.33~7.37(2H, m), 7.50~7.58(3H, m) 7.81~7.84(1H, m) |

TABLE 26

| Ex. No. | Chemical Structure | $^1$H-NMR$\delta$(D$_2$O) |
|---|---|---|
| 98 | (pyrazinyl-C≡C-phenyl-CH$_2$-N(CH$_3$)-(CH$_2$)$_3$-CH(P(O)(ONa)$_2$)$_2$) | 1.56~1.76(5H, m), 2.12(3H, s) 2.41~2.47(2H, m), 3.57(2H, s) 7.26~7.35(2H, m) 7.44~7.46(1H, m), 7.49(1H, s) 8.81(2H, s), 8.93(1H, s) |
| 99 | (phenyl-C≡C-pyridyl-CH$_2$-N(CH$_3$)-(CH$_2$)$_3$-CH(P(O)(ONa)$_2$)$_2$) | 1.60~1.77(3H, m), 1.78~1.86(2H, m) 2.20(3H, s), 2.77~3.05(2H, m) 3.95(2H, s), 7.27~7.33(3H, m) 7.45~7.51(2H, m), 7.90~7.93(1H, m) 8.37~8.42(1H, m), 8.55~8.58(1H, m) |
| 100 | (pyridyl-C≡C-phenyl-CH$_2$-N(CH$_3$)-(CH$_2$)$_3$-CH(P(O)(ONa)$_2$)$_2$) | 1.58~1.80(5H, m), 2.24(3H, s) 2.58~2.65(2H, m), 3.70(2H, s) 7.23~7.32(3H, m), 7.37~7.45(2H, m) 7.73~7.82(1H, m), 8.27~8.33(1H, m) 8.41~8.50(1H, m) |

TABLE 27

| Ex. No. | Chemical Structure | $^1$H-NMR$\delta$(D$_2$O) |
|---|---|---|
| 101 | (MeO-phenyl-CH$_2$-C≡C-phenyl-CH$_2$-N(CH$_3$)-(CH$_2$)$_3$-CH(P(O)(ONa)$_2$)$_2$) | 1.60~1.92(3H, m), 2.02~2.24(2H, m) 2.42(3H, s), 2.52~2.80(2H, m) 3.36(3H, s), 3.38~3.44(2H, m) 3.80~4.00(2H, m), 6.32~6.42(2H, m) 6.44~6.56(1H, m), 6.58~6.70(2H, m) 6.95~7.28(3H, m) |
| 102 | (geranyl-NH-(CH$_2$)$_3$-CH(P(O)(ONa)$_2$)$_2$) | 1.45(3H, s), 1.53(3H, s) 1.55(3H, s), 1.55~1.79(5H, m) 1.95~2.08(4H, m), 2.75~2.82(2H, m) 3.39(2H, d, J=7Hz), 5.00~5.07(1H, m) 5.15(1H, t, J=7Hz) |
| 103 | (geranyl-N(Et)-(CH$_2$)$_3$-CH(P(O)(ONa)$_2$)$_2$) | 0.95(3H, t, J=7Hz), 1.45(3H, s) 1.52(6H, s), 1.50~1.75(5H, m) 1.93~2.13(4H, m), 2.53~2.65(4H, m) 3.21(2H, d, J=7Hz), 5.00~5.05(1H, m) 5.13~5.18(1H, m) |

TABLE 28

| Ex. No. | Chemical Structure | $^1$H-NMR$\delta$(D$_2$O) |
|---|---|---|
| 104 | (geranyl)-N(CH$_2$CH$_2$OH)-(CH$_2$)$_3$-CH(P(ONa)$_2$=O)$_2$ | 1.47(3H, s), 1.53(3H, s), 1.56(3H, s), 1.55~1.67(5H, m), 1.90~2.05(4H, m), 2.40~2.48(2H, m), 2.50~2.59(2H, m), 3.05(2H, d, J=7Hz), 3.35~3.40(2H, m), 5.00~5.70(1H, m), 5.15(1H, t, J=7Hz) |
| 105 | (geranyl)-N(CH$_2$CH$_2$CH$_2$OH)-(CH$_2$)$_3$-CH(P(ONa)$_2$=O)$_2$ | 1.47(3H, s), 1.50(3H, s), 1.51(3H, s), 1.45~1.70(7H, m), 1.93~2.05(4H, m), 2.40~2.58(4H, m), 3.04~3.15(2H, m), 3.42~3.52(2H, m), 5.00~5.70(1H, m), 5.10~5.17(1H, m) |
| 106 | (geranyl)-N(CH$_2$CH$_2$CH$_2$CN)-(CH$_2$)$_3$-CH(P(ONa)$_2$=O)$_2$ | 1.47(3H, s), 1.50(3H, s), 1.52(3H, s), 1.50~1.75(5H, m), 1.84~2.05(6H, m), 2.33~2.45(6H, m), 3.03(2H, d, J=7Hz), 5.00~5.12(1H, m), 5.12~5.18(1H, m) |

TABLE 29

| Ex. No. | Chemical Structure | $^1$H-NMR$\delta$(D$_2$O) |
|---|---|---|
| 107 | (geranyl)-N(cyclopropyl)-(CH$_2$)$_3$-CH(P(ONa)$_2$=O)$_2$ | 0.25~0.30(2H, m), 0.35~0.40(2H, m), 1.45(3H, s), 1.51(6H, s), 1.50~1.70(6H, m), 1.88~2.03(4H, m), 2.42~2.48(2H, m), 3.10(2H, d, J=7Hz), 5.00~5.60(1H, m), 5.20~5.27(1H, m) |
| 108 | (geranyl)-N(cyclohexyl)-(CH$_2$)$_3$-CH(P(ONa)$_2$=O)$_2$ | 0.90~1.34(6H, m), 1.47(3H, s), 1.55(6H, s), 1.40~1.78(9H, m), 1.95~2.05(4H, m), 2.60~2.68(2H, m), 2.70~2.80(1H, m), 3.32~3.38(1H, m), 5.00~5.07(1H, m), 5.12~5.20(1H, m) |
| 109 | (geranyl)-N(CH$_3$)-(CH$_2$)$_3$-C(P(ONa)$_2$=O)$_2$-CH$_2$CH$_2$N(CH$_3$)$_2$ | 1.47(3H, s), 1.52(3H, s), 1.54~1.70(5H, m), 1.77~2.08(8H, m), 2.50~2.58(3H, m), 2.63(6H, s), 2.80~2.90(2H, m), 3.05~3.14(2H, m), 3.45~3.55(2H, m), 4.95~5.04(1H, m), 5.10~5.17(1H, m) |

TABLE 30

| Ex. No. | Chemical Structure | $^1$H-NMRδ(D$_2$O) |
|---|---|---|
| 110 | (farnesyl)-N(Me)-CH$_2$CH$_2$CH$_2$-C(P(ONa)$_2$=O)$_2$-CH$_2$CH$_2$-N(Me)$_2$ | 1.45(6H, s), 1.52(3H, s), 1.57–1.70(5H, m), 1.80–2.09(12H, m), 2.45–2.64(3H, m), 2.67(6H, s), 2.85–2.95(2H, m), 3.16–3.25(2H, m), 3.45–3.51(2H, m), 4.96–5.05(2H, m), 5.13–5.22(1H, m) |
| 111 | (farnesyl)-N(Me)-CH$_2$CH$_2$-N(Me)-CH$_2$CH$_2$CH$_2$-CH(P(ONa)$_2$=O)$_2$ | 1.45(6H, s), 1.52(3H, s), 1.56–1.72(5H, m), 1.82–2.10(10H, m), 2.68(6H, s), 2.84–3.02(6H, m), 3.40–3.62(2H, m), 4.96–5.04(2H, m), 5.12–5.18(1H, m) |
| 112 | HO-C$_6$H$_4$-CH=C(Me)-CH$_2$-N(Me)-CH$_2$CH$_2$CH$_2$-CH(P(ONa)$_2$=O)$_2$ | 1.55–1.75(5H, m), 1.92(3H, s), 2.22(3H, s), 2.45–2.55(2H, s), 3.24(2H, d, J=7Hz), 5.62(2H, d, J=7Hz), 6.48(2H, d, J=8Hz), 7.20(2H, d, J=8Hz) |

TABLE 31

| Ex. No. | Chemical Structure | $^1$H-NMRδ(D$_2$O) |
|---|---|---|
| 113 | (3-MeO-C$_6$H$_4$)-CH=C(Me)-CH$_2$-N(Me)-CH$_2$CH$_2$CH$_2$-CH(P(ONa)$_2$=O)$_2$ | 1.40–1.65(5H, m), 1.90(3H, s), 2.10(3H, s), 2.35(2H, t, J=7Hz), 3.13(2H, d, J=8Hz), 3.69(3H, s), 5.75(1H, t, J=8Hz), 6.76(1H, dd, J=8Hz, 1Hz), 6.88(1H, d, J=1Hz), 6.98(1H, d, J=8Hz), 7.17(1H, t, J=8Hz) |
| 114 | (2-MeO-C$_6$H$_4$)-CH=C(Me)-CH$_2$-N(Me)-CH$_2$CH$_2$CH$_2$-CH(P(ONa)$_2$=O)$_2$ | 1.50–1.72(5H, m), 1.92(3H, s), 2.20(3H, s), 2.40–2.45(2H, m), 3.15(2H, t, J=7Hz), 3.70(3H, s), 5.40(1H, t, J=7Hz), 6.85–6.95(2H, m), 7.08–7.12(1H, m), 7.18–8.03(1H, m) |
| 115 | (4-MeO-C$_6$H$_4$)-CH=C(Me)-CH$_2$-N(Me)-CH$_2$CH$_2$CH$_2$-CH(P(ONa)$_2$=O)$_2$ | 1.50–1.72(5H, m), 1.92(3H, s), 2.18(3H, s), 2.40–2.48(2H, m), 3.20(2H, d, J=7Hz), 4.70(3H, s), 5.70(1H, d, J=7Hz), 6.86(2H, d, J=8Hz), 7.37(2H, d, J=8Hz) |

TABLE 32

| Ex. No. | Chemical Structure | $^1$H-NMR$\delta$(D$_2$O) |
|---|---|---|
| 116 | cyclohexyl-C$_6$H$_4$-C(CH$_3$)=CH-CH$_2$-N(CH$_3$)-(CH$_2$)$_3$-CH[P(O)(ONa)$_2$]$_2$ | 0.90~1.22(4H, m), 1.40~1.95(11H, m) 1.90(3H, s), 2.19~2.30(1H, m) 2.60(3H, s), 2.98~3.10(2H, m) 3.73(2H, d, J=6Hz), 5.61(1H, t, J=6Hz) 7.00(2H, d, J=7Hz), 7.21(2H, d, J=7Hz) |
| 117 | (OHC)(MeO)C$_6$H$_3$-C(CH$_3$)=CH-CH$_2$-N(CH$_3$)-(CH$_2$)$_3$-CH[P(O)(ONa)$_2$]$_2$ | 1.52~1.72(5H, m), 1.92(3H, s) 2.18(3H, s), 2.38~2.48(2H, m) 3.18~3.22(2H, m), 3.80(3H, s) 5.75~5.80(1H, m), 7.01~7.05(1H, m) 7.65~7.75(2H, m), 10.03(1H, s) |
| 118 | (isobutyl)-C$_6$H$_4$-C(CH$_3$)=CH-CH$_2$-N(CH$_3$)-(CH$_2$)$_3$-CH[P(O)(ONa)$_2$]$_2$ | 0.76(6H, d, J=6Hz), 1.28~1.45(3H, m) 1.60~1.90(5H, m), 2.00(3H, s) 2.50(2H, t, J=6Hz), 2.60(3H, s) 2.94(2H, t, J=6Hz), 3.70(2H, d, J=6Hz) 5.70(1H, t, J=6Hz), 7.14(2H, d, J=7Hz) 7.25(2H, d, J=7Hz) |

TABLE 33

| Ex. No. | Chemical Structure | $^1$H-NMR$\delta$(D$_2$O) |
|---|---|---|
| 119 | (isobutyl)-C$_6$H$_4$-C(CH$_3$)=CH-CH$_2$-N(CH$_3$)-(CH$_2$)$_3$-CH[P(O)(ONa)$_2$]$_2$ | 0.80(6H, d, J=6Hz), 1.62~1.96(6H, m) 2.04(3H, s), 2.38~2.48(2H, m) 2.88(3H, br.s), 3.96~4.20(4H, m) 5.68~5.80(1H, m), 7.14(2H, d, J=7Hz) 7.35(2H, d, J=7Hz) |
| 120 | 3,5-(HO)$_2$C$_6$H$_3$-C(CH$_3$)=CH-CH$_2$-N(CH$_3$)-(CH$_2$)$_3$-CH[P(O)(ONa)$_2$]$_2$ | 1.60~1.85(5H, m), 1.90(3H, s) 2.58(3H, s), 2.90~2.98(2H, m) 3.65(2H, d, J=6Hz), 5.65(1H, d, J=6Hz) |
| 121 | morpholino-C$_6$H$_4$-C(CH$_3$)=CH-CH$_2$-N(CH$_3$)-(CH$_2$)$_3$-CH[P(O)(ONa)$_2$]$_2$ | 1.50~1.72(5H, m), 1.92(3H, s) 2.22(3H, s), 2.48~2.55(2H, m) 3.00~3.10(4H, m), 3.24(2H, d, J=6Hz) 3.74~3.81(4H, m), 5.73(1H, t, J=6Hz) 6.95(2H, d, J=7Hz), 7.37(2H, d, J=7Hz) |

TABLE 34

| Ex. No. | Chemical Structure | ¹H-NMRδ(D₂O) |
|---|---|---|
| 122 | (tetrahydroquinoline-N-methyl linked via CH=C(CH₃)-CH₂-N(CH₃)-(CH₂)₃-CH[P(ONa)₂=O]₂) | 1.50–2.00(9H, m), 1.97(3H, s) 2.65(2H, t, J=6Hz), 2.75(6H, s) 3.00(2H, t, J=6Hz), 3.72–3.92(2H, m) 5.68(1H, t, J=6Hz), 6.71(1H, d, J=7Hz) 7.12(1H, s) 7.19(1H, dd, J=7Hz, 2Hz) |
| 123 | (3-HO-phenyl-CH=C(CH₃)-CH₂-N(CH₃)-(CH₂)₃-CH[P(ONa)₂=O]₂) | 1.65–1.81(3H, m), 1.84–1.96(2H, m) 1.98(3H, s), 2.73(3H, s) 3.00–3.18(2H, m), 3.76–3.88(2H, m) 5.70(1H, t, J=8Hz), 6.72–6.75(1H, m) 6.85–6.87(1H, m), 6.92–6.96(1H, m) 7.13–7.19(1H, m) |
| 124 | (3-MOMO-phenyl-CH=C(CH₃)-CH₂-N(CH₃)-(CH₂)₃-CH[P(ONa)₂=O]₂) | 1.58–1.76(3H, m), 1.78–1.88(2H, m) 1.97(3H, s), 2.59(3H, s) 2.73–2.78(2H, m), 3.33(3H, s) 3.68–3.72(2H, m), 5.11(2H, s) 5.68–5.73(1H, m), 6.86–6.92(1H, m) 6.98–7.02(1H, m), 7.05–7.08(1H, m) 7.18–7.24(1H, m) |

TABLE 35

| Ex. No. | Chemical Structure | ¹H-NMRδ(D₂O) |
|---|---|---|
| 125 | (4-piperidinyl-phenyl-CH=C(CH₃)-CH₂-N(CH₃)-(CH₂)₃-CH[P(ONa)₂=O]₂) | 1.38–1.95(11H, m), 1.97(3H, s) 2.69(3H, s), 2.96(4H, t, J=6Hz) 3.00–3.15(2H, m), 3.81(2H, d, J=6Hz) 5.88(1H, t, J=6Hz), 6.95(2H, d, J=7Hz) 7.35(2H, d, J=7Hz) |
| 126 | (3-(1-hydroxyethyl)-phenyl-CH=C(CH₃)-CH₂-N(CH₃)-(CH₂)₃-CH[P(ONa)₂=O]₂) | 1.30(3H, d, J=7Hz), 1.60–1.79(3H, m) 1.82–1.94(2H, m), 2.00(3H, s) 2.70(3H, s), 3.03–3.12(2H, m) 3.77–3.85(2H, m), 4.72–4.80(1H, m) 5.65–5.74(1H, m), 7.15–7.35(4H, m) |
| 127 | (4-F-phenyl-CH=C(CH₃)-CH₂-N(CH₃)-(CH₂)₃-CH[P(ONa)₂=O]₂) | 1.48–1.73(5H, m), 1.93(3H, s) 2.15(3H, s), 2.33–2.43(2H, m) 3.15(2H, d, J=7Hz), 5.73(1H, t, J=7Hz) 6.93–7.33(2H, m), 7.33–7.43(2H, m) |

TABLE 36

| Ex. No. | Chemical Structure | ¹H-NMRδ(D₂O) |
|---|---|---|
| 128 | (4-O₂N-phenyl-CH=C(CH₃)-CH₂-N(CH₃)-(CH₂)₃-CH[P(ONa)₂=O]₂) | 1.60–1.98(5H, m), 2.05(3H, s) 2.75(3H, s), 3.05–3.18(2H, m) 3.89(2H, d, J=7Hz), 5.88(1H, t, J=7Hz) 7.45–7.58(2H, m), 8.30–8.41(2H, m) |

TABLE 36-continued

| Ex. No. | Chemical Structure | ¹H-NMRδ(D₂O) |
|---|---|---|
| 129 | (4-hydroxyphenyl-CH=C(CH₃)-CH₂-N(CH₂CH₂CH₂OH)-CH₂CH₂CH₂-CH(P(=O)(ONa)(OH))(P(=O)(ONa)(OH))) | 1.60–1.92(7H, m), 1.95(3H, s) 3.02–3.12(4H, m), 3.52(2H, t, J=6Hz) 3.92(2H, d, J=10Hz) 5.61(1H, t, J=10Hz) 6.65(2H, d, J=9Hz) 7.25(2H, d, J=9Hz) |
| 130 | (pyridin-3-yl-C(CH₃)=CH-CH₂-N(CH₃)-CH₂CH₂CH₂-CH(P(=O)(ONa)₂)₂) | 1.37–1.70(5H, m), 1.94(3H, s) 2.11(3H, s), 2.33(2H, m) 3.13(2H, d, J=6.5Hz) 5.82(1H, br.t, J=6.5Hz) 7.27(1H, dd, J=8Hz, 5Hz) 7.78(1H, d, J=8Hz), 8.24(1H, d, J=5Hz) 8.46(1H, s) |

TABLE 37

| Ex. No. | Chemical Structure | ¹H-NMR δ (D₂O) |
|---|---|---|
| 131 | (Ph-CH₂CH₂-C(CH₃)=CH-CH₂-N(CH₃)-CH₂CH₂CH₂-CH(P(=O)(ONa)₂)₂) | 1.56(3H, s), 1.46–1.66(5H, m) 2.01(3H, s), 2.27(2H, t, J=7Hz) 2.37(2H, m), 2.66(2H, t, J=7Hz) 3.04(2H, d, J=7Hz), 5.04(1H, t, J=7Hz) 7.06–7.23(5H, m) |
| 132 | (2-methylphenyl-CH₂CH₂-C(CH₃)=CH-CH₂-N(CH₃)-CH₂CH₂CH₂-CH(P(=O)(ONa)₂)₂) | 1.62(3H, s), 1.52–1.72(5H, m) 2.18(3H, s), 2.19(3H, s) 2.23(2H, t, J=8Hz), 2.54(2H, m) 2.67(2H, t, J=8Hz), 3.20(2H, d, J=7Hz) 5.09(1H, t, J=7Hz), 7.00–7.12(4H, m) |
| 133 | (2,4,6-trimethylphenyl-CH₂CH₂-C(CH₃)=CH-CH₂-N(CH₃)-CH₂CH₂CH₂-CH(P(=O)(ONa)₂)₂) | 1.46–1.70(1H, m), 1.65(3H, s) 2.02(2H, m), 2.07(3H, s) 2.14(6H, s), 2.17(3H, s) 2.47(2H, m), 2.60(2H, m) 3.11(2H, d, J=7Hz), 5.21(1H, t, J=7Hz) 6.80(2H, s) |

TABLE 38

| Ex. No. | Chemical Structure | ¹H-NMRδ(D₂O) |
|---|---|---|
| 134 | (3-methylphenyl-CH₂-C(CH₃)=CH-CH₂-N(CH₃)-CH₂CH₂CH₂-CH(P(=O)(ONa)₂)₂) | 1.43(3H, s), 1.40–1.68(5H, m) 2.09(3H, s), 2.16(3H, s) 2.37(2H, m), 3.00(2H, d, J=7Hz) 3.19(2H, s), 5.30(1H, t, J=7Hz) 6.93–7.02(3H, m), 7.11(1H, t) |
| 135 | (pyridin-4-yl-CH₂CH₂-C(CH₃)=CH-CH₂-N(CH₃)-CH₂CH₂CH₂-CH(P(=O)(ONa)₂)₂) | 1.50–1.80(5H, m), 1.61(3H, s) 2.26(3H, s), 2.38(2H, t, J=7Hz) 2.68(2H, dd, J=6.5Hz, 5Hz) 2.75(2H, t, J=7Hz), 3.38(2H, d, J=7Hz) 5.04(1H, t, J=7Hz), 7.19–7.21(2H, m) 8.27(2H, d, J=6Hz) |

TABLE 38-continued

| Ex. No. | Chemical Structure | $^1$H-NMRδ(D$_2$O) |
|---|---|---|
| 136 | (6-methylpyridin-3-yl)-CH$_2$CH$_2$-C(CH$_3$)=CH-CH$_2$-N(CH$_3$)-CH$_2$CH$_2$CH$_2$-CH(P(ONa)$_2$=O)$_2$ | 1.52~1.70(5H, m), 1.57(3H, s)<br>2.13(3H, d, J=3Hz), 2.22~2.34(2H, m)<br>2.30(3H, s), 2.52~2.69(4H, m)<br>3.30(2H, m)<br>4.96(1H, t, J=7.5Hz, 7.5Hz)<br>7.10(1H, dd, J=8Hz, 5Hz)<br>7.47(1H, m), 8.06(1H, m) |

TABLE 39

| Ex. No. | Chemical Structure | $^1$H-NMRδ(D$_2$O) |
|---|---|---|
| 137 | (3,4-dimethoxyphenyl)-CH$_2$CH$_2$-C(CH$_3$)=CH-CH$_2$-N(CH$_3$)-CH$_2$CH$_2$CH$_2$-CH(P(ONa)$_2$=O)$_2$ | 1.38~1.64(5H, m), 1.52(3H, s)<br>1.89(3H, s), 2.22(2H, t, J=7Hz)<br>2.29(2H, m), 2.59(2H, t, J=7Hz)<br>2.97(2H, d, J=7Hz), 3.66(3H, s)<br>3.68(3H, s), 4.99(1H, t, J=7Hz)<br>6.69(1H, br.d, J=8Hz), 6.77(1H, s)<br>6.81(1H, br.d, J=8Hz) |
| 138 | (2,5-dimethoxy-3,6-dimethylphenyl)-CH$_2$CH$_2$-C(CH$_3$)=CH-CH$_2$-N(CH$_3$)-CH$_2$CH$_2$CH$_2$-CH(P(ONa)$_2$=O)$_2$ | 1.45~1.70(5H, s), 1.61(3H, s)<br>1.99(3H, s), 2.04(3H, s)<br>2.10(3H, s), 2.37(2H, m)<br>2.65(2H, t, J=7Hz), 3.02(2H, d, J=7Hz)<br>3.57(3H, s), 3.64(3H, s)<br>5.08(1H, t, J=7Hz), 6.65(1H, s) |
| 139 | (3,4,5-trimethoxyphenyl)-CH$_2$CH$_2$-C(CH$_3$)=CH-CH$_2$-N(CH$_3$)-CH$_2$CH$_2$CH$_2$-CH(P(ONa)$_2$=O)$_2$ | 1.40~1.64(5H, m), 1.54(3H, s)<br>1.86(3H, s), 2.18~2.31(4H, m)<br>2.60(2H, t, J=7Hz), 2.95(2H, d, J=7Hz)<br>3.58(3H, s), 3.69(6H, s)<br>5.00(1H, t, J=7Hz), 6.48(2H, s) |

TABLE 40

| Ex. No. | Chemical Structure | $^1$H-NMRδ(D$_2$O) |
|---|---|---|
| 140 | (pyridin-2-yl)-CH$_2$CH$_2$-C(CH$_3$)=CH-CH$_2$-N(CH$_3$)-CH$_2$CH$_2$CH$_2$-CH(P(ONa)$_2$=O)$_2$ | 1.50~1.76(5H, m), 1.58(3H, s)<br>2.15(3H, s), 2.39(2H, t, J=7.5Hz)<br>2.55(2H, m), 2.82(2H, t, J=7Hz)<br>3.26(2H, d, J=7.5Hz)<br>4.95(1H, t, J=7.5Hz)<br>7.11~7.20(1H, m), 7.61~7.63(1H, m)<br>8.24~8.27(1H, m) |
| 141 | (2,5-dimethylphenyl)-CH$_2$CH$_2$-C(CH$_3$)=CH-CH$_2$-N(CH$_3$)-CH$_2$CH$_2$CH$_2$-CH(P(ONa)$_2$=O)$_2$ | 1.48~1.70(5H, m), 1.59(3H, s)<br>2.08(3H, s), 2.11(3H, s)<br>2.14(3H, s), 2.17(2H, m)<br>2.42(2H, m), 2.61(2H, t, J=7.5Hz)<br>3.07(2H, d, J=7Hz), 5.09(1H, m)<br>6.84~7.00(3H, m) |
| 142 | (2,3-dimethoxyphenyl)-CH$_2$CH$_2$-C(CH$_3$)=CH-CH$_2$-N(CH$_3$)-CH$_2$CH$_2$CH$_2$-CH(P(ONa)$_2$=O)$_2$ | 1.43~1.68(5H, m), 1.56(3H, s)<br>1.95(3H, s), 2.23(2H, t, J=7Hz)<br>2.32(2H, m), 2.66(2H, t, J=7Hz)<br>3.00(2H, d, J=7.5Hz), 3.64(3H, s)<br>3.71(3H, s), 5.01(1H, t, J=7.5Hz)<br>6.76(1H, dd, J=7Hz, 0.5Hz)<br>6.82(1H, dd, J=7Hz, 0.5Hz)<br>6.97(1H, t, J=7Hz) |

TABLE 41

| Ex. No. | Chemical Structure | $^1$H-NMR$\delta$(D$_2$O) |
|---|---|---|
| 143 | (structure with 2,4-dimethoxy-5-methylphenyl, alkenyl chain, N-Me, bisphosphonate P(ONa)$_2$) | 1.35~1.56(5H, m), 1.56(3H, s) 1.95(3H, s), 2.09(3H, s) 2.14(2H, t, J=7Hz), 2.32(2H, m) 2.56(2H, t, J=7Hz), 2.98(2H, d, J=7Hz) 3.65(6H, s), 5.03(1H, t, J=7Hz) 6.69(1H, s), 6.73(1H, s) |
| 144 | (structure with pyridin-3-yl, dienyl chain, N-Me, bisphosphonate) | 1.53~1.72(5H, m), 2.11(3H, s) 2.32(2H, dd, J=7Hz, 14Hz) 2.47(2H, t, J=6.5Hz) 2.66(2H, t, J=7Hz), 3.10(2H, d, J=7Hz) 5.30(1H, dt, J=15.5Hz, 7Hz) 5.66(1H, dt, J=15.5Hz, 7Hz) 7.25(1H, dd, J=8Hz, 5.2Hz) 7.59(1H, dt, J=8Hz, 2Hz) 8.20(1H, dd, J=5.2Hz, 1.6Hz) 8.23(1H, d, J=1.6Hz) |
| 145 | (structure with 3-methoxyphenyl, alkenyl chain, N-Me, bisphosphonate) | 1.36~1.68(5H, m), 1.54(3H, s) 1.93(3H, s), 2.16~2.34(4H, m) 2.63(2H, t, J=7.5Hz), 2.96(2H, d, J=7Hz) 3.66(3H, s), 5.02(1H, t, J=7Hz) 6.68(1H, dd, J=8Hz, 2Hz) 6.72(1H, br.s), 6.76(1H, br.d, J=7.5Hz) 7.13(1H, t, J=8Hz) |

TABLE 42

| Ex. No. | Chemical Structure | $^1$H-NMR$\delta$(D$_2$O) |
|---|---|---|
| 146 | (structure with 3-methylphenyl, alkenyl chain, N-Me, bisphosphonate) | 1.44~1.68(5H, m), 1.56(3H, s) 2.02(3H, s), 2.16(3H, s) 2.26(2H, t, J=7Hz), 2.39(2H, m) 2.63(2H, t, J=7Hz), 3.06(2H, d, J=7Hz) 5.05(1H, m), 6.90~6.97(2H, m) 6.99(1H, br.s), 7.10(1H, t, J=7Hz) |
| 147 | (structure with pyridin-3-yl, dienyl chain, N-Me, bisphosphonate) | 1.44~1.84(5H, m), 2.45(3H, s) 2.78(2H, m), 3.61(2H, d, J=7Hz) 5.54(1H, m), 6.45(1H, t, J=11Hz) 6.62(1H, d) 7.10(1H, dd, J=15Hz, 11Hz) 7.28(1H, dd, J=7Hz, 5Hz) 7.85(1H, d, J=7Hz), 8.24(1H, d, J=5Hz) 8.42(1H, s) |
| 148 | (structure with pyridin-3-yl, alkenyl chain, N-Me, bisphosphonate) | 1.38~1.16(5H, m), 1.52(3H, s) 1.86(3H, s), 2.15~2.29(4H, m) 2.67(2H, t, J=7.5Hz) 2.91(2H, d, J=7Hz), 4.95(1H, t, J=7Hz) 7.22(1H, m), 7.56(1H, m) 8.15~8.22(2H, m) |

TABLE 43

| Ex. No. | Chemical Structure | $^1$H-NMR$\delta$(D$_2$O) |
|---|---|---|
| 149 | 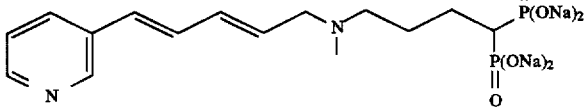 | 1.40~1.70(5H, m), 2.08(3H, s)<br>2.25~2.35(2H, m), 3.04(2H, d, J=14Hz)<br>5.85(1H, dt, J=15Hz, 6.8Hz)<br>6.33(1H, dd, J=15Hz, 7.6Hz)<br>6.45(1H, d, J=16Hz)<br>6.85(1H, dd, J=10Hz, 16Hz)<br>7.26(1H, dd, J=4.8Hz, 6.8Hz)<br>7.80(1H, d, J=7.6Hz)<br>8.20(1H, d, J=4.8Hz), 8.40(1H, s) |
| 150 | 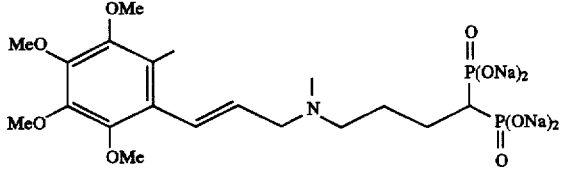 | 1.50~1.80(5H, m), 2.05(3H, s)<br>2.28(3H, s), 2.50~2.60(2H, m)<br>3.25~3.35(2H, m), 3.62(3H, s)<br>3.64(3H, s), 3.74(3H, s)<br>3.78(3H, s), 5.80~5.95(1H, m)<br>6.44(1H, d, J=16Hz) |
| 151 | 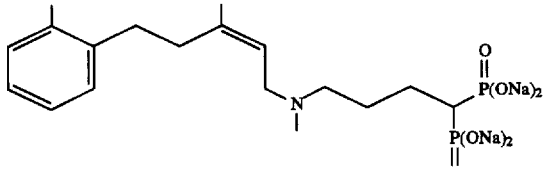 | 1.38~1.66(5H, m), 1.69(3H, s)<br>2.06(3H, s), 2.16~2.23(2H, m)<br>2.21(3H, s), 2.36(2H, m)<br>2.61(2H, t, J=7Hz), 2.80(2H, d, J=7Hz)<br>5.14(1H, t, J=7Hz), 7.02~7.11(4H, m) |

TABLE 44

| Ex. No. | Chemical Structure | $^1$H-NMR$\delta$(D$_2$O) |
|---|---|---|
| 152 | 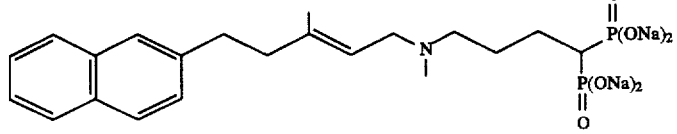 | 1.40~1.69(5H, m), 1.58(3H, s)<br>1.80(3H, s), 2.26(2H, m)<br>2.37(2H, t, J=7Hz), 2.84(2H, t, J=7Hz)<br>2.99(2H, d, J=7Hz), 5.00(1H, t, J=7Hz)<br>7.30~7.41(3H, m), 7.59(1H, s)<br>7.70~7.78(3H, m) |
| 153 | 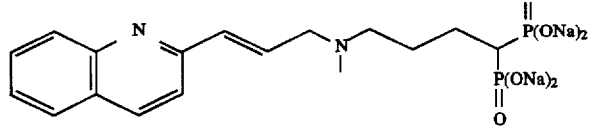 | 1.46~1.70(5H, m), 2.14(3H, s)<br>2.37(2H, t, J=7Hz), 3.19(2H, m)<br>6.60~6.65(2H, m)<br>7.41(1H, dt, J=7Hz, 1.5Hz)<br>7.53(1H, d, J=8.5Hz)<br>7.60(1H, ddd, J=8.5Hz, 7Hz, 1.5Hz)<br>7.68~7.78(2H, m), 8.06(1H, d, J=9Hz) |
| 154 | 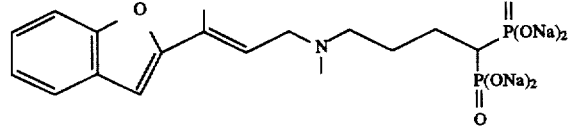 | 1.46~1.72(5H, m), 1.92(3H, s)<br>2.15(3H, s), 2.39(2H, m)<br>3.21(2H, d, J=7Hz), 6.30(1H, t, J=7Hz)<br>6.68(1H, s), 7.12(1H, t, J=7.5Hz)<br>7.19(1H, t, J=7.5Hz)<br>7.37(1H, d, J=8Hz), 7.48(1H, d, J=8Hz) |

TABLE 45

| Ex. No. | Chemical Structure | $^1$H-NMR$\delta$(D$_2$O) |
|---|---|---|
| 155 | (6-methoxynaphthalen-2-yl) derivative with P(ONa)$_2$ bisphosphonate | 1.48~1.72(5H, m), 1.99(3H, s)<br>2.17(3H, s), 2.42(2H, m)<br>3.21(2H, d, J=7.5Hz), 3.76(3H, s)<br>5.89(1H, t, J=7.5Hz)<br>7.02(1H, dd, J=9.5Hz, 2Hz)<br>7.14(1H, br.s), 7.52(1H, d, J=9Hz)<br>7.62(1H, d, J=9Hz)<br>7.65(1H, d, J=9.5Hz), 7.71(1H, s) |
| 156 | naphthalen-2-yl derivative with P(ONa)$_2$ bisphosphonate | 1.50~1.74(5H, m), 2.04(3H, s)<br>2.23(3H, s), 2.49(2H, t, J=7Hz)<br>3.28(2H, d, J=7Hz), 5.92(1H, t, J=7Hz)<br>7.35~7.46(2H, m), 7.58(1H, d, J=9Hz)<br>7.71~7.84(4H, m) |
| 157 | naphthalen-2-yl derivative with P(ONa)$_2$ and COOEt | 1.09(3H, dt, J=7Hz, 1Hz), 1.42(3H, s)<br>1.40~1.66(4H, m), 1.79(3H, s)<br>2.02~2.17(2H, m)<br>2.20(2H, t, J=7.5Hz), 2.36~2.47(1H, m)<br>2.64(2H, t, J=7Hz), 2.97(2H, d, J=7Hz)<br>3.99(2H, m), 4.81(1H, t, J=7Hz)<br>7.11(1H, d, J=8Hz), 7.21~7.30(2H, m)<br>7.34(1H, s), 7.50~7.58(2H, m)<br>7.61(1H, d, J=8Hz) |

TABLE 46

| Ex. No. | Chemical Structure | $^1$H-NMR$\delta$(D$_2$O) |
|---|---|---|
| 158 | 4-benzylphenyl derivative with N and bisphosphonate | 1.44~1.70(5H, m), 2.11(3H, s)<br>2.36(2H, m), 3.10(2H, d, J=7Hz)<br>3.82(2H, s), 6.15(1H, dt, J=16Hz, 7Hz)<br>6.46(1H, d, J=16Hz), 7.08~7.30(9H, m) |
| 159 | 4-(pyridin-3-ylmethyl)phenyl derivative with bisphosphonate | 1.38~1.67(5H, m), 2.11(3H, s)<br>2.35(2H, m), 3.19(2H, d, J=7Hz)<br>3.85(2H, s), 6.16(1H, dt, J=16Hz, 7Hz)<br>6.46(1H, d, J=16Hz), 7.09(2H, d, J=8Hz)<br>7.20(1H, dd, J=5Hz, 7.5Hz)<br>7.27(2H, d, J=8Hz)<br>7.55(1H, dd, J=1Hz, 7.5Hz)<br>8.19(1H, dd, J=1Hz, 5Hz)<br>8.27(1H, s) |
| 160 | phenylcarbamoyloxy-phenyl derivative with bisphosphonate | 1.65~1.94(5H, m), 1.97(3H, s)<br>2.45(3H, s), 2.94~3.04(1H, m)<br>3.07~3.18(1H, m), 3.72~3.90(2H, m)<br>5.67~5.74(1H, m), 6.96~7.06(2H, m)<br>7.11~7.16(1H, m), 7.20~7.32(6H, m) |

TABLE 47

| Ex. No. | Chemical Structure | ¹H-NMRδ(D₂O) |
|---|---|---|
| 161 | (diphenyl vinyl)-CH₂-N(CH₃)-(CH₂)₃-CH(P(O)(ONa)₂)₂ | 1.45~1.65(5H, m), 2.00(3H, s) 3.02(2H, d, J=7Hz), 6.08(1H, t, J=7Hz) 7.08~7.12(4H, m), 7.22~7.38(6H, m) |
| 162 | (phenyl)(4-pyridyl)vinyl-CH₂-N(CH₃)-(CH₂)₃-CH(P(O)(ONa)₂)₂ | 1.48~1.60(5H, m), 2.01~2.05(3H, m) 2.95~3.05(2H, m), 6.10~6.25(1H, m) 7.08~7.38(6H, m), 7.52~7.62(1H, m) 8.15~8.38(2H, m) |
| 163 | (phenyl)(3-pyridyl)vinyl-CH₂-N(CH₃)-(CH₂)₃-CH(P(O)(ONa)₂)₂ | 1.50~1.65(5H, m), 2.05(3H, s) 2.25~2.30(2H, m) 3.00(1H, d, J=7Hz) 3.07(1H, d, J=7Hz) 6.20(1/2H, d, J=7Hz) 6.38(1/2H, d, J=7Hz) 7.05~7.38(7H, m) 8.38(1H, d, J=6Hz), 7.41(1H, d, J=6Hz) |

TABLE 48

| Ex. No. | Chemical Structure | ¹H-NMRδ(D₂O) |
|---|---|---|
| 164 | (phenyl)(2-pyridyl)vinyl-CH₂-N(CH₃)-(CH₂)₃-CH(P(O)(ONa)₂)₂ | 1.50~1.70(5H, m), 2.10(3H, s) 2.25~2.30(2H, m), 3.10(2H, d, J=8Hz) 6.40(1H, t, J=8Hz), 7.10~7.14(2H, m) 7.15~7.22(1H, m), 7.25~7.35(4H, m) 7.63~7.70(1H, m), 8.22~8.28(1H, m) |
| 165 | bis(4-methoxyphenyl)vinyl-CH₂-N(CH₃)-(CH₂)₃-CH(P(O)(ONa)₂)₂ | 1.50~1.60(5H, m), 2.04(3H, s) 2.25~2.30(2H, m), 3.00~3.02(2H, m) 3.65(3H, s), 3.70(3H, s) 5.95~5.98(1H, m) 6.78(1H, d, J=10Hz) 6.86(1H, d, J=10Hz) 7.00(1H, d, J=10Hz) 7.10(1H, d, J=10Hz) |

TABLE 48-continued

| Ex. No. | Chemical Structure | $^1$H-NMR$\delta$(D$_2$O) |
|---|---|---|
| 166 | (2-methylphenyl)-CH$_2$CH$_2$-CH(CH$_3$)-N(CH$_3$)-(CH$_2$)$_3$-CH(P(O)(ONa)$_2$)$_2$ | 1.07(3H, d, J=7Hz), 1.40~1.80(7H, m) 2.05~2.30(1H, m), 2.17(3H, s) 2.23(3H, s), 2.40~2.66(4H, m) 7.00~7.20(4H, m) |

TABLE 49

| Ex. No. | Chemical Structure | $^1$H-NMR$\delta$(D$_2$O) |
|---|---|---|
| 167 | (pyridin-3-yl)-CH$_2$CH$_2$-CH(CH$_3$)-N(CH$_3$)-(CH$_2$)$_3$-CH(P(O)(ONa)$_2$)$_2$ | 1.01(3H, d, J=7Hz), 1.44~1.66(5H, m) 1.70~2.16(2H, m), 2.17(3H, s) 2.42~2.54(3H, m), 2.54~2.80(2H, m) 7.23(1H, dd, J=7.5Hz, 5Hz) 7.62(1H, d, J=7.5Hz) 8.20(1H, br.d, J=5Hz) 8.26(1H, br.s) |
| 168 | (4-MeO-phenyl)-C(O)-CH$_2$-N(CH$_3$)-(CH$_2$)$_3$-CH(P(O)(ONa)$_2$)$_2$ | 1.50~1.84(5H, m), 2.48(3H, s) 2.78~2.88(2H, m), 3.67~3.78(5H, m) 6.82~6.87(2H, m), 7.64~7.70(2H, m) |
| 169 | phenyl-(CH$_2$)$_4$-N(CH$_3$)-(CH$_2$)$_3$-CH(P(O)(ONa)$_2$)$_2$ | 1.12~1.22(2H, m), 1.38~1.68(9H, m) 2.20(3H, s), 2.39~2.52(6H, m) 7.07~7.25(5H, m) |

TABLE 50

| Ex. No. | Chemical Structure | $^1$H-NMR$\delta$(D$_2$O) |
|---|---|---|
| 170 | (pyridin-3-yl)-(CH$_2$)$_4$-N(CH$_3$)-(CH$_2$)$_3$-CH(P(O)(ONa)$_2$)$_2$ | 1.40~2.00(11H, m), 2.10(3H, s) 2.25~2.35(2H, m), 2.60(2H, t, J=8Hz) 7.22(1H, dd, J=5.2Hz, 8Hz) 5.57(1H, d, J=8Hz), 8.19(1H, d, J=5.2Hz) 8.22(1H, s) |
| 171 | phenyl-S-(CH$_2$)$_4$-N(CH$_3$)-(CH$_2$)$_3$-CH(P(O)(ONa)$_2$)$_2$ | 1.40~1.60(9H, m), 2.07(3H, s) 2.25~2.35(4H, m), 2.83~2.90(2H, m) 7.10~7.35(5H, m) |
| 172 | (4-MeO-phenyl)-S-(CH$_2$)$_4$-N(CH$_3$)-(CH$_2$)$_3$-CH(P(O)(ONa)$_2$)$_2$ | 1.35~1.65(9H, m), 2.10(3H, s) 2.25~2.35(4H, m), 2.75~2.80(2H, m) 3.70(3H, s), 6.82~6.87(2H, m) 7.25~7.30(2H, m) |

TABLE 51

| Ex. No. | Chemical Structure | $^1$H-NMRδ(D$_2$O) |
|---|---|---|
| 173 | MeO-C$_6$H$_4$-S-(CH$_2$)$_4$-N(Me)-(CH$_2$)$_3$-CH(P(ONa)$_2$=O)$_2$ | 1.16~1.61(11H, m), 2.10(3H, s) 2.25~2.38(4H, m), 2.71~2.78(2H, m) 3.65(3H, s), 6.80~6.83(2H, m) 7.22~7.28(2H, m) |
| 174 | 2-MeO-C$_6$H$_4$-S-(CH$_2$)$_3$-N(Me)-(CH$_2$)$_3$-CH(P(ONa)$_2$=O)$_2$ | 1.40~1.62(3H, m), 2.10(3H, s) 2.25~2.35(4H, m), 2.75~2.83(2H, m) 3.75(3H, s), 6.87~6.95(2H, m) 7.15~7.20(1H, m), 7.23~7.28(1H, m) |
| 175 | 3-MeO-C$_6$H$_4$-S-(CH$_2$)$_3$-N(Me)-(CH$_2$)$_3$-CH(P(ONa)$_2$=O)$_2$ | 1.45~1.60(9H, m), 2.10(3H, s) 2.30~2.35(4H, m), 2.83~2.92(2H, m) 3.63(3H, m), 6.70~6.75(1H, m) 6.82~6.90(2H, m), 7.15~7.20(1H, m) |

TABLE 52

| Ex. No. | Chemical Structure | $^1$H-NMRδ(D$_2$O) |
|---|---|---|
| 176 | 3-(CH(OH)CH$_3$)-C$_6$H$_4$-O-(CH$_2$)$_3$-N(Me)-(CH$_2$)$_3$-CH(P(ONa)$_2$=O)$_2$ | 1.30(3H, d, J=6Hz), 1.50~1.65(5H, m) 1.80~1.90(2H, m), 2.12(3H, s) 2.29~2.38(2H, m), 2.45~2.50(2H, d) 3.95~4.00(2H, m), 4.73(1H, q) 6.68~6.72(1H, m), 6.85~6.90(2H, m) 7.18~7.25(1H, m) |
| 177 | 4-(CH(OH)CH$_3$)-C$_6$H$_4$-O-(CH$_2$)$_3$-N(Me)-(CH$_2$)$_3$-CH(P(ONa)$_2$=O)$_2$ | 1.30(3H, d, J=7Hz), 1.50~1.65(5H, m) 1.78~1.88(2H, m), 2.10(3H, s) 2.28~2.36(2H, m), 2.42~2.48(2H, m) 3.92~3.98(2H, m), 4.71(1H, q, J=7Hz) 6.82~6.88(2H, d, J=9Hz) 7.20(2H, d, J=9Hz) |
| 178 | Ph-C≡C-(CH$_2$)$_4$-N(Me)-(CH$_2$)$_3$-CH(P(ONa)$_2$=O)$_2$ | 1.30~1.53(6H, m), 1.57~1.75(3H, m) 2.29(2H, t, J=7Hz), 7.19~7.24(3H, m) 7.27~7.34(2H, m) |

TABLE 53

| Ex. No. | Chemical Structure | $^1$H-NMRδ(D$_2$O) |
|---|---|---|
| 179 | Ph-S(=O)-(CH$_2$)$_4$-N(Me)-(CH$_2$)$_3$-CH(P(ONa)$_2$=O)$_2$ | 1.40~1.65(9H, m), 2.15(3H, s) 2.23~2.40(4H, m), 2.83~2.95(2H, m) 7.10~7.35(3H, m), 7.47~7.60(1H, m) |

TABLE 53-continued

| Ex. No. | Chemical Structure | $^1$H-NMR$\delta$(D$_2$O) |
|---|---|---|
| 180 | Phenyl-SO$_2$-NH-(CH$_2$)$_3$-N(CH$_3$)-(CH$_2$)$_3$-CH(P(ONa)$_2$=O)$_2$ | 1.40~1.60(7H, m), 2.02(3H, s)<br>2.20~2.30(4H, m), 2.60(2H, t, J=7Hz)<br>7.38~7.44(3H, m), 7.60~7.63(2H, m) |
| 181 | 4-MeO-C$_6$H$_4$-CH(OH)-(CH$_2$)$_3$-N(CH$_3$)-(CH$_2$)$_3$-CH(P(ONa)$_2$=O)$_2$ | 1.00~1.24(2H, m), 1.34~1.42(2H, m)<br>1.48~1.76(7H, m), 2.17(3H, s)<br>2.34~2.46(4H, m), 4.48~4.53(1H, m)<br>6.87(2H, d, J=8Hz), 7.20(2H, d, J=8Hz) |

TABLE 54

| Ex. No. | Chemical Structure | $^1$H-NMR$\delta$(D$_2$O) |
|---|---|---|
| 182 | benzofuran-2-yl-(CH$_2$)$_3$-N(CH$_3$)-(CH$_2$)$_3$-CH(P(ONa)$_2$=O)$_2$ | 1.50~1.70(5H, m), 1.80~1.90(2H, m)<br>2.08(3H, s), 2.34~2.50(4H, m)<br>2.69(2H, t, J=7Hz), 6.45(1H, s)<br>7.09~7.19(2H, m)<br>7.37(1H, d, J=8Hz)<br>7.44(1H, d, J=8Hz) |
| 183 | pyridin-3-yl-CH$_2$-C$_6$H$_4$-(CH$_2$)$_2$-N(CH$_3$)-(CH$_2$)$_3$-CH(P(ONa)$_2$=O)$_2$ | 1.56~1.89(7H, m), 2.50~2.57(5H, m)<br>2.81~2.89(4H, m), 3.86(2H, s)<br>7.10(4H, s)<br>7.22(1H, dd, J=8Hz, 5Hz)<br>7.57(1H, dt, J=8Hz, 1.5Hz)<br>8.21(1H, dd, J=5Hz, 1.5Hz)<br>8.30(1H, d, J=1.5Hz) |
| 184 | 3,4-(MeO)$_2$-C$_6$H$_3$-CH$_2$-C$_6$H$_4$-(CH$_2$)$_2$-N(CH$_3$)-(CH$_2$)$_3$-CH(P(ONa)$_2$=O)$_2$ | 1.45~1.67(5H, m), 2.14(3H, s)<br>2.32~2.39(2H, m), 2.44~2.51(2H, m)<br>2.58~2.65(2H, m), 3.60(3H, m)<br>3.63(3H, s), 3.69(2H, s)<br>6.64(1H, dd, J=8.0Hz, 1.8Hz)<br>6.72(1H, br.d, J=1.8Hz)<br>6.74(1H, d, J=8.0Hz)<br>7.02(2H, d, J=8.5Hz)<br>7.05(2H, d, J=8.5Hz) |

TABLE 55
| Ex. No. | Chemical Structure | $^1$H-NMR$\delta$(D$_2$O) |
|---|---|---|
| 185 | 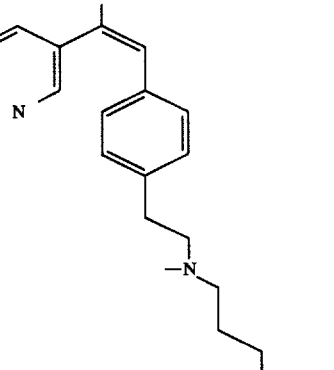 | 1.40~1.70(5H, m), 2.02(3H, s) 2.12(3H, s), 2.28~2.60(6H, m) 6.52(1H, s), 6.75(2H, d, J=8Hz) 6.84(2H, d, J=8Hz), 7.20(1H, m) 7.48(1H, m), 8.04(1H, s) 8.20(1H, m) |
| 186 | 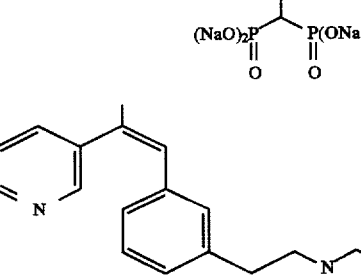 | 1.50~1.70(5H, m), 2.08(3H, s) 2.16~2.34(4H, m), 2.36~2.48(2H, m) 6.54(1H, s), 6.58(1H, s) 6.72~7.06(3H, m), 7.22~7.60(2H, m) 8.08(1H, s), 8.20~8.28(1H, m) |
TABLE 56
| Ex. No. | Chemical Structure | $^1$H-NMR$\delta$(D$_2$O) |
|---|---|---|
| 187 | 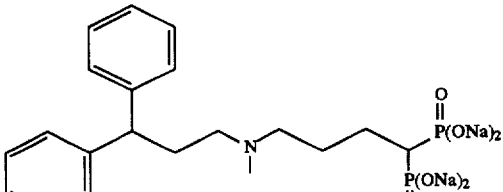 | 1.45~1.60(5H, m), 2.08(3H, s) 2.10~2.30(6H, m), 3.84(1H, t, J=7Hz) 7.05~7.14(2H, m), 7.18~7.30(8H, m) |
| 188 | 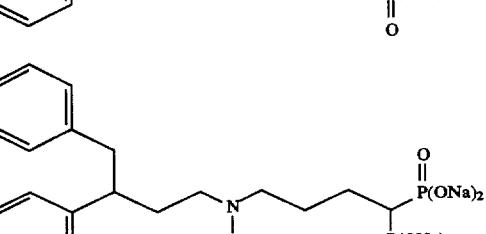 | 1.45~1.60(5H, m), 1.70~1.85(2H, m) 2.00(3H, s), 2.20~2.38(4H, m) 2.70~2.93(5H, m), 6.95~7.18(10H, m) |

TABLE 57
| Ex. No. | Chemical Structure | $^1$H-NMR$\delta$(D$_2$O) |
|---|---|---|
| 189 | 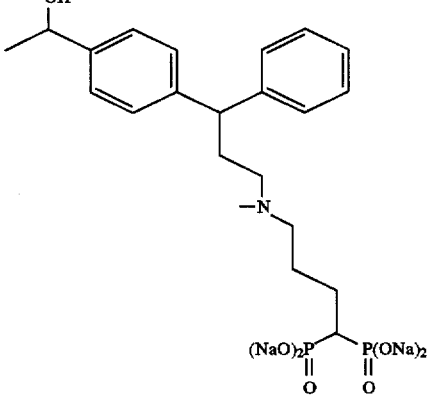 | 1.26(3H, d, J=7Hz), 1.48~1.64(5H, m) 2.10~2.23(2H, m), 2.15(3H, s) 2.30~2.43(4H, m), 3.85(1H, t, J=7Hz) 7.06~7.30(9H, m) |
| 190 | 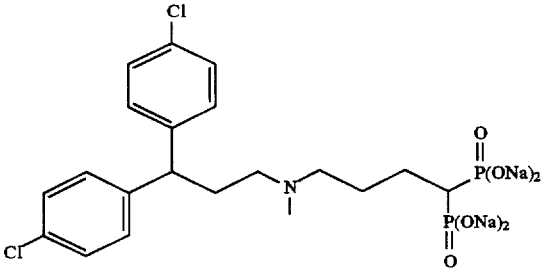 | 1.55~1.75(5H, m), 2.20~2.30(2H, m) 2.50(3H, s), 2.65~2.72(2H, m) 2.75~2.80(2H, m), 3.82(1H, t, J=7Hz) 7.10~7.18(8H, m) |
TABLE 58
| Ex. No. | Chemical Structure | $^1$H-NMR$\delta$(D$_2$O) |
|---|---|---|
| 191 | 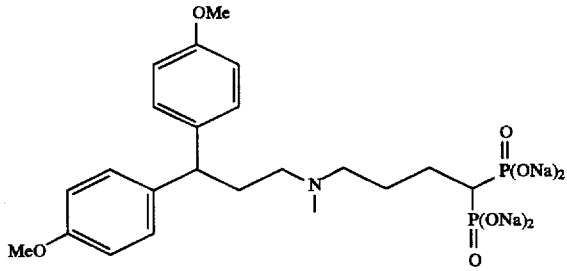 | 1.45~1.60(5H, m), 2.00(3H, s) 2.00~2.10(2H, m), 2.15~2.28(4H, m) 3.70(1H, t, J=7Hz), 6.75(4H, d, J=10Hz) 7.10(4H, d, J=10Hz) |
| 192 | 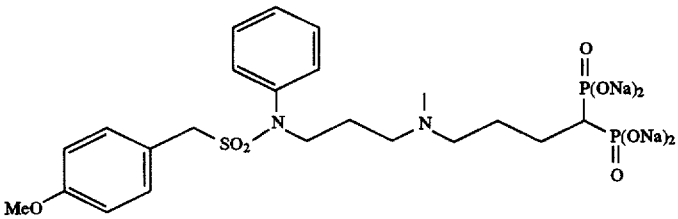 | 1.32~1.58(7H, m), 1.85(3H, s) 2.02~2.18(4H, m), 3.00~3.05(2H, m) 3.65(3H, s), 4.19(2H, s) 6.80(2H, d, J=8Hz), 7.12(2H, d, J=8Hz) 7.45~7.50(2H, m), 7.52~7.58(1H, m) 7.64~7.70(2H, m) |

TABLE 59

| Ex. No. | Chemical Structure | $^1$H-NMR$\delta$(D$_2$O) |
| --- | --- | --- |
| 193 | (phenyl-piperidine-N-(CH$_2$)$_3$-CH(P(ONa)$_2$=O)$_2$) | 1.42~1.77(9H, m), 2.07(2H, t, J=12Hz)<br>2.32(2H, t, J=7Hz)<br>2.49(1H, tt, J=15Hz, 4Hz)<br>2.99(2H, d, J=12Hz), 7.09~7.15(1H, m)<br>7.18~7.28(4H, m) |
| 194 | (benzyl-piperidine-N-(CH$_2$)$_3$-CH(P(ONa)$_2$=O)$_2$) | 1.10~1.25(2H, m), 1.46~1.70(8H, m)<br>2.07(2H, t, J=12Hz)<br>2.38~2.48(4H, m), 2.96(2H, t, J=12Hz)<br>7.10~7.16(3H, m), 7.22(2H, t, J=8Hz) |
| 195 | (3-carbamoylbenzyl-piperidine-N-(CH$_2$)$_3$-CH(P(ONa)$_2$=O)$_2$) | 1.05~1.13(2H, m), 1.40~1.68(8H, m)<br>1.83~2.08(2H, m), 2.20~2.41(2H, m)<br>2.53~2.58(2H, m), 2.78~2.95(2H, m)<br>7.25~7.35(2H, m), 7.44~7.53(2H, m) |

TABLE 60

| Ex. No. | Chemical Structure | $^1$H-NMR$\delta$(D$_2$O) |
| --- | --- | --- |
| 196 | (4-(1-hydroxyethyl)phenyl-CH$_2$-piperidine-N-(CH$_2$)$_3$-CH(P(ONa)$_2$=O)$_2$) | 1.06~1.22(2H, m), 1.30(3H, d, J=8Hz)<br>1.40~1.70(8H, m), 2.01(2H, t, J=12Hz)<br>2.28~2.48(4H, m), 2.85~2.98(2H, m)<br>4.74(1H, q, J=8Hz), 7.11(2H, d, J=8Hz)<br>7.19(2H, d, J=8Hz) |
| 197 | (4-(1-hydroxybutyl)phenyl-CH$_2$-piperidine-N-(CH$_2$)$_3$-CH(P(ONa)$_2$=O)$_2$) | 0.73(3H, t, J=8Hz), 1.00~1.24(2H, m)<br>1.24~1.41(2H, m), 1.46~1.87(10H, m)<br>2.40~2.53(2H, m), 2.60~2.78(2H, m)<br>2.87~3.04(2H, m), 3.32~3.35(2H, m)<br>4.53(1H, t, J=7Hz), 7.11(2H, d, J=8Hz)<br>7.18(2H, d, J=8Hz) |
| 198 | (4-methoxyphenyl-CH(OH)-piperidine-N-(CH$_2$)$_3$-CH(P(ONa)$_2$=O)$_2$) | 0.97~1.10(2H, m), 1.15~1.29(1H, m)<br>1.47~1.67(6H, m), 1.81~1.92(2H, m)<br>1.99(1H, t, J=12Hz), 2.24~2.44(2H, m)<br>2.81(1H, d, J=12Hz), 2.97(1H, d, J=12Hz)<br>3.68(3H, s), 4.17(1H, d, J=8Hz)<br>6.86(2H, dt, J=8Hz, 3Hz)<br>7.16(2H, dt, J=8Hz, 3Hz) |

TABLE 61

| Ex. No. | Chemical Structure | $^1$H-NMR$\delta$(D$_2$O) |
|---|---|---|
| 199 | 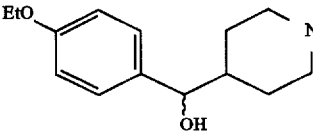 | 1.21(3H, t, J=7Hz), 1.30~1.35(2H, m)<br>1.35~1.50(1H, m), 1.54~1.85(6H, m)<br>2.05(1H, d, J=14Hz), 2.55~2.78(2H, m)<br>2.90(2H, t, J=9Hz), 3.29(1H, d, J=14Hz)<br>3.45(1H, d, J=14Hz)<br>3.97(2H, qualt, J=7Hz)<br>4.23(1H, d, J=8Hz), 6.85(2H, d, J=8Hz)<br>7.16(2H, d, J=8Hz) |

Examples 200 to 204

The compounds of Examples 200 to 204 listed in Tables 62 and 63 were prepared by preparing diphosphonic acid ester derivatives in a similar manner to that of the Example 4 and deprotecting the ester derivatives in a similar manner to that of the Example 14.

TABLE 62

| Ex. No. | Chemical Structure | $^1$H-NMR$\delta$(D$_2$O) |
|---|---|---|
| 200 | 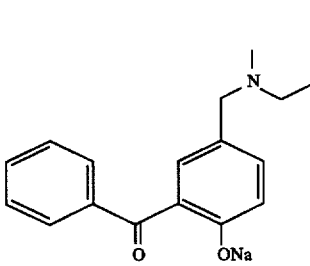 | 1.7~1.9(5H, m), 2.28(3H, s)<br>2.66(2H, t, J=7Hz), 3.64(2H, s)<br>6.67(1H, d, J=8Hz), 7.19(1H, d, J=2Hz)<br>7.32(1H, dd, J=2Hz, 8Hz)<br>7.51(2H, t, J=8Hz), 7.64(1H, t, J=8Hz)<br>7.78(2H, d, J=8Hz) |
| 201 | 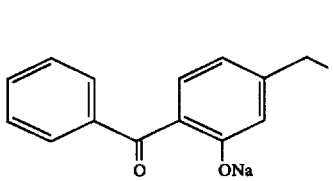 | 1.6~1.9(5H, m), 2.18(3H, s)<br>2.50(2H, t, J=7Hz), 3.49(2H, s)<br>6.54(1H, d, J=8Hz), 6.60(1H, s)<br>7.23(1H, d, J=8Hz), 7.58(2H, t, J=8Hz)<br>7.61(1H, t, J=8Hz), 7.75(2H, d, J=8Hz) |
| 202 | 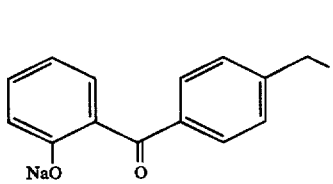 | 1.7~1.9(5H, m), 2.16(3H, s)<br>2.53(2H, t, J=7Hz), 3.66(2H, s)<br>6.57(1H, t, J=8Hz), 6.68(1H, d, J=8Hz)<br>7.24(1H, dd, J=2Hz, 8Hz)<br>7.31~7.36(1H, m), 7.46(2H, d, J=8Hz)<br>7.76(2H, d, J=8Hz) |

TABLE 63

| Ex. No. | Chemical Structure | $^1$H-NMR$\delta$(D$_2$O, DSS) |
|---|---|---|
| 203 | 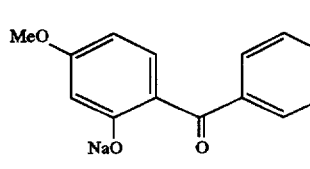 | 1.7~1.9(5H, m), 2.17(3H, s)<br>2.52(2H, t, J=7Hz), 3.66(2H, s)<br>3.82(3H, s)<br>6.18(1H, dd, J=2Hz, 9Hz)<br>6.21(1H, d, J=2Hz), 7.26(1H, d, J=9Hz)<br>7.45(2H, d, J=8Hz), 7.67(2H, d, J=8Hz) |

TABLE 63-continued

| Ex. No. | Chemical Structure | $^1$H-NMR$\delta$($D_2O$, DSS) |
|---|---|---|
| 204 | (4-fluoro-2-(sodiooxycarbonyl)phenyl)-[4-[[N-methyl-N-(4,4-bis(sodiophosphono)butyl)amino]methyl]phenyl]methanone | 1.7–1.9(5H, m), 2.17(3H, s)<br>2.51(2H, t, J=J=7Hz), 3.62(1H, d, J=8Hz)<br>3.65(1H, d, J=8Hz), 6.27–6.36(2H, m)<br>7.25(1H, t, J=8Hz), 7.42–7.46(2H, m)<br>7.73(2H, d, J=8Hz) |

Examples 205 to 209

The compounds of Examples 205 to 209 listed in Tables 64 and 65 were prepared by preparing diphosphonic acid ester derivatives in a similar manner to that of the Example 5 and deprotecting the ester derivatives in a similar manner to that of the Example 14.

TABLE 64

| Ex. No. | Chemical Structure | $^1$H-NMR$\delta$($D_2O$) |
|---|---|---|
| 205 | (geranyl piperidine diphosphonate sodium salt) | 1.48(3H, s), 1.55(3H, s)<br>1.56–1.88(8H, m), 1.92–2.11(6H, m)<br>2.81(2H, t, J=12Hz), 3.34–3.44(2H, m)<br>3.56(2H, d, J=8Hz), 4.98–5.05(1H, m)<br>5.13(1H, t, J=8Hz) |
| 206 | (farnesyl piperidine diphosphonate sodium salt) | 1.43(3H, s), 1.46(3H, s)<br>1.53(3H, s), 1.54–1.66(2H, m)<br>1.68–2.02(8H, m), 2.18–2.27(2H, m)<br>2.52–2.62(2H, m), 2.70(2H, t, J=8Hz)<br>3.17–3.24(2H, m), 4.96–5.04(2H, m) |
| 207 | (3-phenylpropyl piperidine diphosphonate sodium salt) | 0.92–1.06(2H, m), 1.47–1.62(3H, m)<br>1.64–1.84(5H, m), 1.92(2H, t, J=12Hz)<br>2.26(2H, t, J=8Hz), 2.50(2H, t, J=8Hz)<br>2.80(2H, d, J=12Hz), 7.10–7.27(5H, m) |

TABLE 65

| Ex. No. | Chemical Structure | $^1$H-NMR$\delta$($D_2O$) |
|---|---|---|
| 208 | (3-(benzofuran-2-yl)propyl piperidine diphosphonate sodium salt) | 1.08–1.31(2H, m), 1.55–1.68(2H, m)<br>1.75–2.10(7H, m), 2.75–2.88(2H, m)<br>3.00–3.08(2H, m), 3.42–3.50(2H, m)<br>6.48(1H, s), 7.10–7.20(2H, m)<br>7.38(1H, d, J=8Hz), 7.45(1H, d, J=8Hz) |
| 209 | (3-styrylbenzyl piperidine diphosphonate sodium salt) | 0.95–1.08(2H, m), 1.50–1.62(3H, m)<br>1.70(2H, broad d, J=13Hz)<br>1.79(1H, tt, J=22Hz, 7Hz)<br>2.05(2H, broad, t, J=12Hz)<br>2.82(2H, broad d, J=12Hz), 3.48(2H, s)<br>7.15(2H, s), 7.17(1H, d, J=8Hz)<br>7.21(1H, t, J=8Hz), 7.29(1H, t, J=8Hz)<br>7.31(2H, t, J=8Hz), 7.43(1H, d, J=8Hz)<br>7.46(1H, s), 7.51(2H, d, J=8Hz) |

Examples 210 and 211

The compounds of Examples 210 and 211 listed in Table 66 were prepared by preparing diphosphonic acid ester derivatives in a similar manner to that of the Example 9 and deprotecting the ester derivatives in a similar manner to that of the Example 14.

TABLE 66

| Ex. No. | Chemical Structure | $^1$H-NMR δ(D$_2$O) |
|---|---|---|
| 210 | (structure) | 2.02(2H, quint, J=8Hz)<br>2.27(3H, s), 2.77(1H, t, J=18Hz)<br>3.12(2H, t, J=8Hz), 4.00(2H, t, J=8Hz)<br>7.24(1H, t, J=8Hz), 7.33(2H, t, J=8Hz)<br>7.47(2H, d, J=8Hz), 7.65(1H, s) |
| 211 | (structure) | 1.05~1.18(2H, m), 1.41~1.55(3H, m)<br>1.76(2H, quint, J=8Hz)<br>1.88(2H, t, J=12Hz), 2.30(2H, t, J=8Hz)<br>2.42(2H, d, J=7Hz), 2.74~2.87(3H, m)<br>3.15(2H, t, J=8Hz), 7.09~7.17(3H, m)<br>7.22(2H, t, J=8Hz) |

Examples 212 to 229

The compounds of Examples 212 to 229 listed in Tables 67 to 72 were prepared by preparing diphosphonic acid ester derivatives in a similar manner to that of the Example 10 and deprotecting the ester derivatives in a similar manner to that of the Example 14.

TABLE 67

| Ex. No. | Chemical Structure | $^1$H-NMR δ(D$_2$O) |
|---|---|---|
| 212 | (structure) | 1.45(3H, s), 1.52(3H, s)<br>1.57(3H, s), 1.61~1.82(7H, m)<br>2.00~2.08(4H, m), 2.56(3H, s)<br>2.86~2.98(2H, m), 3.38~3.56(6H, m)<br>4.96~5.02(1H, m)<br>5.11~5.17(1H, t, J=7Hz) |
| 213 | (structure) | 1.48(6H, s), 1.50~1.76(11H, m)<br>1.85~2.08(8H, m), 3.43(2H, t, J=6Hz)<br>3.93(2H, d, J=6Hz), 5.02~5.10(2H, m)<br>5.22~5.29(1H, m) |
| 214 | (structure) | 1.42(3H, s), 1.68(1H, tt, J=7Hz, 21Hz)<br>2.16(3H, s), 2.38(2H, tt, J=7Hz, 15Hz)<br>3.16(2H, s), 5.54(1H, t, J=7Hz)<br>6.96(1H, d, J=7.5Hz)<br>6.99(1H, d, J=7.5Hz), 7.04(1H, s)<br>7.11(1H, t, J=7.5Hz) |

TABLE 68

| Ex. No. | Chemical Structure | $^1$H-NMRδ(D$_2$O) |
|---|---|---|
| 215 | (2-methylphenyl-CH$_2$CH$_2$-C(CH$_3$)=CH-CH$_2$-CH(P(ONa)$_2$=O)$_2$) | 1.60(3H, s)<br>1.81(1H, tt, J=22Hz, 6.5Hz)<br>2.10(2H, t, J=8Hz), 2.19(3H, s)<br>2.32~2.47(2H, m), 2.57~2.64(2H, m)<br>5.34(1H, t, J=7Hz), 7.00~7.19(4H, m) |
| 216 | (2,4,6-trimethylphenyl-CH$_2$CH$_2$-C(CH$_3$)=CH-CH$_2$-CH(P(ONa)$_2$=O)$_2$) | 1.63(3H, s), 1.64(1H, m)<br>1.95(2H, m), 2.07(3H, s)<br>2.16(6H, s), 2.39(2H, m)<br>2.58(2H, m), 5.47(1H, t, J=7Hz)<br>6.79(2H, s) |
| 217 | (pyridin-3-yl-CH$_2$CH$_2$-C(CH$_3$)=CH-CH$_2$-CH(P(ONa)$_2$=O)$_2$) | 1.40~1.62(1H, m), 1.54(3H, s)<br>2.17(2H, t, J=7.5Hz)<br>2.23~2.38(2H, m), 2.63(2H, t, J=7.5Hz)<br>5.39(1H, t, J=6.5Hz), 7.22(1H, m)<br>7.60(1H, br.d, J=8Hz), 8.17(1H, m)<br>8.24(1H, s) |

TABLE 69

| Ex. No. | Chemical Structure | $^1$H-NMRδ(D$_2$O) |
|---|---|---|
| 218 | (phenyl-CH$_2$CH$_2$-C(CH$_3$)=CH-CH=CH-CH$_2$-CH(P(ONa)$_2$=O)$_2$) | 1.56~1.72(1H, m), 1.64(3H, s)<br>2.23(2H, t, J=7.5Hz)<br>2.33~2.48(2H, m), 2.58~2.66(2H, m)<br>5.68~5.78(2H, m), 6.19~6.29(1H, m)<br>7.06~7.24(5H, m) |
| 219 | (phenyl-C≡C-CH$_2$CH$_2$CH$_2$-CH(P(ONa)$_2$=O)$_2$) | 1.57~1.83(5H, m), 2.33(2H, t, J=7Hz)<br>7.19~7.26(3H, m), 7.28~7.37(2H, m) |
| 220 | (3-MeO-phenyl-CH$_2$CH$_2$-C(CH$_3$)=CH-CH=CH-CH$_2$-CH(P(ONa)$_2$=O)$_2$) | 1.50~1.80(1H, m), 1.64(3H, s)<br>2.23(2H, t, J=7.5Hz), 2.43(2H, m)<br>2.62(2H, t, J=7.5Hz), 3.68(3H, s)<br>5.72~5.82(2H, m)<br>6.23(1H, dd, J=14.5Hz, 11Hz)<br>6.69(1H, dd, J=8Hz, 2.5Hz)<br>6.74~6.80(2H, m), 7.14(1H, t, J=7.5Hz) |

TABLE 70

| Ex. No. | Chemical Structure | $^1$H-NMRδ(D$_2$O) |
|---|---|---|
| 221 | (2,3,4,5-tetramethoxyphenyl-CH$_2$CH$_2$-C(CH$_3$)=CH-CH$_2$CH$_2$-C(CH$_3$)=CH-CH$_2$CH$_2$-C(CH$_3$)=CH-CH$_2$-CH(P(ONa)$_2$=O)$_2$) | 1.34~1.60(1H, m), 1.35(3H, s)<br>1.46(3H, s), 1.61(3H, s)<br>1.69~1.78(2H, m),<br>1.79~1.90(4H, m)<br>1.90~1.97(2H, m), 1.99(3H, s)<br>2.32(2H, dt, J=6.5Hz, 15Hz)<br>3.16(2H, d, J=7Hz, 3.62(3H, s)<br>3.63(3H, s),<br>3.74(3H, s), 3.75(3H, s)<br>4.86(1H, t, J=7Hz),<br>4.93(1H, t, J=6.5Hz)<br>5.13(1H, t, J=6.5Hz) |

TABLE 70-continued

| Ex. No. | Chemical Structure | $^1$H-NMR$\delta$(D$_2$O) |
|---|---|---|
| 222 | naphthalene-CH=C(CH$_3$)-CH$_2$-CH(P(O)(ONa)$_2$)-P(O)(ONa)$_2$ | 1.84(1H, tt, J=21Hz, 6.5Hz) 2.07(3H, s), 2.65(2H, m) 6.24(1H, t, J=7Hz), 7.34~7.43(2H, m) 7.67(1H, d, J=8.5Hz), 7.74~7.83(3H, m) 7.86(1H, s) |
| 223 | naphthalene-CH$_2$CH$_2$-CH$_2$-CH=C(CH$_3$)-CH$_2$-CH(P(O)(ONa)$_2$)-P(O)(ONa)$_2$ | 1.60(1H, tt, J=22Hz, 6.5Hz) 1.61(3H, s), 2.26~2.42(4H, m) 2.81(2H, dd, J=8.5Hz, 7.0Hz) 5.46(1H, t, J=6Hz), 7.34~7.43(3H, m) 7.66(1H, s), 7.74~7.80(3H, m) |

TABLE 71

| Ex. No. | Chemical Structure | $^1$H-NMR$\delta$(D$_2$O) |
|---|---|---|
| 224 | quinoline-CH$_2$CH$_2$-CH=C(CH$_3$)-CH$_2$-CH(P(O)(ONa)$_2$)-P(O)(ONa)$_2$ | 1.56(3H, s), 1.54~1.71(1H, m) 2.31(2H, t, J=7.5Hz), 2.24~2.46(2H, m) 2.91(2H, t, J=7.5Hz), 5.37(1H, m) 7.33(1H, d, J=8.5Hz), 7.42(1H, m) 7.61(1H, m), 7.73~8.81(2H, m) 8.10(1H, d, J=8.5Hz) |
| 225 | naphthalene-CH$_2$CH$_2$-CH=C(CH$_3$)-CH$_2$-CH(P(O)(Me)(ONa))-P(O)(ONa)$_2$ | 1.20(3H, d, J=14Hz), 1.45~1.60(1H, m) 1.59(3H, s), 2.23~2.44(4H, m) 2.78(2H, t, J=8Hz), 5.40(1H, t, J=8Hz) 7.32~7.41(3H, m), 7.64(1H, s) 7.74(3H, t, J=8Hz) |
| 226 | MeO-naphthalene-CH$_2$CH$_2$-CH=C(CH$_3$)-CH$_2$-CH(P(O)(ONa)$_2$)-P(O)(ONa)$_2$ | 1.44~1.71(1H, m), 1.61(3H, s) 2.27(2H, t, J=8Hz), 2.30~2.42(2H, m) 2.77(2H, t, J=8Hz), 3.81(3H, s) 5.45(1H, m) 7.07(1H, dd, J=8.5Hz, 2.5Hz) 7.21(1H, br.s), 7.35(1H, d, J=8.5Hz) 7.60(1H, s), 7.64~7.70(2H, m) |

TABLE 72

| Ex. No. | Chemical Structure | $^1$H-NMR$\delta$(D$_2$O) |
|---|---|---|
| 227 | naphthalene-CH$_2$CH$_2$-C(CH$_3$)=CH-CH$_2$-CH(P(O)(ONa)$_2$)-P(O)(ONa)$_2$ | 1.56(3H, s), 1.50~1.67(1H, m) 2.22~2.46(4H, m) 2.78(2H, t, J=8Hz), 5.40(1H, m) 7.32~7.40(2H, m) 7.43(1H, d, J=8.5Hz) 7.69(1H, s), 7.73~7.79(3H, m) |
| 228 | pyridine-thiophene-(CH$_2$)$_5$-CH(P(O)(ONa)$_2$)-P(O)(ONa)$_2$ | 1.20~1.30(2H, m), 1.35~1.50(2H, m) 1.50~1.70(5H, m), 2.70(2H, t, J=8Hz) 6.74(1H, d, J=3.6Hz) 7.14(1H, d, J=3.6Hz) 7.24(1H, dd, J=4.8Hz, 8Hz) 7.80(1H, d, J=8Hz) 8.19(1H, d, J=4.8Hz), 8.53(1H, s) |

TABLE 72-continued

| Ex. No. | Chemical Structure | $^1$H-NMR$\delta$(D$_2$O) |
|---|---|---|
| 229 | [structure: benzyl-phenyl-CH=CH-CH$_2$-CH(P(ONa)$_2$=O)$_2$] | 1.67(1H, tt, J=7Hz, 22Hz)<br>2.54(2H, tt, J=7Hz, 15Hz)<br>3.82(2H, s), 6.32(1H, d, J=16Hz)<br>6.48(1H, dt, J=16Hz, 7Hz)<br>7.06–7.14(3H, m), 7.14–7.24(4H, m)<br>7.27(2H, d, J=8Hz) |

Examples 230 to 235

The compounds of Examples 230 to 235 listed in Tables 73 and 74 were prepared by preparing diphosphonic acid ester derivatives in a similar manner to those of the Examples 11 and 12 and deprotecting the ester derivatives in a similar manner to that of the Example 14.

TABLE 73

| Ex. No. | Chemical Structure | $^1$H-NMR$\delta$(D$_2$O) |
|---|---|---|
| 230 | [farnesyl-phenyl-CH(P(ONa)$_2$=O)$_2$ meta substituted] | 1.47(3H, s), 1.51(3H, s), 1.53(3H, s)<br>1.78(3H, s), 1.88–1.93(2H, m)<br>1.95–2.00(2H, m), 3.15(1H, t, J=20Hz)<br>5.03–5.08(1H, m), 5.10–5.16(1H, m)<br>5.21(1H, s), 7.02–7.07(1H, m)<br>7.13–7.18(1H, m), 7.22–7.28(2H, m) |
| 231 | [farnesyl-furan-CH(P(ONa)$_2$=O)$_2$] | 1.49(3H, s), 1.54(3H, s), 1.56(3H, s)<br>1.93–2.06(4H, m), 3.23(2H, d, J=8Hz)<br>3.28(1H, t, J=22Hz), 5.05–5.12(1H, m)<br>5.30(1H, t, J=8Hz), 5.87(1H, d, J=3Hz)<br>6.09(1H, d, J=3Hz) |
| 232 | [farnesyl-thiophene-CH(P(ONa)$_2$=O)$_2$] | 1.50(trans), 1.53(cis)(3H, s)<br>1.55(trans), 1.57(cis)(3H, s)<br>1.74(cis), 1.83(trans)(3H, s)<br>2.00–2.35(4H, m)<br>3,34(cis), 3.36(trans)(1H, t, J=24Hz)<br>5.05–5.20(1H, m)<br>6.24(cis), 6.30(trans)(1H, s)<br>6.69–6.73(1H, m), 6.79–6.83(1H, m) |

TABLE 74

| Ex. No. | Chemical Structure | $^1$H-NMR$\delta$(D$_2$O) |
|---|---|---|
| 233 | [farnesyl-thiophene-CH(P(ONa)$_2$=O)$_2$] | 1.46(3H, s), 1.48(3H, s), 1.53(3H, s)<br>1.75(cis), 1.83(trans)(3H, s)<br>1.80–2.35(8H, m)<br>3.34(cis), 3.36(trans)(1H, t, J=24Hz)<br>6.24(cis), 6.30(trans)(1H, s)<br>6.69–6.73(1H, m), 6.79–6.83(1H, m) |
| 234 | [farnesyl-thiophene-CH$_2$-CH(P(ONa)$_2$=O)$_2$] | 1.46(3H, s), 1.48(3H, s), 1.53(3H, s)<br>1.75(cis), 1.83(trans)(3H, s)<br>1.80–2.35(8H, m)<br>2.70(1H, tt, J=24Hz 4Hz)<br>3.00(trans), 3.03(cis)(1H, t, J=15Hz)<br>5.05–5.16(2H, m)<br>6.27(cis), 6.30(trans)(1H, s)<br>6.69–6.73(1H, m), 6.79–6.83(1H, m) |

TABLE 74-continued

| Ex. No. | Chemical Structure | $^1$H-NMR$\delta$(D$_2$O) |
|---|---|---|
| 235 | (pyridyl-C(CH$_3$)=CH-phenyl-CH(P(O)(ONa)$_2$)$_2$) | 2.08(3H, s), 3.10(1H, t, J=23Hz)<br>6.41(1H, d, J=7Hz), 6.60(1H, s)<br>6.79(1H, t, J=8Hz), 7.14(1H, d, J=7Hz)<br>7.18–7.26(2H, m)<br>7.61(1H, br.d, J=8Hz)<br>8.23–8.30(2H, m) |

Examples 236 to 250

The compounds of Examples 236 to 250 listed in Tables 75 to 80 were prepared by preparing diphosphonic acid ester derivatives in a similar manner to that of the Example 13 and deprotecting the ester derivatives in a similar manner to that of the Example 14.

TABLE 75

| Ex. No. | Chemical Structure | $^1$H-NMR$\delta$(D$_2$O) |
|---|---|---|
| 236 | (4-acetylphenyl-CH$_2$-N(CH$_3$)-(CH$_2$)$_3$-CH(P(O)(ONa)$_2$)$_2$) | 1.73–2.08(5H, m), 2.60(3H, s)<br>2.77(3H, s), 2.95–3.05(2H, m)<br>4.17(2H, s), 7.63(2H, d, J=9Hz)<br>8.03(2H, d, J=9Hz) |
| 237 | (4-acetylphenyl-C(CH$_3$)=CH-CH$_2$-N(CH$_3$)-(CH$_2$)$_3$-CH(P(O)(ONa)$_2$)$_2$) | 1.64–1.79(3H, m), 1.82–1.96(2H, m)<br>2.04(3H, s), 2.52(3H, s), 2.73(3H, s)<br>3.03–3.17(2H, m), 3.83–3.91(2H, m)<br>5.84(1H, t, J=7Hz), 7.50(2H, d, J=9Hz)<br>7.85(2H, d, J=9Hz) |
| 238 | (3-acetylphenyl-C(CH$_3$)=CH-CH$_2$-N(CH$_3$)-(CH$_2$)$_3$-CH(P(O)(ONa)$_2$)$_2$) | 1.60–1.93(5H, m), 1.95(3H, s)<br>2.67(3H, s), 2.98–3.10(2H, m)<br>3.76–3.84(2H, m), 5.63–5.72(1H, m)<br>7.18–7.34(1H, m), 7.47–7.58(1H, m)<br>7.60–7.73(2H, m) |

TABLE 76

| Ex. No. | Chemical Structure | $^1$H-NMR$\delta$(D$_2$O) |
|---|---|---|
| 239 | (3-acetyl-4-methoxyphenyl-C(CH$_3$)=CH-CH$_2$-N(CH$_3$)-(CH$_2$)$_3$-CH(P(O)(ONa)$_2$)$_2$) | 1.50–1.67(5H, m), 1.90(3H, s)<br>2.15(3H, s)<br>2.35–2.40(2H, m)<br>2.40–2.48(3H, m), 3.14(2H, d, J=8Hz)<br>3.75(3H, s), 5.72(1H, t, J=8Hz)<br>6.98(1H, d, J=9Hz), 7.52–7.58(2H, m) |

TABLE 76-continued

| Ex. No. | Chemical Structure | $^1$H-NMR$\delta$(D$_2$O) |
|---|---|---|
| 240 | 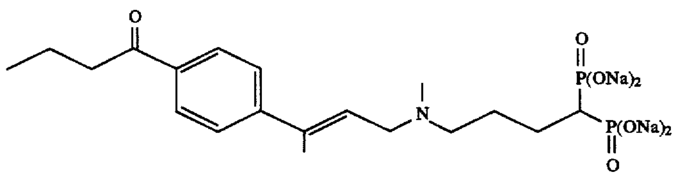 | 0.88(3H, t, J=7Hz), 1.57~1.84(5H, m) 1.85~1.94(2H, m), 2.10(3H, s) 2.64(3H, s), 2.96~3.03(4H, m) 3.77(2H, d, J=7Hz), 5.95(1H, t, J=7Hz) 7.58(2H, d, J=9Hz), 7.92(2H, d, J=9Hz) |
| 241 | 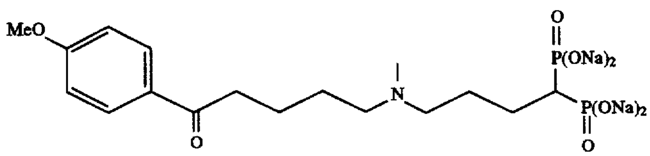 | 1.40~1.69(11H, m), 2.18(3H, s) 2.38~2.46(4H, m), 3.76(3H, s) 6.95(2H, d, J=8Hz), 7.88(2H, d, J=8Hz) |

TABLE 77

| Ex. No. | Chemical Structure | $^1$H-NMR$\delta$(D$_2$O) |
|---|---|---|
| 242 | 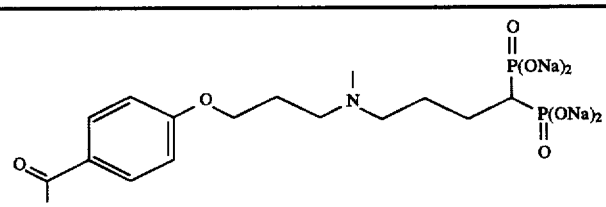 | 1.50~1.62(5H, m), 1.80~1.90(2H, m) 2.28~2.35(2H, m), 2.40~2.50(3H, m) 4.01(2H, t, J=6Hz), 6.90(2H, d, J=9Hz) 7.80(2H, d, J=9Hz) |
| 243 | 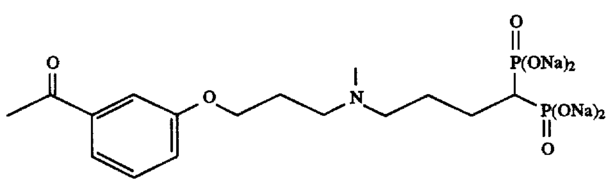 | 1.42~1.65(5H, m), 1.80~1.90(2H, m) 2.10(3H, s), 2.27~2.35(2H, m) 2.46(3H, s), 3.95~4.00(4H, m) 7.10~7.15(1H, m), 7.30~7.35(2H, m) 7.42~7.47(1H, m) |
| 244 | 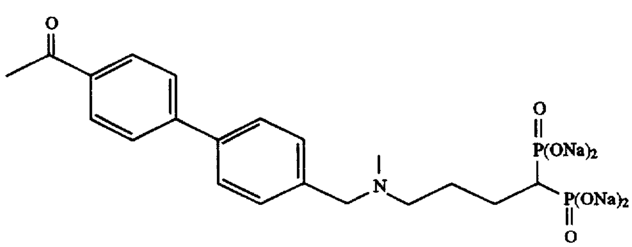 | 1.55~1.76(5H, m), 2.08(3H, s) 2.37(3H, t, J=8Hz), 2.56(3H, s) 3.53(2H, s), 7.39(2H, d, J=8Hz) 7.63(2H, d, J=8Hz), 7.71(2H, d, J=8Hz) 7.95(2H, d, J=8Hz) |

TABLE 78

| Ex. No. | Chemical Structure | $^1$H-NMR$\delta$(D$_2$O) |
|---|---|---|
| 245 | 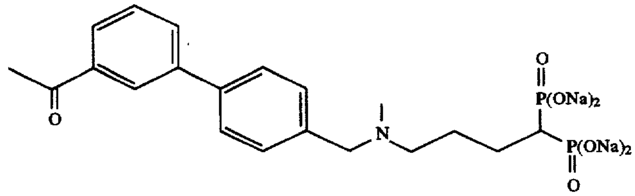 | 1.52~1.72(5H, m), 2.05(3H, s) 2.34(2H, t, J=8Hz), 2.55(3H, s) 3.50(2H, s), 7.35(2H, d, J=8Hz) 7.48(1H, t, J=8Hz), 7.55(2H, d, J=8Hz) 7.81(2H, t, J=8Hz), 8.05(1H, s) |

TABLE 78-continued
| Ex. No. | Chemical Structure | $^1$H-NMRδ(D$_2$O) |
|---|---|---|
| 246 | 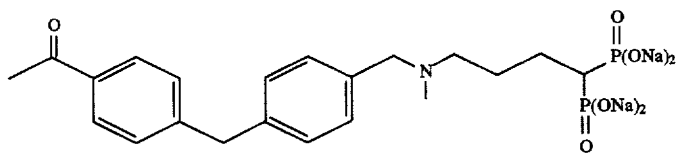 | 1.52~1.69(5H, m), 2.00(3H, s)<br>2.31(2H, t, J=8Hz), 2.48(3H, s)<br>3.41(2H, s), 3.92(2H, s)<br>7.14(2H, d, J=8Hz), 7.18(2H, d, J=8Hz)<br>7.29(2H, d, J=8Hz), 7.79(2H, d, J=8Hz) |
| 247 | 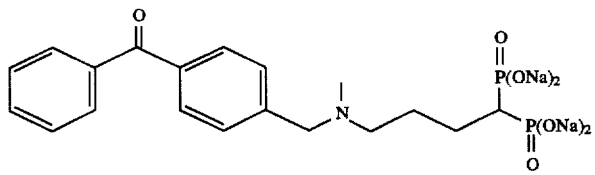 | 1.54~1.75(5H, m), 2.06(3H, s)<br>2.37(2H, t, J=7.5Hz), 3.55(2H, s)<br>7.39(2H, d, J=8.0Hz)<br>7.44(2H, d, J=8.0Hz)<br>7.58(1H, tt, J=7.5Hz, 1.5Hz)<br>7.62~7.67(4H, m) |
TABLE 79
| Ex. No. | Chemical Structure | $^1$H-NMRδ(D$_2$O) |
|---|---|---|
| 248 | 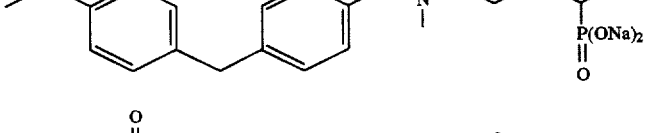 | 1.88~2.06(5H, m), 2.38(3H, s)<br>2.64~2.72(2H, m), 2.84(3H, s)<br>3.14~3.28(4H, m), 3.78(2H, s)<br>7.38~7.43(2H, m), 7.46~7.50(2H, m)<br>7.54~7.58(2H, m), 8.08~8.12(2H, m) |
| 249 | 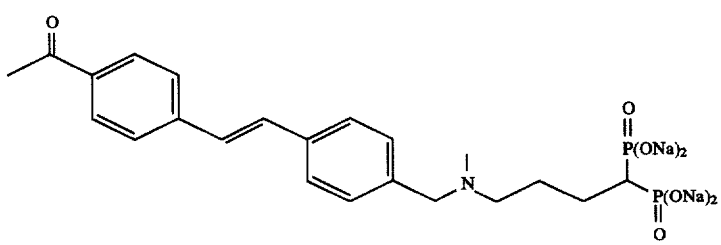 | 1.55~1.88(5H, m), 2.38~2.48(6H, m)<br>2.82~2.88(2H, m), 3.95~3.98(2H, m)<br>7.12~7.20(2H, m), 7.31~7.35(2H, m)<br>7.48~7.56(4H, m), 7.79~7.84(2H, m) |

TABLE 80

| Ex. No. | Chemical Structure | $^1$H-NMR$\delta$(D$_2$O) |
|---|---|---|
| 250 | 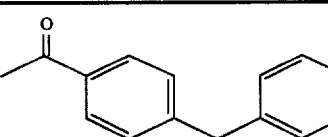 | 1.45–1.65(5H, m), 2.10(3H, s) 2.13–2.38(7H, m), 2.41–2.49(2H, m) 3.95(1H, t, J=8Hz), 7.08–7.15(1H, m) 7.20–7.30(4H, m), 7.39(2H, d, J=8Hz) 7.79(2H, d, J=8Hz) |

Examples 251 to 265

The compounds of Examples 281 to 285 listed in Tables 81 to 85 were prepared by preparing diphosphonic acid ester derivatives in a similar manner to that of the Example 7 and deprotecting the ester derivatives in a similar manners to that of the Example 15.

TABLE 81

| Ex. No. | Chemical Structure | $^1$H-NMR$\delta$(D$_2$O) |
|---|---|---|
| 251 | 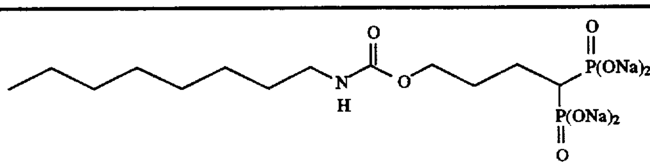 | 0.87(3H, t, J=7Hz), 1.22–1.36(10H, m) 1.43–1.53(2H, m), 1.65–1.93(5H, m) 2.90(2H, t, J=6Hz), 4.07(2H, t, J=6Hz) |
| 252 | 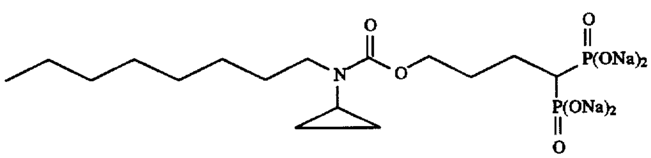 | 0.57–0.62(2H, m), 0.70–0.76(2H, m) 0.78(3H, t, J=6Hz), 1.15(10H, m) 1.44–1.54(2H, m), 1.64–1.88(5H, m) 2.50–2.57(1H, m), 3.21(2H, t, J=6Hz) 4.02(2H, t, J=7Hz) |
| 253 | 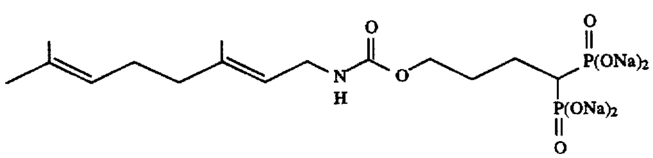 | 1.47(3H, s), 1.52(6H, s) 1.53(3H, s), 1.57–1.77(5H, m) 1.87–2.02(4H, m), 3.55(2H, d, J=8Hz) 3.92(2H, t, J=6Hz), 5.03(1H, t, J=8Hz) 5.08(1H, t, J=8Hz) |

TABLE 82

| Ex. No. | Chemical Structure | $^1$H-NMR$\delta$(D$_2$O) |
|---|---|---|
| 254 | 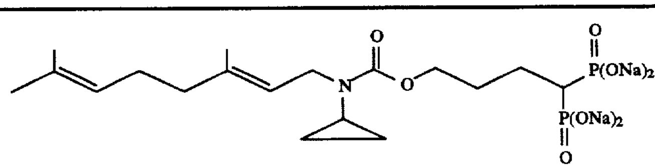 | 0.58–0.72(4H, m), 1.50(3H, s) 1.56(3H, s), 1.58(3H,s) 1.60–1.85(5H, m), 1.90–1.98(4H, m) 2.41–2.50(1H, m), 3.77–3.84(2H, m) 4.01(2H, t, J=6Hz), 4.98–5.14(2H, m) |

TABLE 82-continued

| Ex. No. | Chemical Structure | $^1$H-NMR$\delta$(D$_2$O) |
|---|---|---|
| 255 | (geranyl-N(cyclohexyl)-C(=O)-O-CH$_2$CH$_2$CH$_2$-CH(P(ONa)$_2$=O)$_2$) | 1.08~1.28(4H, m), 1.38~1.96(22H, m) 3.56~3.72(3H, m), 3.87~3.94(2H, m) 4.86~4.94(2H, m) |
| 256 | (morpholino-(CH$_2$)$_3$-NH-C(=O)-O-CH$_2$CH$_2$CH$_2$-CH(P(ONa)$_2$=O)$_2$) | 1.52~1.80(7H, m), 2.27(2H, t, J=8Hz) 2.35~2.47(4H, m), 2.97~3.05(2H, m) 3.58~3.64(4H, m), 3.89~3.97(2H, m) |

TABLE 83

| Ex. No. | Chemical Structure | $^1$H-NMR$\delta$(D$_2$O) |
|---|---|---|
| 257 | (2-oxopyrrolidin-1-yl-(CH$_2$)$_3$-NH-C(=O)-O-CH$_2$CH$_2$CH$_2$-CH(P(ONa)$_2$=O)$_2$) | 1.62(2H, quint, J=7Hz) 1.66~1.85(5H, m) 1.91(2H, quint, J=8Hz) 2.28(2H, t, J=8Hz), 2.97(2H, t, J=7Hz) 3.17(2H, t, J=7Hz), 3.36(2H, t, J=8Hz) 3.89~4.00(2H, m) |
| 258 | (PhCH$_2$CH$_2$-NH-C(=O)-O-CH$_2$CH$_2$CH$_2$-CH(P(ONa)$_2$=O)$_2$) | 1.61~1.79(5H, m), 2.64(2H, t, J=7Hz) 3.17~3.27(2H, m), 3.81~3.90(2H, m) 7.10~7.16(3H, m), 7.19~7.25(2H, m) |
| 259 | (2-MeO-C$_6$H$_4$-CH$_2$CH$_2$-NH-C(=O)-O-CH$_2$CH$_2$CH$_2$-CH(P(ONa)$_2$=O)$_2$) | 1.60~1.80(5H, m), 2.82(2H, t, J=7Hz) 3.18(2H, t, J=7Hz), 3.70(3H, s) 3.81~3.92(2H, m), 6.82~6.91(2H, m) 7.03~7.09(1H, m), 7.13~7.18(1H, m) |

TABLE 84

| Ex. No. | Chemical Structure | $^1$H-NMR$\delta$(D$_2$O) |
|---|---|---|
| 260 | (4-Cl-C$_6$H$_4$-CH$_2$CH$_2$-NH-C(=O)-O-CH$_2$CH$_2$CH$_2$-CH(P(ONa)$_2$=O)$_2$) | 1.63~1.83(5H, m), 2.62(2H, t, J=7Hz) 3.13~3.24(2H, m), 3.78~3.88(2H, m) 7.07(2H, d, J=9Hz), 7.22(2H, d, J=9Hz) |
| 261 | (4-MeO-C$_6$H$_4$-CH$_2$CH$_2$-NH-C(=O)-O-CH$_2$CH$_2$CH$_2$-CH(P(ONa)$_2$=O)$_2$) | 1.63~1.82(5H, m), 2.56(2H, t, J=7Hz) 3.10~3.22(2H, m), 3.63(3H, s) 3.78~3.90(2H, m), 6.77(2H, d, J=9Hz) 7.03(2H, d, J=9Hz) |

TABLE 84-continued

| Ex. No. | Chemical Structure | $^1$H-NMR$\delta$(D$_2$O) |
|---|---|---|
| 262 | MeO-C6H3(OMe)-CH2CH2-NH-C(O)-O-(CH2)3-CH(P(O)(ONa)2)2 | 1.47~1.74(5H, m), 2.53~2.62(2H, m) 3.12~3.24(2H, m), 3.66(6H, s) 3.80~3.87(2H, m), 6.65~6.85(3H, m) |

TABLE 85

| Ex. No. | Chemical Structure | $^1$H-NMR$\delta$(D$_2$O) |
|---|---|---|
| 263 | Ph-(CH2)3-NH-C(O)-O-(CH2)3-CH(P(O)(ONa)2)2 | 1.36(2H, quint, J=8Hz) 1.51(2H, quint, J=8Hz) 1.58~1.80(5H, m), 2.51(2H, t, J=8Hz) 2.98(2H, t, J=7Hz), 3.90~2.97(2H, m) 7.10~7.18(3H, m), 7.20~7.25(2H, m) |
| 264 | 2-Pyridyl-CH2CH2-NH-C(O)-O-(CH2)3-CH(P(O)(ONa)2)2 | 1.47~1.72(5H, m), 2.73~2.80(2H, m) 3.24~3.37(2H, m), 3.77~3.87(2H, m) 7.11~7.20(2H, m), 7.61~7.68(1H, m) 8.24~8.30(1H, m) |
| 265 | Imidazolyl-(CH2)3-NH-C(O)-O-(CH2)3-CH(P(O)(ONa)2)2 | 1.55~1.88(7H, m), 2.90~2.98(2H, m) 3.86~3.98(4H, m), 6.84(1H, s) 7.02(1H, s), 7.74(1H, s) |

Examples 266 to 274

The compounds of Examples 266 to 274 listed in Tables 86 to 88 were prepared by preparing diphosphonic acid ester derivatives in a similar manner to that of the Example 1 and deprotecting the ester derivatives in a similar manner to that of the Example 16.

TABLE 86

| Ex. No. | Chemical Structure | $^1$H-NMR$\delta$(D$_2$O) |
|---|---|---|
| 266 | 3-Pyridyl-CH2CH2-C6H4-CH2-N(Me)-(CH2)3-CH(P(O)(OH)2)2 | 1.61~2.00(5H, m), 2.62(3H, s) 2.88~3.15(6H, m), 4.06(1H, d, J=14Hz) 4.20(1H, d, J=14Hz), 7.10(1H, s) 7.18(1H, d, J=8Hz), 7.21(1H, d, J=8Hz) 7.29(1H, t, J=8Hz) 7.80(1H, dd, J=9Hz, 6Hz) 8.26(1H, d, J=9Hz), 8.32(1H, s) 8.46(1H, d, J=6Hz) |

TABLE 86-continued

| Ex. No. | Chemical Structure | ¹H-NMRδ(D₂O) |
|---|---|---|
| 267 | 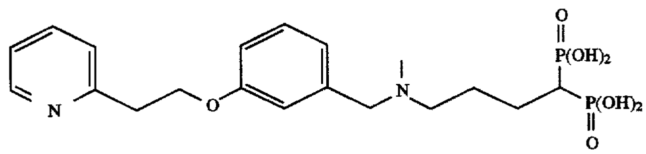 | 1.62~2.00(5H, m), 2.65(3H, s)<br>2.92~3.00(1H, m), 3.04~3.13(1H, m)<br>3.43(2H, t, J=6Hz), 4.07(1H, d, J=14Hz)<br>4.23(1H, d, J=14Hz), 4.38(2H, t, J=6Hz)<br>6.90~6.95(2H, m), 6.97(1H, d, J=8Hz)<br>7.25~7.31(1H, m), 7.76~7.81(1H, m)<br>7.91(1H, d, J=8Hz)<br>8.38(1H, dt, J=1Hz, 8Hz)<br>8.54(1H, dd, J=8Hz, 1Hz) |
| 268 | 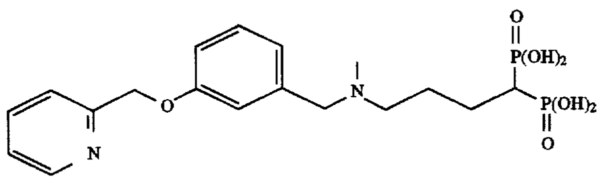 | 1.64~2.02(5H, m), 2.68(3H, s)<br>2.93~3.04(1H, m), 3.04~3.16(1H, m)<br>4.13(1H, d, J=12Hz), 4.28(1H, d, J=12Hz)<br>5.43(2H, s), 7.05~7.13(3H, m)<br>7.33~7.39(1H, m), 7.77~7.84(1H, m)<br>7.92~7.97(1H, m), 8.35~8.40(1H, m)<br>8.60~8.65(1H, m) |

TABLE 87

| Ex. No. | Chemical Structure | ¹H-NMRδ(D₂O) |
|---|---|---|
| 269 | 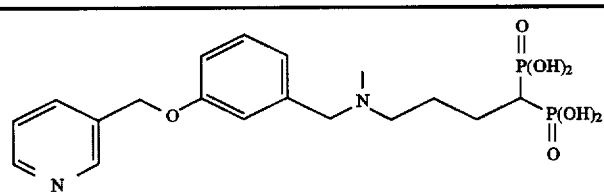 | 1.60~2.00(5H, m), 2.65(3H, s)<br>2.90~2.99(1H, m), 3.02~3.11(1H, m)<br>4.09(1H, d, J=14Hz), 4.24(1H, d, J=14Hz)<br>5.30(2H, s), 7.0~7.08(3H, m)<br>7.32(1H, t, J=8Hz)<br>7.93(1H, dd, J=8Hz, 6Hz)<br>8.53(1H, dt, J=8Hz, <1Hz)<br>8.61(1H, d, J=6Hz)<br>8.76(1H, d, J=<1Hz) |
| 270 | 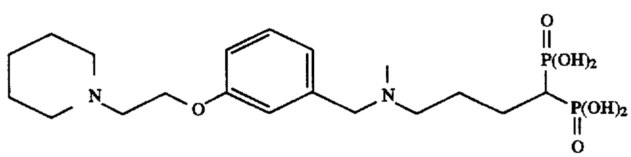 | 1.33(1H, tq, J=4Hz, 13Hz)<br>1.51~2.00(10H, m), 2.05~2.13(2H, m)<br>2.66(3H, s), 2.80(2H, dt, J=4Hz, 13Hz)<br>2.93~3.02(1H, m), 3.06~3.13(1H, m)<br>3.16(2H, t, J=8Hz), 3.43(2H, d, J=13Hz)<br>4.04(2H, t, J=7Hz), 4.07(1H, d, J=14Hz)<br>4.25(1H, d, J=14Hz), 6.94~7.00(3H, m)<br>7.30(1H, t, J=8Hz) |
| 271 | 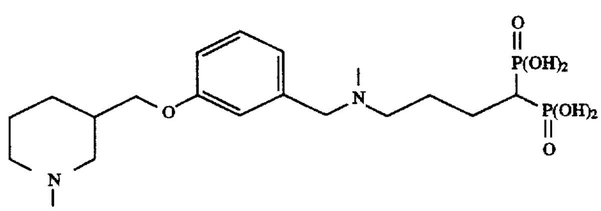 | 1.22~1.33(1H, m), 1.60~2.28(10H, m)<br>2.67(3H, s), 2.71~2.84(5H, m)<br>2.93~3.03(1H, m), 3.06~3.18(1H, m)<br>3.34~3.41(1H, m), 3.49~3.57(1H, m)<br>3.79~3.86(1H, m), 3.93~4.00(1H, m)<br>4.07(1H, d, J=12Hz), 4.23(1H, d, J=12Hz)<br>6.94~7.00(3H, m), 7.30(1H, t, J=8Hz) |

TABLE 88

| Ex. No. | Chemical Structure | ¹H-NMRδ(D₂O) |
|---|---|---|
| 272 | | 1.64~2.02(5H, m), 2.32~2.43(1H, m)<br>2.52~2.60(2H, m), 2.68(3H, s)<br>2.76(3H, s), 2.79~3.04(4H, m)<br>3.08~3.17(1H, m), 3.37~3.44(1H, m)<br>3.46~3.54(1H, m), 4.12(1H, d, J=14Hz)<br>4.29(1H, d, J=14Hz), 7.24(2H, d, J=8Hz)<br>7.37(2H, d, J=8Hz) |

TABLE 88-continued

| Ex. No. | Chemical Structure | $^1$H-NMR$\delta$(D$_2$O) |
|---|---|---|
| 273 | (structure) | 1.48~1.78(5H, m), 2.14(2H, q, J=8Hz)<br>2.79(2H, t, J=7Hz), 2.89(2H, t, J=8Hz)<br>4.36(2H, t, J=8Hz), 7.37~7.45(2H, m)<br>7.56~7.65(2H, m) |
| 274 | (structure) | 1.66~1.97(5H, m), 2.21~2.38(2H, m)<br>2.75(3H, s), 2.98~3.26(2H, m)<br>4.26(2H, t, J=8Hz), 7.37~7.45(3H, m)<br>7.53~7.57(2H, m), 7.72(1H, d, J=2Hz)<br>8.73(1H, d, J=2Hz) |

Examples 275 to 280

The compounds of Examples 275 to 280 listed in Tables 89 and 90 were prepared by preparing diphosphonic acid ester derivatives in a similar manner to that of the Example 2 and deprotecting the ester derivatives in a similar manner to that of the Example 16.

TABLE 89

| Ex. No. | Chemical Structure | $^1$H-NMR$\delta$(D$_2$O) |
|---|---|---|
| 275 | (structure) | 1.28~1.40(2H, m), 1.66~1.92(7H, m)<br>1.99(1H, tt, J=24Hz, 7Hz)<br>2.47(2H, d, J=6Hz)<br>2.75(2H, broad t, J=12Hz)<br>2.98(2H, t, J=8Hz)<br>3.44(2H, broad d, J=12Hz)<br>3.70(3H, s), 6.73~6.80(3H, m)<br>7.28(1H, t, J=8Hz) |
| 276 | (structure) | 1.34~1.47(2H, m), 1.64~1.92(8H, m)<br>2.71~2.82(4H, m)<br>2.97(2H, broad t, J=8Hz)<br>3.42~3.50(2H, m), 7.84~7.90(1H, m)<br>8.32~8.38(1H, m), 8.48~8.57(2H, m) |
| 277 | (structure) | 1.23~1.40(2H, m), 1.42~1.60(2H, m)<br>1.60~1.98(12H, m)<br>2.52(2H, d, J=7Hz), 2.69~2.84(4H, m)<br>2.96(2H, t, J=8Hz), 3.26~3.34(2H, m)<br>3.38~3.48(2H, m), 7.29(2H, d, J=8Hz)<br>7.27(2H, d, J=8Hz) |

TABLE 90

| Ex. No. | Chemical Structure | $^1$H-NMRδ(D$_2$O) |
|---|---|---|
| 278 | (pyridin-3-yl)methylene-piperidine-N-(CH$_2$)$_3$-CH(P(OH)$_2$(=O))$_2$ | 1.64–1.98(5H, m), 2.42–2.54(1H, m)<br>2.60–2.68(2H, m), 2.68–2.78(1H, m)<br>2.80–2.90(1H, m), 3.08(2H, t, J=7Hz)<br>3.45–3.55(1H, m), 3.55–3.65(1H, m)<br>6.49(1H, s), 7.88–7.93(1H, m)<br>8.29–8.33(1H, m), 8.47–8.53(2H, m) |
| 279 | 4-F-C$_6$H$_4$-C(=O)-CH(piperidine)-N-(CH$_2$)$_3$-CH(P(OH)$_2$(=O))$_2$ | 1.67–2.12(9H, m), 2.97–3.12(4H, m)<br>3.53–3.70(3H, m), 7.10–7.17(2H, m)<br>7.85–7.95(2H, m) |
| 280 | (pyridin-2-yl)-CH$_2$-O-piperidine-N-(CH$_2$)$_3$-CH(P(OH)$_2$(=O))$_2$ | 1.64–1.94(7H, m), 2.14(1H, d, J=15Hz)<br>2.26(1H, d, J=15Hz)<br>2.90(1H, dt, J=2Hz, 12Hz)<br>3.03(2H, t, J=8Hz)<br>3.17(1H, dt, J=2Hz, 12Hz),<br>3.34(1H, d, J=12Hz), 3.55(1H, d, J=12Hz)<br>3.75–3.86(1H, m), 7.76–7.87(2H, m)<br>8.33–8.40(1H, m), 8.55–8.60(1H, m) |

Example 281

The compound of Example 281 listed in Table 91 was prepared by preparing a diphosphonic acid ester derivative in a similar manner to that of the Example 9 and deprotecting the ester derivative in a similar manner to that of the Example 16.

TABLE 91

| Ex. No. | Chemical Structure | $^1$H-NMRδ(D$_2$O) |
|---|---|---|
| 281 | C$_6$H$_5$-(CH$_2$)$_4$-N(H)-(CH$_2$)$_3$-N(H)-CH(P(OH)$_2$)(P(OH)$_2$(=O)) | 1.18–1.28(2H, m), 1.48–1.68(4H, m)<br>1.96–2.16(2H, m), 2.50(2H, t, J=8Hz)<br>2.70(3H, s), 2.87–3.20(4H, m)<br>3.29(2H, t, J=8Hz), 3.37(1H, t, J=20Hz)<br>7.08–7.18(3H, m), 7.21(2H, t, J=8Hz) |

Examples 282 to 288

The compounds of Examples 282 to 288 listed in Tables 92 to 94 were prepared by preparing diphosphonic acid ester derivatives in a similar manner to that of the Example 3 and deprotecting the ester derivatives in a similar manner to those of Examples 17 and 18.

TABLE 92

| Ex. No. | Chemical Structure | $^1$H-NMRδ(D$_2$O) |
|---|---|---|
| 282 | MeO-C$_6$H$_4$-C(CH$_3$)=CH-CH$_2$-N(COONa)-(CH$_2$)$_3$-CH(P(ONa)$_2$(=O)) | 1.30–1.72(4H, m), 1.92(3H, s)<br>2.21(3H, s), 2.27–2.40(1H, m)<br>2.41–2.52(2H, m), 3.22(2H, d, J=6Hz)<br>5.68(1H, t, J=6Hz), 6.83(1H, d, J=9Hz)<br>7.32(1H, d, J=9Hz) |

TABLE 92-continued

| Ex. No. | Chemical Structure | $^1$H-NMR$\delta$(D$_2$O) |
|---|---|---|
| 283 | (structure: 2-methylphenyl-CH$_2$CH$_2$-C(CH$_3$)=CH-CH$_2$-N(CH$_3$)-(CH$_2$)$_3$-CH(COONa)-P(ONa)$_2$=O) | 1.30–1.70(4H, m), 1.60(3H, s)<br>1.85–2.47(5H, m), 2.06(3H, s)<br>2.18(3H, s), 2.64(2H, t, J=8Hz)<br>3.03(2H, d, J=6.5Hz)<br>5.18(1H, t, J=6.5Hz)<br>6.97–7.18(4H, m) |
| 284 | (structure: 2-naphthyl-CH$_2$CH$_2$-C(CH$_3$)=CH-CH$_2$-N(CH$_3$)-(CH$_2$)$_3$-CH(COONa)-P(ONa)$_2$=O) | 1.14–1.29(2H, m), 1.36–1.64(2H, m)<br>1.61(3H, s), 1.95(3H, s)<br>2.27(1H, ddd, J=21Hz, 12Hz, 3.5Hz)<br>2.39–2.49(4H, m), 2.86(2H, t, J=7Hz)<br>3.32(2H, d, J=8Hz), 4.91(1H, t, J=8Hz)<br>7.31(1H, d, J=8.5Hz), 7.34–7.42(2H, m)<br>7.57(1H, s), 7.69–7.79(3H, m) |

TABLE 93

| Ex. No. | Chemical Structure | $^1$H-NMR$\delta$(D$_2$O) |
|---|---|---|
| 285 | (structure: 3-pyridyl-thienyl-CH$_2$-N(CH$_3$)-(CH$_2$)$_3$-CH(COONa)-P(ONa)$_2$=O) | 1.30–1.70(4H, m), 2.08(3H, s)<br>2.25–2.40(3H, m), 3.62(2H, s)<br>6.88(1H, d, J=3.6Hz)<br>7.19(1H, d, J=3.6Hz)<br>7.28(1H, dd, J=4.8Hz, 8Hz)<br>7.85(1H, t, J=8Hz)<br>8.22(1H, d, J=4.8Hz)<br>8.58(1H, s) |
| 286 | (structure: 3-pyridyl-CH$_2$CH$_2$-phenyl-CH$_2$-N(CH$_3$)-(CH$_2$)$_3$-CH(COONa)-P(ONa)$_2$=O) | 1.22–1.53(3H, m), 1.56–1.69(1H, m)<br>1.85(3H, s), 2.14–2.28(2H, m)<br>2.34(1H, ddd, J=20Hz, 13Hz, 3Hz)<br>2.82(4H, s), 3.31(2H, s), 6.89(1H, s)<br>6.97(1H, d, J=8Hz), 7.01(1H, d, J=8Hz)<br>7.13(1H, t, J=8Hz)<br>7.15(1H, dd, J=8Hz, 5Hz)<br>7.46(1H, dt, J=8Hz, 2Hz)<br>8.06(1H, d, J=2Hz)<br>8.14(1H, dd, J=5Hz, 2Hz) |
| 287 | (structure: phenyl-CH=CH-phenyl-CH$_2$-N(CH$_3$)-(CH$_2$)$_3$-CH(COONa)-P(ONa)$_2$=O) | 1.30–1.55(3H, m), 1.56–1.71(1H, m)<br>2.08(3H, s), 2.30–2.46(3H, m)<br>3.51(2H, s), 7.08–7.10(2H, m)<br>7.12–7.22(2H, m), 7.23–7.31(3H, m)<br>7.38–7.42(2H, m), 7.44–7.49(2H, m) |

TABLE 94

| Ex. No. | Chemical Structure | $^1$H-NMR$\delta$(D$_2$O) |
|---|---|---|
| 288 | (structure: thienyl-C(CH$_3$)=CH-thienyl-CH$_2$-N(CH$_3$)-(CH$_2$)$_3$-CH(COONa)-P(ONa)$_2$=O) | 1.37–1.70(4H, m), 2.03(3H, s)<br>2.23(3H, s), 2.29–2.42(3H, m)<br>3.69(2H, s), 6.88(1H, d, J=4Hz)<br>6.92–6.97(2H, m), 7.02(1H, s)<br>7.12(1H, dd, J=4Hz, 1Hz)<br>7.20(1H, dd, J=6Hz, 1Hz) |

Examples 289 add 290

The compounds of Examples 289 and 290 listed in Table 95 were prepared by preparing diphosphonic acid ester derivatives in a similar manner to that of the Example 8 and deprotecting the ester derivatives in a similar manner to those of the Examples 17 and 18.

TABLE 95

| Ex. No. | Chemical Structure | $^1$H-NMR$\delta$(D$_2$O) |
|---|---|---|
| 289 | (geranyl-NH-C(O)-O-(CH$_2$)$_3$-CH(COONa)-P(ONa)$_2$=O) | 1.35–1.78(13H, m)<br>1.85–1.92(2H, m), 1.94–2.02(2H, m)<br>2.38–2.48(1H, m), 3.53(2H, d, J=7Hz)<br>3.88(2H, t, J=7Hz), 4.96–5.08(2H, m) |
| 290 | (geranyl-N(CH$_3$)-C(O)-O-(CH$_2$)$_3$-CH(COONa)-P(ONa)$_2$=O) | 1.36–1.76(13H, m)<br>1.86–2.03(4H, m), 2.30–2.40(1H, m)<br>2.68(3H, s), 3.68–3.79(2H, m)<br>3.91(2H, t, J=7Hz), 4.84–5.07(2H, m) |

Examples 291 to 293

The compounds of Examples 291 to 293 listed in Table 96 were prepared by preparing triethyl 1-carboxyphosphonate from 1-bromo-3-methyl-5-(2- naphthyl)-2-pentene and triethyl phosphonoacetate in a similar manner to that of the Example 10 and deprotecting the ester in a similar manner to those of Examples 17 and 18.

TABLE 96

| Ex. No. | Chemical Structure | $^1$H-NMR$\delta$(D$_2$O) |
|---|---|---|
| 291 | (2-naphthyl-CH$_2$CH$_2$-C(CH$_3$)=CH-CH$_2$-CH(COOEt)-P(ONa)$_2$=O) | 0.93(3H, t, J=7.5Hz), 1.58(3H, s)<br>2.10–2.22(1H, m), 2.29(2H, t, J=7Hz)<br>2.34–2.48(2H, m)<br>2.78(2H, br.t, J=7Hz)<br>3.58–3.72(2H, m), 4.94(1H, m)<br>7.31(1H, br.d, J=8Hz)<br>7.34–7.42(2H, m), 7.58(1H, br.s)<br>7.71–7.80(3H, m) |
| 292 | (2-naphthyl-CH$_2$CH$_2$-C(CH$_3$)=CH-CH$_2$-CH(COONa)-P(ONa)$_2$=O) | 1.59(3H, s), 2.16–2.43(5H, m)<br>2.78(2H, t, J=5Hz)<br>5.11(1H, m), 7.33–7.43(3H, m)<br>7.64(1H, s), 7.72–7.79(3H, m) |
| 293 | (2-naphthyl-CH$_2$CH$_2$-C(CH$_3$)=CH-CH$_2$-C(OH)(COONa)-P(ONa)$_2$=O) | 1.56(3H, s), 2.25(2H, t, J=8Hz)<br>2.3–2.4(1H, m), 2.6–2.7(1H, m)<br>2.77(2H, t, J=8Hz), 5.00(1H, t, J=6Hz)<br>7.3–7.4(3H, m), 7.63(1H, s)<br>7.7–7.8(3H, m) |

Example 294

The compound of Example 294 listed in Table 97 was prepared by preparing a phosphonic acid ester derivative in a similar manner to that of the Example 6 and deprotecting the ester derivative in a similar manner to that of the Example 19.

TABLE 97

| Ex. No. | Chemical Structure | $^1$H-NMRδ(D$_2$O, DDS) |
|---|---|---|
| 294 | (farnesyl)N(Me)CH$_2$CH(OH)CH$_2$CH(COONa)P(O)(ONa)$_2$ | 1.61(6H, s), 1.68(3H, s)<br>1.74(3H, s), 1.97–2.24(8H, m)<br>2.51(0.4H, ddd, J=4Hz, 11Hz, 23Hz)<br>2.72(3H, s), 2.98–3.14(2H, m)<br>3.62–3.76(2H, m)<br>3.84–3.92(0.6H, m)<br>3.99–4.07(0.4H, m)<br>5.14–5.21(2H, m), 5.32(1H, t, J=8Hz) |

Examples 295 to 300

The diphosphonic acid ester derivatives listed in Tables 98 and 99 were prepared from phosphonic acid ester derivatives in a similar manner to those of the Examples 21 and 22.

TABLE 98

| Ex. No. | Chemical Structure | $^1$H-NMR |
|---|---|---|
| 295 | [structure with MOM-O-phenyl, N(Me), phosphonate pivaloyloxymethyl ester] | δ(CDCl$_3$);<br>1.08–1.25(27H, m)<br>1.93–2.52(11H, m)<br>2.72–2.84(2H, m), 3.17–3.25(2H, m)<br>3.46(3H, s), 5.28(2H, s)<br>5.46–5.90(7H, m), 6.93–7.08(3H, m)<br>7.20–7.29(1H, m) |
| 296 | [3-methoxybenzyl-piperidine-propyl phosphonate structure] | δ(D$_2$O);<br>1.12(9H, s), 1.32(2H, br.q, J=13Hz)<br>1.63–2.00(10H, m)<br>2.47(2H, d, J=8Hz)<br>2.73(2H, br.t, J=13Hz)<br>2.95(2H, t, J=8Hz)<br>3.42(2H, d, J=13Hz)<br>3.68(3H, s), 5.40(2H, d, J=12Hz)<br>6.70–6.78(3H, m), 7.17(1H, t, J=8Hz) |
| 297 | [4-fluorobenzoyl-piperidine structure with phosphonate] | δ(D$_2$O);<br>0.97–1.01(9H, m), 1.60–2.01(9H, m)<br>2.86–3.00(4H, m), 3.45–3.60(3H, m)<br>5.34(2H, d, J=14Hz)<br>7.60(2H, t, J=9Hz)<br>7.85(2H, dd, J=9Hz, 5Hz) |

TABLE 99

| Ex. No. | Chemical Structure | $^1$H-NMR |
|---|---|---|
| 298 | [4-fluorobenzoyl-piperidine structure with bis-pivaloyloxymethyl diphosphonate] | δ(CDCl$_3$);<br>1.17–1.24(27H, m)<br>1.60–1.70(5H, m), 2.00–2.24(6H, m)<br>2.40–2.55(2H, m), 2.92–3.20(3H, m)<br>5.60–5.76(5H, m), 5.84–5.89(1H, m)<br>7.12–7.19(2H, m), 7.93–7.98(2H, m) |

TABLE 99-continued

| Ex. No. | Chemical Structure | ¹H-NMR |
|---|---|---|
| 299 | [structure with OH-CH(CH₃)-phenyl-CH₂-phenyl-CH₂-N(CH₃)-(CH₂)₃-CH(P(O)(ONa)₂)(P(O)(ONa)(OEt))] | δ(D₂O); 1.06(3H, t, J=8Hz), 1.29(3H, d, J=7Hz) 1.52–1.80(5H, m), 2.18(3H, s) 2.52(2H, t, J=8Hz), 3.60–3.82(4H, m) 3.86(2H, s), 4.72(1H, q, J=8Hz) 7.13–7.23(8H, m) |
| 300 | [structure with CH₃-C(O)-phenyl-CH₂-phenyl-CH₂-N(CH₃)-(CH₂)₃-CH(P(O)(ONa)₂)(P(O)(ONa)(OEt))] | δ(D₂O); 1.05(3H, t, J=8Hz), 1.50–1.74(5H, m) 2.07(3H, s), 2.37(2H, t, J=8Hz) 2.46–2.49(3H, m), 3.49(2H, s) 3.68–3.83(2H, m), 3.94(2H, s) 7.18(2H, d, J=8Hz), 7.22(2H, d, J=8Hz) 7.29(2H, d, J=8Hz), 7.79(2H, d, J=8Hz) |

Examples 301 to 367

The compounds of Examples 301 to 367 listed in Tables 100 to 122 were prepared by preparing diphosphonic acid ester derivatives in a similar manner to that of the Example 1 and deprotecting the ester derivatives in a similar manner to that of the Example 14.

TABLE 100

| Ex. No. | Chemical Structure | ¹H-NMR |
|---|---|---|
| 301 (634) | [6-fluorobenzothiazol-2-yl-N(CH₃)-(CH₂)₃-CH(P(O)(ONa)₂)₂] | δ(D₂O); 1.45(1H, tt, J=6Hz, 23Hz) 1.55–1.83(4H, m), 3.02(3H, s) 3.34(2H, t, J=7Hz) 6.93(1H, dt, J=3Hz, 9Hz) 7.20(1H, dd, J=5Hz, 9Hz) 7.28(1H, dd, J=3Hz, 9Hz) |
| 302 (684) | [indol-3-yl-CH₂-N(CH₃)-(CH₂)₃-CH(P(O)(ONa)₂)₂] | δ(D₂O); 1.50–1.80(5H, m), 2.22(3H, s) 2.51–2.57(2H, m), 3.87(2H, s) 7.03(1H, t, J=7Hz), 7.10(1H, t, J=7Hz) 7.30(1H, s), 7.37(1H, d, J=7Hz) 7.60(1H, d, J=7Hz) |
| 303 (693) | [indol-2-yl-CH₂-N(CH₃)-(CH₂)₃-CH(P(O)(ONa)₂)₂] | δ(D₂O); 1.46–1.72(5H, m), 2.06(3H, s) 2.30(2H, t, J=8Hz), 3.61(2H, s) 6.34(1H, s), 6.98(1H, t, J=8Hz) 7.04(1H, t, J=8Hz), 7.32(1H, t, J=8Hz) 7.47(1H, d, J=8Hz) |

TABLE 101

| Ex. No. | Chemical Structure | ¹H-NMR |
|---|---|---|
| 304 (660) | (5-methoxyindol-3-yl)methyl-N-methyl-aminobutyl bisphosphonate structure | δ(D₂O); 1.50~1.80(5H, m), 2.16(3H, s) 2.45~2.53(2H, m), 3.73(3H, s) 3.77(2H, s), 6.77(1H, dd, J=8Hz, 2Hz) 7.13(1H, s), 7.27~7.31(2H, m) |
| 305 (689) | (1-methylbenzimidazol-2-yl)methyl-NH-aminobutyl bisphosphonate structure | δ(D₂O); 1.43~1.80(5H, m), 3.27(3H, s) 3.92(2H, br.s), 4.17(2H, br.s) 7.03(3H, br.s), 7.33(1H, br.s) |
| 306 (667) | (benzimidazol-2-yl)methyl-N-methyl-aminobutyl bisphosphonate structure | δ(D₂O); 1.58~1.75(5H, m), 2.13(3H, s) 2.38(2H, t, J=7Hz), 3.75(2H, s) 7.15~7.20(2H, m), 7.48~7.53(2H, m) |

TABLE 102

| Ex. No. | Chemical Structure | ¹H—NMR |
|---|---|---|
| 307 (679) | (indazol-3-yl)methyl-N-methyl-aminobutyl bisphosphonate structure | δ(D₂O); 1.52~1.75(5H, m), 2.15(3H, s) 2.43~2.52(2H, m), 3.93(2H, s) 7.10(1H, t, J=8Hz), 7.32(1H, t, J=8Hz) 7.45(1H, d, J=8Hz), 7.75(1H, d, J=8Hz) |
| 308 (676) | (quinoxalin-2-yl)methyl-N-methyl-aminobutyl bisphosphonate structure | δ(D₂O); 1.47~1.85(5H, m) 2.88(3H, d, J=32Hz) 3.92~4.05(2H, m) 4.72(2H, d, J=32 Hz) 7.68~7.77(2H, m), 7.91~7.97(2H, m) 8.70(1H, s) |

TABLE 102-continued

| Ex. No. | Chemical Structure | $^1$H—NMR |
|---|---|---|
| 309 (752) | 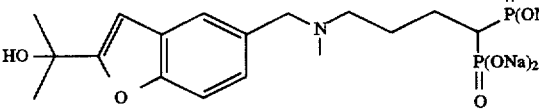 | δ(D$_2$O); 1.50(6H, s), 1.52~1.70(5H, m) 2.02(3H, s), 2.32(2H, t, J=7Hz) 3.52(2H, s,), 6.59(1H, s) 7.16(1H, d, J=8Hz), 7.34(1H, d, J=8Hz) 7.44(1H, s) |

TABLE 103

| Ex. No. | Chemical Structure | $^1$H—NMR |
|---|---|---|
| 310 (510) | 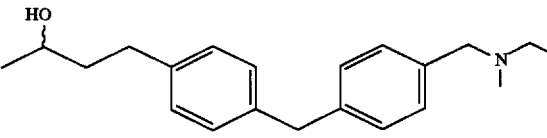 | δ(D$_2$O); 0.90(3H, d, J=6Hz), 1.24~1.50(2H, m) 1.56~1.85(5H, m), 2.20~2.39(5H, m) 2.83(2H, br,), 3.41~3.59(1H, m) 3.62(2H, s), 3.84(2H, s) 6.73~7.12(8H, m) |
| 311 (642) | 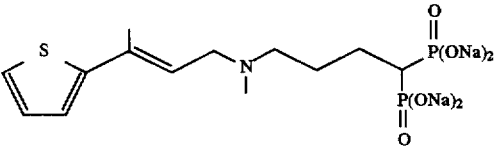 | δ(D$_2$O); 1.45~1.65(5H, m), 1.85(3H, s) 2.10(3H, s), 2.35(2H, t, J=7Hz) 3.12(2H, d, J=7Hz), 5.89(1H, d, J=7Hz) 6.90(1H, dd, J=6Hz, 4Hz) 7.01(1H, d, J=4Hz), 7.15(1H, d, J=6Hz) |
| 312 (691) | 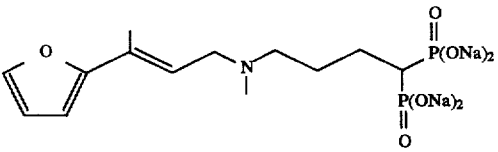 | δ(D$_2$O); 1.40~1.65(5H, m), 1.80(3Hs, ) 2.08(3H,s ), 2.28~2.38(2H, m) 3.10(2H, d, J=7Hz), 3.18(3H, s) 5.87(1H, s, J=7Hz), 6.25(1H, d, J=3Hz) 6.32(1H, dd, J=3Hz, 1Hz) 7.30(1H, d, J=1Hz) |

TABLE 104

| Ex. No. | Chemical Structure | $^1$H—NMR |
|---|---|---|
| 313 (558) | 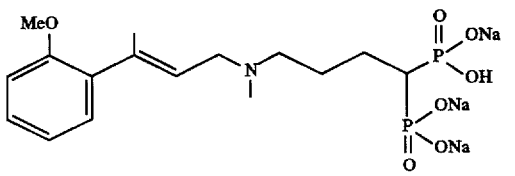 | δ(D$_2$O); 1.55~1.68(5H, m), 1.82(3H, s) 2.20(3H, s), 2.42~2.48(2H, m) 3.13~3.18(2H, m), 3.67(3H, s) 5.39(2H, t, J=8Hz) 6.82~6.95(2H, m), 7.05~7.08(1H, m) 7.15~7.20(1H, m) |
| 314 (665) | 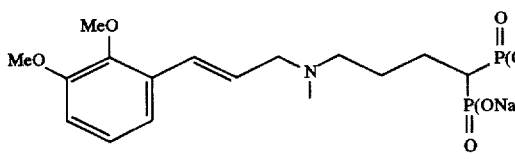 | δ(D$_2$O); 1.45~1.68(5H, m), 2.11(3H, m) 2.30~2.39(2H, m), 3.12(2H, d, J=7Hz) 3.61(3H, s), 3.72(3H, s) 6.22(1H, dt, J=7Hz, 16Hz) 6.69(1H, d, J=16Hz) 6.87(1H, d, J=9Hz), 7.00(1H, t, J=9Hz) 7.10(1H, d, J=9Hz) |
| 315 (647) | 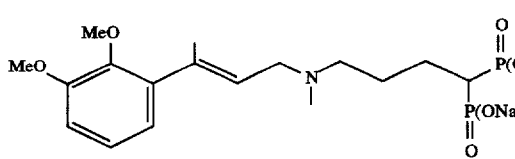 | δ(D$_2$O); 1.50~1.66(5H, m), 1.87(3H, s) 2.16(3H, s), 2.38~2.42(2H, m) 3.13(2H, d, J=7Hz), 3.60(3H, s) 3.73(3H, s), 5.43(1H, t, J=7Hz) 6.75(1H, d, J=9Hz), 6.90(1H, d, J=9Hz) 7.00(1H, t, J=9Hz) |

TABLE 105

| Ex. No. | Chemical Structure | $^1$H—NMR |
|---|---|---|
| 316 (643) | MeO, MeO, MeO substituted phenyl—CH=C(Me)—CH₂—N(Me)—(CH₂)₃—CH[P(ONa)₂=O]₂ | δ(D₂O); 1.40~1.65(5H, m), 1.81(3H, s) 2.10(3H, s), 2.30~2.38(2H, m) 3.08(2H, d, J=7Hz), 3.63(3H, s) 3.65(3H, s), 3.68(3H, s) 5.38(1H, t, J=6Hz), 6.68 (1H, d, J=9Hz) 6.83(1H, d, J=9Hz) |
| 317 (641) | MeO-phenyl—CH=C(Me)—CH₂—N(CN)—(CH₂)₃—CH[P(ONa)₂=O]₂ | δ(D₂O); 1.42~1.90(8H, m), 3.02(2H, t, J=7Hz) 3.65(3H, s), 3.70(2H, d, J=7Hz) 5.35(1H, t, J=7Hz), 6.86(1H, t, J=9Hz) 6.93(1H, d, J=9Hz), 7.08(1H, d, J=9Hz) 7.19(1H, t, J=7Hz) |
| 318 (731) | MeO-phenyl—C(Me)=C(Me)—C(Me)₂—N(Me)—(CH₂)₃—CH[P(ONa)₂=O]₂ | δ(D₂O); 1.31(3H, s), 1.44~1.69(5H, m) 1.79(3H, s), 2.12(3H, s) 2.25~2.42(2H, m) 3.00(1H, d, J=13Hz) 3.12(1H, d, J=13Hz) 3.66(3H, m), 6.89(1H, t, J=9Hz) 6.94~7.01(2H, m), 7.18(1H, t, J=9Hz) |

TABLE 106

| Ex. No. | Chemical Structure | $^1$H—NMR |
|---|---|---|
| 319 (639) | MeO-phenyl—CH=C(Me)—CH₂—NH—(CH₂)₃—CH[P(ONa)₂=O]₂ | δ(D₂O); 1.38~1.75(5H, m), 1.80(3H, s) 2.42~2.45(1H, m), 2.45~2.59(2H, m) 3.25(2H, d, J=7Hz), 3.65(3H, s) 3.36(1H, t, J=7Hz), 6.80~6.95 (2H, m) 7.05(1H, d, J=9Hz), 7.18(1H, t, J=9Hz) |
| 320 (686) | thiophene(OMe)—C(Me)=CH—CH₂—N(Me)—(CH₂)₃—CH[P(ONa)₂=O]₂ | δ(D₂O); 1.40~1.62(5H, m), 1.89(3H, s) 2.08(3H, s), 2.27~2.36(2H, m) 3.04(2H, d, J=7Hz), 3.70(3H, s) 5.90(1H, t, J=7Hz), 6.84(1H, d, J=5Hz) 7.05(1H, d, J=5Hz) |
| 321 (657) | HO—CH(Me)—thiophene—C(Me)=CH—CH₂—N(Me)—(CH₂)₃—CH[P(ONa)₂=O]₂ | δ(D₂O); 1.37(3H, d, J=7Hz), 1.38~1.62(5H, m) 1.89(3H, s), 2.08(3H, s) 2.25~2.34(2H, m), 3.07(2H, d, J=7Hz) 4.89(1H, q, J=7Hz), 5.82(1H, t, J=7Hz) 6.75(1H, d, J=4Hz), 6.82(1H, d, J=4Hz) |

TABLE 107

| Ex. No. | Chemical Structure | ¹H—NMR |
|---|---|---|
| 322 (554) | (structure) | δ(D₂O); 1.32(6H, d, J=7Hz), 1.67~1.98(5H, m) 2.04(3H, s), 2.74(3H, s) 2.96~3.20(2H, m), 3.76~3.49(2H, m) 3.76~3.94(2H, m), 4.79(2H, q, J=7Hz) 5.72(1H, t, J=7Hz), 7.24(1H, s) 7.28(2H, s) |
| 323 (652) | (structure) | δ(D₂O); 1.42~1.67(5H, m), 1.84(3H, s) 2.14(3H, s), 2.31~2.38(2H, br,) 2.53(6H, s), 3.10(2H, d, J=7Hz) 5.34~5.40(1H, m), 6.91~6.96(1H, m) 7.04~7.08(2H, m), 7.14~7.20(1H, m) |
| 324 (682) | (structure) | δ(D₂O); 1.39(9H, s), 1.50~1.68(5H, m) 1.74(3H, s), 2.12(3H, s) 2.31~2.38(2H, m), 3.05(2H, d, J=7Hz) 5.45(1H, t, J=7Hz), 6.00(1H, d, J=3Hz) 6.03(1H, t, J=3Hz), 7.11(1H, d, J=3Hz) |

TABLE 108

| Ex. No. | Chemical Structure | ¹H—NMR |
|---|---|---|
| 325 (655) | (structure) | δ(D₂O); 1.27(3H, d, J=7Hz), 1.42~1.65(5H, m) 1.80(3H, s), 2.13(3H, s) 2.32~2.40(2H, m), 3.09(2H, d, J=7Hz) 3.65(3H, s), 4.68(1H, q, J=7Hz) 5.39(1H, t, J=7Hz), 6.92(1H, d, J=9Hz) 7.03(1H, s), 7.17(1H, d, J=9Hz) |
| 326 (668) | (structure) E:Z = 1:1 | δ(D₂O); 1.42~1.62 (5H, m), 1.81(1.5H, s) 1.85(1.5H, s), 1.97(1.5H, s) 2.08(1.5H, s), 2.12~2.19(1H, m) 2.26~2.35(1H, m), 2.57(1.5H, s) 2.60(1.5H, s), 2.60~2.72(1H, m) 3.07(1H, d, J=7Hz), 3.68(3H, s) 4.08(1H, s), 4.15(1H, s) 5.50(1H, t, J=7Hz), 5.59(1H, t, J=7Hz) 6.80~6.87(2H, m), 6.93(1H, d, J=5Hz) 6.98(1H, d, J=5Hz), 7.08(1H, d, J=9Hz) 7.13(1H, d, J=9Hz), 7.60(1H, d, J=5Hz) |
| 327 (669) | (structure) E:Z = 1:1 | δ(D₂O); 1.32~1.62(5H, m), 1.85(3H, s) 1.98(1.5H, s), 2.12(1.5H, s) 2.14~2.18(1H, m), 2.31~2.40(4H, m) 2.65~2.73(1H, m), 3.07(1H, d, J=7Hz) 5.42~5.52(1H, m) 6.78(0.5H, d, J=5Hz) 6.86(0.5H, d, J=5Hz) 7.32(0.5H, d, J=5Hz) 7.40(0.5H, d, J=7Hz) |

TABLE 109

| Ex. No. | Chemical Structure | ¹H—NMR |
|---|---|---|
| 328 (625) | (6-chloro-2H-chromen-3-yl)methyl-N-methyl substituted bisphosphonate structure | δ(D₂O); 1.53~1.52(5H, m), 2.20(3H, s) 2.40~2.49(2H, m), 3.15(2H, s) 4.60(2H, s), 6.35(1H, s) 6.66(1H, d, J=8Hz) 6.97~7.02(2H, m) |
| 329 (626) | 8-methoxy chroman-derived vinyl-N-methyl bisphosphonate structure | δ(D₂O); 1.53~1.70(5H, m), 2.12(3H, s) 2.32~2.42(2H, m), 2.60(2H, t, J=7Hz) 3.15(2H, d, J=8Hz), 3.70(3H, s) 4.10(2H, t, J=7Hz), 6.07(1H, t, J=8Hz) 6.80~6.85(2H, m), 7.20(1H, t, J=8Hz) |
| 330 (628) | chroman-3-yl-methyl-N-methyl bisphosphonate structure | δ(D₂O); 1.48~1.63(5H, m), 2.11(3H, s) 2.15~2.37(5H, m) 2.42(1H, dd, J=15Hz, 10Hz) 2.78(1H, dd, J=16Hz, 7Hz) 3.75(1H, t, J=10Hz) 4.13(1H, d, J=10Hz) 6.69(1H, d, J=8Hz), 6.80(1H, t, J=8Hz) 6.99~7.05(2H, m) |

TABLE 110

| Ex. No. | Chemical Structure | ¹H—NMR |
|---|---|---|
| 331 (650) | 1,4-benzodioxan-2-ylmethyl-N-methyl bisphosphonate structure | δ(D₂O); 1.48~1.67(5H, m), 2.18(3H, s) 2.30~2.42(2H, m) 2.50(1H, dd, J=4Hz, 13Hz) 2.62(1H, dd, J=8Hz, 13Hz) 3.88(1H, dd, J=7Hz, 12Hz) 4.17(1H, d, J=12Hz) 4.30~4.36(1H, m), 6.75~6.85(4H, m) |
| 332 (659) | 1,3-benzodioxol-2-ylmethyl-N-methyl bisphosphonate structure | δ(D₂O); 1.49~1.80(5H, m), 2.61~2.79(3H, m) 3.36~3.54(2H, m) 3.80~3.98(2H, br. s) 5.95~6.10(1H, m), 6.55~6.68(4H, m) |
| 333 (651) | 5-methoxy-indol-3-yl-ethyl-amino bisphosphonate structure | δ(D₂O); 1.40~1.70(5H, m), 2.50~2.61(2H, m) 2.76~2.88(4H, m), 3.73(3H, s) 6.72~6.78(1H, m), 7.05~7.12(2H, m) 7.23~7.28(1H, m) |

TABLE 111

| Ex. No. | Chemical Structure | $^1$H—NMR |
|---|---|---|
| 334 (672) | (5-methoxy-1-methylindol-3-yl-ethyl)-NH-(CH₂)₃-CH(P(O)(ONa)₂)₂ | δ(D₂O); 1.50(1H, tt, J=22Hz, 5Hz) 1.53–1.70(4H, m) 2.58(2H, t, J=7Hz), 2.82(4H, br. s) 3.55(3H, s), 3.72(3H, s) 6.78(1H, dd, J=2Hz, 8Hz) 6.98(1H, s), 7.05(1H, d, J=2Hz) 7.20(1H, d, J=8Hz) |
| 335 (673) | (5-methoxy-1-cyanomethylindol-3-yl-ethyl)-NH-(CH₂)₃-CH(P(O)(ONa)₂)₂ | δ(D₂O); 1.53–1.80(5H, m), 2.83–2.92(2H, m) 2.98(2H, t, J=7Hz), 3.12–3.20(2H, m) 3.73(3H, s,), 6.80(1H, dd, J=8Hz, 2Hz) 7.02(1H, d, J=2Hz), 7.07(1H, s) 7.10(1H, d, J=8Hz) |

TABLE 112

| Ex. No. | Chemical Structure | $^1$H—NMR |
|---|---|---|
| 336 (685) | (5-methoxy-1-methoxymethylindol-3-yl-ethyl)-N(Me)-(CH₂)₃-CH(P(O)(ONa)₂)₂ | δ(D₂O); 1.50–1.68(5H, m), 2.22(3H, s), 2.40–2.49(2H, m), 2.62–2.70(2H, m) 2.76–2.83(2H, m), 3.07(3H, s) 3.72(3H, s), 5.32(2H, s) 6.81(1H, dd, J=2Hz, 8Hz) 7.07(1H, d, J=2Hz), 7.12(1H, s) 7.32(1H, d, J=8Hz) |
| 337 (664) | (2-methoxyphenyl-ethyl)-N(Me)-(CH₂)₃-CH(P(O)(ONa)₂)₂ | δ(D₂O); 1.50–1.65(5H, m), 2.19(3H, s) 2.38(2H, t, J=6Hz), 2.47–2.55(2H, m) 2.64–2.72(2H, m), 3.69(3H, s) 6.82(1H, t, J=9Hz), 6.89(1H, d, J=9Hz) 7.12(1H, d, J=9Hz) |
| 338 (730) | (2-methoxyphenyl-propyl)-N(Me)-(CH₂)₃-CH(P(O)(ONa)₂)₂ | δ(D₂O); 1.45–1.68(5H, m), 2.12(3H, s) 2.32–2.41(4H, m), 2.26(2H, t, J=7Hz) 3.70(3H, s), 6.82(1H, t, J=9Hz) 6.92(1H, d, J=9Hz), 7.10–7.15(2H, m) |

TABLE 113

| Ex. No. | Chemical Structure | ¹H—NMR |
|---|---|---|
| 339 (646) | [structure: 2,3-dimethoxyphenyl-propyl-N(Me)-butyl-CH(P(ONa)₂=O)₂] | δ(D₂O); 1.40~1.70(7H, m), 2.07(3H, s) 2.23~2.38(4H, m), 2.47(2H, t, J=7Hz) 3.61(1H, s), 3.70(3H, s) 6.78(1H, d, J=9Hz), 6.81(1H, d, J=9Hz) 6.97(1H, t, J=9Hz) |
| 340 (765) | [structure: 4-(1-hydroxy-2-methylpropyl)phenyl-propyl-N(Me)-butyl-CH(P(ONa)₂=O)₂] | δ(D₂O); 0.63(3H, d, J=7Hz), 0.70(3H, d, J=7Hz) 0.98(1H, t, J=7Hz), 1.45~1.68(5H, m) 2.12(3H, s), 2.32~2.41(4H, m) 2.26(2H, d, J=7Hz), 4.18~4.20(1H, m) 6.82(2H, d, J=9Hz), 7.22(2H, 2H, d, J=9Hz) |
| 341 (619) | [structure: 4-fluorophenyl-N(Me)-ethyl-N(Me)-butyl-CH(P(ONa)₂=O)₂] | δ(D₂O/DSS); 1.62~1.78(5H, m), 2.24(3H, s) 2.44(2H, t, J=7Hz), 2.56(2H, t, J=8Hz) 2.82(3H, s), 3.40(2H, t, J=8Hz) 6.95~7.00(2H, m), 7.03~7.12(2H, m) |

TABLE 114

| Ex. No. | Chemical Structure | ¹H—NMR |
|---|---|---|
| 342 (690) | [structure: 4-fluorophenyl-N(SO₂Me)-propyl-N(Me)-butyl-CH(P(ONa)₂=O)₂] | δ(D₂O); 1.39~1.56(7H, m), 1.96(3H, s) 2.18(2H, t, J=7Hz), 2.30(2H, t, J=8Hz) 2.93(3H, s), 3.52(2H, t, J=7Hz) 7.06(2H, t, J=9Hz) 7.29(2H, dd, J=9Hz, 5Hz) |
| 343 (597) | [structure: 2-methoxyphenyl-N(Me)-ethyl-N(Me)-butyl-CH(P(ONa)₂=O)₂] | δ(D₂O); 1.42~1.61(5H, m), 2.05(3H, s) 2.25(2H, t, J=7Hz), 2.37~2.44(2H, m) 2.54(3H, s), 2.95~3.02(2H, m) 3.71(3H, m), 6.85(1H, t, J=8Hz) 6.89(1H, d, J=8Hz), 6.98(1H, t, J=8Hz) 7.03(1H, t, J=8Hz) |
| 344 (658) | [structure: 2-thienyl-CO-propyl-N(Me)-butyl-CH(P(ONa)₂=O)₂] | δ(D₂O); 1.50~1.66(5H, m), 1.73~1.81(2H, m) 2.14(3H, s), 2.33~2.40(4H, m) 2.91(2H, t, J=7Hz) 7.10(1H, dd, J=4Hz, 5Hz) 7.73~7.76(1H, m) 7.82(1H, dd, J=1Hz, 4Hz) |

TABLE 115

| Ex. No. | Chemical Structure | ¹H—NMR |
|---|---|---|
| 345 (635) | [structure: benzyl-CH(COONa)-NH-propyl-CH(P(ONa)₂=O)₂] | δ(D₂O); 1.43~1.72(5H, m) 2.74(1H, dd, J=13Hz, 9Hz) 2.98(1H, dd, J=12Hz, 4Hz) 3.79(2H, s), 4.01~4.08(1H, m) 7.10~7.18(3H, m), 7.18~7.25(2H, m) |

TABLE 115-continued

| Ex. No. | Chemical Structure | $^1$H—NMR |
|---|---|---|
| 346 (638) | (structure) | δ(D$_2$O); 1.50~1.80(5H, m), 2.60~2.68(1H, m) 2.79(2.87 (1H, m), 3.72~3.93(2H, m) 3.93~4.05(1H, m), 6.43(2H, d, J=8Hz) 6.87(2H, d, J=8Hz) |

TABLE 116

| Ex. No. | Chemical Structure | $^1$H—NMR |
|---|---|---|
| 347 (627) | (structure) | δ(D$_2$O); 1.51~1.68(6H, m), 1.68~1.77(1H, m) 1.77~1.97(2H, m), 2.15 (3H, s) 2.33~2.42(2H, m), 2.42~2.53(2H, m) 2.71~2.80(1H, m), 3.68(3H, s) 4.03~4.15(2H, m), 6.73~6.82(3H, m) |
| 348 (583) | (structure) | δ(D$_2$O); 1.59~1.81(5H, m), 2.40~2.49(2H, m) 2.61~2.71(2H, m), 2.83~2.93(2H, m) 3.23~3.33(2H, m), 3.66(3H, s) 5.93(1H, s), 6.87(1H, t, J=7Hz) 6.92(1H, d, J=8Hz), 7.08(1H, d, J=7Hz) 7.19(1H, t, J=8Hz) |
| 349 (605) | (structure) | δ(D$_2$O); 1.50~1.70(9H, m), 2.08~2.20(2H, m) 2.32~2.42(2H, m), 2.83~2.91(1H, m) 2.97~3.06(2H, m), 3.69(3H, s) 6.86~6.93(2H, m), 7.13(1H, t, J=8Hz) 7.19(1H, d, J=8Hz) |

TABLE 117

| Ex. No. | Chemical Structure | $^1$H—NMR |
|---|---|---|
| 350 (683) | (structure) | δ(D$_2$O); 1.54~1.66(6H, m), 1.72~1.83(1H, m) 2.29(1H, t, J=9Hz), 2.34~2.81(8H, m) 3.67(3H, m), 6.82(1H, t, J=8Hz) 6.88(1H, d, J=8Hz), 7.07~7.15(2H, m) |

TABLE 117-continued

| Ex. No. | Chemical Structure | ¹H—NMR |
|---|---|---|
| 351 (671) | (structure) | δ(D₂O/DSS); 1.68~1.86(5H, m), 2.56~2.67(4H, m) 2.81(2H, t, J=7Hz), 3.45(2H, s) 3.84(3H, s), 6.59(1H, s) 7.02~7.10(2H, m), 7.31(1H, t, J=8Hz) 7.44(1H, d, J=8Hz) |
| 352 (621) | (structure) | δ(D₂O); 1.5~1.68(5H, m), 2.26~2.32(2H, m) 2.40(2H, t, J=7Hz), 2.47~2.60(4H, m) 3.04~3.14(1H, m), 3.58(2H, s) 7.29(1H, t, J=7Hz), 7.44(1H, d, J=7Hz) 7.54(1H, t, J=7Hz), 7.59(1H, t, J=7Hz) |

TABLE 118

| Ex. No. | Chemical Structure | ¹H—NMR |
|---|---|---|
| 353 (620) | (structure) | δ(D₂O); 1.15~1.19(2H, m) 1.33(1H, dq, J=2Hz, 7Hz) 1.44~1.64(6H, m), 1.80~1.94(2H, m) 1.97(1H, dt, J=1Hz, 7Hz) 2.24(2H, t, J=7Hz), 2.66~2.72(1H, m) 2.81(1H, br. d, J=12Hz) 2.88(1H, d, J=18Hz) 2.91(1H, br. d, J=12Hz) 3.08(1H, d, J=18Hz) 7.28(1H, t, J=7Hz), 7.45(1H, d, J=7Hz), 7.55(1H, d, J=7Hz), 7.56(1H, t, J=7Hz) |
| 354 (632) | (structure) | δ(D₂O); 1.50~1.75(7H, m), 1.85~1.97(2H, m) 2.24~2.40(4H, m), 2.54(3H, s) 2.55~2.70(2H, m), 6.94(1H, t, J=7Hz) 7.07(1H, d, J=7Hz), 7.43(1H, t, J=7Hz) 7.50(1H, d, J=7Hz) |
| 355 (633) | (structure) | δ(D₂O); 1.47~1.66(7H, m), 1.83~1.93(2H, m) 2.20~2.32(2H, m), 2.68(2H, br. s) 4.36~4.41(2H, m), 7.16~7.20(1H, m) 7.22~7.26(1H, m), 7.25(1H, s) 7.32(1H, t, J=8Hz) |

TABLE 119

| Ex. No. | Chemical Structure | ¹H—NMR |
|---|---|---|
| 356 (637) | (structure: 2-methoxyphenyl-O-piperidinyl-N-(CH₂)₃-CH(P(ONa)₂=O)₂) | δ(D₂O); 1.49~1.64(7H, m), 1.84~1.93(2H, m) 2.10~2.25(2H, m), 2.27(1H, t, J=7Hz) 2.70~2.80(2H, m), 3.69(3H, s) 4.27(1H, br. s) 6.84(1H, dt, J=2Hz, 7Hz) 6.91(1H, dt, J=2Hz, 7Hz) 6.94(1H, dd, J=2Hz, 7Hz) 6.97(1H, dd, J=2Hz, 7Hz) |
| 357 (631) | (structure: 2-cyanophenyl-O-piperidinyl-N-(CH₂)₃-CH(P(ONa)₂=O)₂) | δ(D₂O); 1.50~1.75(7H, m), 1.80~1.95(2H, m) 2.20~2.38(4H, m), 2.45~2.70(2H, m) 4.50~4.62(1H, m), 6.96(1H, t, J=7Hz) 7.10(1H, d, J=7Hz), 7.50(1H, t, J=7Hz) 7.56(1H, t, J=7Hz) |
| 358 (596) | (structure: 2-MeO-phenyl-piperazinyl-(CH₂)₃-CH(P(ONa)₂=O)₂) | δ(D₂O); 1.46~1.67(5H, m), 2.30(2H, t, J=7Hz) 2.4~3.1(8H, br. m), 3.69(3H, s) 6.83~6.92(2H, m), 6.95~7.03(2H, m) |

TABLE 120

| Ex. No. | Chemical Structure | ¹H—NMR |
|---|---|---|
| 359 (613) | (structure: 4-fluorophenyl-piperidinyl-N(Me)-(CH₂)₃-CH(P(ONa)₂=O)₂) | δ(D₂O); 1.43~1.65(7H, m) 1.83(2H, d, J=12Hz), 2.11(3H, s) 2.37~2.62(5H, m) 3.42(2H, d, J=Hz) 6.90~7.00(4H, m) |
| 360 (666) | (structure: 2-MeO, CN-cyclohexyl-N(Me)-(CH₂)₃-CH(P(ONa)₂=O)₂) | δ(D₂O/DSS); 1.65~1.92(9H, m) 2.07(2H, d, J=12Hz), 2.33(3H, s) 2.51(2H, d, J=11Hz) 2.62(2H, t, J=7Hz) 2.70(1H, tt, J=11Hz, 3Hz) 3.93(3H, s), 7.08(1H, t, J=8Hz) 7.17(1H, d, J=8Hz), 7.39~7.46(2H, m) |
| 361 (694) | (structure: MeSO₂-N(Me)-phenyl-C(=O)-piperidinyl-N-(CH₂)₃-CH(P(ONa)₂=O)₂) | δ(D₂O); 1.43~1.65(7H, m), 1.70~1.80(2H, m) 2.10(2H, t, J=10Hz) 2.24~2.33(2H, m), 2.86~2.96(2H, m) 2.92~2.33(2H, m), 2.86~2.96(2H, m) 2.92(3H, s), 3.02(3H, s) 3.30~3.40(1H, m), 7.41(2H, d, J=8Hz) 7.87(2H, d, J=8Hz) |

TABLE 121

| Ex. No. | Chemical Structure | $^1$H—NMR |
|---|---|---|
| 362 (678) | (structure: sulfonamide-phenyl-C(O)-piperidine-N-(CH2)3-CH(P(ONa)2=O)2 with -S(O)2-NH- group) | δ(D₂O); 1.56–1.80(7H, m), 1.80–1.86(2H, m) 2.23(2H, t, J=12Hz) 2.38–2.48(2H, m), 2.93(3H, s) 3.01(2H, dd, J=12Hz, 2Hz) 3.40–3.50(1H, m), 7.00(2H, d, J=8Hz) 7.86(2H, d, J=8Hz) |
| 363 (724) | (structure with -S(O)2-N(CH2CN)- on phenyl) | δ(D₂O); 1.43–1.91(9H, m), 2.03–2.47(4H, m) 2.85–3.12(2H, m), 3.02(3H, s) 3.30–3.43(1H, m), 4.68–4.74(2H, m) 7.42–7.52(2H, m), 7.77–7.95(2H, m) |
| 364 (715) | (structure with -S(O)2-N(Et)- on phenyl) | δ(D₂O); 1.05(3H, t, J=7Hz), 1.55–1.82(7H, m) 1.84–1.93(2H, m) 2.23(2H, t, J=11Hz), 2.37–2.48(2H, m), 2.98–3.12(2H, m) 3.09(3H, s), 3.45–3.54(1H, m) 3.75(2H, q, J=7Hz), 7.53(2H, d, J=8Hz) 8.03(2H, d, J=8Hz) |

TABLE 122

| Ex. No. | Chemical Structure | $^1$H-NMR |
|---|---|---|
| 365 (515) | (structure: CH(OH)(CH3)-phenyl-thiophene-CH2-N(Me)-(CH2)3-CH(P(ONa)2=O)2) | δ(D₂O); 1.33(3H, d, J=8Hz), 1.45–1.70(5H, m) 2.09(3H, s), 2.32(2H, t, J=8Hz) 3.65(2H, s), 4.78(1H, q, J=8Hz) 6.89(1H, d, J=4Hz), 7.17–7.21(2H, m) 7.29(1H, t, J=8Hz) 7.45(1H, dt, J=8Hz, 1Hz) 7.51(1H, t, J=1Hz) |
| 366 (640) | (cinnamyl-type structure with N-acetyl) | δ(D₂O); 1.45–1.80(5H, m), 1.85(3H, s) 1.98(1.5H, s), 2.01(1.5H, s) 3.16–3.28(2H, m), 3.66(3H, s) 3.98(1H, d, J=7Hz), 4.03(1H, d, J=7Hz) 5.21(0.5H, t, J=7Hz) 5.28(0.5H, t, J=7Hz) 6.81–6.93(2H, m), 7.01–7.08(1H, m) 7.12–7.21(1H, m) |
| 367 (729) | (MeO-phenyl-(CH2)2-N(Me)-C(O)-CH2- with diphosphonate) | δ(D₂O); 1.50–1.72(3H, m), 1.73–1.98(4H, m) 2.55(2H, t, J=7Hz), 2.92(3H, s) 3.04–3.17(4H, m), 6.85(1H, t, J=9Hz) 6.91(1H, d, J=9Hz) 7.14(1H, dd, J=9Hz) |

Example 368

The compound of Example 368 listed in Table 123 was prepared by preparing a diphosphonic acid ester derivative in a similar manner to that of the Example 5 and deprotecting the ester derivative in a similar manner to that of the Example 14.

TABLE 123

| Ex. No. | Chemical Structure | ¹H-NMR |
|---|---|---|
| 368 | 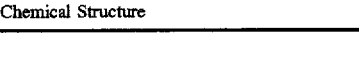 | δ(D$_2$O);<br>0.87–1.03(2H, m), 1.43–1.57(3H, m)<br>1.66(2H, d, J=12Hz)<br>1.72(1H, tt, J=22Hz, 6Hz)<br>1.99(2H, t, J=12Hz)<br>2.75(2H, d, J=12Hz), 3.54(2H, s)<br>6.33(1H, s), 7.47(1H, d, J=8Hz)<br>6.95(1H, t, J=8Hz), 7.04(1H, t, J=8Hz)<br>7.31(1H, d, J=8Hz) |

Example 369 to 374

The compounds of Examples 369 to 374 listed in Tables 124 and 125 were prepared by preparing diphosphonic acid ester derivatives in a similar manner to that of the Example 10 and deprotecting the ester derivatives in a similar manner to that of the Example 14.

TABLE 124

| Ex. No. | Chemical Structure | ¹H-NMR |
|---|---|---|
| 369 (754) | 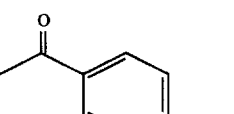 | δ(D$_2$O);<br>1.55(3H, s), 1.75(1H, tt, J=7Hz, 21Hz)<br>2.14–2.41(4H, m), 2.48(3H, s)<br>2.68(2H, t, J=7Hz), 5.23–5.30(1H, m)<br>7.24–7.34(2H, m), 7.78(2H, d, J=8Hz) |
| 370 (759) | 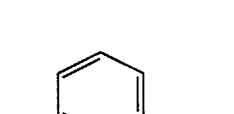 | δ(D$_2$O);<br>1.32–1.42(4H, m), 1.60–1.84(5H, m)<br>3.68(3H, s), 4.52(1H, t, J=6Hz)<br>6.86(1H, dd, J=3Hz, 8Hz)<br>6.93–7.01(2H, m), 7.18(1H, t, J=8Hz) |
| 371 (760) | 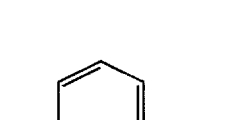 | δ(D$_2$O);<br>1.28–1.87(7H, m), 2.65(2H, t, J=7Hz)<br>3.73(3H, s), 6.84–7.03(1H, m)<br>7.10–7.28(3H, m) |

TABLE 125

| Ex. No. | Chemical Structure | ¹H-NMR |
|---|---|---|
| 372 (750) | 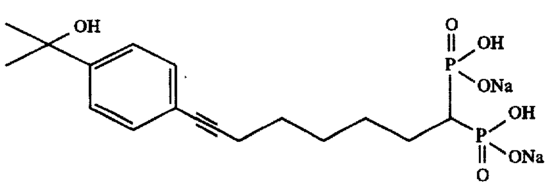 | δ(D$_2$O);<br>1.29(6H, s), 1.30–1.52(6H, m)<br>1.62–1.77(2H, m)<br>1.90(1H, tt, J=6Hz, 22Hz)<br>2.29(2H, t, J=6Hz), 7.17(2H, d, J=8Hz)<br>7.26(2H, d, J=8Hz) |

TABLE 125-continued

| Ex. No. | Chemical Structure | ¹H-NMR |
|---|---|---|
| 373 (610) | MeO-C₆H₄-N(piperidine-4-yl)-CH₂CH₂-CH(P(ONa)₂=O)(P(ONa)₂=O) | δ(D₂O/DSS); 1.31~1.59(5H, m) 1.72(1H, tt, J=22Hz, 7Hz) 1.77~1.92(4H, m) 2.59(2H, t, J=11Hz) 3.35(2H, d, J=11Hz) 3.85(3H, s), 6.97~7.06(2H, m) 7.10~7.20(2H, m) |
| 374 (609) | MeO-C₆H₄-N(piperidin-4-ylidene)=CH-CH₂-CH(P(ONa)₂=O)(P(ONa)₂=O) | δ(D₂O/DSS); 1.73(1H, tt, J=21Hz, 1.73Hz) 2.38(2H, t, J=5Hz), 2.47~2.62(4H, m) 2.99(4H, b. s), 3.87(3H, s) 5.63(1H, t, J=7Hz), 7.00(1H, t, J=8Hz) 7.05(1H, d, J=8Hz), 7.10~7.17(2H, m) |

Example 375

The compound of Example 375 listed in Table 126 was prepared by preparing a diphosphonic acid ester derivative in a similar manner to those of the Examples 11 and 12 and deprotecting the ester derivative in a similar manner to that of the Example 14.

TABLE 126

| Ex. No. | Chemical Structure | ¹H-NMR |
|---|---|---|
| 375 (732) | [structure with P(ONa)₂ groups on benzylidene-N-cinnamyl arrangement with 4-F-phenyl] | δ(D₂O/DSS); 2.86(3H, s), 3.17(1H, t, J=23Hz) 4.02(2H, d, J=6Hz) 6.25(1H, dt, J=16Hz, 6Hz) 6.61(1H, d, J=16Hz) 6.98(2H, d, J=8Hz), 7.07(2H, t, J=9Hz) 7.38~7.44(4H, m) |

Example 376 to 384

The compounds of Examples 376 to 384 listed in Tables 127 to 129 were prepared by preparing diphosphonic acid ester derivatives in a similar manner to that of the Example 13 and deprotecting the ester derivatives in a similar manner to that of the Example 14.

TABLE 127

| Ex. No. | Chemical Structure | ¹H-NMR |
|---|---|---|
| 376 (548) | 3-acetylphenyl-thiophene-CH₂-N(Me)-(CH₂)₃-CH(P(ONa)₂=O)₂ | δ(D₂O); 1.47~1.70(5H, m), 2.10(3H, s) 2.33(2H, t, J=7Hz), 2.50(3H, s) 3.66(2H, s), 6.90(1H, d, J=4Hz) 7.21(1H, d, J=4Hz), 7.37(1H, t, J=8Hz) 7.71(2H, dt, J=8Hz, 2Hz) 7.96(1H, t, J=2Hz) |

TABLE 127-continued

| Ex. No. | Chemical Structure | ¹H-NMR |
|---|---|---|
| 377 (543) | (structure: 4-acetylphenyl-thiophene-CH₂-N(CH₃)-(CH₂)₃-CH(P(ONa)₂=O)₂) | δ(D₂O); 1.50~1.70(5H, m), 2.09(3H, s) 2.32(2H, t, J=7Hz), 2.43(3H, s) 3.65(2H, s), 6.89(1H, d, J=4Hz) 7.24(1H, d, J=4Hz) 7.51(2H, dt, J=8Hz, 2Hz) 7.73(2H, dt, J=8Hz, 2Hz) |
| 378 (511) | (structure: CH₃-CO-CH₂-CH₂-phenyl-CH₂-phenyl-CH₂-N(CH₃)-(CH₂)₃-CH(P(ONa)₂=O)₂) | δ(D₂O); 1.60~1.75(3H, m), 1.81~1.90(2H, m) 1.94(3H, s), 2.46(3H, s) 2.50~2.61(4H, m) 2.97(2H, br. t, J=8Hz), 3.74(2H, br) 4.03(2H, br. s), 6.86~7.02(4H, m) 7.07~7.23(4H, m) |

TABLE 128

| Ex. No. | Chemical Structure | ¹H-NMR |
|---|---|---|
| 379 (514) | (structure with P(=O)(OEt)(ONa) groups) | δ(D₂O); 1.05(6H, t, J=7Hz), 1.55~1.85(5H, m) 2.28(3H, s), 2.47(3H, s) 2.57~2.65(2H, m, 3.70~3.83(6H, m) 3.93(2H, s), 7.18(1H, d, J=8Hz) 7.23(1H, d, J=8Hz), 7.27(1H, d, J=8Hz) 7.77(1H, d, J=8Hz) |
| 380 (648) | (structure with OMe and P(ONa)₂ groups) | δ(D₂O); 1.45~4.65(5H, m), 1.82(3H, s) 2.14(3H, s), 2.36~2.40(2H, m) 2.42(3H, s), 3.10(2H, d, J=7Hz) 3.75(3H, s), 5.43(1H, t, J=7Hz) 6.96(1H, d, J=9Hz), 7.61(1H, d, J=2Hz) 7.80(1H, dd, J=9Hz, 2Hz) |
| 381 (656) | (thiophene structure with P(ONa)₂ groups) | δ(D₂O); 1.47~1.63(5H, m), 1.92(3H, s) 2.08(3H, s), 2.30(2H, t, J=7Hz) 2.40(3H, s), 3.11(2H, d, J=7Hz) 6.01(1H, t, J=7Hz), 7.07(1H, d, J=4Hz) 7.65(1H, d, J=4Hz) |

TABLE 129

| Ex. No. | Chemical Structure | ¹H-NMR |
|---|---|---|
| 382 (555) | (diacetyl phenyl structure with P(ONa)₂ groups) | δ(D₂O); 1.63~1.83(3H, m), 1.88~1.97(2H, m) 2.09(3H, s), 2.56(6H, s) 2.76(3H, s), 3.12(2H, t, J=7Hz) 3.88(2H, d, J=7Hz), 5.85(1H, t, J=7Hz) 8.07(2H, s), 8.22(1H, s) |

TABLE 129-continued

| Ex. No. | Chemical Structure | $^1$H-NMR |
|---|---|---|
| 383 (645) | [structure: 2-acetyl-6-substituted pyridine with branched chain bearing N and two P(ONa)₂ groups] | δ(D₂O); 1.15(3H, d, J=7Hz), 1.55~1.85(7H, m) 1.97(3H, s), 2.08~2.33(4H, m) 2.77~2.86(1H, m), 7.45(1H, d, J=8Hz) 7.72~7.83(2H, m) |
| 384 (751) | [structure: 4-acetylphenyl chain with N and two P(ONa)₂ groups] | δ(D₂O); 1.42~1.76(7H, m), 2.10(3H, s) 2.20~2.40(4H, m), 2.48(3H, s) 2.52~2.60(2H, t, J=7Hz) 7.27(2H, d, J=8Hz), 7.78(2H, d, J=8Hz) |

Example 385 to 425

The compounds of Examples 385 to 425 listed in Tables 130 to 143 were prepared by preparing diphosphonic acid ester derivatives in a similar manner to that of tie Example 1 and deprotecting the ester derivatives in a similar manner to that of the Example 16.

TABLE 130

| Ex. No. | Chemical Structure | $^1$H-NMR |
|---|---|---|
| 385 (738) | [structure: benzofuran with hydroxyethyl substituent, CH₂N chain with two P(OH)₂ groups] | δ(D₂O); 1.36(3H, d, J=7Hz), 1.65~1.82(2H, m) 1.84~2.00(2H, m) 1.99(1H, tt, J=7Hz, 24Hz) 2.76(3H, s), 3.05(1H, dt, J=7Hz, 12Hz) 3.15(1H, dt, J=7Hz, 12Hz) 4.38(1H, d, J=14Hz), 4.47(1H, d, J=14Hz) 4.86(1H, q, J=7Hz), 7.01(1H, s) 7.30(1H, dd, J=2Hz, 9Hz) 7.43(1H, d, J=9Hz), 7.55(1H, d, J=2Hz) |
| 386 (733) | [structure: benzofuran with hydroxyethyl substituent, CH₂N chain with two P(OH)₂ groups] | δ(D₂O—NaOD); 1.42(3H, d, J=7Hz), 1.48~1.68(5H, m) 2.02(3H, s), 2.32(2H, t, J=7Hz) 3.52(2H, s), 4.85(1H, q, J=7Hz) 6.59(1H, s), 7.14(1H, dd, J=2Hz, 8Hz) 7.33(1H, d, J=8Hz), 7.43(1H, s) |
| 387 (696) | [structure: quinoline-6-ylmethyl with N chain and two P(OH)₂ groups] | δ(D₂O); 1.62~1.95(5H, m), 2.84(3H, br.) 4.01(2H, br.), 4.58(2H, br.) 7.68~7.85(3H, m), 7.97(1H, d, J=8Hz) 8.64~8.82(2H, m) |

TABLE 131

| Ex. No. | Chemical Structure | ¹H-NMR |
|---|---|---|
| 388 (630) | (MeO-benzothiazole)-N(Me)-CH₂CH₂CH₂-CH(P(OH)₂=O)(P(OH)₂=O) | δ(D₂O); 1.38~1.77(5H, m), 2.97(3H, br. s) 3.24~3.31(2H, m), 3.71(3H, s) 6.74(1H, dd, J=4Hz, 8Hz) 6.87(1H, dt, J=4Hz, 8Hz) 7.09(1H, dd, J=4Hz, 8Hz) |
| 389 (680) | (benzothiazole)-CH₂-N(Me)-CH₂CH₂CH₂-CH(P(OH)₂=O)(P(OH)₂=O) | δ(D₂O); 1.57~1.86(5H, m), 2.64(3H, s) 2.94~3.00(2H, m), 4.60(2H, br.) 7.31(1H, t, J=8Hz), 7.40(1H, t, J=8Hz) 7.78(1H, d, J=8Hz), 7.84(1H, d, J=8Hz) |
| 390 (721) | (benzothiazole)-CH₂-N(CH₂CH₂OH)-CH₂CH₂CH₂-CH(P(OH)₂=O)(P(OH)₂=O) | δ(D₂O); 1.54~1.82(5H, m) 3.35~3.42(2H, br.) 3.50~3.54(2H, br.) 3.92~4.03(2H, br.) 4.35~4.45(2H, m), 7.37~7.51(2H, m) 7.90~7.97(2H, m) |

TABLE 132

| Ex. No. | Chemical Structure | ¹H-NMR |
|---|---|---|
| 391 (756) | (1,4-naphthoquinone-2-yl)-CH₂-N(Me)-CH₂CH₂CH₂-CH(P(OH)₂=O)(P(OH)₂=O) | δ(D₂O); 1.69~1.86(2H, m), 1.92~2.03(2H, m) 2.11(1H, tt, J=5Hz, 23Hz) 2.76(3H, s), 3.07~3.25(2H, m) 4.00(1H, d, J=13Hz) 4.32(1H, d, J=13Hz) 7.11(1H, s), 7.68~7.73(2H, m) 7.85~7.91(1H, m), 7.91~7.96(1H, m) |
| 392 (764) | (3-MeO, 2-OMe-phenyl)-CH(OH)-(thiophene)-CH₂-N(Me)-CH₂CH₂CH₂-CH(P(OH)₂=O)(P(OH)₂=O) | δ(D₂O); 1.72~1.98(4H, m) 1.97(1H, tt, J=6Hz, 23Hz) 2.63(3H, s), 2.87~2.98(1H, m) 3.02~3.12(1H, m), 3.52(3H, s) 3.70(3H, s), 4.26(1H, dd, J=15Hz, 2Hz) 4.38(1H, dd, J=15Hz, 3Hz), 6.20(1H, s) 6.77(1H, d, J=3Hz) 6.94(1H, dd, J=8Hz, 1Hz) 6.98~7.03(2H, m), 7.07(1H, t, J=8Hz) |
| 393 (600) | (thiophen-3-yl)-C(Me)=CH-CH₂-N(Me)-CH₂CH₂CH₂-CH(P(OH)₂=O)(P(OH)₂=O) | δ(D₂O); 1.60~1.78(2H, m), 1.79~2.00(6H, m) 2.65(3H, s), 2.89~3.00(1H, m) 3.01~3.10(1H, m) 3.75(1H, dd, J=13Hz, 7Hz) 3.81(1H, dd, J=13Hz, 7Hz) 5.80(1H, d, J=7Hz), 7.20(1H, d, J=5Hz) 7.24(1H, d, J=5Hz), 7.34(1H, s) |

TABLE 133

| Ex. No. | Chemical Structure | ¹H-NMR |
|---|---|---|
| 394 (599) | (N-methylpyrrol-2-yl structure) | δ(D₂O); 1.65~2.08(8H, m), 2.45(3H, s) 2.95~3.02(1H, m), 3.05~3.18(1H, m) 3.50(3H, s), 3.77(1H, dd, J=13Hz, 7Hz) 3.85(1H, dd, J=13Hz, 7Hz) 5.40(1H, d, J=7Hz) |
| 395 (581) | (N-methylpyrrol-3-yl structure) | δ(D₂O); 1.65~1.80(2H, m), 1.80~2.05(6H, m) 2.65(3H, s), 2.89~2.99(1H, m) 3.03~3.12(1H, m), 3.45(3H, s) 3.70(1H, dd, J=13Hz, 7Hz) 3.79(1H, dd, J=13Hz, 7Hz) 5.60(1H, t, J=7Hz) |
| 396 (644) | (2-nitrophenyl structure) | δ(D₂O); 1.28~1.63(5H, m) 1.83(s) and 1.87(total 3H, s) 1.92(s) and 2.07(total 3H, s) 2.06(br.) and 2.28(total 2H, br.) 2.49~2.54(m) and 3.02~3.08 (total 2H, m) 5.32~5.40(m) and 5.44~5.50 (total 1H, m) 7.21~7.40(2H, m), 7.48~7.58(2H, m) 7.77(d, J=9Hz) and 7.89(total 2H, d, J=9Hz) |

TABLE 134

| Ex. No. | Chemical Structure | ¹H-NMR |
|---|---|---|
| 397 (662) | (2,6-dimethoxyphenyl structure) | δ(D₂O); 1.65~2.06(5H, m), 2.65(3H, s) 2.86~2.95(1H, m), 3.02~3.14(1H, m) 3.53~3.63(1H, m), 3.65(6H, s) 3.66~3.75(1H, m), 6.27~6.38(1H, m) 6.52(2H, d, J=8Hz) 6.82(1H, d, J=15Hz) 7.10(1H, d, J=8Hz) |
| 398 (603) | (2-methoxy-4-fluorophenyl structure) | δ(D₂O); 1.64~2.02(8H, m) 2.70(3H, s), 2.92~3.02(1H, m) 3.05~3.15(1H, m), 3.62(3H, s) 3.68(1H, dd, J=13Hz, 7Hz) 3.79(1H, dd, J=13Hz, 7Hz) 5.36(1H, t, J=7Hz) 6.55(1H, dd, J=9Hz, 9Hz) 6.68(1H, d, J=9Hz) 6.99(1H, dd, J=9Hz, 9Hz) |
| 399 (601) | (2,4-dimethoxyphenyl structure) | δ(D₂O); 1.63~2.05(8H, m), 2.68(3H, s) 2.92~3.01(1H, m), 3.05~3.16(1H, m) 3.62(3H, s), 3.63(3H, s) 3.66(1H, dd, J=13Hz, 7Hz) 3.78(1H, dd, J=13Hz, 7Hz) 5.35(1H, t, J=7Hz), 6.42(1H, d, J=9Hz) 6.47(1H, s), 6.97(1H, J=9Hz) |

TABLE 135

| Ex. No. | Chemical Structure | ¹H-NMR |
|---|---|---|
| 400 (622) | (structure) | δ(D₂O); 1.65~2.05(8H, m), 2.73(3H, s) 2.95~3.07(1H, m), 3.08~3.20(4H, m) 3.68(3H, s), 3.70~3.94(2H, m) 4.41(1H, d, J=7Hz), 4.47(1H, d, J=7Hz) 5.40(1H, t, J=7Hz), 6.95(1H, d, J=9Hz) 7.22(1H, d, J=9Hz), 7.28(1H, s) |
| 401 (623) | (structure) | δ(D₂O); 1.35~1.66(5H, m), 1.70(3H, s) 2.10(3H, s), 2.26~2.34(2H, m) 3.05(2H, d, J=7Hz), 3.64(6H, s) 5.20~5.24(1H, m), 6.63(2H, d, J=8Hz) 7.25(1H, t, J=8Hz) |
| 402 (614) | (structure) | δ(D₂O); 1.34~1.64(5H, m), 1.67(3H, s) 2.09(3H, s), 2.30(2H, br.) 3.03(2H, d, J=7Hz), 3.62(6H, s) 3.67(3H, s), 5.18(1H, br.) 6.19(2H, s) |

TABLE 136

| Ex. No. | Chemical Structure | ¹H-NMR |
|---|---|---|
| 403 (688) | (structure) | δ(D₂O); 1.64~1.98(5H, m), 2.74(3H, br.) 2.91~3.22(2H, m), 3.64~3.92(2H, m) 6.33~6.43(1H, m), 6.52~6.65(1H, m) 7.62~8.02(4H, m), 8.57~8.80(2H, m) |
| 404 (594) | (structure) | δ(D₂O); 1.63~1.92(5H, m), 1.96(3H, s) 2.72(3H, s), 3.06(2H, br.) 3.84(2H, br.), 5.82(2H, s) 5.87(1H, t, J=7Hz), 6.69~6.82(3H, m) |
| 405 (592) | (structure) | δ(D₂O); 1.62~2.12(5H, m), 1.94(3H, s) 2.70(3H, s), 2.93~3.30(1H, m) 3.06~3.18(1H, m) 3.75(1H, dd, J=8Hz, 14Hz) 3.84 1H, dd, J=8Hz, 14Hz) 4.14(4H, m), 5.63(1H, br. t, J=7Hz) 6.76(1H, d, J=9Hz), 6.87~6.93(2H, m) |

TABLE 137

| Ex. No. | Chemical Structure | ¹H-NMR |
|---|---|---|
| 406 (624) | (structure) | δ(D₂O); 1.38~1.53(5H, m), 1.74(3H, s) 1.87(3H, s), 2.05(2H, br.) 2.52(2H, d, J=6Hz), 3.63(6H, s) 5.53(1H, t, J=6Hz), 6.61(2H, d, J=8Hz) 7.17(1H, t, J=8Hz) |

TABLE 137-continued

| Ex. No. | Chemical Structure | $^1$H-NMR |
|---|---|---|
| 407 (615) | 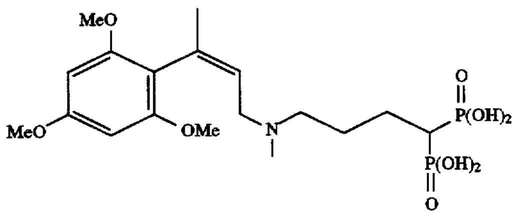 | δ(D$_2$O); 1.28~1.58(5H, m), 1.72(3H, s) 1.86(3H, s), 2.02~2.08(2H, m) 2.52(2H, d, J=6Hz), 3.62(6H, s) 3.67(3H, s), 5.52(1H, t, J=6Hz) 6.19(2H, s) |
| 408 (580) | 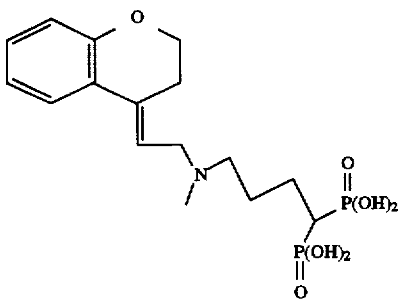 | δ(D$_2$O); 1.67~1.98(4H, m) 2.00(1H, tt, J=24Hz, 8Hz) 2.63(2H, t, J=8Hz), 2.72(3H, s) 2.96~3.05(1H, m), 3.09~3.19(1H, m) 3.79(1H, dd, J=9Hz, 15Hz) 3.89(1H, dd, J=9Hz, 15Hz) 4.10(2H, t, J=8Hz), 6.01(1H, t, J=9Hz) 6.77(1H, d, J=8Hz), 6.88(1H, t, J=8Hz) 7.15(1H, t, J=8Hz), 7.57(1H, d, J=8Hz) |

TABLE 138

| Ex. No. | Chemical Structure | $^1$H-NMR |
|---|---|---|
| 409 (716) | 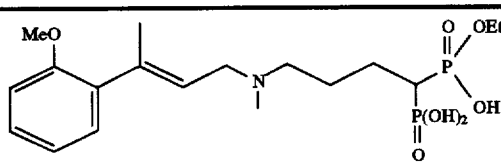 | δ(D$_2$O—NaOD); 1.20(3H, t, J=7Hz), 1.48~1.70(3H, m) 1.85~1.94(2H, m), 1.94(3H, d, J=1Hz) 2.85(3H, s), 3.11~3.28(4H, m) 3.67(3H, s), 3.89(2H, d, J=8Hz) 5.47(1H, dt, J=1Hz, 8Hz) 6.88(1H, dt, J=1Hz, 8Hz) 6.93(1H, d, J=8Hz) 7.08(1H, dd, J=2Hz, 8Hz) 7.22(1H, dt, J=2Hz, 8Hz) |
| 410 (617) | 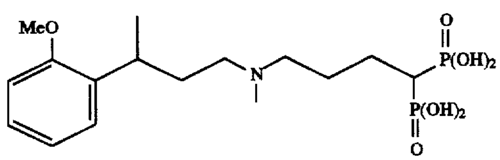 | δ(D$_2$O); 1.08(3H, d, J=7Hz), 1.61~2.05(8H, m) 2.62(3H, s), 2.85~3.02(4H, m) 3.03~3.15(2H, m), 3.64(3H, s) 6.87~6.95(2H, m), 7.11~7.19(2H, m) |
| 411 (653) | 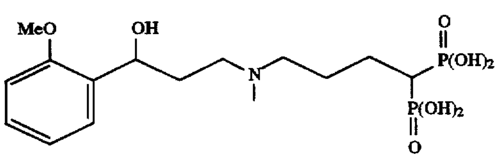 | δ(D$_2$O+NaOD/DSS); 1.56(1H, tt, J=22Hz, 5Hz) 1.60~1.75(4H, m), 1.98(2H, q, J=7Hz) 2.18(3H, s), 2.38~2.42(3H, m) 2.54(1H, dt, J=13Hz, 8Hz) 3.85(3H, s), 5.04(1H, t, J=7Hz) 7.03~7.10(2H, m), 7.36(1H, t, J=8Hz) 7.40(1H, d, J=8Hz) |

TABLE 139

| Ex. No. | Chemical Structure | $^1$H-NMR |
|---|---|---|
| 412 (727) | [structure: 4-(methylthio)phenyl-CH2CH2CH2-N(CH3)-CH2CH2CH2-CH(P(O)(OH)2)2] | δ(D$_2$O); 1.63–1.98(7H, m), 2.34(3H, s) 2.50–2.57(2H, m), 2.67(3H, s) 2.86–3.10(4H, m), 7.10(2H, d, J=8Hz) 7.16(2H, d, J=8Hz) |
| 413 (728) | [structure: 4-(methylsulfonyl)phenyl-CH2CH2CH2-N(CH3)-CH2CH2CH2-CH(P(O)(OH)2)2] | δ(D$_2$O); 1.63–1.98(6H, m), 2.02–2.20(1H, m) 2.60–2.73(2H, m), 2.67(3H, s) 2.87–3.10(4H, m), 3.08(3H, s) 7.37(2H, d, J=8Hz), 7.72(2H, d, J=8Hz) |
| 414 (718) | [structure: 4-hydroxyphenyl-CH2CH2CH2-N(CH3)-CH2CH2CH2-CH(P(O)(OH)2)2] | δ(D$_2$O); 1.60–2.07(8H, m), 2.70(3H, s) 2.92–3.01(1H, m), 3.05–3.15(1H, m) 3.75(1H, dd, J=15Hz, 7Hz) 3.82(1H, dd, J=15Hz, 7Hz) 5.61(1H, t, J=7Hz), 6.72(2H, d, J=9Hz) 7.22(2H, d, J=9Hz) |

TABLE 140

| Ex. No. | Chemical Structure | $^1$H-NMR |
|---|---|---|
| 415 (703) | [structure: 4-(hydroxymethyl)phenyl-CH2CH2CH2-N(CH3)-CH2CH2CH2-CH(P(O)(OH)2)2] | δ(D$_2$O); 1.62–2.00(7H, m), 2.57(2H, t, J=7Hz) 2.67(3H, s), 2.87–2.97(2H, m) 2.99–3.07(2H, m), 4.45(2H, s) 7.14(2H, d, J=8Hz), 7.19(2H, d, J=8Hz) |
| 416 (704) | [structure: 4-(1-hydroxyethyl)phenyl-CH2CH2CH2-N(CH3)-CH2CH2CH2-CH(P(O)(OH)2)2] | δ(D$_2$O); 1.30(3H, d, J=7Hz), 1.62–2.00(7H, m) 2.57(2H, t, J=8Hz), 2.67(3H, s) 2.88–2.97(2H, m), 3.00–3.10(2H, m) 4.73(1H, q, J=7Hz), 7.13(2H, d, J=8Hz) 7.21(2H, d, J=8Hz) |
| 417 (747) | [structure: 4-(2-hydroxypropan-2-yl)phenyl-CH2CH2CH2-N(CH3)-CH2CH2CH2-CH(P(O)(OH)2)2] | δ(D$_2$O); 1.40(6H, s), 1.62–1.95(6H, m) 1.95(1H, tt, J=22Hz, 5Hz) 2.56(2H, t, J=7Hz), 2.68(3H, s) 2.88–2.98(2H, m), 3.01–3.10(2H, m) 7.15(2H, d, J=8Hz), 7.31(2H, d, J=8Hz) |

TABLE 141

| Ex. No. | Chemical Structure | $^1$H-NMR |
|---|---|---|
| 418 (746) | [structure: 2,5-dimethyl-1,4-benzoquinone-3-yl-CH2CH2CH2-N(CH3)-CH2CH2CH2-CH(P(O)(OH)2)2] | δ(D$_2$O); 1.60–1.91(6H, m), 1.77(6H, s) 1.82(3H, s) 2.00(1H, tt, J=22Hz, 5Hz) 2.35(2H, t, J=7Hz), 2.69(3H, s) 2.91–3.02(2H, m), 3.02–3.14(2H, m) |

TABLE 141-continued

| Ex. No. | Chemical Structure | ¹H-NMR |
|---|---|---|
| 419 (663) | (structure: 2,6-dimethoxyphenyl-propyl-N(Me)-butyl-gem-bisphosphonate) | δ(D₂O); 1.63–2.06(7H, m), 2.55(3H, s) 2.84–3.05(6H, m), 3.68(6H, s) 6.58(2H, d, J=8Hz), 7.12(1H, t, J=8Hz) |
| 420 (674) | (structure: benzothiazol-2-yl-propyl-N(Me)-butyl-gem-bisphosphonate) | δ(D₂O); 1.55–1.85(5H, m), 2.08–2.17(2H, m) 2.64(3H, s), 2.93–3.11(6H, m) 7.31(1H, t, J=8Hz), 7.40(1H, t, J=8Hz) 7.78(1H, d, J=8Hz), 7.84(1H, d, J=8Hz) |

TABLE 142

| Ex. No. | Chemical Structure | ¹H-NMR |
|---|---|---|
| 421 (742) | (structure: 1,3-dihydroxyindan-2-yl-propyl-N(Me)-butyl-gem-bisphosphonate) | δ(D₂O); 1.56–2.01(6H, m)2.10(1H, tt, J=6Hz, 23Hz)2.32(d, J=5Hz) and 2.45(total 2H, d, J=5Hz) 2.73(d, J=5Hz)and 3.17(total 3H, d, J=5Hz)2.94–3.20(4H, m) 4.52–4.58(2H, t, J=7Hz) 7.18–7.30(4H, m) |
| 422 (743) | (structure: 1,3-dihydroxyindan-2-yl-propyl-N(Me)-butyl-gem-bisphosphonate isomer) | δ(D₂O); 1.57–2.02(6H, m)2.09(1H, tt, J=6Hz, 22Hz)2.34(d, J=4Hz) and 2.47(total 2H, d, J=4Hz) 2.74(d, J=4Hz)and 3.16(total 2H, d, J=4Hz)2.94–3.21(4H, m), 4.54–4.61(2H, m)7.22–7.32 (4H, m) |
| 423 (598) | (structure: chroman-4-yl-ethyl-N(Me)-butyl-gem-bisphosphonate) | δ(D₂O); 1.64–2.10(9H, m), 2.70(3H, s) 2.80–2.90(1H, m), 2.92–3.25(4H, m) 3.99–4.13(2H, m), 6.70(1H, d, J=8Hz) 6.84(1H, dt, J=1Hz, 8Hz) 7.04(1H, dt, J=1Hz, 8Hz) 7.10(1H, dd, J=2Hz, 8Hz) |

TABLE 143

| Ex. No. | Chemical Structure | $^1$H-NMR |
|---|---|---|
| 424 (552) | (structure) | δ(CDCl$_3$); 1.45(3H, d, J=7Hz), 1.87~2.23(6H, m) 2.38(1H, tt, J=6Hz, 21Hz)2.57(3H, s), 2.84~2.98(2H, br.)3.93(2H, s), 3.96~4.16(2H, br.)4.28~4.41(2H, m), 4.47~4.57(1H, m)4.60~4.70(1H, m), 4.84(1H, q, J=7Hz)7.12(2H, d, J=8Hz), 7.18(2H, d, J=8Hz)7.28(2H, d, J=8Hz), 7.36(2H, d, J=8Hz) |
| 425 (553) | (structure) | δ(CDCl$_3$); 1.76~2.25(6H, m), 2.45~2.68(1H, m) 2.52(3H, s), 2.56(3H, s)2.82~2.94 (2H, br.), 3.97(2H, s)4.02~4.14(2H, br.) 4.21~4.33(2H, m), 4.44~4.54(1H, m) 4.64~4.74(1H, m), 7.15(2H, d, J=8Hz) 7.24(2H, d, J=8Hz), 7.38(2H, d, J=8Hz) 7.86(2H, d, J=8Hz) |

Examples 426 to 439

The compounds of Examples 426 to 439 listed in Tables 144 to 148 were prepared by preparing diphosphonic acid ester derivatives in a similar manner to that of tie Example 2 and deprotecting the ester derivatives in a similar manner to that of the Example 16.

TABLE 144

| Ex. No. | Chemical Structure | $^1$H-NMR |
|---|---|---|
| 426 (602) | (structure) | δ(D$_2$O); 1.70~2.10(5H, m), 2.85~3.09(3H, m) 3.10~3.25(3H, m), 3.48(2H, t, J=7Hz) 3.65(3H, s), 3.66(3H, s) 6.65(1H, s), 6.83(1H, s) |
| 427 (675) | (structure) | δ(D$_2$O—NaOD); 1.44~1.67(5H, m) 1.74(2H, br. q, J=12Hz) 1.94(2H, br. d, J=12Hz) 2.11(2H, br. t, J=12Hz) 2.30(2H, t, J=7Hz) 2.97(2H, br. d, J=12Hz) 3.04(1H, tt, J=4Hz, 12Hz) 7.01(1H, tt, J=2Hz, 10Hz) 7.18(1H, dt, J=10Hz, 2Hz) 7.70(1H, dd, J=4Hz, 10Hz) |
| 428 (595) | (structure) | δ(D$_2$O); 1.67~2.13(8H, m), 2.43~2.55(2H, m) 3.00~3.12(2H, m), 3.15~3.31(2H, m) 3.35~3.43(2H, m), 3.70(3H, s) 6.90(1H, t, J=8Hz), 6.95(1H, d, J=8Hz) 7.25(1H, t, J=8Hz), 7.32(1H, d, J=8Hz) |

TABLE 145

| Ex. No. | Chemical Structure | ¹H-NMR |
|---|---|---|
| 429 (612) | 4-F-C6H4-piperazine-(CH2)3-CH(P(OH)2=O)(P(OH)2=O) | δ(D₂O+NaOD/DSS); 1.70~1.90(5H, m), 2.49(2H, t, J=7Hz) 2.74(4H, br. s), 3.14(4H, br. s) 7.07~7.16(4H, m) |
| 430 (710) | 3-NC-C6H4-CH2-piperidin-4-yl-N-(CH2)3-CH(P(OH)2=O)(P(OH)2=O) | δ(D₂O); 1.24~1.37(2H, m), 1.57~1.82(8H, m) 2.53(2H, d, J=7Hz), 2.55~2.62(2H, m) 2.84(2H, d, J=7Hz), 3.25~3.35(2H, m) 7.32~7.37(1H, m), 7.42(1H, d, J=8Hz) 7.45~7.51(2H, m) |
| 431 (708) | 3-NC-C6H4-CH=piperidin-4-ylidene-N-(CH2)3-CH(P(OH)2=O)(P(OH)2=O) | δ(D₂O); 1.62~2.02(5H, m), 2.50~2.57(2H, m) 2.75~2.83(2H, m), 2.87~2.96(1H, m) 3.03(2H, br. t, J=8Hz) 3.41~3.58(3H, m), 6.01(1H, s) 7.33~7.40(2H, m), 7.45~7.52(2H, m) |

TABLE 146

| Ex. No. | Chemical Structure | ¹H-NMR |
|---|---|---|
| 432 (697) | 3-NC-C6H4-C(=O)O-piperidin-4-yl-N-(CH2)3-CH(P(OH)2=O)(P(OH)2=O) | δ(D₂O); 1.80~2.30(9H, m), 3.00~3.22(4H, m) 3.40~3.47(2H, m), 3.53~3.60(1H, m) 5.23(1H, br.), 7.48~7.55(1H, m) 7.83~7.88(1H, m)8.12~8.27(2H, m) |
| 433 (698) | 3-NC-C6H4-NH-C(=O)-piperidin-4-yl-N-(CH2)3-CH(P(OH)2=O)(P(OH)2=O) | δ(D₂O); 1.63~1.98(7H, m), 2.02~2.10(2H, m) 2.58~2.68(1H, m)2.92(2H, br. t, J=12Hz)3.02(2H, t, J=7Hz) 3.55(2H, br. d, J=12Hz)7.32~7.43 (2H, m), 7.50~7.55(1H, m)7.72~7.75 (1H, m) |
| 434 (701) | 2-thienyl-C(=O)-piperidin-4-yl-N-(CH2)3-CH(P(OH)2=O)(P(OH)2=O) | δ(D₂O); 1.64~1.94(5H, m) 2.08(2H, br. d, J=12Hz) 2.98(2H, br. t, J=12Hz) 3.05(2H, t, J=7Hz), 3.51~3.62(3H, m) 7.12(1H, t, J=5Hz), 7.80(1H, d, J=5Hz) 7.88(1H, d, J=5Hz) |

TABLE 147

| Ex. No. | Chemical Structure | $^1$H-NMR |
|---|---|---|
| 435 (670) | (2-MeO-phenyl)C(O)-piperidine-N-(CH$_2$)$_3$-CH(P(O)(OH)$_2$)$_2$ | δ(D$_2$O—CD$_3$OD); 1.63~2.06(7H, m) 2.08(2H, br. d, J=12Hz) 2.94(2H, dt, J=4Hz, 12Hz) 3.04(2H, t, J=7Hz), 3.50~3.60(3H, m) 3.79(3H, s)6.97(1H, dt, J=1Hz, 7Hz) 7.07(1H, d, J=8Hz), 7.43~7.51(2H, m) |
| 436 (722) | (4-HOCH$_2$-phenyl)C(O)-piperidine-N-(CH$_2$)$_3$-CH(P(O)(OH)$_2$)$_2$ | δ(D$_2$O—NaOD); 1.62~1.82(7H, m) 1.93(2H, br. d, J=12Hz) 2.26(2H, br. t, J=12Hz) 2.45(2H, t, J=7Hz) 3.56(1H, tt, J=4Hz, 12Hz) 4.75(3H, s), 7.56(2H, d, J=7Hz) 8.02(2H, d, J=7Hz) |
| 437 (714) | (4-(CH$_3$CH(OH))-phenyl)C(O)-piperidine-N-(CH$_2$)$_3$-CH(P(O)(OH)$_2$)$_2$ | δ(D$_2$O—NaOD); 1.34(3H, d, J=7Hz), 1.60~1.81(7H, m) 1.93(2H, br. d, J=12Hz) 2.63(2H, br. t, J=12Hz) 2.74(2H, t, J=7Hz) 3.26(2H, br. d, J=12Hz) 3.55(1H, tt, J=4Hz, 12Hz) 4.85(1H, q, J=7Hz), 7.40(2H, d, J=8Hz) 7.85(2H, d, J=8Hz) |

TABLE 148

| Ex. No. | Chemical Structure | $^1$H-NMR |
|---|---|---|
| 438 (717) | (4-CH$_3$C(O)-phenyl)C(O)-piperidine-N-(CH$_2$)$_3$-CH(P(O)(OH)$_2$)$_2$ | δ(D$_2$O—NaOD); 1.54~1.75(7H, m)1.86(2H, br. d, J=12Hz)2.32(2H, br. t, J=12Hz) 2.48(2H, t, J=7Hz), 2.57(3H, s) 3.06(2H, br. d, J=12Hz)3.48(1H, tt, J=4Hz, 12Hz)7.92(2H, d, J=7Hz), 7.97(2H, d, J=7Hz) |
| 439 (723) | (4-CH$_3$CH$_2$C(O)-phenyl)C(O)-piperidine-N-(CH$_2$)$_3$-CH(P(O)(OH)$_2$)$_2$ | δ(D$_2$O—NaOD): 1.20(3H, t, J=7Hz), 1.61~1.82(7H, m) 1.94(2H, br. d, J=12Hz)2.24(2H, br. t, J=12Hz)2.45(2H, t, J=7Hz)3.08(2H, br. d, J=12Hz)3.55(1H, tt, J=4Hz, 12Hz) 3.59(2H, q, J=7Hz), 8.07~8.13(4H, m) |

Example 440

The compound of Example 440 listed in Table 149 was prepared by preparing a diphosphonic acid ester derivative in a similar manner to that of the Example 3 and deprotecting the ester derivative in a similar manner to those of Examples 17 and 18.

TABLE 149

| Ex. No. | Chemical Structure | ¹H-NMR |
|---|---|---|
| 440 | [Structure: benzyl-phenyl-CH₂CH₂-CH(CH₃)-N(CH₃)-CH₂CH₂CH₂-CH(COONa)-P(ONa)₂=O] | δ(D₂O): 0.92(3H, d, J=7Hz), 1.20–1.35(2H, m) 1.35–1.50(2H, m), 2.10(3H, s) 2.25–2.55(5H, m), 2.60–2.65(1H, m) 3.48(1H, q, J=7Hz), 3.80(2H, s) 6.95–7.02(3H, s), 7.95–7.20(6H, m) |

Example 441

The compound of Example 411 listed in Table 150 was prepared by preparing triethyl 1-carboxy-phosphonate from 1-bromo-3-methyl-5-(2-naphthyl)-2-pentene and triethyl phosphonoacetate in a similar manner to that of the Example 10 and deprotecting the ester in a similar manner to those of Example 17 and 18.

TABLE 150

| Ex. No. | Chemical Structure | ¹H-NMR |
|---|---|---|
| 441 | [Structure: acetyl-naphthyl-CH₂CH₂-C(CH₃)=CH-CH₂-CH(COONa)-P(ONa)₂=O] | δ(D₂O); 1.55(3H, s), 2.15–2.37(5H, m) 2.55(3H, s), 2.75(2H, t, J=6Hz) 5.02–5.08(1H, m), 7.33–7.38(1H, m) 7.59(1H, s), 7.62–7.78(3H, m) 8.30(1H, s) |

Examples 442 to 504

The diphosphonic acid ester derivatives listed in Tables 151 to 171 were prepared from phosphonic acid ester derivatives in a similar manner to those of the Examples 21 and 22.

TABLE 151

| Ex. No. | Chemical Structure | ¹H-NMR |
|---|---|---|
| 442 (539) | [Structure with HO-CH(CH₃)-phenyl-thiophene-CH₂-N-chain-P(O)(OH)(OCH₂OC(O)C(CH₃)₃), P(OH)₂=O] | δ(CDCl₃); 1.19(18H, s), 1.21(9H, s) 1.51(3H, d, J=7Hz), 1.93–2.25(4H, m) 2.37–2.53(1H, m), 2.76(3H, s) 4.47(2H, s), 4.93(1H, q, J=7Hz) 5.62–5.69(3H, m)5.74(2H, dd, J=5Hz, 15Hz)5.84(1H, dd, J=5Hz, 10Hz)7.24 (1H, s), 7.26(1H, s)7.40(2H, d, J=8Hz), 7.54(2H, d, J=8Hz) |
| 443 (536) | [Structure with pyridyl-thiophene-CH₂-N-chain-P(O)(OH)(OCH₂OC(O)C(CH₃)₃), P(OH)₂=O] | δ(D₂O); 1.00(9H, s), 1.62–1.98(4H, m) 2.75(3H, s), 2.93–3.18(3H, m) 4.42–4.58(2H, m), 5.32–5.40(2H, m) 7.25–7.28(1H, m), 7.46–7.49(1H, m) 7.76–7.81(1H, m), 8.45–8.50(2H, m) 8.85(1H, s) |

TABLE 151-continued

| Ex. No. | Chemical Structure | ¹H-NMR |
|---|---|---|
| 444 (512) | [structure] | δ(D₂O); 1.03(9H, s), 1.24(3H, d, J=7Hz) 1.57~2.04(5H, m), 2.58(3H, s) 2.84(3H, s), 2.92~3.08(2H, m) 3.78(2H, br. d, J=14Hz)3.95~4.20 (2H, m), 5.30~5.60(3H, m)7.02~7.30 (8H, m) |

TABLE 152

| Ex. No. | Chemical Structure | ¹H-NMR |
|---|---|---|
| 445 (531) | [structure] | δ(D₂O); 1.02(6H, s), 1.05(3H, s) 1.65~1.95(7H, m), 1.95~2.14(1H, m) 2.73(3H, s), 2.90~3.04(1H, m) 3.07~3.20(1H, m), 3.65(1H, s) 3.70~3.82(2H, m), 5.32~5.42(3H, m) 6.82~6.95(2H, m), 7.02~7.08(1H, m) 7.17~7.23(1H, m) |
| 446 (527) | [structure] | δ(D₂O); 1.03(9H, s), 1.63~2.05(5H, m) 2.00(3H, s), 2.73(3H, s) 2.95~3.03(1H, m), 3.07~3.17(1H, m) 3.75~3.90(2H, m), 5.36~5.40(2H, m) 5.67(1H, t, J=8Hz), 6.99(2H, t, J=9Hz) 7.38(2H, dd, J=5Hz, 9Hz) |
| 447 (523) | [structure] | δ(D₂O); 0.98(9H, s), 1.63~2.12(8H, m) 2.47(3H, br. s), 2.73(3H, br. s) 2.93~3.19(2H, m), 3.72~3.91(2H, m) 5.30~5.43(2H, m), 5.66~5.77(1H, m) 7.29~7.40(1H, m), 7.54~7.62(1H, m) 7.68~7.83(2H, m) |

TABLE 153

| Ex. No. | Chemical Structure | ¹H-NMR |
|---|---|---|
| 448 (520) | [structure] | δ(D₂O); 1.01(6H, s), 1.05(3H, s)1.27~1.33 (3H, m), 1.64~2.08(8H, m)2.67(3H, s), 2.82~3.17(2H, m)3.73~3.92(2H, m), 4.72~4.81(1H, m)5.33~5.43(2H, m), 5.68(1H, t, J=7Hz)7.18~7.36(4H, m) |
| 449 (545) | [structure] | δ(CDCl₃); 1.30~1.40(6H, m), 2.02(3H, s) 2.05~2.22(7H, m), 2.78(3H, s) 3.00~3.05(2H, m), 3.45(3H, s) 5.52~5.56(1H, m), 5.75~5.82(1H, m) 6.82~6.95(2H, m), 7.08~7.10(1H, m) 7.22~7.25(1H, m) |

TABLE 153-continued

| Ex. No. | Chemical Structure | $^1$H-NMR |
|---|---|---|
| 450 (562) | 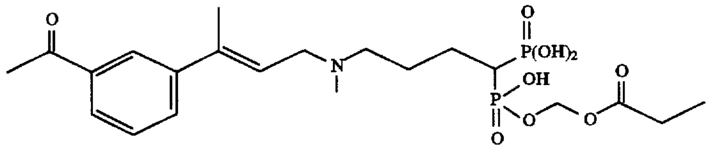 | δ(CDCl$_3$); 1.03(3H, t, J=7Hz), 1.90~2.30(7H, m) 2.14(3H, s), 2.58(3H, s)2.68~2.88(2H, br.), 3.24(3H, br.)3.50~3.72(1H, br.) 3.50~3.72(1H, br. 3.78~4.07(2H, br.) 4.20~4.38(1H, br.)5.48~5.61(2H, m) 5.89~6.03(1H, br.)7.33~7.49(1H, m), 7.61~7.71(1H, m)7.74~7.97(2H, m) |

TABLE 154

| Ex. No. | Chemical Structure | $^1$H-NMR |
|---|---|---|
| 451 (589) | 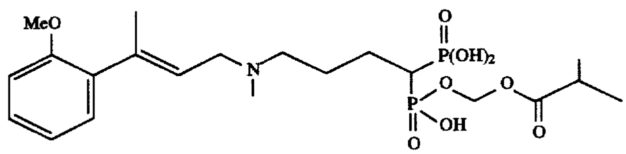 | δ(CDCl$_3$); 1.08(6H, d, J=7Hz), 1.92~2.38(5H, m) 2.04(3H, s), 2.42~2.52(1H, m)2.77 (3H, br. s), 2.93~3.25(2H, m)3.72~3.93 (2H, m), 3.77(3H, s)5.48~5.64(3H, m), 6.80~6.93(2H, m)7.07~7.13(1H, m), 7.20~7.29(1H, m) |
| 452 (559) | 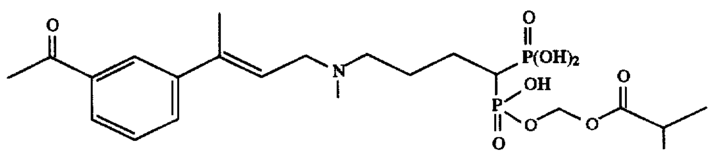 | δ(CDCl$_3$); 1.04(6H, d, J=7Hz), 1.92~2.20(4H, m) 2.18(3H, s), 2.35~2.60(2H, m)2.64 (3H, s), 2.80(3H, s)2.92~3.02 (1H, br.)3.10~3.26(1H, br.)3.82~4.02 (2H, br.)5.60~5.80(2H, br.), 5.98(1H, br.) 7.36~7.48(1H, m), 7.62~7.68(1H, m) 7.73~7.96(2H, m) |
| 453 (567) | 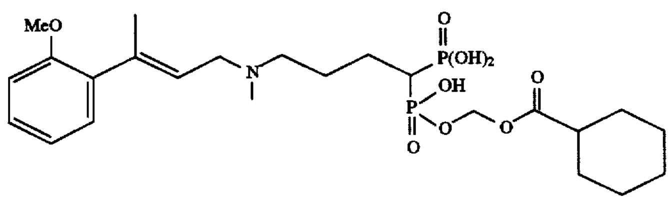 | δ(D$_2$O); 1.15~1.58(12H, m)1.58~1.82(6H, m), 1.82~2.02(6H, m)2.15(3H, s), 2.30~2.42 (2H, m)2.55~2.65(1H, m), 2.85~2.90 (2H, m)3.82(3H, s), 5.50~5.75(5H, m) 6.90~7.02(2H, m), 7.10~7.19(1H, m) 7.22~7.33(1H, m) |

TABLE 155

| Ex. No. | Chemical Structure | $^1$H-NMR |
|---|---|---|
| 454 (573) | 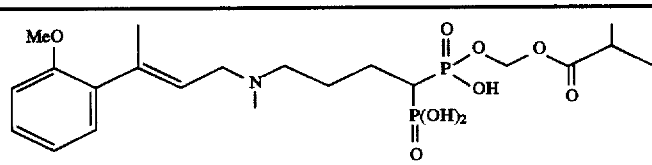 | δ(CD$_3$OD/TMS); 1.29(6H, d, J=7Hz)1.94~2.17(7H, m) 2.43(1H, tt, J=24Hz, 7Hz), 2.91(3H, s) 3.1~3.2(2H, m), 3.82(3H, s)3.91(1H, dd, J=13Hz, 8Hz)4.00(1H, dd, J=13Hz, 8Hz) 5.52(1H, t, J=8Hz), 5.67(2H, d, J=13Hz) 6.93(1H, t, J=8Hz), 7.00(1H, d, J=8Hz) 7.14(1H, dd, J=8Hz, 2Hz)7.29(1H, dt, J=8Hz, 2Hz) |
| 455 (576) | 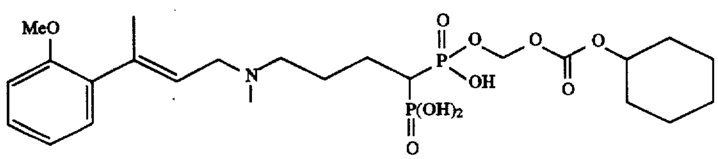 | δ(CDCl$_3$); 1.13~1.46(6H, m), 1.64~1.75(2H, br.) 1.83~1.94(2H, br.), 1.98~2.28(4H, m) 2.07(3H, s), 2.44(1H, br. t, J=24Hz) 2.79(3H, br. s), 2.92~3.27(2H, m) 3.73~3.93(2H, m), 3.80(3H, s) 4.55~4.64(1H, m), 5.55(1H, br. t, J=7Hz) 5.58~5.67(2H, m), 6.88(1H, d, J=8Hz) 6.92(1H, t, J=8Hz), 7.12(1H, d, J=8Hz) 7.21~7.32(1H, m) |

TABLE 155-continued

| Ex. No. | Chemical Structure | ¹H-NMR |
|---|---|---|
| 456 (587) | (structure) | δ(CD₃OD/TMS); 1.73(3H, s), 2.37(2H, t, J=8Hz) 2.41~2.52(1H, m), 2.60~2.74(1H, m) 2.82~2.93(3H, m), 2.88(3H, s) 2.91(3H, s), 5.16(1H, t, J=8Hz) 5.58~5.66(2H, m), 7.32(1H, dd, J=8Hz, 2Hz)7.35~7.43(2H, m), 7.60(1H, s) 7.72~7.80(3H, m) |

TABLE 156

| Ex. No. | Chemical Structure | ¹H-NMR |
|---|---|---|
| 457 (537) | (structure) | δ(D₂O); 1.01~1.05(18H, m) 1.62~1.80(2H, m), 1.80~1.98(3H, m) 2.75(3H, s), 2.95~3.18(2H, m) 4.42~4.50(2H, s), 5.32~5.42(4H, m) 7.25~7.28(1H, m), 7.46~7.49(1H, m) 7.77~7.82(1H, m), 8.45~8.51(2H, m) 8.95(1H, s) |
| 458 (513) | (structure) | δ(CDCl₃); 1.12~1.24(18H, m) 1.45(3H, d, J=6Hz), 1.73~2.17(4H, m)2.31(1H, br.), 2.62(3H, s) 2.78(3H, br.), 2.80~2.90(2H, m) 3.10~3.30(2H, m), 4.72~4.88(2H, m) 5.46~5.67(5H, m), 7.06~7.38(8H, m) |
| 459 (532) | (structure) | δ(D₂O); 1.01(6H, s), 1.05~1.08(12H, m) 1.60~1.65(4H, m), 1.95(3H, s) 2.18~2.32(1H, m), 2.65~2.68(2H, m) 3.68(3H, s), 5.35~5.58(5H, m) 6.82~6.98(2H, m), 7.03~7.10(1H, m) 7.19~7.23(1H, m) |

TABLE 157

| Ex. No. | Chemical Structure | ¹H-NMR |
|---|---|---|
| 460 (521) | (structure) | δ(CDCl₃); 1.13(9H, s), 1.19(9H, s) 1.46(3H, d, J=6Hz), 1.84~2.44(5H, m) 2.18(3H, br. s), 2.77(3H, br. s) 3.04~3.27(2H, m), 3.98~4.26(2H, m) 4.87(1H, q, J=6Hz), 5.48~5.77(4H, m) 5.96~6.08(1H, m), 7.18~7.28(3H, m) 7.61~7.68(1H, br.) |
| 461 (524) | (structure) | δ(CDCl₃); 1.12(18H, s), 1.88~2.48(5H, m) 2.16(3H, s), 2.60(3H, s)2.80(3H, br. s), 2.90~3.25(2H, br.), 3.80~4.02 (1H, br.)4.17~4.37(1H, br.)5.30~5.77 (4H, m), 5.90~6.04(1H, )7.36~7.51 (1H, m), 7.64~7.72(1H, m)7.76~8.03 (2H, m) |

TABLE 157-continued

| Ex. No. | Chemical Structure | ¹H-NMR |
|---|---|---|
| 462 (748) | 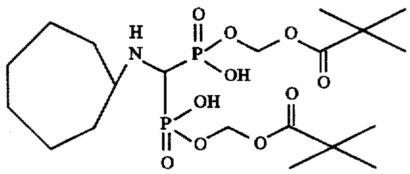 | δ(CDCl₃); 1.22(18H, s), 1.36~1.65(6H, m) 1.65~1.90(4H, m), 2.10~2.28(2H, m) 3.37~3.51(1H, m)3.59(1H, t, J=20Hz), 5.65(2H, s)5.68(2H, s) |

TABLE 158

| Ex. No. | Chemical Structure | ¹H-NMR |
|---|---|---|
| 463 (611) | 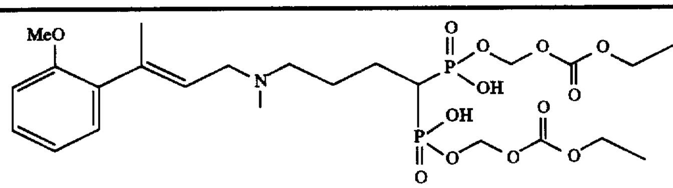 | δ(CD₃OD); 1.23~1.38(6H, m), 1.90~2.20(7H, m) 2.35~2.52(1H, m), 3.15(3H, s) 3.45(2H, t, J=7Hz), 3.82(1H, s) 4.18~4.23(4H, m), 4.33(2H, q, J=7Hz) 5.25~5.38(2H, m), 5.40~5.73(3H, m) 6.88~6.98(2H, m), 7.15(1H, d, J=9Hz) 7.25(1H, t, J=7Hz) |
| 464 (590) | 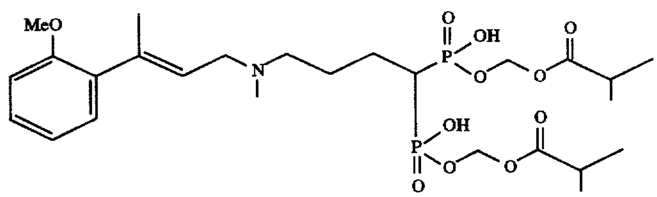 | δ(CDCl₃); 1.12~1.22(12H, m)1.92~2.24(4H, m), 2.07(3H, s)2.36~2.64(3H, m), 2.77(3H, br. s)2.90~3.24(2H, m), 3.75~3.94(2H, m) 3.81(3H, s), 5.55(1H, br. t, J=8Hz) 5.60~5.83(4H, m), 6.87(1H, d, J=8Hz) 6.93(1H, t, J=8Hz)7.10(1H, dd, J=2Hz, 8Hz)7.24~7.32(1H, m) |
| 465 (568) | 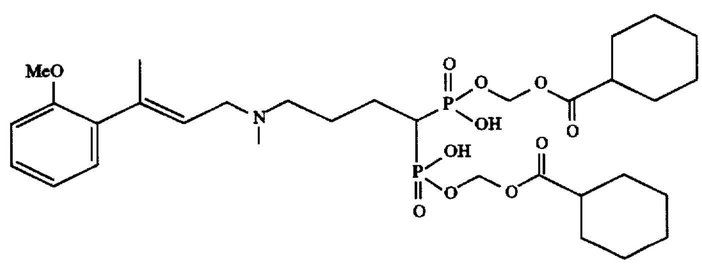 | δ(CD₃OD); 1.18~1.58(12H, m)1.60~1.85(6H, m), 1.85~2.05(8H, m)2.15(3H, s), 2.32~2.42 (1H, m)2.85~2.88(2H, m), 3.82(3H, s) 5.45~5.78(5H, m), 6.90~7.02(2H, m) 7.10~7.18(1H, m), 7.25~7.35(1H, m) |

TABLE 159

| Ex. No. | Chemical Structure | ¹H-NMR |
|---|---|---|
| 466 (575) | 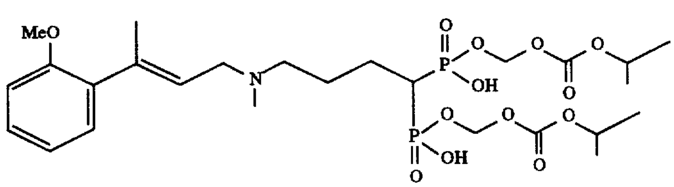 | δ(CD₃OD/TMS); 1.28(6H, d, J=7Hz), 1.30(6H, d, J=7Hz) 2.11(3H, s), 2.76(1H, tt, J=24Hz, 7Hz) 3.82(3H, s), 3.92(1H, dd, J=13Hz, 8Hz) 4.00(1H, dd, J=13Hz, 8Hz) 5.54(1H, t, J=8Hz), 5.60~5.75(4H, m) 6.93(1H, t, J=8Hz), 7.00(1H, d, J=8Hz) 7.15(1H, d, J=8Hz), 7.29(1H, t, J=8Hz) |

TABLE 159-continued

| Ex. No. | Chemical Structure | $^1$H-NMR |
|---|---|---|
| 467 (577) | 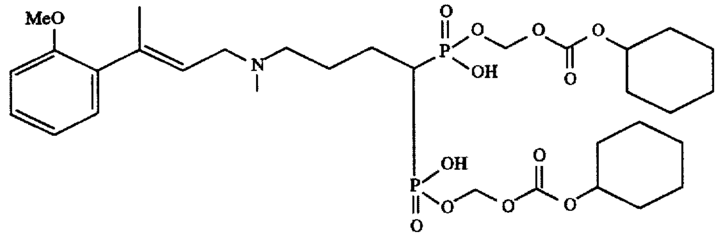 | δ(CDCl$_3$); 1.14~1.57(12H, m), 1.65~1.77(4H, br.) 1.84~1.96(4H, br.), 1.97~2.28(4H, m) 2.06(3H, s), 2.46(1H, br. t, J=22Hz) 2.79(3H, s), 2.89~2.99(1H, br.) 3.08~3.18(1H, br.), 3.75~3.97(2H, m) 3.81(3H, s), 4.57~4.68(2H, m) 5.55(1H, br. t, J=8Hz), 5.62~5.83(4H, m) 6.88(1H, d, J=8Hz), 6.94(1H, t, J=8Hz) 7.11(1H, dd, J=3Hz, 8Hz) 7.24~7.32(1H, m) |
| 468 (585) | 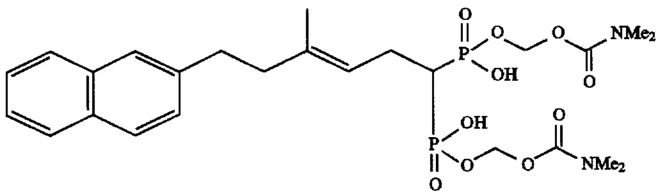 | δ(CDCl$_3$/TMS); 1.69(3H, s), 2.34(2H, d, J=8Hz) 2.46(1H, tt, J=25Hz, 7Hz) 2.56~2.72(2H, m), 2.77~2.94(2H, m) 2.89(12H, s), 5.27(1H, t, J=8Hz) 5.58~5.70(4H, m)7.33(1H, dd, J=8Hz, 2Hz), 7.36~7.47(2H, m), 7.62(1H, s) 7.73~7.81(3H, m) |

TABLE 160

| Ex. No. | Chemical Structure | $^1$H-NMR |
|---|---|---|
| 469 (588) | 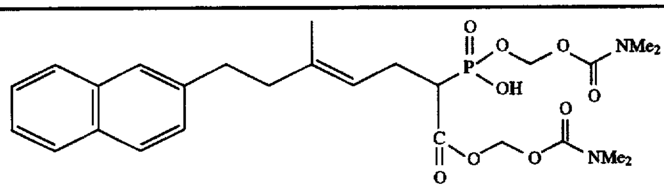 | δ(CD$_3$OD/TMS); 1.72(3H, s), 2.36(2H, t, J=8Hz) 2.42~2.53(1H, m), 2.62~2.74(1H, m) 2.83~2.88(2H, m), 2.84(3H, s) 2.87(3H, s), 2.90(3H, s)2.92(3H, s) 2.96(1H, ddd, J=22Hz, 11Hz, 4Hz) 5.09(1H, t, J=8Hz), 5.56~5.67(4H, m) 7.32(1H, d, J=8Hz), 7.36~7.46(2H, m) 7.60(1H, s), 7.73~7.83(3H, m) |
| 470 (525) | 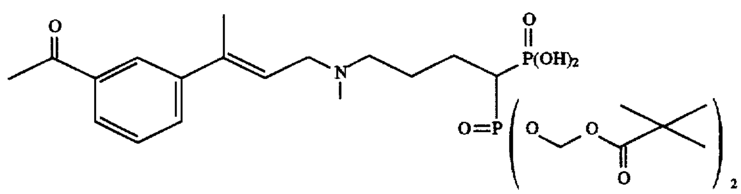 | δ(CDCl$_3$); 1.14(9H, s), 1.17(9H, s) 1.85~2.33(4H, m), 2.18(3H, s) 2.42(1H, tt, J=5Hz, 23Hz) 2.63(3H, br. s), 2.78(3H, br. s) 2.90~3.13(1H, br.), 3.40~3.62(1H, br.) 4.12~4.41(2H, br.), 5.46~5.76(4H, m) 5.92~6.03(1H, m), 7.42~7.50(1H, m) 7.64~7.72(1H, m), 7.85~7.92(1H, m) 7.96~8.03(1H, br.) |
| 471 (516) | 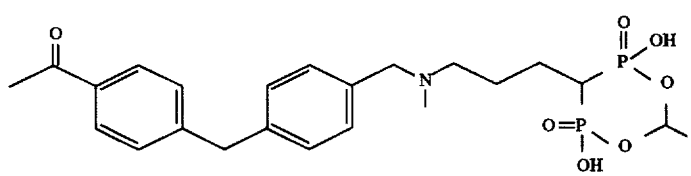 | δ(D$_2$O—CD$_3$OD); 1.14(d, J=7Hz)and 1.26(3H, d, J=7Hz) 1.49~2.11(5H, m), 2.28(3H, s) 2.52(3H, s), 2.77~2.89(1H, m) 2.92~3.04(1H, m), 3.73(2H, br.) 3.88~3.94(1H, m), 4.07~4.16(1H, m) 5.50(1H, q, J=5Hz), 7.00~7.10(2H, m) 7.16(1H, d, J=8Hz), 7.51(1H, t, J=8Hz) |

TABLE 161

| Ex. No. | Chemical Structure | ¹H-NMR |
|---|---|---|
| 472 (541) | 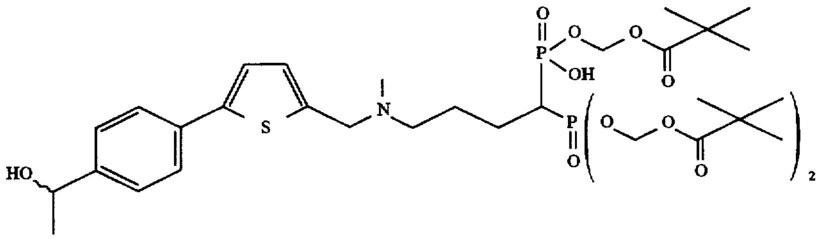 | δ(CD₃OD); 1.19(9H, s), 1.42(3H, d, J=7Hz) 1.90~2.18(4H, m) 2.20(1H, tt, J=7Hz, 24Hz) 2.86(3H, s), 3.19(2H, br. s) 4.57(2H, s), 4.85(1H, q, J=7Hz) 5.60(2H, d, J=12Hz), 7.35(1H, d, J=3Hz)7.39(1H, d, J=3Hz), 7.42 (2H, d, J=8Hz)7.62(2H, d, J=8Hz) |
| 473 (544) | 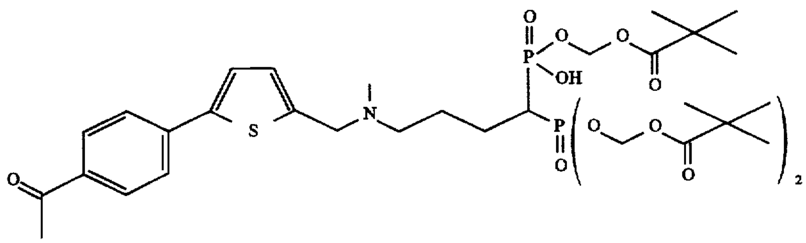 | δ(CDCl₃—CD₃OD); 1.188(9H, s), 1.203(9H, s), 1.205(9H, s), 1.70~2.03(5H, m) 2.25(3H, m), 2.41(2H, t, J=7Hz) 2.60(3H, s), 3.73(2H, s) 5.54(1H, dd, J=5Hz, 12Hz) 5.60~5.69(3H, m) 5.72(1H, dd, J=5Hz, 12Hz) 5.80(1H, dd, J=5Hz, 10Hz) 6.91(1H, d, J=4Hz,), 7.28 (1H, d, J=4Hz)7.65(2H, d, J=8Hz), 7.95(2H, d, J=8Hz) |
| 474 (538) | 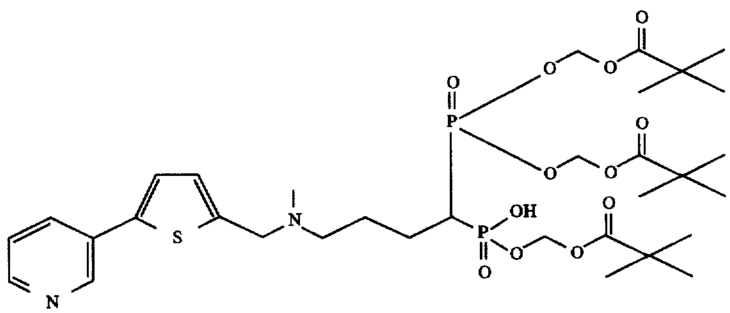 | δ(CDCl₃); 1.15~1.22(27H, m), 1.98~2.15 (4H, m)2.15~2.28(2H, m), 2.38~2.55(1H, m)4.48~4.61 (2H, m), 5.62~5.92(6H, m) 7.30~7.38(2H, m), 7.82~7.88 (1H, m)8.55~8.60(1H, m), 8.95 (1H, s) |

TABLE 162

| Ex. No. | Chemical Structure | ¹H—NMR |
|---|---|---|
| 475 (556) | 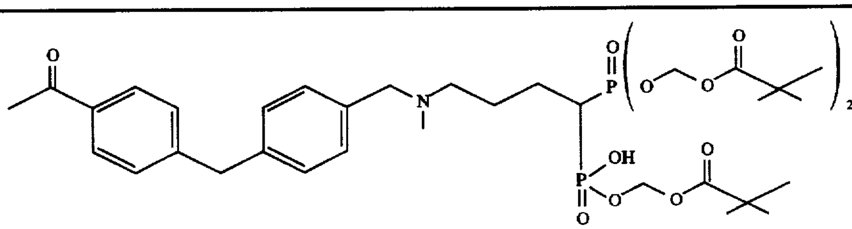 | δ(CDCl₃); 1.16(9H, s), 1.19(18H, s) 1.79~2.28(5H, m), 2.57(3H, s) 2.64(3H, br. s), 2.85~2.96(1H, br.) 3.05~3.16(1H, br.), 3.29~3.55(2H, br.), 4.04(2H, s) 5.58~5.89(6H, m), 7.19~7.30(4H, m) 7.22(2H, d, J=8Hz), 7.89(2H, d, J=8Hz) |
| 476 (533) | 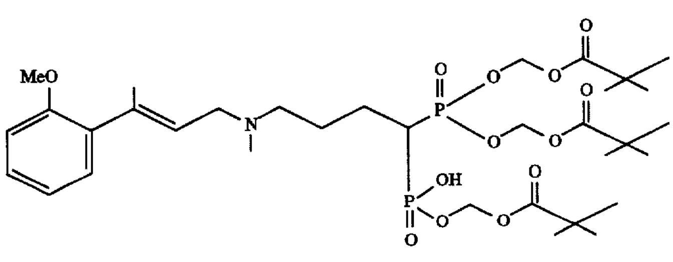 | δ(CD₃OD); 1.18~1.24(27H, m), 2.05(3H, m) 2.06~2.30(6H, m), 2.35~2.52(1H, m) 2.78(2H, d, J=8Hz), 3.80(3H, s) 5.52~5.58(1H, d, J=8Hz) 5.60~5.85(6H, m), 6.82~6.95(2H, m) 7.08~7.12(1H, m), 7.22~7.30(1H, m) |

TABLE 162-continued

| Ex. No. | Chemical Structure | ¹H—NMR |
|---|---|---|
| 477 (530) | 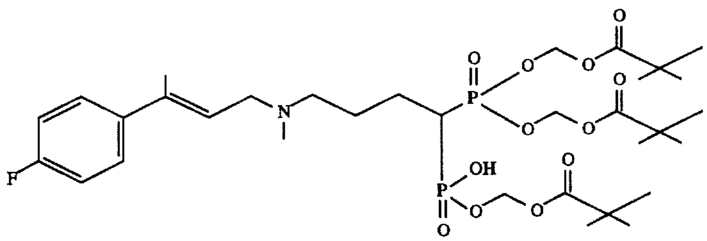 | δ(CDCl₃); 1.17(9H, s), 1.20(9H, s), 1.21(9H, s) 2.13(3H, s), 1.89~2.29(4H, m) 2.41(1H, t, J=24Hz), 2.77(3H, s) 2.70~3.06(2H, m), 3.80~4.00(2H, m) 5.57~5.84 (6H, m), 5.90 (1H, t, J=8Hz) 7.04(2H, dd, J=9Hz) 7.42(2H, dd, J=5Hz,, 9Hz) |

TABLE 163

| Ex. No. | Chemical Structure | ¹H—NMR |
|---|---|---|
| 478 (526) | 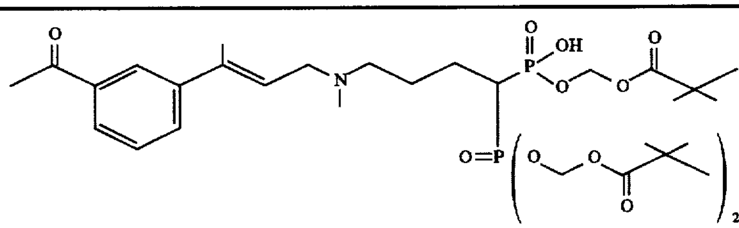 | δ(CDCl₃); 1.16(9H, s), 1.19(9H, s), 1.20(9H, s) 1.89~2.31(4H, m), s.18 (3H, s) 2.42(1H, tt, J=5Hz, 23Hz), 2.64(3H, s) 2.79(3H, s), 2.83~3.04(1H, br.) 3.09~3.27(1H, br.), 3.82~4.05(2H, m) 5.58~5.83(6H, m), 6.02(1H, t, J=7Hz) 7.47(1H, t, J=8Hz), 7.67(1H, d, J=8Hz) |
| 479 (522) | 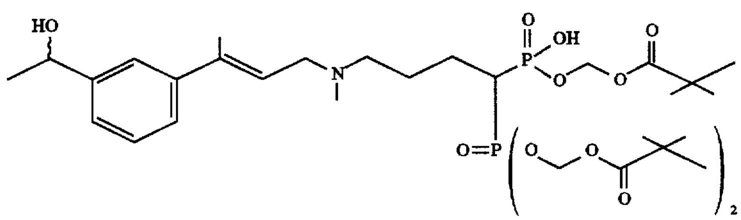 | δ(CDCl₃); 1.14(9H, s), 1.18(18H, s) 1.46(3H, d, J=6Hz), 1.86~2.52(5H, m) 2.19(3H, s), 2.92~3.28(4H, br.) 3.38~3.54(1H, br.), 4.14~4.26(2H, m) 4.87(1H, q, J=6Hz), 5.43~5.80(6H, m) 5.98~6.14(1H, m), 7.20~7.29(3H, m) 7.62~7.70(1H, br.) |
| 480 (692) | 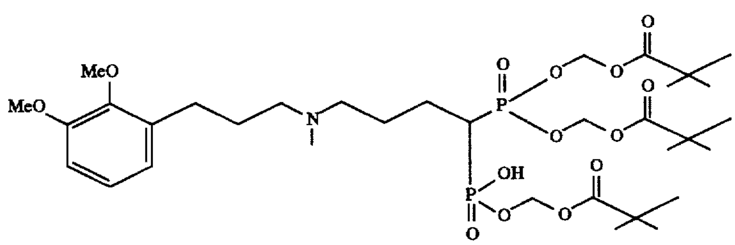 | δ(CD₃OD); 1.20(9H, s), 1.22(9H, s), 1.23(9H, s) 1.85~2.13(6H, m) 2.40(1H, dd, J=20Hz, 7Hz) 2.72(2H, t, J=7Hz), 2.83(3H, s) 3.00~3.30(4H, m), 3.80(3H, s) 3.83(3H, s), 5.55~5.79(6H, m) 6.82(1H, d, J=9Hz),6.90(1H, d, J=9Hz) 7.00(1H, dd, J=9Hz) |

TABLE 164

| Ex. No. | Chemical Structure | ¹H—NMR |
|---|---|---|
| 481 (706) | 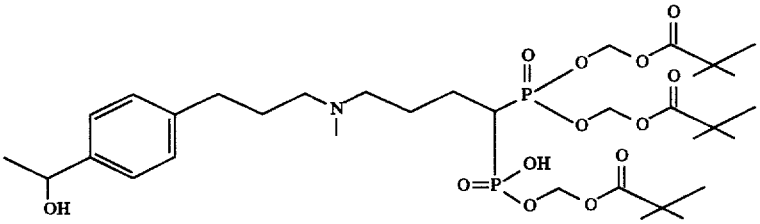 | δ(CDCl₃); 1.18(9H, m), 1.22(18H, m) 1.47(3H, d, J=6Hz), 1.82~2.46(7H, m) 2.60~3.16(6H, m), 2.70(3H, s) 4.86(1H, q, J=6Hz), 5.61 (2H, d, J=11Hz) 5.62(1H, d, J=10Hz) 5.66~5.76(2H, m) 5.80(1H, dd, J=5Hz, 10Hz) 7.17(2H, d, J=9Hz), 7.31(2H, d, J=9Hz) |
| 482 (705) | 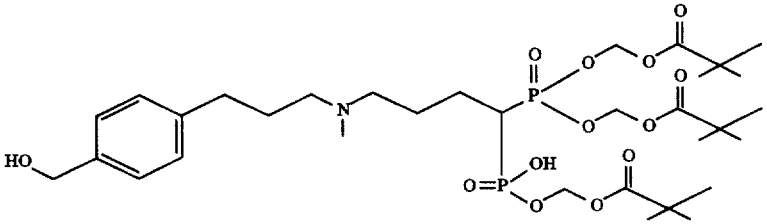 | δ(CDCl₃); 1.18(9H, s), 1.22(18H, s) 1.80~2.45(7H, m), 2.56~3.17(6H, m) 2.68(3H, s), 4.63(2H, s) 5.57~5.65(3H, m), 5.67~5.75(2H, m) 5.80(1H, dd, J=5Hz, 10Hz) 7.17(2H, d, J=8Hz), 7.30(2H, d, J=8Hz) |
| 483 (582) | 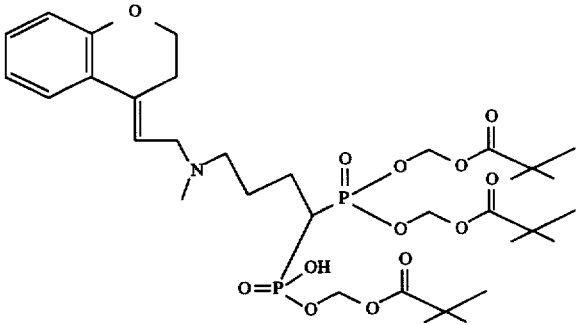 | δ(CDCl₃); 1.12(9H, s), 1.14(18H, s) 1.75~2.23(4H, m), 2.34(1H, t, J=24Hz) 2.70(3H, s), 2.77~2.94(1H, m) 3.00~3.20(1H, m), 3.55~3.65(2H, m) 3.75~4.00(2H, m), 5.48~5.80(6H, m) 6.08~6.18(1H, m), 6.74~6.91(2H, m) 7.10~7.20(1H, m), 7.55~7.64(1H, m) |

TABLE 165

| Ex. No. | Chemical Structure | ¹H—NMR |
|---|---|---|
| 484 (695) | 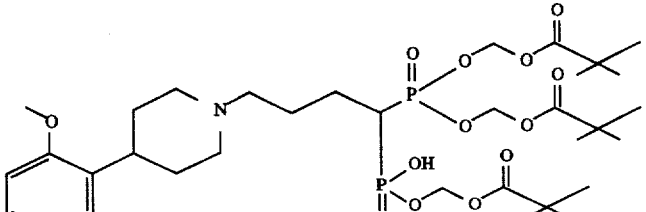 | δ(CDCl₃); 1.19(9H, s), 1.22(18H, s) 1.90~2.29(8H, m), 2.50(1H, t, J=25Hz) 2.34~2.73(2H, m), 2.93~3.05(1H, m) 3.06~3.21(2H, m), 3.56~3.71(2H, m) 3.82(3H, s), 5.62~5.78(5H, m) 5.83~5.90(1H, m), 6.85(1H, d, J=8Hz) 6.93(1H, t, J=8Hz), 7.17~7.25(2H, m) |
| 485 (606) | 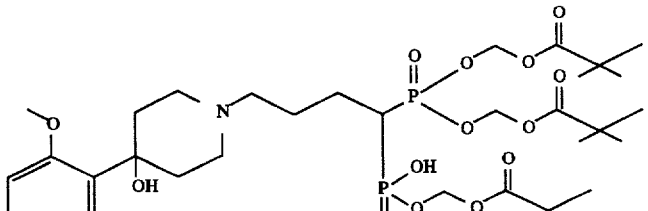 | δ(CDCl₃); 1.16(9H, s), 1.22(18H, s) 1.94~2.21(6H, m), 2.39(1H, t, J=24Hz) 2.60~2.72(2H, m), 2.96~3.22(4H, m) 3.49~3.63(2H, m), 3.90(3H, s) 5.54~5.81(6H, m), 6.92(1H, d, J=8Hz) 6.98(1H, d, J=8Hz), 7.25(1H, d, J=8Hz) 7.36(1H, d, J=8Hz) |

TABLE 165-continued

| Ex. No. | Chemical Structure | $^1$H—NMR |
|---|---|---|
| 486 (584) | 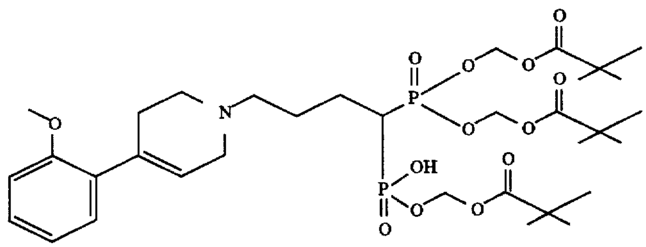 | δ(CDCl$_3$); 1.13(9H, s), 1.15(18H, s) 1.86~2.25(4H, m), 2.34(1H, t, J=24Hz) 2.60~2.90(2H, m), 3.00~3.34(4H, m) 3.42~3.61(2H, m), 3.75(3H, s) 5.53~5.72(6H, m), 5.72~5.80(1H, m) 6.81(1H, d, J=8Hz), 6.87(1H, t, J=8Hz) 7.10(1H, dd, J=2Hz, 8Hz) 7.17~7.26(1H, m) |

TABLE 166

| Ex. No. | Chemical Structure | $^1$H—NMR |
|---|---|---|
| 487 (709) | 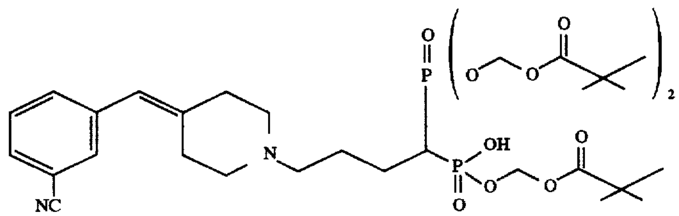 | δ(CDCl$_3$); 1.21(9H, s), 1.23(18H, s) 1.70~2.22(5H, m), 2.38~2.68(4H, m) 2.75~3.18(4H, m), 3.63~3.96(2H, m) 5.58~5.77(5H, m) 5.87(1H, dd, J=6Hz, 10Hz), 6.41(1H, s) 7.38~7.48(3H, m), 7.54(1H, d, J=8Hz) |
| 488 (713) | 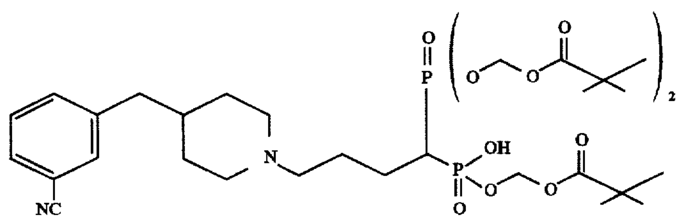 | δ(CDCl$_3$); 1.21(9H, s), 1.23(18H, s) 1.62~1.96(5H, m), 1.98~2.23(4H, m) 2.34~2.53(3H, m), 2.66(2H, d, J=8Hz) 2.89~2.98(1H, m), 3.04~3.13(1H, m) 3.63(1H, br. d, J=13Hz) 3.76(1H, br. d, J=13Hz) 5.58~5.76(5H, m) 5.85(1H, dd, J=6Hz, 10Hz) 7.37~7.44(2H, m), 7.47(1H, s) 7.49~7.54(1H, m) |
| 489 (749) | 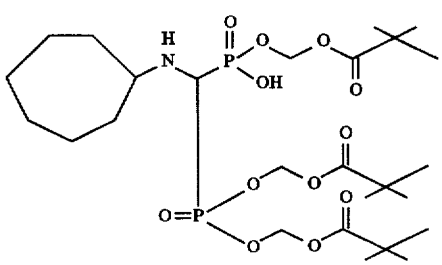 | δ(CDCl$_3$); 1.22(9H, s), 1.24(18H, s) 1.36~1.66(6H, m), 1.68~1.96(4H, m) 2.01~2.10(1H, m), 2.23~2.33(1H, m) 3.31~3.42(1H, m), 3.61(1H, t, J=20Hz) 5.58(1H, dd, J=13Hz, 6Hz) 5.68(1H, dd, J=13Hz, 6Hz) 5.76~5.89(4H, m) |

TABLE 167
| Ex. No. | Chemical Structure | $^1$H—NMR |
|---|---|---|
| 490 (563) | 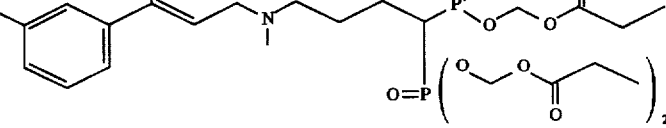 | δ(CDCl$_3$); 1.04~1.24(9H, m), 1.93~2.50(9H, m), 2.29(3H, s), 2.53~2.63(2H, m), 2.65(3H, s), 3.25(3H, br. s) 3.63~3.86(2H, m), 4.26~4.36(1H, m), 4.42~4.50(1H, m), 5.57~5.80(6H, m) 5.82(1H, br. t, J=7Hz) 7.48(1H, t, J=8Hz), 7.67(1H, d, J=8Hz) 7.92(1H, d, J=8Hz), 8.01(1H, s) |
| 491 (591) | 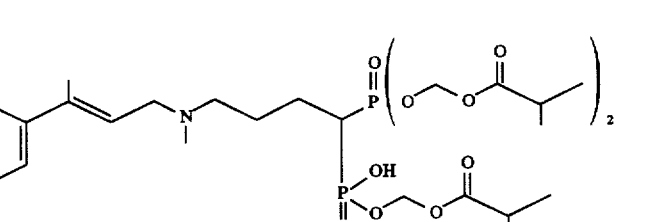 | δ(CDCl$_3$); 1.10~1.21(18H m), 1.92~2.20(4H, m), 2.06(3H, s), 2.35~2.66(4H, m), 2.79(3H, br. s), s.20~3.03(1H, m) 3.10~3.22(1H, m), 3.76~3.94(2H, m) 3.81(3H, s), 5.56(1H, br. t, J=8Hz) 5.60~5.83(6H, m), 6.88(1H, d, J=8Hz) 6.92(1H, t, J=8Hz), 7.09(1H, d, J=8Hz) 7.24~7.32(1H, m) |
| 492 (608) | 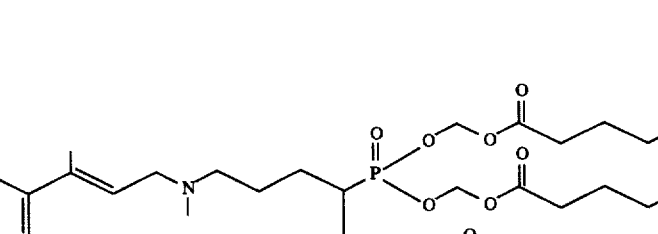 | δ(CD$_3$OD); 0.90~0.97(9H, m), 1.32~1.41(6H, m) 1.55~1.65(6H, m), 1.90~2.18(7H m) 2.35~2.50(7H, m), 2.90(3H, s) 3.05~3.20(2H, m), 3.82(3H, s) 3.85~4.00(2H, m), 5.50~5.75(7H, m) 6.93(1H, t, J=9Hz), 7.00(1H, d, J=9Hz) 7.14(1H, d, J=9Hz), 7.28(1H, t, J=9Hz) |

TABLE 168

| Ex. No. | Chemical Structure | ¹H—NMR |
|---|---|---|
| 493 (569) | 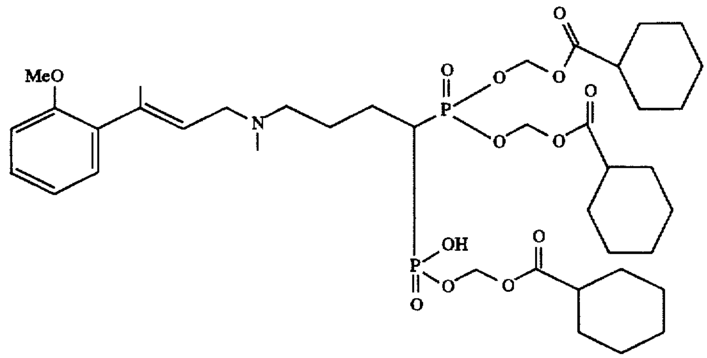 | δ(CDCl₃); 1.15~1.30(8H, m), 1.30~1.45(6H, m) 1.55~1.79(8H, m), 1.82~1.95(6H, m) 1.83~1.95(6H, m), 2.05(3H, s) 2.20~2.38(4H, m), 2.76(2H, d, J=7Hz) 5.52(1H, t, J=7Hz), 5.60~5.80(6H, m) 6.86(1H, d, J=7Hz), 6.93(1H, t, J=7Hz) 7.07(1H, d, J=7Hz), 7.22(1H, t, J=7Hz) |
| 494 (560) | 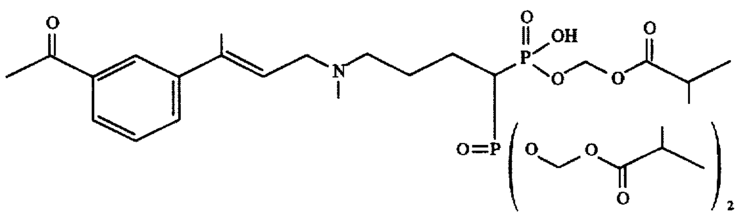 | δ(CDCl₃); 1.10(6H, d, J=7Hz), 1.13~1.18(12H, m) 1.94~2.22(4H, m), 2.19(3H, s) 2.36~2.66(4H, m), 2.64(3H, s) 2.78(3H, s), 2.90~3.02(2H, br.) 3.10~3.29(1H, br.), 3.81~4.04(2H, br.) 5.59~5.81(6H, m), 6.00(1H, br. t, J=8Hz) 7.46(1H, t, J=8Hz), 7.67(1H, br. d, J=8Hz) 7.88(1H, d, J=8Hz), 7.99(1H, s) |
| 495 (607) | 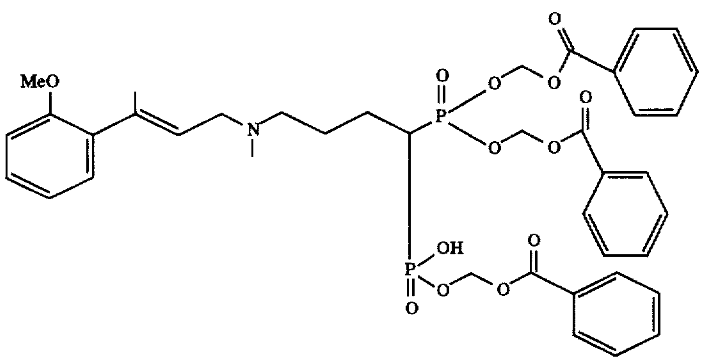 | δ(CD₃OD); 1.92~2.12(7H, m), 2.48~2.63(1H, m) 2.80(3H, s), 2.95~3.07(2H, m) 3.75~3.90 (5H, m), 5.45(2H, t, J=7Hz) 5.81~6.02(6H, m), 6.91(1H, t, J=9Hz) 6.97(1H, d, J=9Hz), 7.12(1H, d, J=9Hz) 7.25(1H, t, J=9Hz), 7.37~7.48(6H, m) 7.50~7.62(3H, m), 7.92~8.01(4H, m) 8.01~8.08(2H, m) |

TABLE 169

| Ex. No. | Chemical Structure | ¹H—NMR |
|---|---|---|
| 496 (586) | 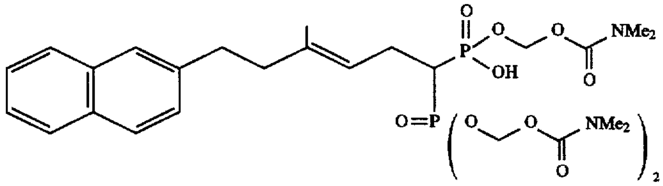 | δ(CDCl₃/TMS); 1.71(3H, s), 2.35(2H, d, J=8Hz) 2.57(1H, tt, J=24Hz, 7Hz) 2.60~2.76(2H, m), 2.80~2.95(2H, m) 2.92(18H, s), 5.35(1H, t, J=8Hz) 5.63~5.76(6H, m), 7.37~7.46(2H, m) 7.33(1H, dd, J=8Hz, 2Hz) 7.37~7.46(2H, m), 7.61(1H, s) 7.72~7.81(3H, m) |

TABLE 169-continued

| Ex. No. | Chemical Structure | $^1$H—NMR |
|---|---|---|
| 497 (557) | 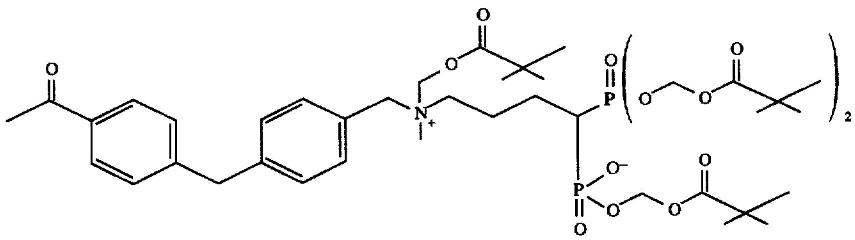 | δ(CDCl$_3$); 1.16(9H, s), 1.18(18H, s), 1.27(9H, s) 1.88~2.68(5H, m), 2.58(3H, s) (3H,s) 3.13(3H, br. s), 3.50~3.63(1H, m) 3.75~3.90(1H, m), 4.04(1H, s) 4.68(1H, t, J=13Hz), 4.84(1H, d, J=13Hz) 5.06~5.16(2H, m), 5.54~5.84(6H, m) 7.16~7.34(4H, m), 7.48(2H, m) 7.89(2H, d, J=8Hz) |
| 498 (570) | 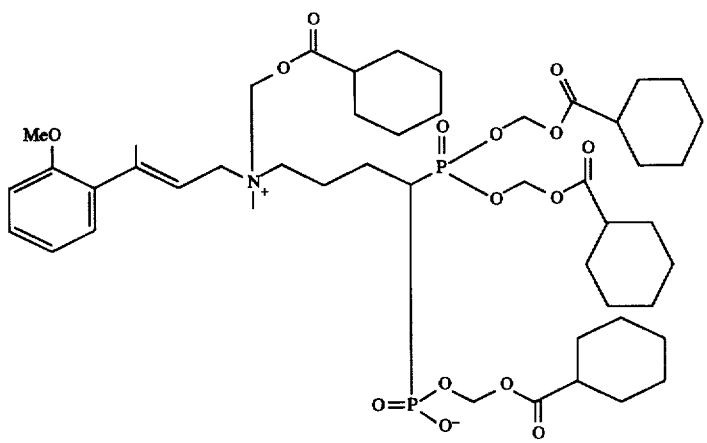 | δ(CD$_3$OD); 1.15~1.60(20H, m) 1.60~2.07(22H, m) 2.07~2.25(5H, m), 2.30~2.48(4H, m) 2.55~2.65(1H, m), 3.12(3H, s) 3.35~3.42(2H, m), 3.82(3H, s) 4.20(1H, s, J=8Hz), 5.12(2H, s) 5.52~5.80(7H, m) 6.95(1H, dd, J=9Hz, 9Hz) 7.01(1H, ,d, J=9Hz), 7.18(1H, d, J=9Hz) 7.30(1H, dd, J=9Hz, 9Hz) |

TABLE 170

| Ex. No. | Chemical Structure | $^1$H—NMR |
|---|---|---|
| 499 (549) | 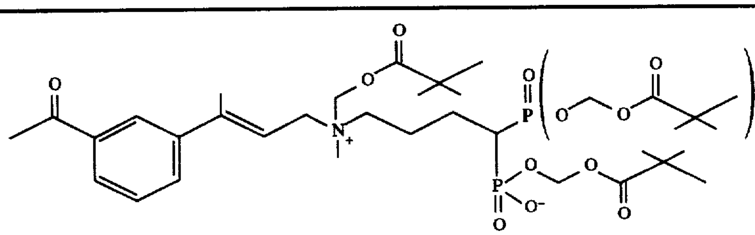 | δ(CDCl$_3$); 1.18(36H, br. s), 1.70~2.03(4H, m) 2.10~2.19(1H, m), 2.29(3H, br. s) 2.65(3H, s), 3.25(3H, br. s) 3.44~3.54(2H, m), 4.23~4.36(2H, m) 4.80~5.25(2H, br.), 5.50~5.85(6H, m) 5.91~6.02(1H, m), 7.49(1H, t, J=8Hz) 7.69(1H, d, J=8Hz), 7.92(1H, d, J=8Hz) 8.00~8.04(1H, m) |
| 500 (561) | 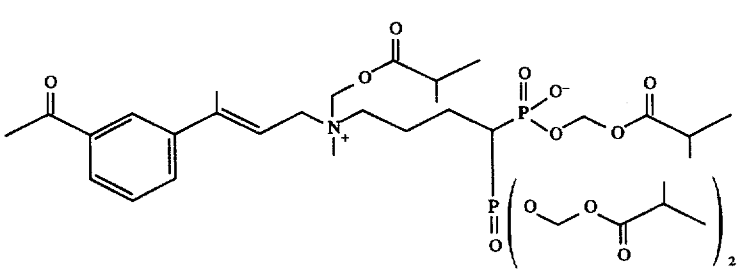 | δ(CDCl$_3$); 1.07~1.17 (18H, m), 1.24 (6H, d, J=7Hz) 1.93~2.40 (5H, m), 2.27 (3H, s) 2.42~2.83 (4H, m), 2.63 (3H, s) 3.23 (3H, s), 3.57~3.85 (2H, m) 4.25~4.34 (1H, m), 4.38~4.47 (1H, m) 5.31~5.39 (2H, m), 5.56~5.81 (6H, m) 5.93 (1H, br. t, J=8Hz), 7.47 (1H, t, J=8Hz) 7.67(1H, d, J=8Hz), 7.91(1H, d, J=8Hz) 8.00(1H, s) |

TABLE 170-continued

| Ex. No. | Chemical Structure | ¹H—NMR |
|---|---|---|
| 501 (574) | (structure) | δ(CD₃OD/TMS); 1.28(6H, d, J=7Hz), 1.35(6H, d, J=7Hz) 2.15(3H, s), 2.43(1H, tt, J=24Hz, 7Hz) 3.14(3H, s), 3.4~3.5(2H, m) 3.83(3H, s), 4.22(2H, d, J=8Hz) 5.34(2H, s), 5.6~5.7(3H, m) 6.95(1H, t, J=8Hz), 7.01(1H, d, J=8Hz) 7.17(1H, dd, J=8Hz, 2Hz), 7.30(1H, dt, J=2Hz, 8Hz) |

TABLE 171

| Ex. No. | Chemical Structure | ¹H—NMR |
|---|---|---|
| 502 (578) | (structure) | δ(CDCl₃); 1.13~1.58(18H, m), 1.63~1.81(6H, br.) 1.83~1.96(6H, br.), 1.98~2.15(2H, m) 2.13(3H, s), 2.21~2.37(2H, m) 2.49(1H, br. t, J=23Hz), 3.27(3H, s) 3.66~3.80(2H, m), 3.82(3H, s) 4.12~4.23(1H, m), 4.26~4.35(1H, m) 4.56~4.72(3H, m), 5.28~5.37(2H, m) 5.52(1H, br. t, J=8Hz) 5.61~5.85(4H, m), 6.89(1H, d, J=8Hz) 6.94(1H, t, J=8Hz), 7.11(1H, d, J=8Hz) 7.25~7.32(1H, m) |
| 503 (546) | (structure) | δ(CDCl₃); 1.22(27H, s), 1.51(3H, d, J=7Hz) 1.70~2.04(4H, m), 2.25(3H, d, J=2Hz) 2.41(2H, dt, J=2Hz, 7Hz) 2.58(1H, dtt, J=2Hz,7Hz, 24Hz) 3.35(2H, s), 3.79(3H, dd, J=5Hz, 14Hz) 4.92(1H, q, J=7Hz), 5.66~5.75(6H, m) 6.84(1H, d, J=3Hz), 7.13(1H, d, J=3Hz) 7.37(2H, d, J=8Hz), 7.56(2H, d, J=8Hz) |
| 504 (700) | (structure) | δ(CD₃OD); 1.23(27H, s), 1.85~2.05(7H, m) 2.72(2H, t, J=7Hz), 2.86(3H, s) 3.02~3.22(2H, m), 3.81(3H, s) 3.82(3H, dd, J=12Hz, 3Hz) 3.83(3H, s), 5.62~5.78(6H, m) 6.80(1H, d, J=9Hz), 6.85(1H, d, J=9Hz) 7.00(1H, d, J=9Hz) |

Example 505

Tetraethyl 5-{4-(4-fluorobenzoyl)piperidino}-(E)-3-pentenylidene-1,1-diphosphonate

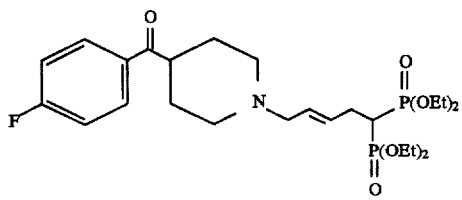

2.4 g of the tetraethyl 5-acetoxy-(E)-3-pentenylidene-1,1-diphosphonate prepared in the Preparative Example 14 was dissolved in 40 ml of tetrahydrofuran, followed by the addition of 1.45 g of 4-(4-fluorobenzoyl)piperidine hydrochloride, 8.4 ml of triethylamine and 280 mg of tetrakis(triphenyl-phosphine) palladium. The obtained mixture was heated at 50° C. for 8 hours under a nitrogen flow while stirring. The reaction solution was distilled to remove the solvent. The residue was purified by silica gel column chromatography [conc. aqueous ammonia/methanol/dichloromethane (1/10/50 to 1/10/25)] to thereby give 2.1 g of the title compound.

$^1$H-NMR δ(CDCl$_3$): 1.35(12H, t, J=7HZ), 2.82~2.88(4H, m), 2.02~2.10(2H, m), 2.38(1H, tt, J=23 Hz, 7 Hz), 2.61~2.75(2H, m), 2.96~3.03(4H, m), 3.13~3.22(1H, m), 4.14~4.23(6H, m), 5.61(1H, dr, J=15 Hz, 7 Hz), 5.79(1H, dr, J=7 Hz, 7 Hz), 7.12(2H, t, J=9 Hz), 7.96(2H, dd, J=9 Hz, 6 Hz)

Example 506

Tetraethyl 4-[3-[2-(2-methoxyphenyl)ethyl]-1-methylformamidin-1-yl]-1,1,-butanediphosphonate acetate

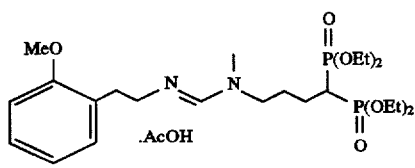

A mixture comprising 1.6 g of the tetraethyl 4-methylamino-1,1-butanediphosphonate prepared in the Preparative Example 1, 1.2 g of the 1,1-dimethyl-3-[2-(2-methoxyphenyl)ethyl]formamidine prepared in the Preparative Example 15, a catalytic amount of ammonium sulfate and 2 ml of toluene was heated in an oil bath at 120° C. for 5 hours. After cooling, the resultant reaction solution was subjected to silica gel column chromatography and then elution with 0 to 30 % (15% acetic acid/methanol)/chloroform was effected. 950 mg of the title compound was obtained.

$^1$H-NMR δ(CDCl$_3$): 1.31~1.38(12H, m), 1.75~1.88(4H, m), 2.04(3H, s), 2.94(2H, s, J=7 Hz), 3.14(3H, s), 3.20(2H, t, J=7 Hz), 3.59(2H, t, J=7 Hz), 3.83(3H, s), 4.12~4.23(8H, m), 6.82~6.92(2H, m), 7.05(1H, s), 7.15(1H, d, J=8 Hz), 7.22(1H, t, J=8 Hz)

Example 507

Tetraethyl N-[4-(4-fluorophenyl)-4-methyl-3-butenyl]carbamoylmethanediphosphonate (a) 4-(4-fluorophenyl)-4-methyl-3-butenylisocyanate

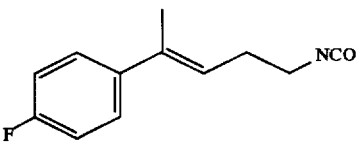

A mixture comprising 1.4 g of 5-(4-fluorophenyl)-5-methyl-4-pentenoic acid, 1 ml of thionyl chloride and 30 ml of benzene was heated in an oil bath at 80° C. for 2 hours and then concentrated to give a carboxylic acid chloride. The whole amount of this carboxylic acid chloride was dissolved in 15 ml of acetone and the resultant solution was dropwise added to 30 ml of an aqueous solution of 1 g of sodium azide while cooling with ice. After reacting at that temperature for 2 hours, the reaction mixture was extracted with benzene. The benzene phase was washed twice with water and once with a saturated aqueous solution of common salt, followed by drying over anhydrous magnesium sulfate. The magnesium sulfate was removed by filtration.

The benzene solution as the filtrate was partially concentrated under a reduced pressure to remove water and then heated under reflux for 2 hours. The reaction solution was concentrated to give a crude product of 4-(4-fluorophenyl)-4-methyl-3-butenyl-isocyanate.

This isocyanate was used for the next step as it was without further purification.

(b) Tetraethyl N-[4-(4-fluorophenyl-4-methyl-3-butenyl]carbamoylmethanediphosphonate

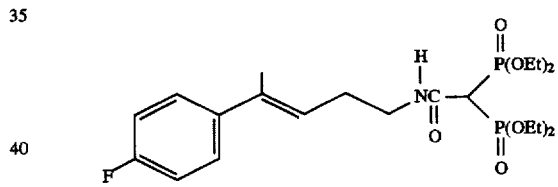

2.5 g of tetraethyl methanediphosphonate was dropwise added to a mixture comprising 300 mg of sodium hydride and 30 ml of N,N-dimethylformamide while stirring. the obtained mixture was stirred for 2 hours to give a clear reaction solution. The whole amount of the isocyanate prepared in the step (a) was added thereto and then the reaction was carried out at room temperature for 2 hours. The reaction solution was extracted with ethyl acetate-diluted hydrochloric acid system. The organic phase was subjected to silica gel column chromatography and then elution with 0 to 5 % methanol/chloroform was effected. 1.07 g of the title compound was obtained.

$^1$H-NMR δ(CDCl$_3$): 1.28(6H, t, J=7 Hz), 1.34(6H, t, J=7 Hz), 2.03(3H, s), 2.45(2H, q, J=7 Hz), 3.42(2H, q, J=7 Hz), 3.57(1H, t, J=23 Hz), 4.10~4.27(8H, m), 5.70(1H, t, J=7 Hz), 6.98(2H, t, J=9 Hz), 7.06(1H, t, J=7 Hz), 7.34(2H, dd, J=9 Hz, 5 Hz)

Example 508

Tetraethyl 4-[N-methyl-2-(5-bromobenzofuran-2-yl)-2-hydroxyethylamino]butylidene-1,1-diphosphonate

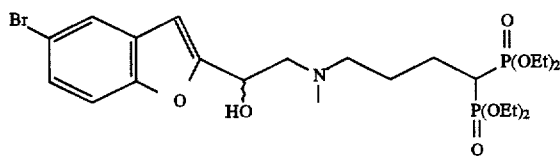

A mixture comprising 1 g of the tetraethyl 4-methylamino-1,1-butanediphosphonate prepared in Preparative Example 1, 2 g of the 5-bromo-2-(1,2-epoxyethyl)benzofuran synthesized according to the process described in J. Heterocyclic Chem., 28, p.1395 (1991), 10 ml of benzene and 10 ml of methanol was heated under reflux for 5 hours. The reaction mixture was distilled to remove the solvent. The residue was purified by silica gel column chromatography (2 to 5% methanol/dichloromethane) to thereby give 0.2 g of the title compound.

$^1$H-NMR δ(CDCl$_3$): 1.35(12H, t, J=7 Hz), 1.83(2H, quin, J=8 Hz), 1.92~2.08(2H, m), 2.32(3H, s), 2.48(1H, J=7 Hz, 24 Hz), 2.44~2.51(1H, m), 2.54~2.62(1H, m), 2.68(1H, dd, J=3 Hz, 12 Hz), 2.86(1H, dd, J=10 Hz, 12 Hz), 4.13~4.23 (8H, m), 4.83(1H, dd, J=3 Hz, 10 Hz), 6.64(1H, s), 7.31(1H, d, J=8 Hz), 7.34(1H, d, J=8 Hz), 7.66(1H, s)

Examples 509 to 512

The compounds of Examples 509 to 512 listed in Tables 172 and 173 were prepared by preparing diphosphonic acid ester derivatives in a similar manner to that of the Example 505 and deprotecting the ester derivatives in a similar manner to that of the Example 14.

TABLE 172

| Ex. No. | Chemical Structure | $^1$H — NMR |
|---|---|---|
| 509 (744) | | δ(D$_2$O); 1.30(3H, s), 1.57(1H, tt, J=20Hz, 7Hz) 1.79(3H, s), 2.07(3H, s) 2.33~2.45(2H, m) 3.83(1H, dd, J=15Hz, 8Hz) 2.92~3.00(2H, m), 3.07(1H, d, J=12Hz) 3.66(3H, s), 5.44(1H, td, J=Hz, 16Hz) 5.87(1H, td, J=8Hz, 16Hz) 6.90(1H, t, J=9Hz), 6.95~6.99(2H, m) 7.19(1H, t, J=9Hz) |
| 510 (745) | | δ(D$_2$O); 1.40~1.63(3H, m), 1.67~1.88(2H, m) 1.99~2.05(2H, m), 2.30~2.43(2H, m) 2.80~2.90(4H, m), 3.25~3.35(2H, m) 5.40(1H, td, J=8Hz, 16Hz) 5.82(1H, td, J=8Hz, 16Hz) 7.08(2H, t, J=8Hz) 7.88(2H, dd, J=8Hz, 6Hz) |
| 511 (740) | | δ(D$_2$O); 1.59~1.75(3H, m), 2.18(3H, s) 2.32~2.54(7H, m), 3.01(2H, d, J=7Hz) 3.70(3H, s), 5.40(1H, td, J=7Hz, 16Hz) 5.84(1H, td, J=7Hz, 16Hz) 6.82(1H, t, J=9Hz), 6.90(1H, d, J=9Hz) 7.07~7.16(2H, m) |

TABLE 173

| Ex. No. | Chemical Structure | $^1$H — NMR |
|---|---|---|
| 512 (766) | | δ(CD$_2$O); 1.56(1H, tt, J=20Hz, 7Hz), 2.10(3H, s) 2.30~2.48(4H, m), 2.61~2.68(2H, m) 2.90(2H, d, J=7Hz) 5.40(1H, td, J=7Hz, 16Hz) 5.82(1H, td, J=7Hz, 16Hz) 6.81(1H, t, J=9Hz), 6.90(1H, d, J=9Hz) 7.08~7.17(2H, m) |

Examples 513 and 514

The compounds of Examples 513 and 514 listed in Table 174 were prepared by preparing diphosphonic acid ester derivatives in a similar manner to that of the Example 508 and deprotecting the ester derivatives in a similar manner to that of the Example 14.

TABLE 174

| Ex. No. | Chemical Structure | $^1$H—NMR |
|---|---|---|
| 513 (755) | [Br-benzofuran-CH(OH)-CH$_2$-N(CH$_3$)-(CH$_2$)$_3$-CH(P(ONa)$_2$=O)$_2$] | δ(D$_2$O); 1.50–1.68(5H, m), 2.14(3H, s) 2.35–2.44(2H, m) 2.78(1H, dd, J=8Hz, 12Hz) 2.84(1H, dd, J=7Hz, 12Hz) 4.95(1H, t, J=7Hz), 6.66(1H, s) 7.31 (1H, s), 7.65(1H, s) |
| 514 (757) | [benzofuran-CH(OH)-CH$_2$-N(CH$_3$)-(CH$_2$)$_3$-CH(P(ONa)$_2$=O)$_2$] | δ(D$_2$O); 1.54–1.70(5H, m), 2.15(3H, s) 2.36–2.44(2H, m) 2.80(1H, dd, J=8Hz, 12Hz) 2.87(1H, dd, J=7Hz, 12Hz) 4.93(1H, t, J=7Hz), 6.70(1H, s) 7.14(1H, t, J=8Hz), 7.21(1H, t, J=8Hz) 7.41(1H, d, J=8Hz), 7.51(1H, d, J=8Hz) |

Examples 515 and 516

The compounds of Examples 515 and 516 listed in Table 175 were prepared by preparing diphosphonic acid ester derivatives in a similar manner to that of the Example 5 and deprotecting the ester derivatives in a similar manner to that of the Example 16.

TABLE 175

| Ex. No. | Chemical Structure | $^1$H—NMR |
|---|---|---|
| 515 (702) | [HO-CH(CH$_3$)-phenyl-thiophene-CH$_2$-N(piperidine)-CH$_2$-CH(P(OH)$_2$=O)$_2$] | δ(D$_2$O); 1.24(2H, br. q, J=12Hz) 1.48(3H, d, J=7Hz), 1.55–1.71(3H, m) 1.75–1.91(3H, m) 2.31(2H, br. t, J=12Hz) 3.01(2H, br. d, J=12Hz), 3.86(2H, s) 4.81(1H, q, J=7Hz), 6.99(1H, d, J=3Hz) 7.25(1H, d, J=3Hz) 7.34(2H, dt, J=2Hz, 8Hz) 7.58(2H, dt, J=2Hz, 8Hz) |
| 516 (687) | [benzothiazole-CH$_2$-N(piperidine)-CH$_2$-CH(P(OH)$_2$=O)$_2$] | δ(D$_2$O); 1.24–1.35(2H, m), 1.56–1.70(2H, m) 1.80–1.98(4H, m), 3.04(2H, t, J=2Hz) 3.54(2H, d, J=12Hz), 4.62(2H, br.) 7.40(1H, t, J=8Hz), 7.46(1H, t, J=8Hz) 7.92(2H, t, J=8Hz) |

Examples 517 to 525

The compounds of Examples 517 to 525 listed in Tables 176 to 178 were prepared by preparing diphosphonic acid ester derivatives in a similar manner to that of the Example 10 and deprotecting the ester derivatives in a similar manner to that of the Example 16.

TABLE 176

| Ex. No. | Chemical Structure | ¹H—NMR |
|---|---|---|
| 517 (753) | 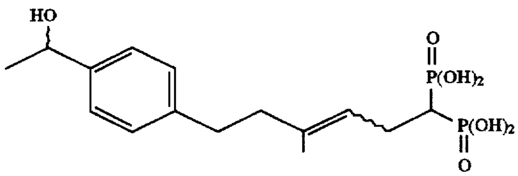 | δ(D₂O); 1.30(3H, d, J=7Hz) 1.53(s) and 1.57(total 3H, s) 1.62~1.98(1H, m), 2.04~2.45(4H, m) 2.59(2H, br. t, J=7Hz) 4.73(1H, q, J=7Hz), 5.22(1H, br.) 7.11~7.23(4H, m) |
| 518 (736) | 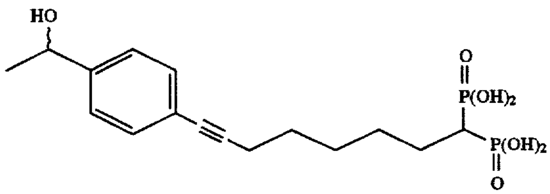 | δ(D₂O); 1.27(3H, d, J=6Hz), 1.29~1.51(6H, m) 1.62~1.78(2H, m) 1.88(1H, tt, J=6Hz, 22Hz) 2.28(2H, t, J=6Hz), 4.73(1H, q, J=6Hz) 7.18(2H, d, J=8Hz), 7.26(2H, d, J=8Hz) |
| 519 (737) | 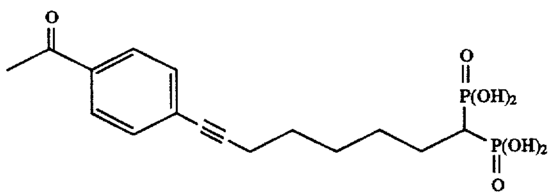 | δ(D₂O); 1.18~1.28(2H, m), 1.30~1.47(4H, m) 1.62~1.80(2H, m), 1.90~2.09(1H, m) 2.11~2.22(2H, br.), 2.30(3H, s) 7.07(2H, d, J=8Hz), 7.48(2H, d, J=8Hz) |

TABLE 177

| Ex. No. | Chemical Structure | ¹H—NMR |
|---|---|---|
| 520 (629) | 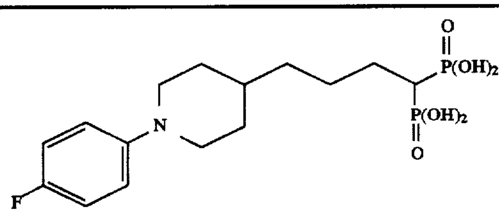 | δ(D₂O + NaOD/DSS); 1.25~1.82(10H, m) 1.90(2H, d, J=13Hz) 2.66(2H, t, J=12Hz) 3.45(2H, d, J=12Hz) 7.05~7.17(4H, m) |
| 521 (604) | 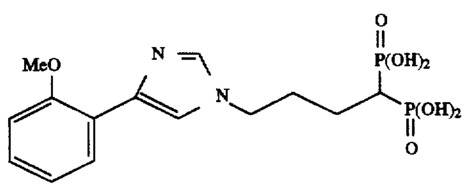 | δ(D₂O); 1.62~2.07(5H, m), 3.80(3H, s) 4.07(2H, t, J=7Hz), 6.97(1H, t, J=8Hz) 7.03(1H, d, J=8Hz), 7.28(1H, t, J=8Hz) 7.57(1H, d, J=8Hz), 7.68(1H, s) 8.16(1H, s) |
| 522 (720) | 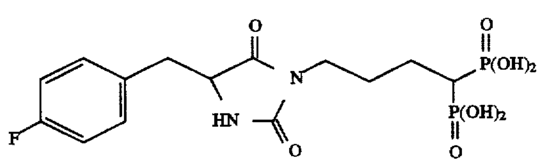 | δ(D₂O + NaOD/DSS); 1.51(1H, tt, J=22Hz, 5Hz) 1.57~1.74(4H, m), 3.00(1H, d, J=14Hz) 3.08(1H, d, J=14Hz) 3.15~3.21(2H, m), 7.06(2H, t, J=9Hz) 7.21(2H, dd, J=9Hz, 5Hz) |

TABLE 178

| Ex. No. | Chemical Structure | $^1$H—NMR |
|---|---|---|
| 523 (725) | 4-F-C6H4-CH=C(N(Me)C(=O)-)-C(=O)-NH-(CH2)3-CH(P(OH)2=O)(P(OH)2=O) | δ(D$_2$O + NaOD/DSS); 1.70–1.90(5H, m), 3.19(3H, s) 3.59(2H, t, J=7Hz), 6.63(1H, s) 7.16(2H, t, J=9Hz) 7.78(2H, dd, J=9Hz, 5Hz) |
| 525 (726) | 4-F-C6H4-CH2-CH(N(Me)C(=O)-)-C(=O)-NH-(CH2)3-CH(P(OH)2=O)(P(OH)2=O) | δ(D$_2$O + NaOD/DSS); 1.32–1.56(2H, m), 1.58–1.73(2H, m) 2.02(1H, br. t, J=24Hz) 3.04(3H, s), 3.13–3.31(4H, m) 4.41(1H, t, J=4Hz), 7.07(2H, t, J=9Hz) 7.14(2H, dd, J=9Hz, 5Hz) |
| 525 (719) | 4-F-C6H4-CH=C(NHC(=O)-)-C(=O)-NH-(CH2)3-CH(P(OH)2=O)(P(OH)2=O) | δ(D$_2$O + NaOD/DSS); 1.67–1.87(5H, m), 3.53(2H, t, J=7Hz) 6.47(1H, s), 7.16(2H, t, J=9Hz) 7.86(2H, dd, J=9Hz, 6Hz) |

Examples 526 to 528

The compounds of Examples 528 to 528 listed in Table 179 were prepared by preparing diphosphonic acid ester derivatives in a similar manner to that of the Example 13 and deprotecting the ester derivatives in a similar manner to that of the Example 18.

TABLE 179

| Ex. No. | Chemical Structure | $^1$H—NMR |
|---|---|---|
| 526 (734) | Acetyl-benzofuran-CH2-N(Me)-(CH2)3-CH(P(OH)2=O)(P(OH)2=O) | δ(D$_2$O + NaOD); 1.50–1.72(5H, m), 2.03(3H, s) 2.35(2H, t, J=7Hz), 2.47(3H, s) 3.56(2H, s) 7.41(1H, dd, J=2Hz, 9Hz) 7.47(1H, d, J=9Hz), 7.65(1H, d, J=2Hz) 7.70(1H, s) |
| 527 (739) | Acetyl-benzofuran-CH2-N(Me)-(CH2)3-CH(P(OH)2=O)(P(OH)2=O) | δ(D$_2$O); 1.66–1.82(2H, m), 1.86–2.06(3H, m) 2.54(3H, s), 2.78(3H, s) 3.02–3.11(1H, m), 3.13–3.24(1H, m) 4.42(1H, d, J=14Hz), 4.52(1H, d, J=14Hz) 7.12(1H, s), 7.51(1H, d, J=9Hz) 7.88(1H, dd, J=2Hz, 9Hz) 8.21(1H, d, J=2Hz) |
| 528 (762) | (MeO)(OMe)-C6H3-C(=O)-thiophene-CH2-N(Me)-(CH2)3-CH(P(OH)2=O)(P(OH)2=O) | δ(D$_2$O); 1.73(2H, qd, J=16Hz, 8Hz) 1.97(1H, tt, J=22Hz, 6Hz), 2.01(2H, m) 2.72(3H, s), 2.97–3.09(1H, m) 3.09–3.23(1H, m), 3.56(3H, s) 3.77(3H, s), 4.43(1H, d, J=14Hz) 4.56(1H, d, J=14Hz), 6.88–6.92(1H, m) 7.08–7.18(2H, m), 7.24(1H, d, J=4Hz) 7.39(1H, d, J=4Hz) |

Examples 529 to 531

The compounds of Examples 529 to 531 listed in Table 180 were prepared by preparing diphosphonic acid ester derivatives in a similar manner to that of the Example 508 and deprotecting the ester derivatives in a similar manner to that of the Example 16

TABLE 180

| Ex. No. | Chemical Structure | ¹H—NMR |
|---|---|---|
| 529 (661) | MeO-phenyl-CH₂CH₂-N=CH-N(Me)-CH₂CH₂CH₂-CH(P(OH)₂=O)(P(OH)₂=O) | δ(D₂O + NaOD/DSS); 1.56(1H, tt, J=22Hz, 5Hz) 1.60–1.83(4H, m), 2.83(2H,t, J=7Hz) 2.87(3H, s), 3.16(2H, t, J=8Hz) 3.45(2H, t, J=7Hz), 3.84(3H, s) 6.99(1H, t, J=8Hz), 7.06(1H, d, J=8Hz) 7.21(1H, d, J=8Hz), 7.30(1H, t, J=8Hz) |
| 530 (636) | MeO-phenyl-CH₂-N=CH-N(Me)-CH₂CH₂CH₂-CH(P(OH)₂=O)(P(OH)₂=O) | δ(D₂O + NaOD/DSS); 1.58(1H, tt, J=22Hz, 5Hz) 1.61–1.86(4H, m), 2.87(3H, s) 3.22(2H, t, J=8Hz), 3.85(3H, s) 4.35(2H, s), 6.95–7.10(2H, m) 7.25–7.40(2H, m), 7.65(1H, s) |
| 531 (677) | MeO-phenyl-CH=C(N-cycle)- with P(OH)₂ groups | δ(D₂O + NaOD/DSS); 1.75–2.04(5H, m) 2.98(2H, dt, J=2Hz, 6Hz), 3.39(3H, s) 3.51–3.59(4H, m), 3.88 (3H, s) 7.07–7.15(2H, m), 7.40–7.48(2H, m) 7.53(1H, t, J=2Hz) |

Example 532

The compound of Examples 532 listed in Table 181 was prepared by preparing a diphosphonic acid ester derivative in a similar manner to that of the Example 507 and deprotecting the ester derivative in a similar manner to that of the Example 16.

TABLE 181

| Ex. No. | Chemical Structure | ¹H—NMR |
|---|---|---|
| 532 (711) | F-phenyl-C(Me)=CH-CH₂CH₂-NH-CH₂-CH(P(OH)₂=O)(P(OH)₂=O) | δ(D₂O + NaOD/DSS); 2.40(3H, s), 2.47(2H, q, J=7Hz) 3.34(2H, t, J=7Hz), 5.82(1H, t, J=7Hz) 7.10(2H, t, J=9Hz) 7.48(2H, dd, J=9Hz, 5Hz) |

Example 533

1-Chloro-4-(3,4-methylenedioxybenzyl)amino-6-nitrophthalazine and 1-Chloro-4-(3,4-methylenedioxbenzyl)amino-7-nitrophthalazine (a) 1.4-Dichloro-6-nitrophthalazine

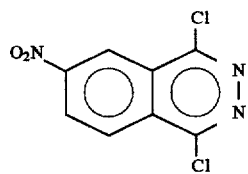

10 g of 2,3-dihydro-6-nitro-1,4-phthalazinedione was suspended in 50 ml of phosphorus oxychloride, followed by the addition of 10 ml of diisopropylethylamine thereto. The resultant mixture was heated under reflux for four hours. The reaction mixture was distilled under reduced pressure to remove excess phosphorus oxychloride. Ethyl acetate was added to the residue thus obtained to give a solution. The obtained solution was washed with water and a saturated aqueous solution of common salt successively, dried over magnesium sulfate and subjected to vacuum concentration to remove the solvent. Thus, the title compound was obtained in a crude form, which was used in the subsequent step without further purification.

¹H-NMR δ(CDCl₃): 8.56(1H, dd, J=9.0, 0.5 Hz), 8.83 (1H, dd, J=9.0, 2.0 Hz), 9.20(1H, dd, J=2.0, 0.5 Hz)

(b) 1-Chloro-4-(3,4-methylenedioxybenzyl)amino-6-nitrophthalazine and 1-Chloro-4-(3,4-methylenedioxybenzyl)amino-7-nitrophthalazine

239

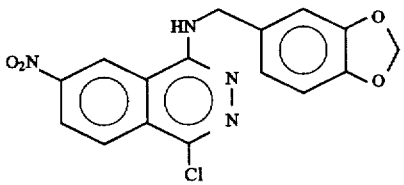

and

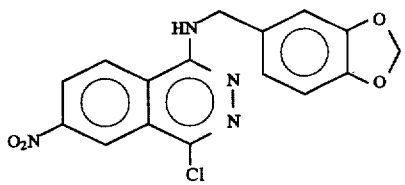

3.5 g of the 1,4-dichloro-6-nitrophthalazine prepared in the step (a) was dissolved in 100 ml of ethanol, followed by the addition thereto of 2.17 g of piperonylamine and 3 ml of triethylamine. The resultant mixture was heated under reflux for 12 hours. The reaction mixture was distilled under reduced pressure to remove the solvent. Water was added to the residue thus obtained to give a solution. The obtained aqueous solution was extracted with methylene chloride. The organic phase was dried over magnesium sulfate and then subjected to vacuum concentration to remove the solvent. The residue was purified by silica gel column chromatography [n-hexane/ethyl acetate (2: 1 to 1: 1)]. Thus, 1.8 g of 1-chloro-4-(3,4-methylenedioxybenzyl) amino-6-nitrophthalazine was obtained from less polar fractions as a yellow solid and 1.2 g of 1-chloro-4-(3,4-methylene-dioxybenzyl)amino-7-nitrophthalazine was obtained from more polar fractions as a yellow solid.

1-Chloro-4-(3,4-methylenedioxybenzyl)amino-6-nitrophthalazine

Elementary analysis

|      | C (%) | H (%) | N (%) |
|------|-------|-------|-------|
| cal. | 53.57 | 3.09  | 15.62 |
| found| 53.60 | 3.11  | 15.60 |

Mass (M/Z): 359 (MH⁺)
m.p.: from 186.5 to 188° C.
$^1$H-NMR δ(CDCl$_3$): 4.80(2H, d, J=5.0 Hz), 5.73(1H, t, J=5.0 Hz), 5.95(2H, s), 6.78(1H, d, J=8.0 Hz), 6.92(1H, dd, J=8.0, 2.0 Hz), 6.94(1H, d, J=2.0 Hz), 8.37(1H, d, J=9.0 Hz), 8.64(1H, dd, J=9.0, 2.0 Hz), 8.73(1H, d, J=2.0 Hz)

1Chloro-4-(3,4-methylene-dioxybenzyl)amino-7-nitrophthalazine

Elementary analysis

|      | C (%) | H (%) | N (%) |
|------|-------|-------|-------|
| cal. | 53.57 | 3.09  | 15.62 |
| found| 53.70 | 3.15  | 15.54 |

Mass (M/Z): 359 (MH⁺)
m.p.: from 240°to 242° C. (decomp.)
$^1$H-NMR δ(CDCl$_3$): 4.78(2H, d, J=5.0 Hz), 5.52(1H, t, J=5.0 Hz), 5.96(2H, s), 6.78(1H, d, J=8.0 Hz), 6.91(1H, dd, J=8.0, 1.5 Hz), 6.93(1H, d, J=1.5 Hz), 7.98(1H, d, J=9.0 Hz), 8.59(1H, dd, J=9.0, 2.0 Hz), 9.05(1H, d, J=2.0 Hz )

We claim:

240

1. A phosphonic acid derivative represented by the following general formula (I) or a pharmacologically acceptable salt thereof:

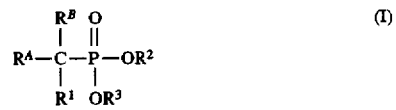

wherein R$^1$ represents a hydrogen atom;

R$^2$ and R$^3$ may be the same or different from each other and each represents a hydrogen atom, a lower alkyl group which may have a substituent, an alkali metal or a prodrug ester forming group having the formula

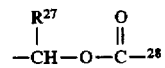

wherein R$^{27}$ represents a hydrogen atom or a lower alkyl group; and R$^{28}$ represents an alkyl group which has 1 to 12 carbon atoms and may have a substituent, a cycloalkyl group, an aryl group which may have a substituent, an alkoxy group which has 1 to 12 carbon atoms and may have a substituent, a cycloalkyloxy group, an aryloxy group which may have a substituent, an alkylamino group which has 1 to 12 carbon atoms and may have a substituent, a cycloalkylamino group or an aromatic amino group which may have a substituent;

R$^4$ represents a group represented by the formula:

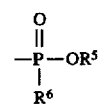

wherein R$^5$ represents a hydrogen atom, a lower alkyl group, an alkali metal or a prodrug ester forming group; and R$^6$ represents a lower alkyl group or a group represented by the formula: —OR$^7$ (wherein R$^7$ represents a hydrogen atom, a lower alkyl group, an alkali metal or said prodrug ester forming group as defined above); and R$^B$ represents a group represented by the formula: S—T— wherein S represents a group represented by the formula:

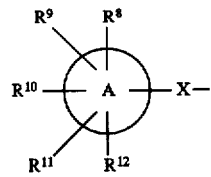

wherein ring A represents a phenyl ring; and X represents a single bond, an alkylene chain which may have a substituent, or an alkylene chain having one double bond within the chain which may have a substituent; R$^8$, R$^9$, R$^{10}$, R$^{11}$ and R$^{12}$ may be the same or different from one another and each represents (1) a hydrogen atom,
(2) an alkyl group which may have a substituent,
(3) an alkenyl group which may have a substituent,
(4) a lower alkoxy group which may have a substituent,
(5) a carbamoyl group which may have a substituent,
(6) a carbamoyloxy group which may have a substituent,
(7) a hydroxyl group, (8) an acyl group,
(9) a halogen atom,
(10) a group represented by the following formula:

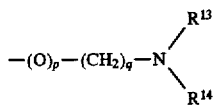

wherein $R^{13}$ and $R^{14}$ may be the same or different from each other and each represents a lower alkyl group which may have a substituent; p is 0 or 1; and q is an integer of 0 to 4) or (11) a group represented by the formula:

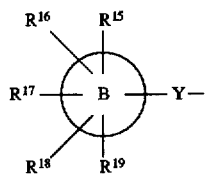

wherein $R^{15}$, $R^{16}$, $R^{17}$, $R^{18}$ and $R^{19}$ may be the same or different from one another and each represents a hydrogen atom, a hydroxyl group, a lower alkyl group or a lower alkoxy group which may have a substituent; ring B represents a phenyl ring; and Y represents an alkylene chain which may have a substituent, an alkylene chain having at least one double bond in the chain which may have a substituent, an alkylene chain having at least one triple bond within the chain which may have a substituent, a group represented by the formula:

a group represented by the formula: —O—, or a single bond, or alternatively two adjacent groups of $R^8$, $R^9$, $R^{10}$, $R^{11}$ and $R^{12}$ may together form a ring; and T represents (1) a group represented by the formula:

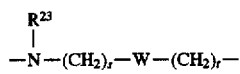

(wherein $R^{23}$ represents a cycloalkyl group, a cycloalkylalkyl group, a lower alkyl group which have a substituent or a lower alkenyl group which may have a substituent; W represents a group represented by the formula: —O—, or a single bond; and s and t are independent of each other and are each an integer of 0 to 4).

2. A pharmaceutical composition which comprises a therapeutically effective amount of the phosphonic acid derivative or the pharmacologically acceptable salt thereof as set forth in claim 1 and a pharmaceutically acceptable filler.

3. A method for medically treating a disease against which a squalene synthetase inhibiting action is efficacious which comprises administering a therapeutically effective amount of the phosphonic acid derivative or the pharmacologically acceptable salt thereof as set forth in claim 1 to a patient suffering from said disease against which a squalene synthetase inhibiting action is efficacious.

4. A method for medically treating hyperlipemia which comprises administering a therapeutically effective amount of the phosphonic acid derivative or the pharmacologically acceptable salt thereof as set forth in claim 1 to a patient suffering from hyperlipemia.

5. A method for medically treating hypertension which comprises administering a therapeutically effective amount of the phosphonic acid derivative or the pharmacologically acceptable salt thereof as set forth in claim 1 to a patient suffering from hypertension.

6. A phosphonic acid derivative represented by the following general formula (I) or a pharmacologically acceptable salt thereof:

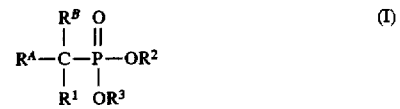

wherein $R^1$ represents a hydrogen atom;

$R^2$ and $R^3$ may be the same or different from each other and each represents a hydrogen atom, a lower alkyl group which may have a substituent, an alkali metal or a prodrug ester forming group having the formula

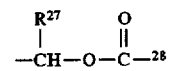

wherein $R^{27}$ represents a hydrogen atom or a lower alkyl group; and $R^{28}$ represents an alkyl group which has 1 to 12 carbon atoms and may have a substituent, a cycloalkyl group, an aryl group which may have a substituent, an alkoxy group which has 1 to 12 carbon atoms and may have a substituent, a cycloalkyloxy group, an aryloxy group which may have a substituent, an alkylamino group which has 1 to 12 carbon atoms and may have a substituent, a cycloalkylamino group or an aromatic amino group which may have a substituent;

$R^4$ represents a group represented by the formula:

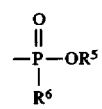

wherein $R^5$ represents a hydrogen atom, a lower alkyl group, an alkali metal or a prodrug ester forming group; and $R^6$ represents a lower alkyl group or a group represented by the formula: —$OR^7$ wherein $R^7$ represents a hydrogen atom, a lower alkyl group, an alkali metal or a prodrug ester forming group as defined above; and $R^B$ represents a group represented by the formula: S—T— wherein S represents a group represented by the formula:

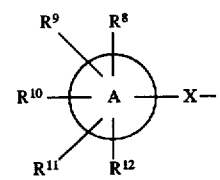

wherein ring A represents a phenyl ring; X is an alkylene chain having one double bond in the chain; $R^8$, $R^9$, $R^{10}$, $R^{11}$ and $R^{12}$ each represents a hydrogen atom;

and T represents a group represented by the formula:

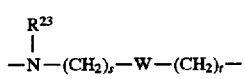

(wherein R²³ represents a hydrogen atom, a cycloalkyl group, a cycloalkylalkyl group, a lower alkyl group which have a substituent or a lower alkenyl group which may have a substituent; W represents a single bond; and s and t are independent of each other and are each an integer of 0 and 4.

7. A compound having the formula

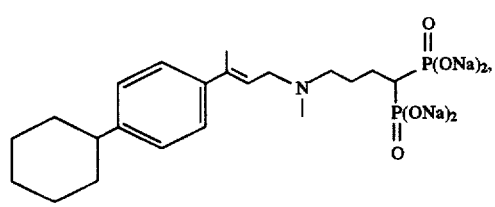

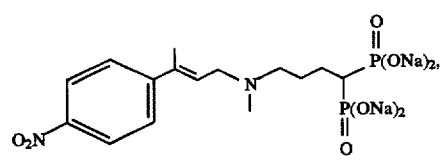

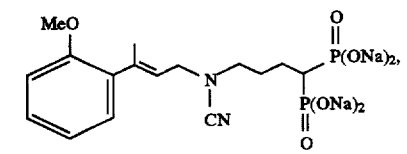

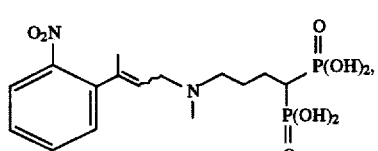

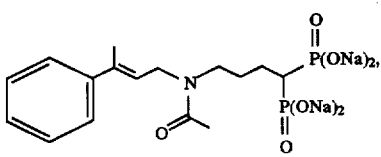

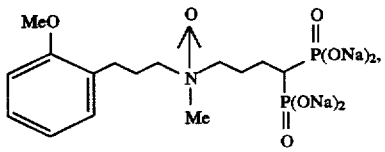

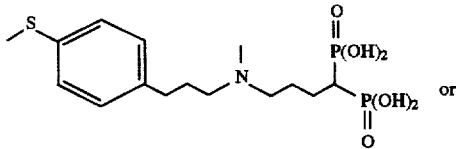 or

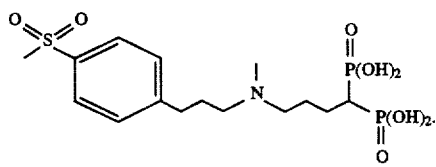

8. A phosphonic acid derivative according to claim 1 from the group consisting of

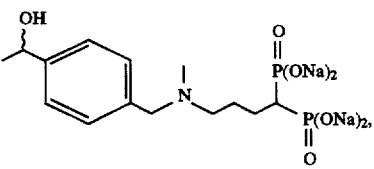

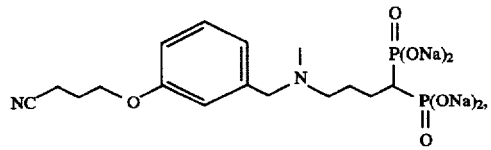

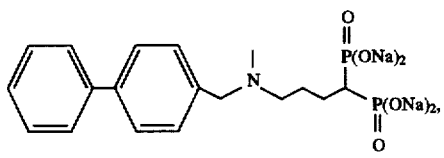

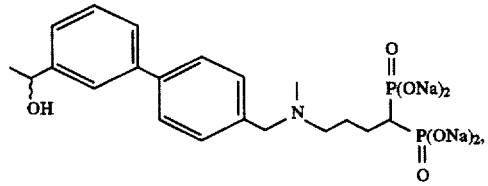

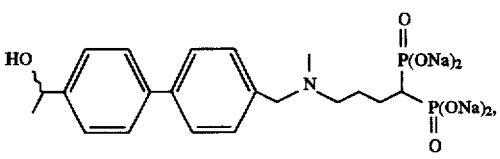

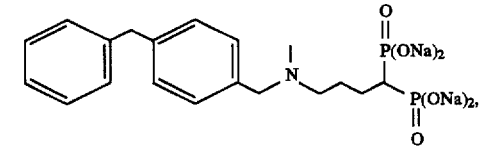

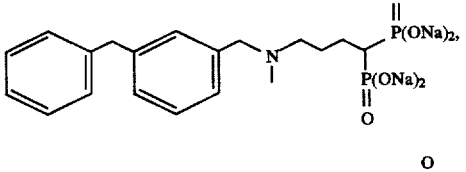

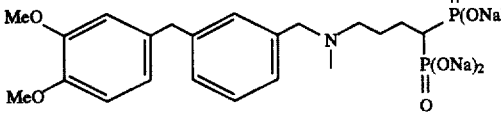

245
-continued
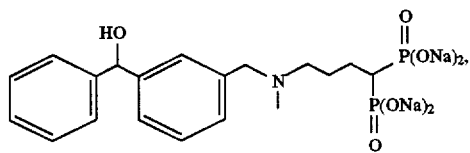
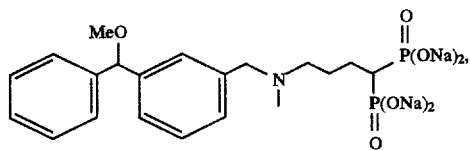
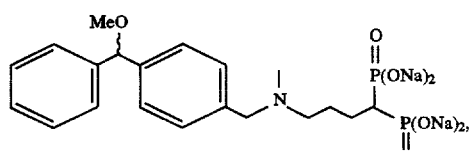
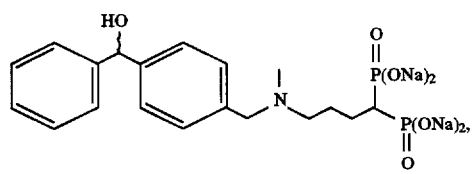
246
-continued
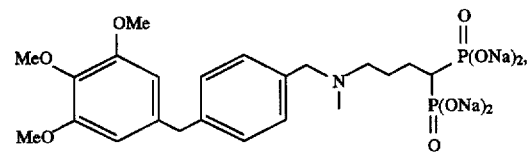
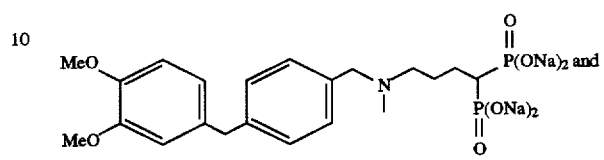
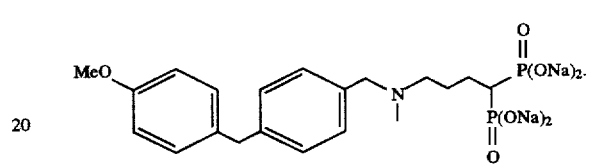
9. A phosphonic acid derivative according to claim 1 selected from the group consisting of
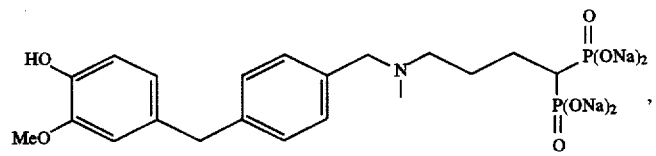
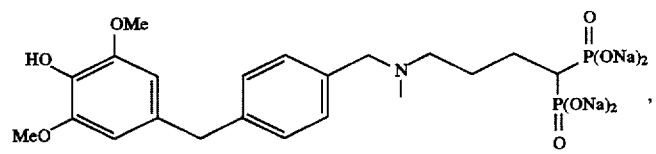
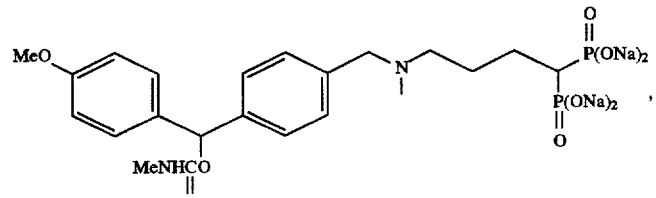
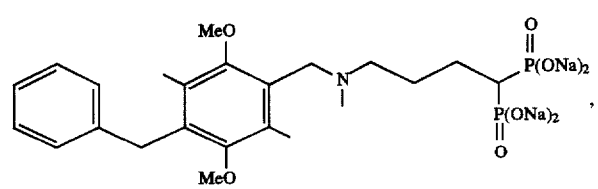

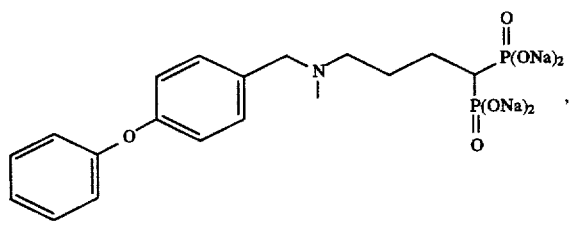
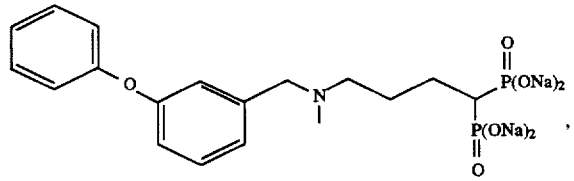
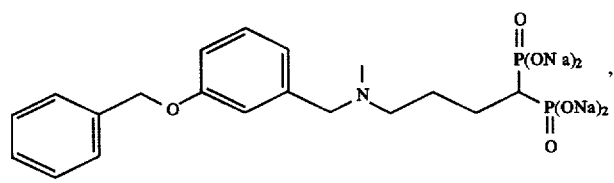
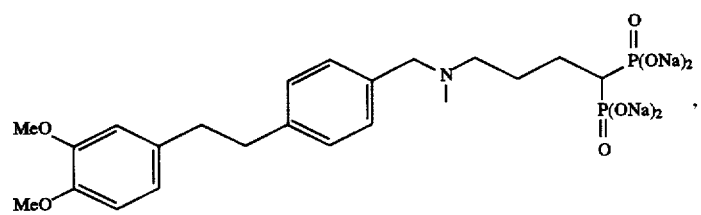
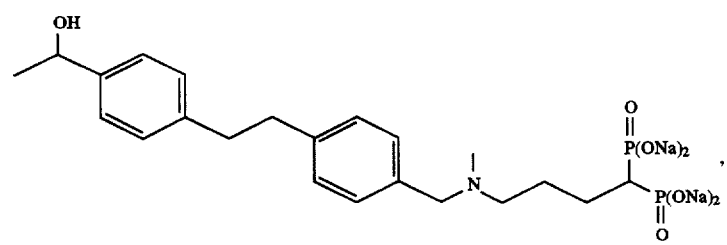
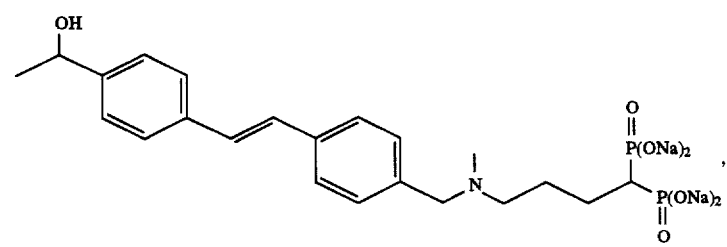
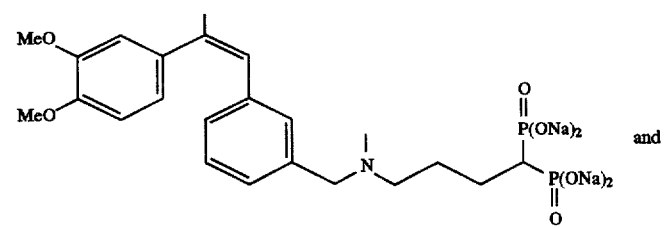
and -continued
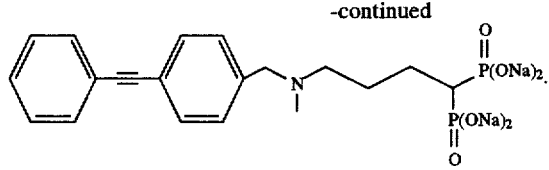
10. A phosphonic acid derivative according to claim 1 selected from the group consisting of
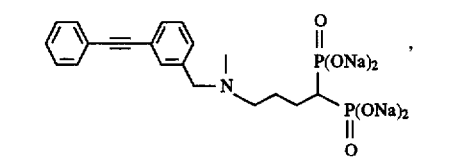,
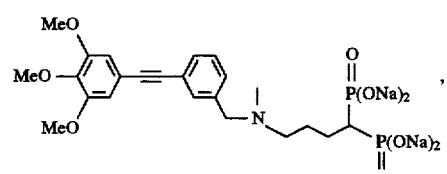,
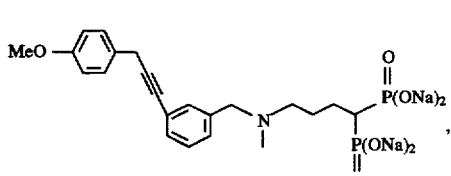,
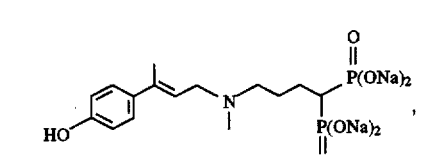,
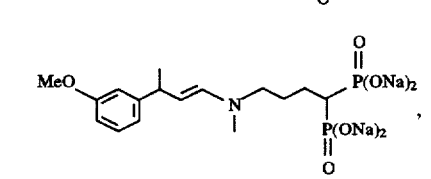,
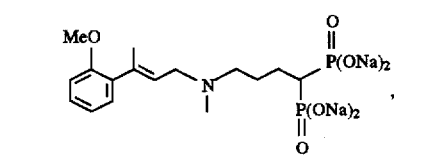,
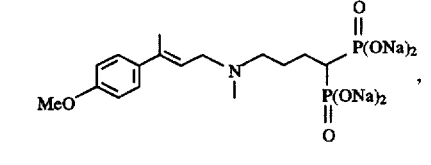,
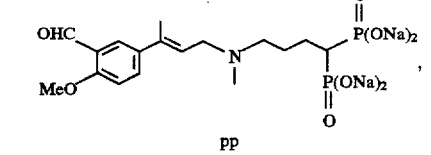,
pp
-continued
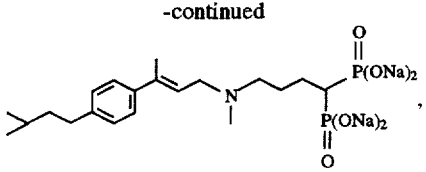,
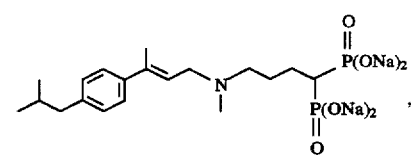,
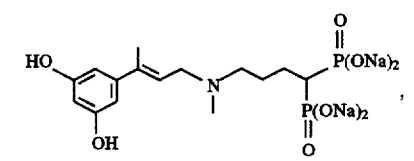,
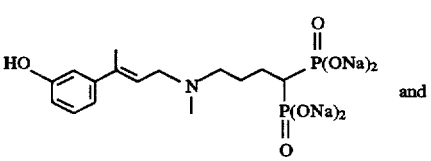 and
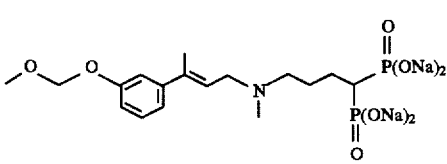
11. A phosphonic acid derivative according to claim 1 selected from the group consisting of
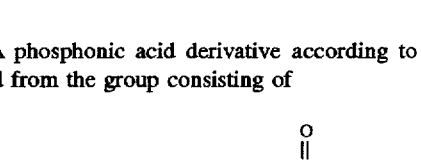,
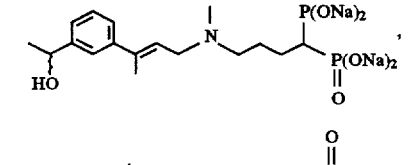,
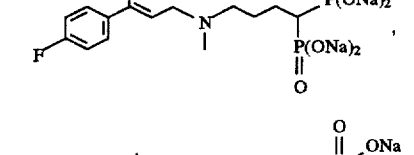,

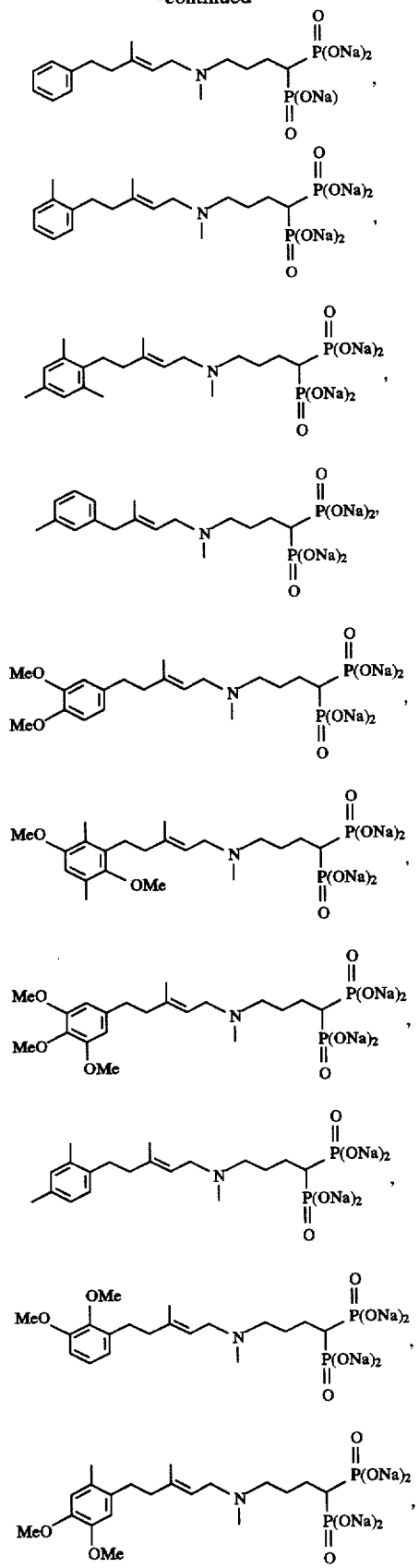
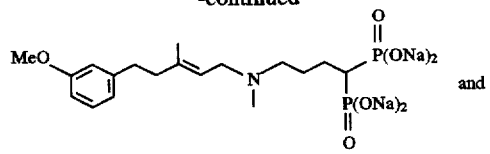
12. A phosphonic acid derivative according to claim 1 selected from the group consisting of
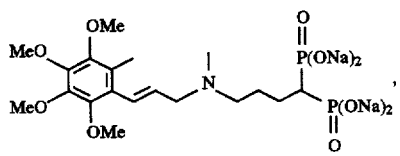
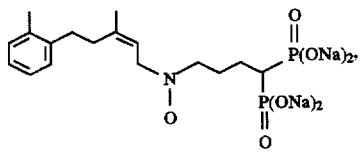
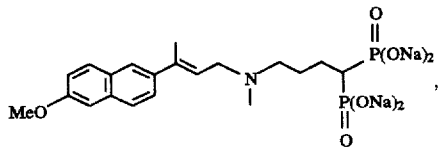
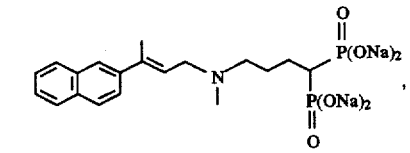
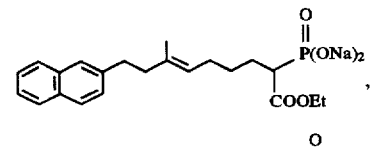
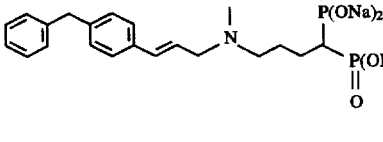
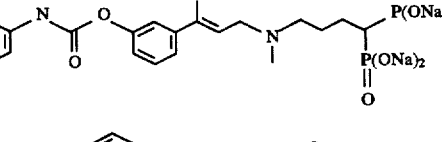
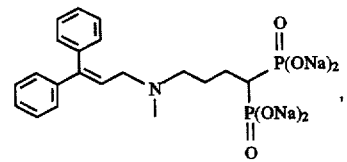

253
-continued
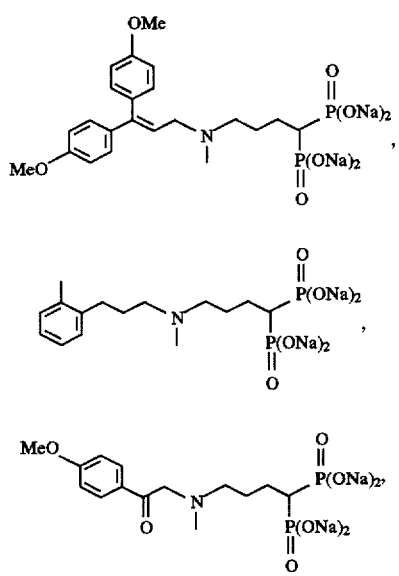
254
-continued
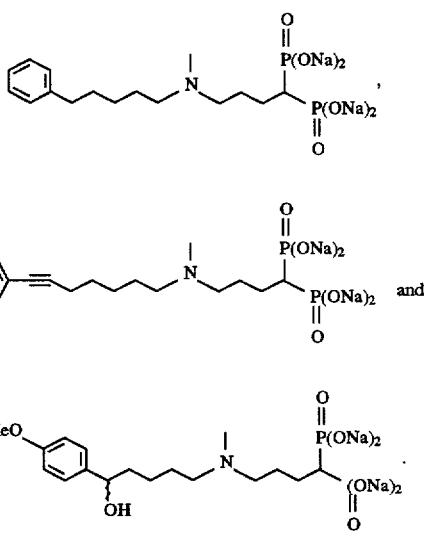
13. A phosphonic acid derivative according to claim 1 selected from the group consisting of
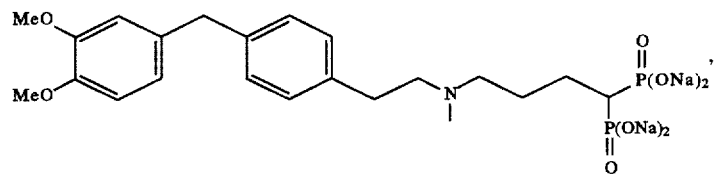
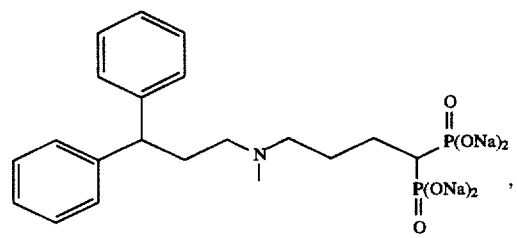
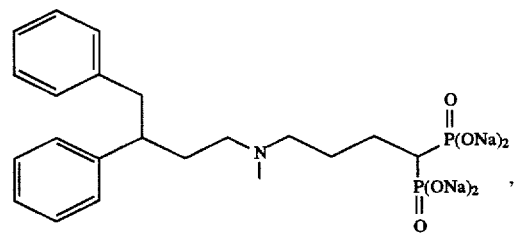

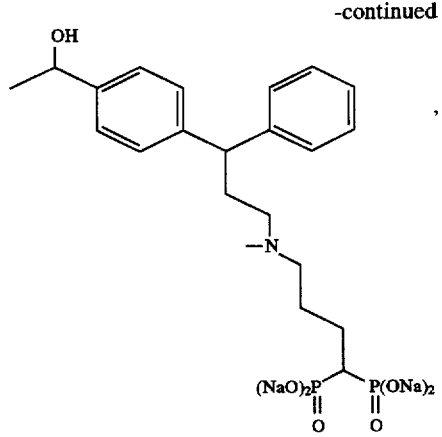
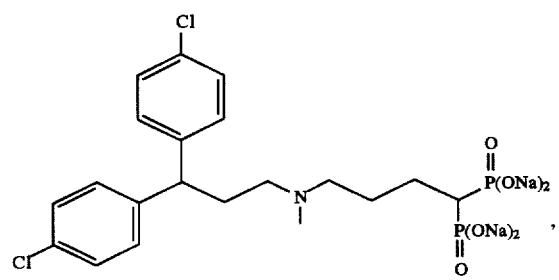
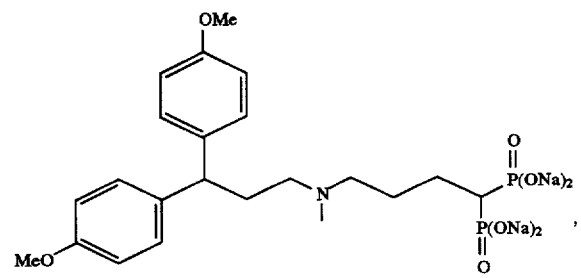
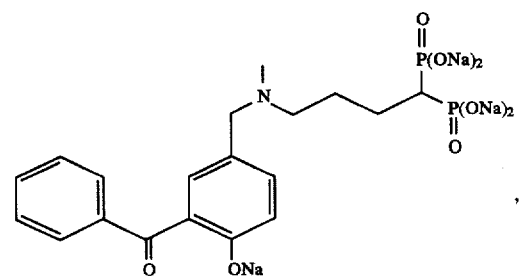
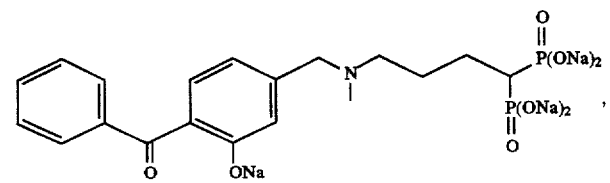
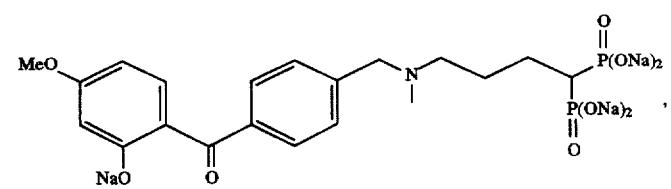

-continued
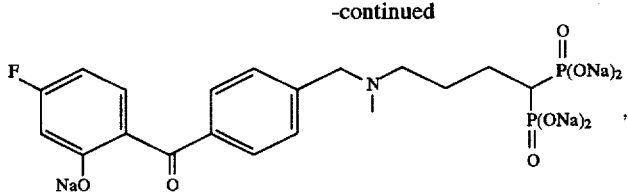
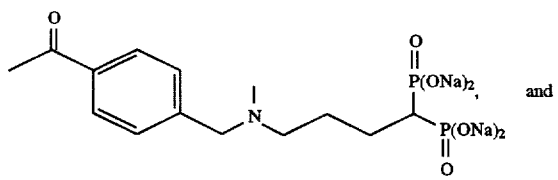
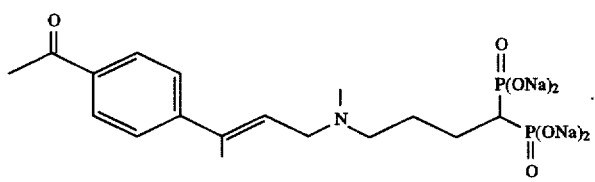
14. A phosphonic acid derivative according to claim 1 selected from the group consisting of
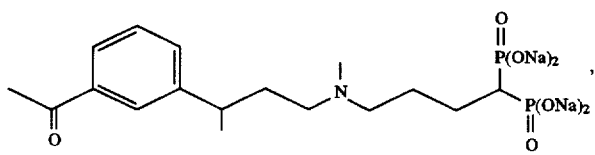
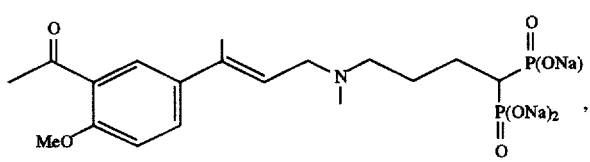
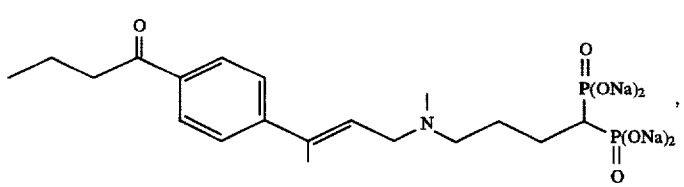
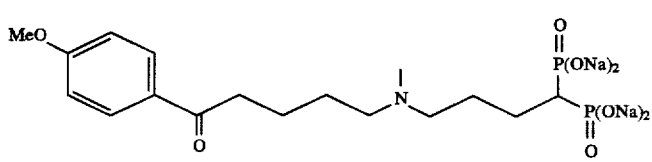
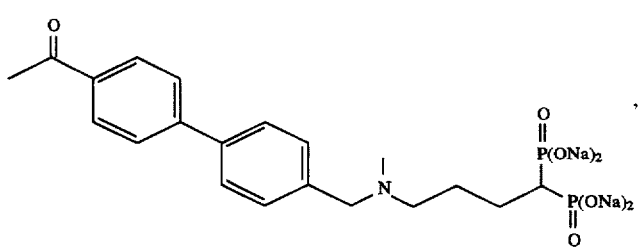

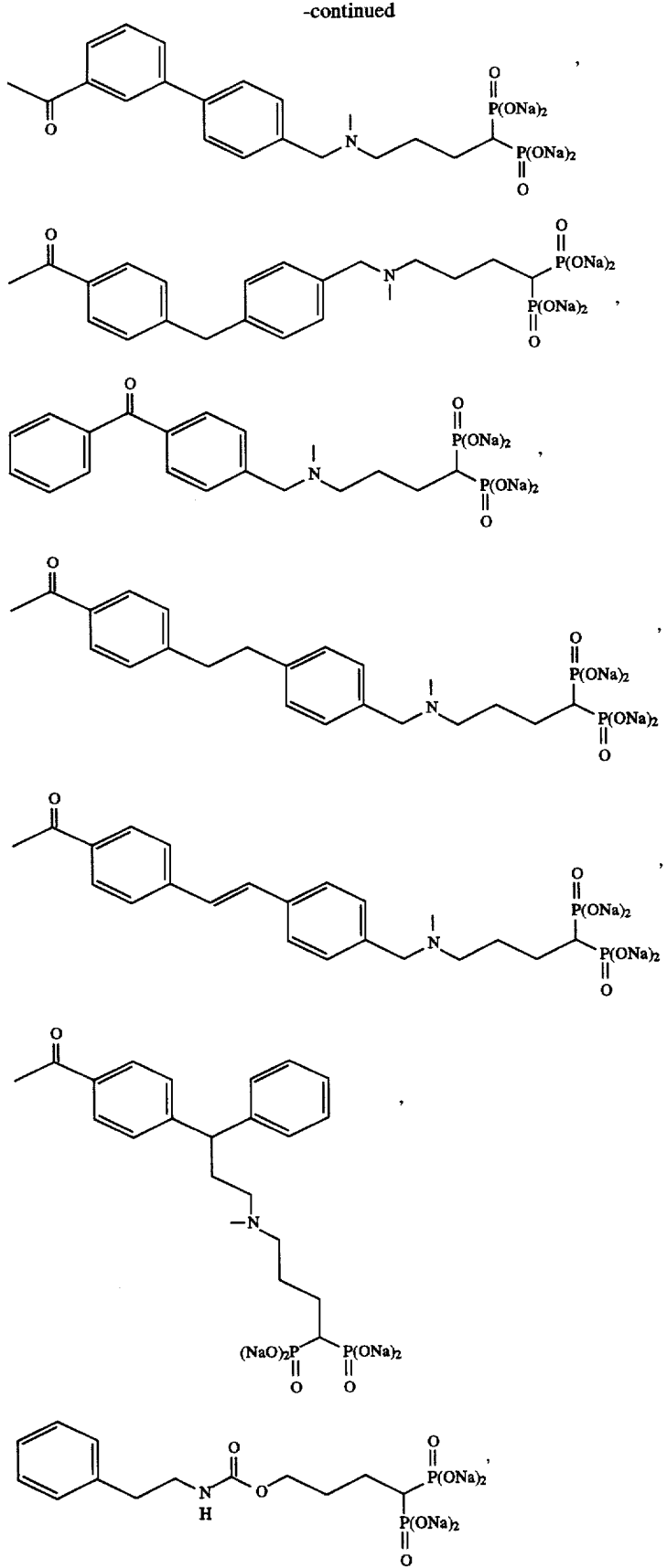

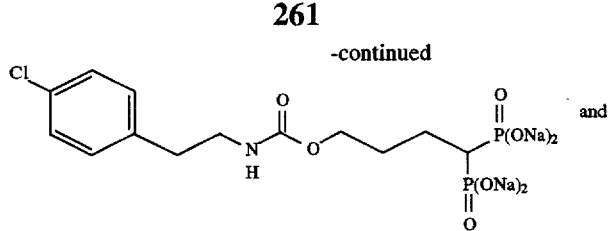
and
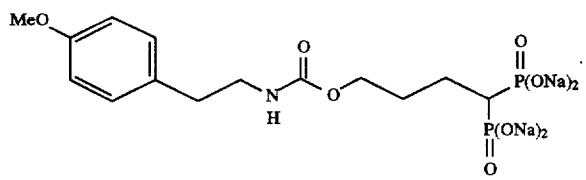
15. A phosphonic acid derivative according to claim 1 selected from the group consisting of
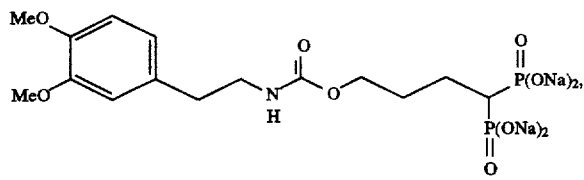
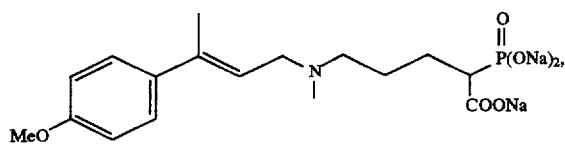
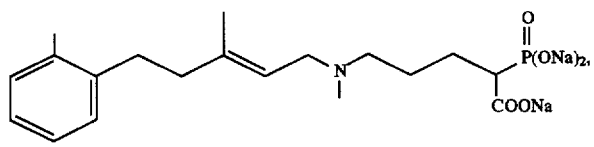
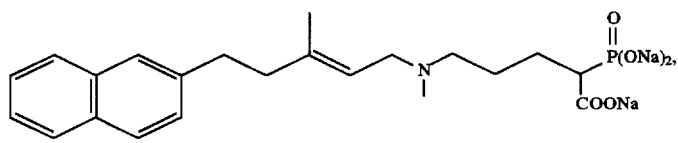
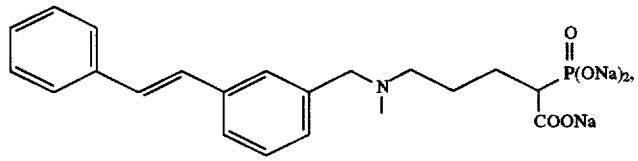
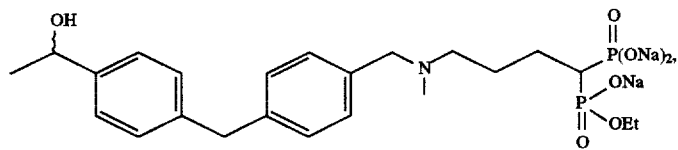
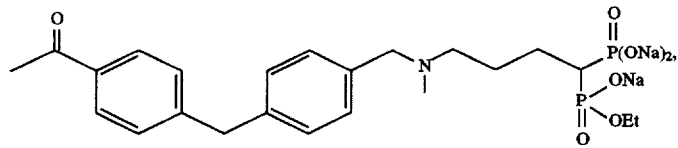

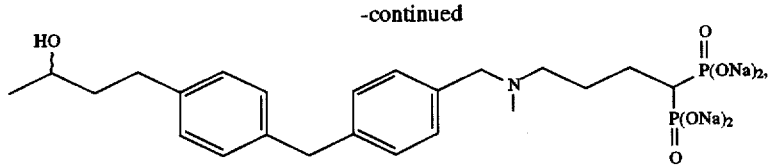
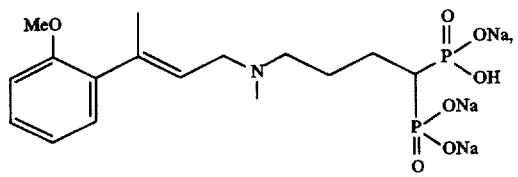
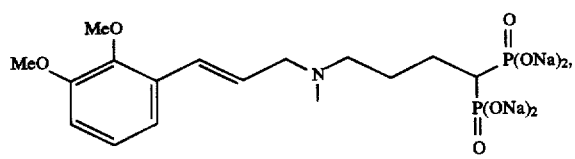
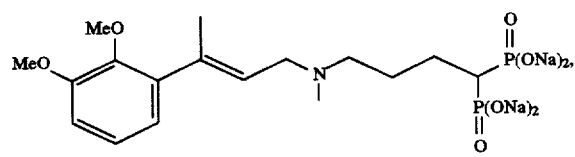
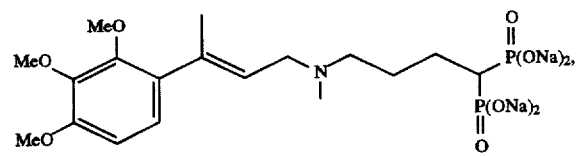
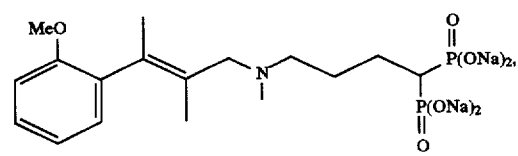
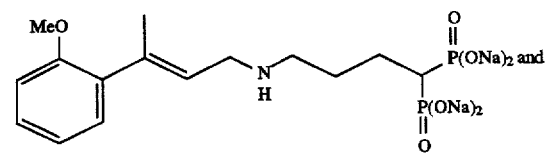
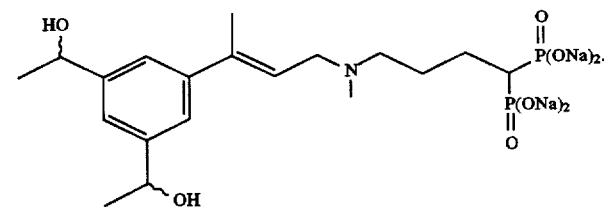
16. A phosphonic acid derivative according to claim 1 selected from the group consisting of
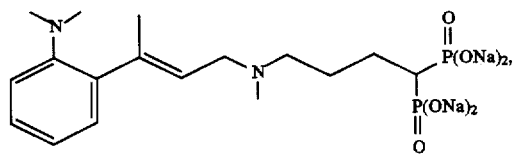

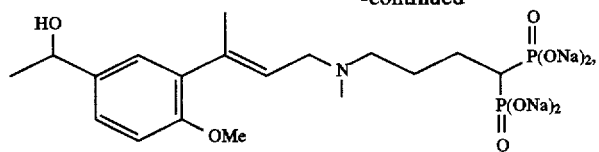
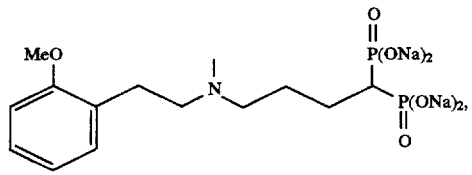
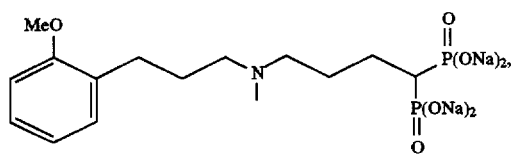
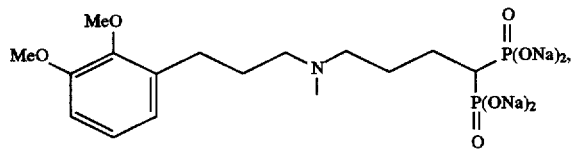
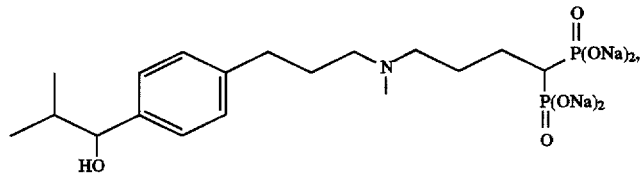
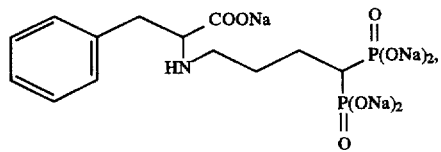
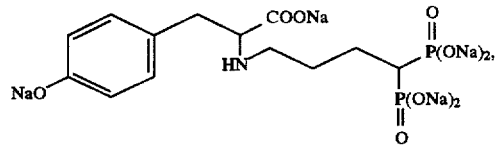
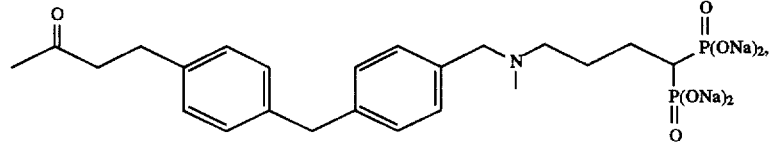
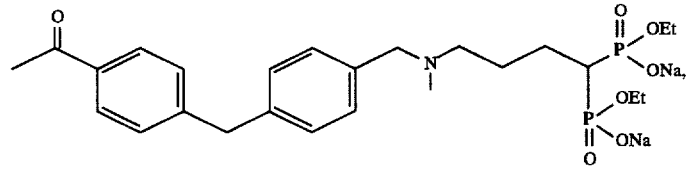
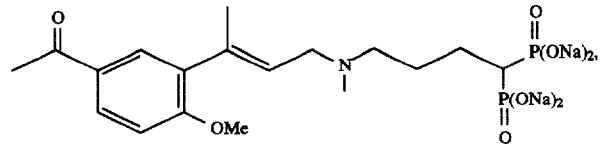

-continued
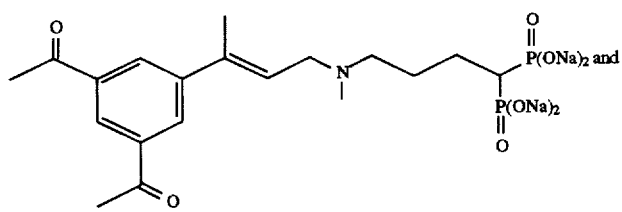
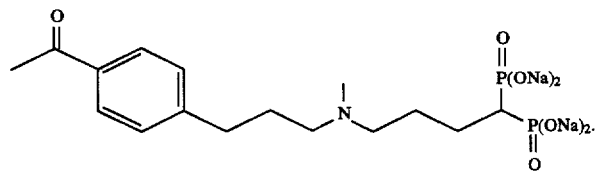
17. A phosphonic acid derivative according to claim 1 selected from the group consisting of
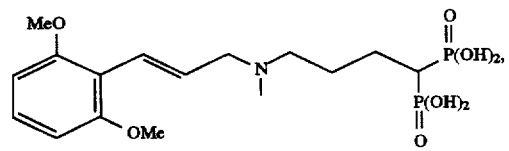
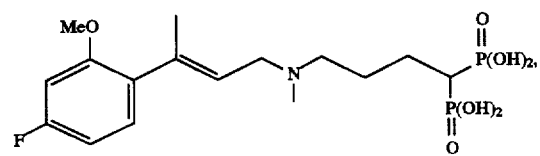
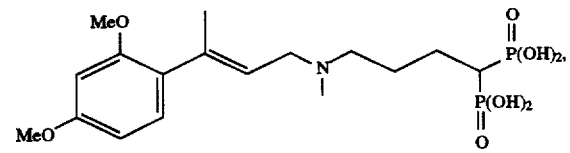
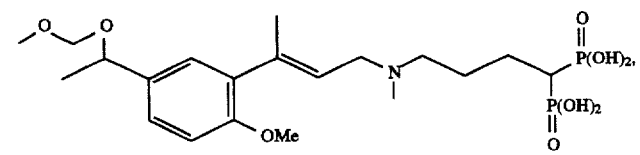
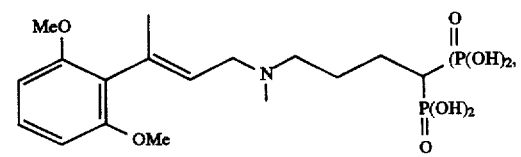
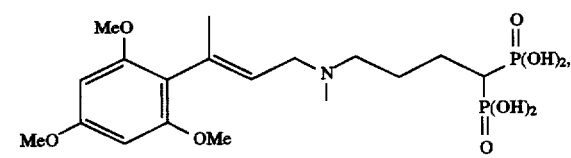

-continued
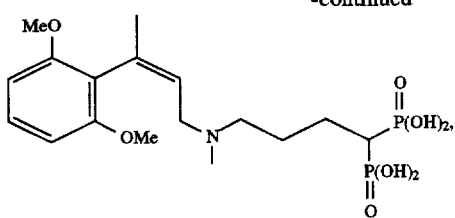
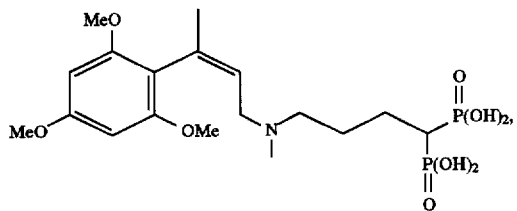
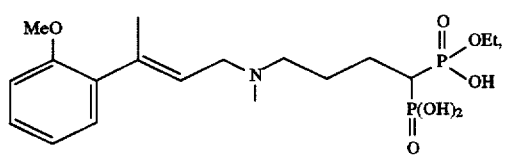
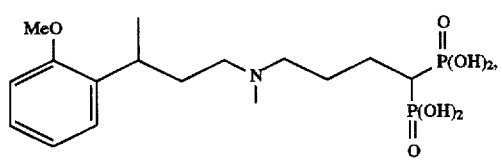
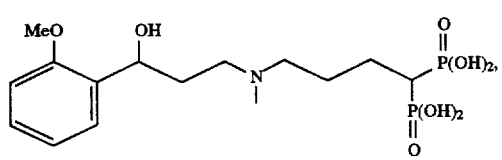
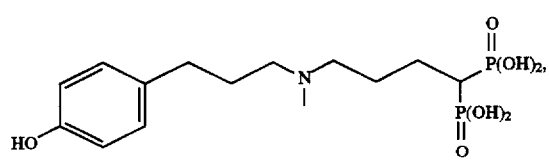
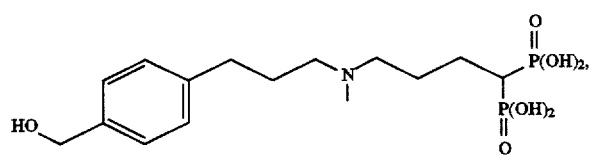
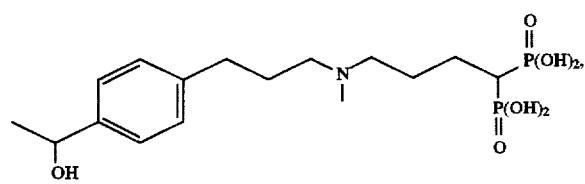
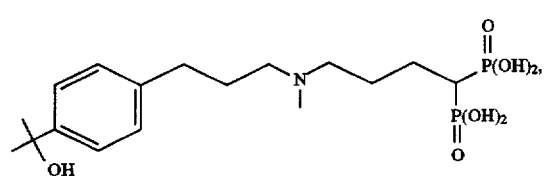

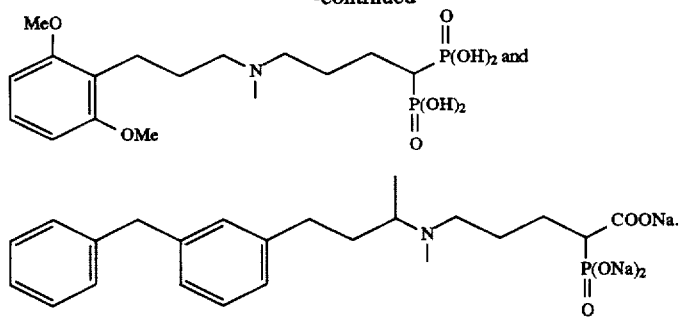
18. A phosphonic acid derivative according to claim 1 selected from the group consisting of
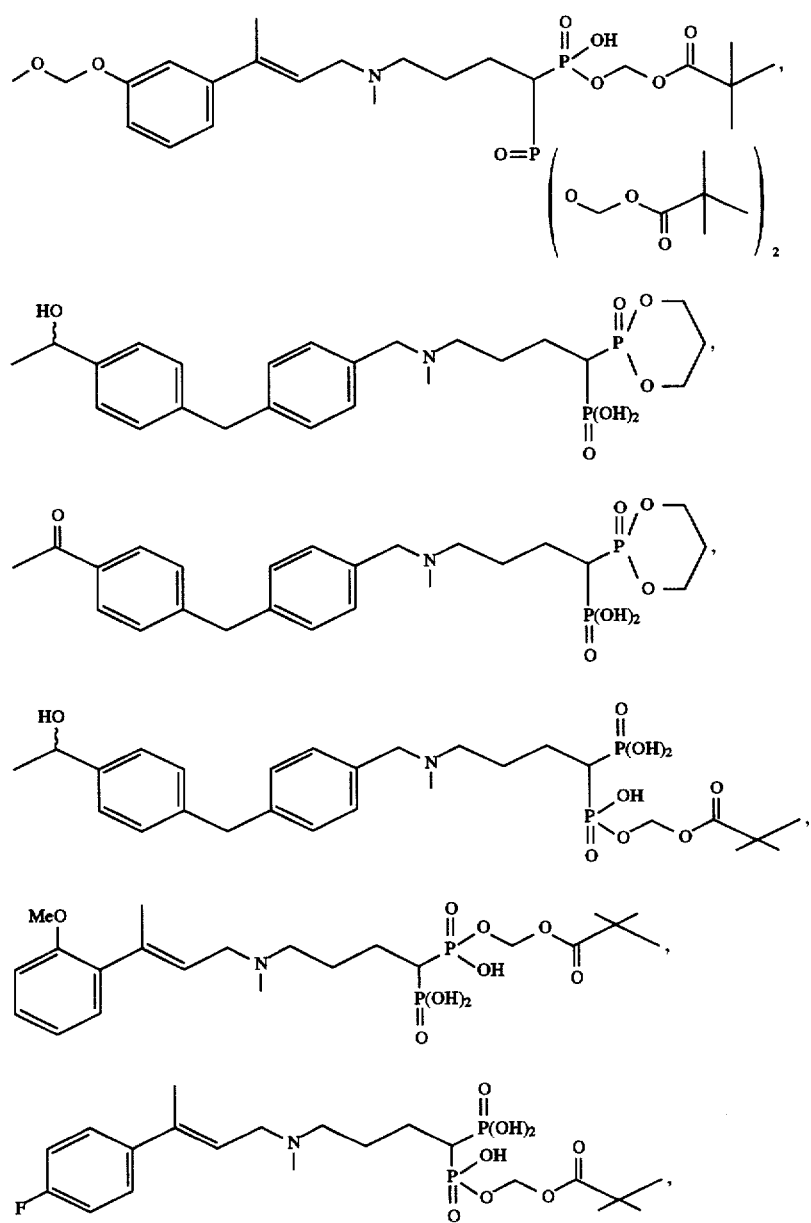

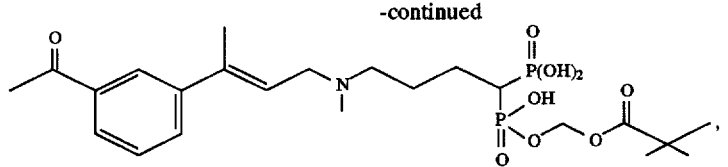
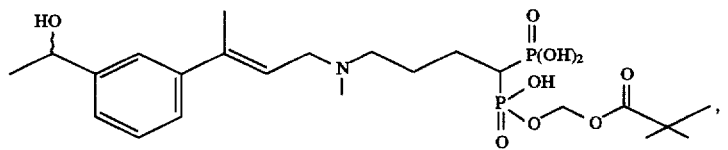
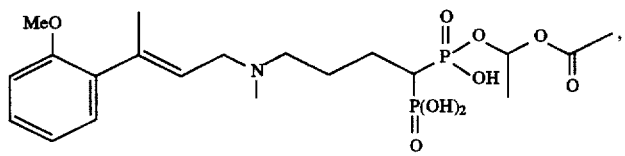
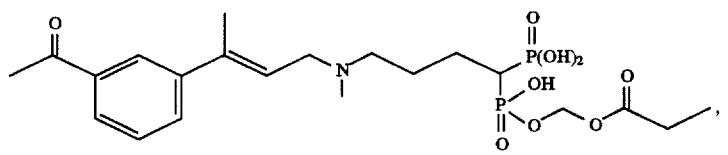
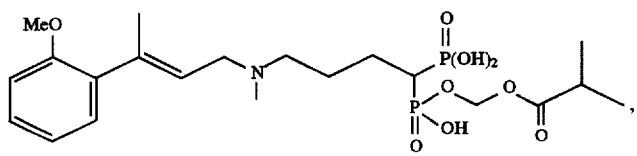
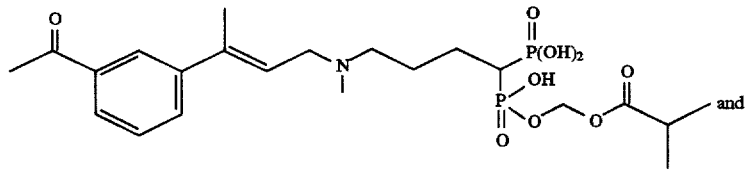
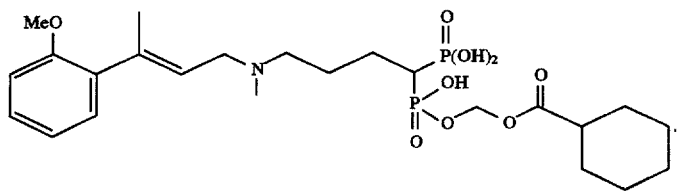
19. A phosphonic acid derivative according to claim 1 selected from the group consisting of
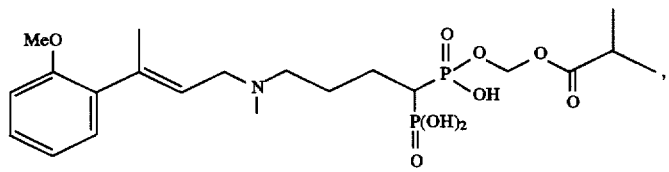
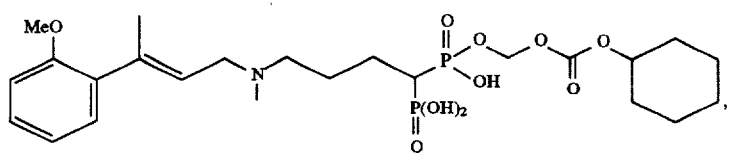

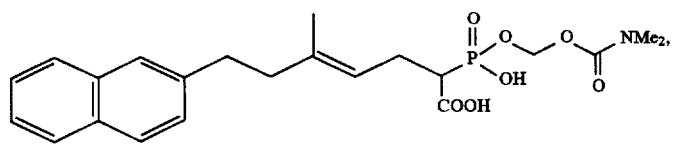
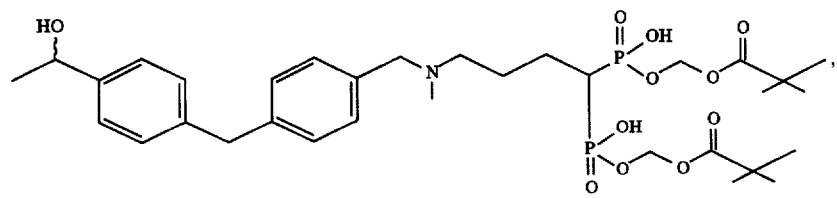
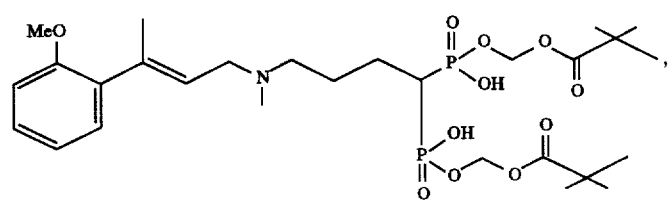
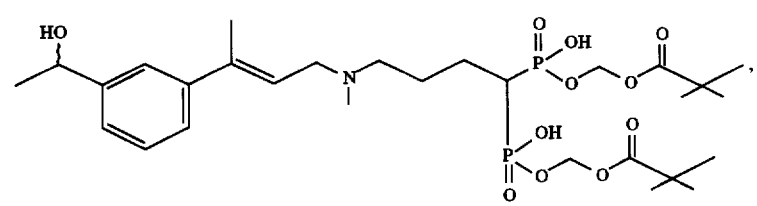
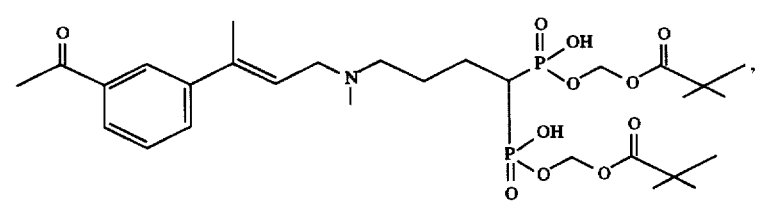
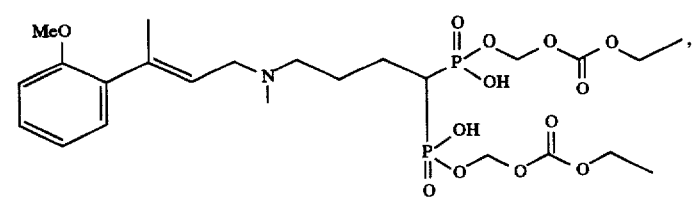
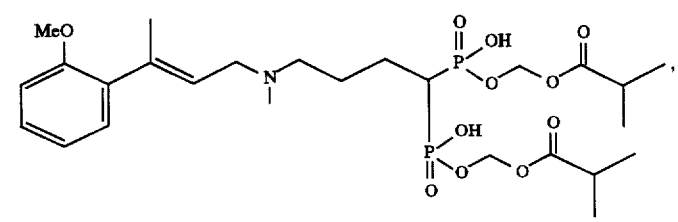

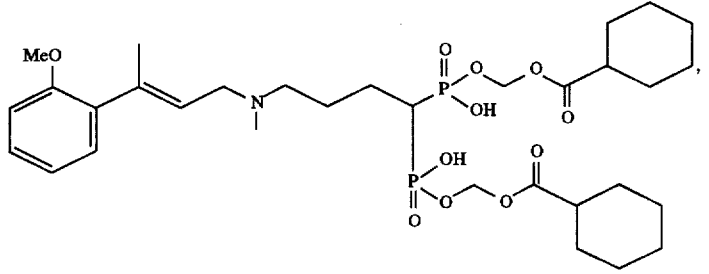
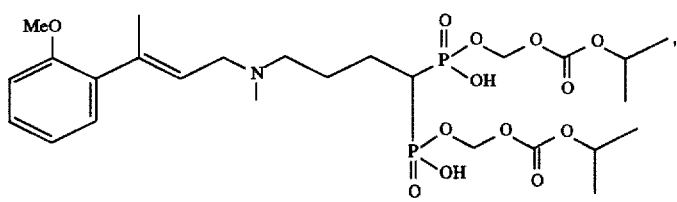
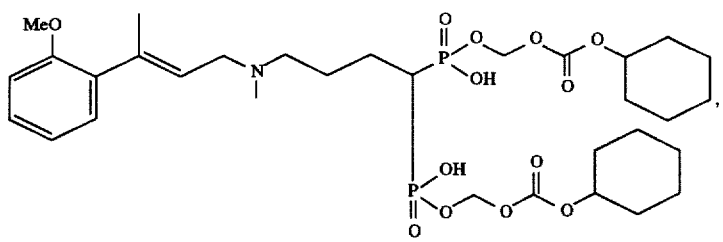
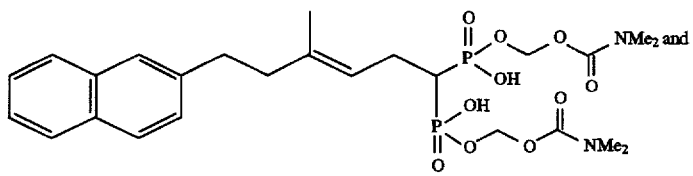
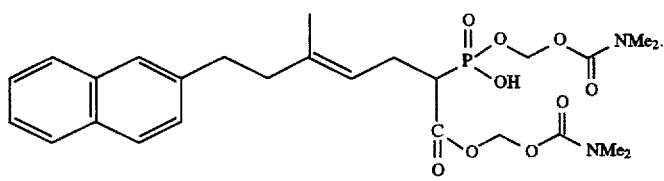
20. A phosphonic acid derivative according to claim 1 selected from the group consisting of
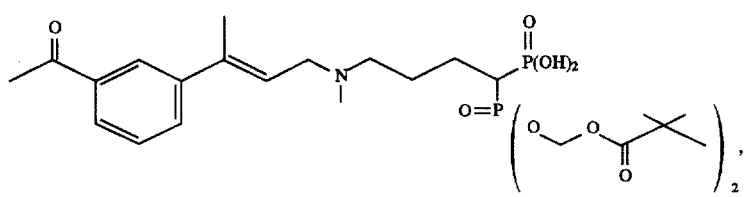
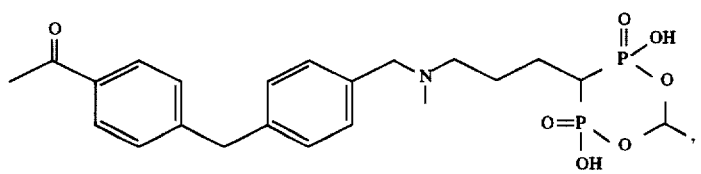

-continued
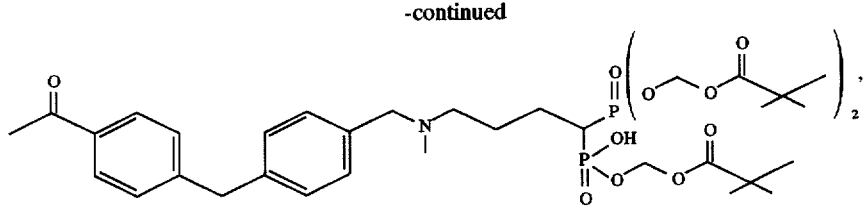
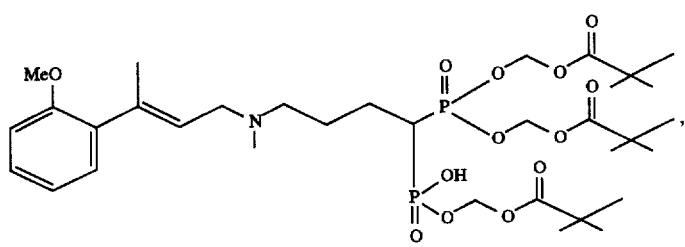
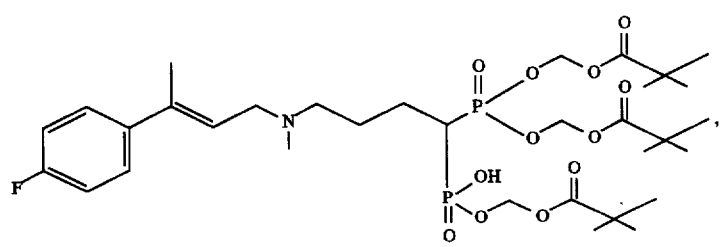
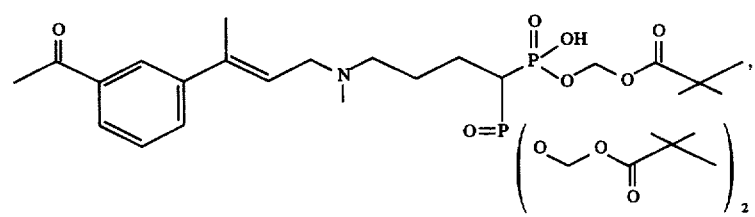
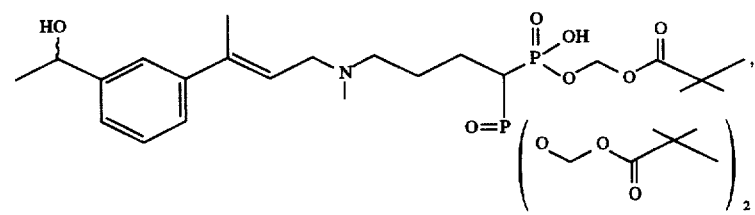
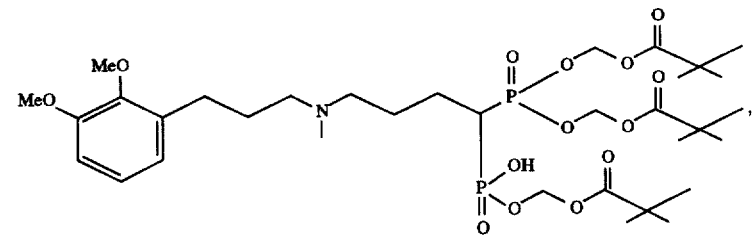
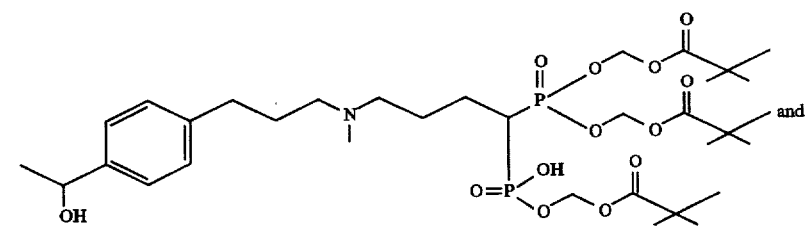

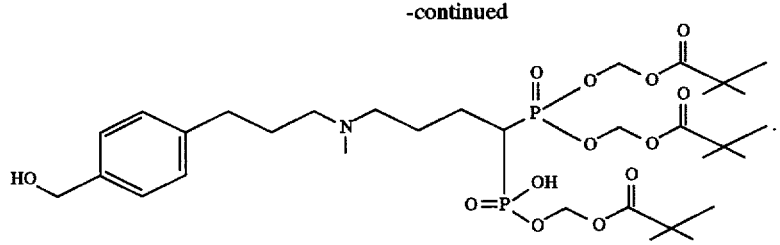
21. A phosphonic acid derivative according to claim 1 selected from the group consisting of
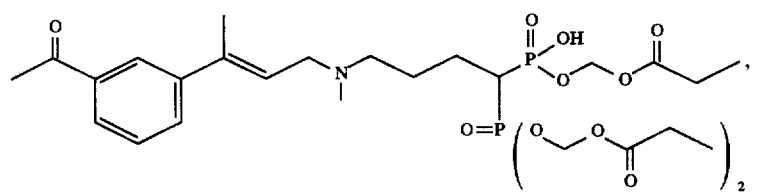
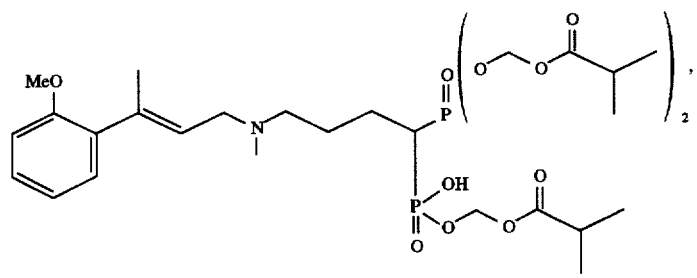
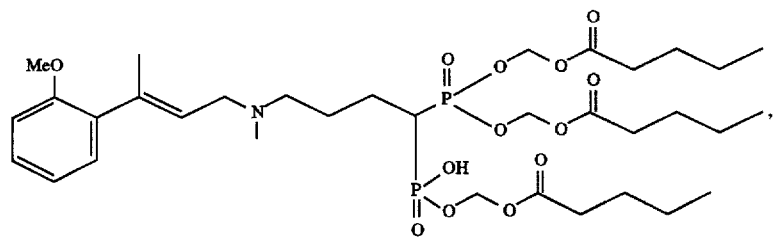
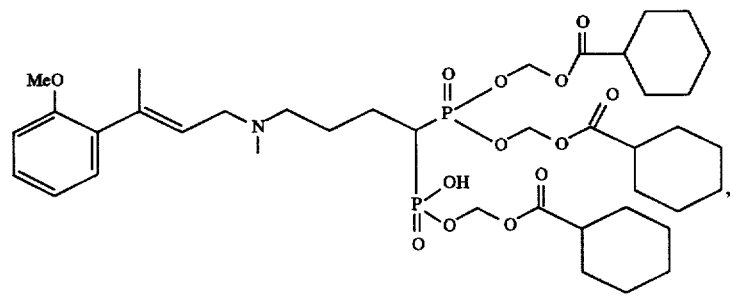
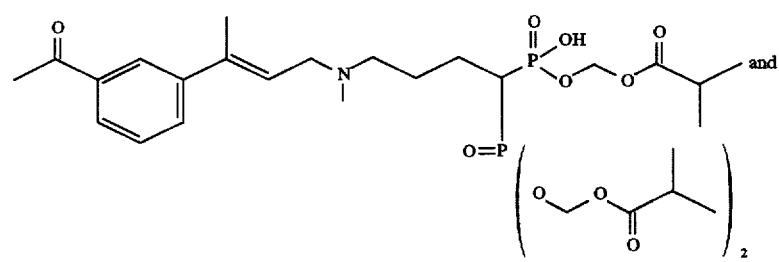

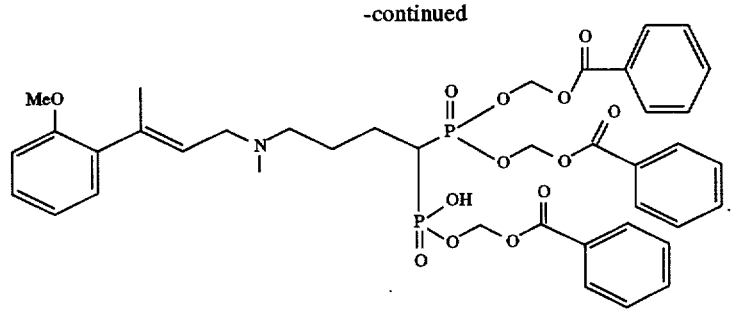
* * * * *